United States Patent
Protopopova et al.

(10) Patent No.: US 7,456,222 B2
(45) Date of Patent: Nov. 25, 2008

(54) ANTI TUBERCULAR DRUG: COMPOSITIONS AND METHODS

(75) Inventors: Marina Nikolaevna Protopopova, Silver Springs, MD (US); Richard Edward Lee, Cordova, TN (US); Richard Allan Slayden, Ft. Collins, CO (US); Clifton E. Barry, III, Germantown, MD (US); Elena Bogatcheva, Bethesda, MD (US); Leo Einck, McLean, VA (US)

(73) Assignees: Sequella, Inc., Rockville, MD (US); The United States of America as represented by the Secretary, Department of Health and Human Services, Washington, DC (US)

( * ) Notice: Subject to any disclaimer, the term of this patent is extended or adjusted under 35 U.S.C. 154(b) by 55 days.

(21) Appl. No.: 11/173,192

(22) Filed: Jul. 1, 2005

(65) Prior Publication Data

US 2006/0148904 A1    Jul. 6, 2006

Related U.S. Application Data

(63) Continuation-in-part of application No. 11/145,499, filed on Jun. 3, 2005, which is a continuation of application No. 10/441,146, filed on May 19, 2003, now abandoned, which is a continuation-in-part of application No. 10/147,587, filed on May 17, 2002, now Pat. No. 6,951,961.

(60) Provisional application No. 60/381,220, filed on May 17, 2002.

(51) Int. Cl.
*A61K 31/132* (2006.01)
*A61K 31/135* (2006.01)
*A61K 31/44* (2006.01)
*A61K 31/445* (2006.01)

(52) U.S. Cl. ............. 514/648; 514/306; 514/317; 514/649; 514/653; 514/654; 514/655; 514/659; 514/660; 564/316; 564/320; 564/355; 564/366; 564/368; 564/369; 564/370; 564/453; 564/454; 564/455; 564/457; 546/134; 546/194; 546/246

(58) Field of Classification Search ............. None
See application file for complete search history.

(56) References Cited

U.S. PATENT DOCUMENTS

| | | | |
|---|---|---|---|
| 2,623,878 A | 12/1952 | Isler et al. |
| 3,176,040 A | 3/1965 | Wilkinson et al. |
| 3,553,257 A | 1/1971 | Halmos et al. |
| 3,579,586 A | 5/1971 | Zoja |
| 3,579,587 A | 5/1971 | Zoja |
| 3,718,655 A | 2/1973 | Ferrer-Salat et al. |
| 3,769,347 A | 10/1973 | Kazan |
| 3,829,493 A | 8/1974 | Butula et al. |
| 3,847,991 A | 11/1974 | Bernardi et al. |
| 3,855,300 A | 12/1974 | Takahashi et al. |
| 3,878,201 A | 4/1975 | Tomcufcik |
| 3,931,152 A | 1/1976 | Tomcufcik et al. |
| 3,931,157 A | 1/1976 | Child et al. |
| 3,944,608 A | 3/1976 | Singh |
| 3,944,616 A | 3/1976 | Kazan |
| 3,944,617 A | 3/1976 | Singh |
| 3,944,618 A | 3/1976 | Singh |
| 3,944,619 A | 3/1976 | Singh |
| 3,953,513 A | 4/1976 | Oppici |
| 3,979,457 A | 9/1976 | Fujii et al. |
| 4,006,234 A | 2/1977 | Child et al. |
| RE29,358 E | 8/1977 | Tomcufcik |
| RE29,588 E | 3/1978 | Halmos et al. |
| 4,150,030 A | 4/1979 | Singh |
| 4,262,122 A | 4/1981 | Lees et al. |
| 4,450,274 A | 5/1984 | Park |
| 5,104,875 A | 4/1992 | Jurgen et al. |
| 5,439,891 A | 8/1995 | Kapil et al. |
| 5,922,282 A | 7/1999 | Ledley |
| 5,985,935 A | 11/1999 | Kharazmi et al. |
| 2003/0236225 A1 | 12/2003 | Protopopova et al. |
| 2004/0033986 A1 | 2/2004 | Protopopova et al. |

FOREIGN PATENT DOCUMENTS

| | | |
|---|---|---|
| FR | 2007524 | 4/1969 |
| GB | 729332 | 5/1955 |
| GB | 961317 | 6/1964 |
| GB | 1234349 | 6/1971 |
| RU | 2168986 | 6/2001 |
| WO | WO 99/51213 A2 | 10/1999 |

OTHER PUBLICATIONS

Database CAPLUS on STN, Acc. No. 1973:38547, Hamilton-Miller, Chemotherapy (1973), 18(3), p. 154-61 (abstract).*
Database CAPLUS on STN, Acc. No. 2003:49639, Lee et al., Journal of Combinational Chemistry (2003), 5(2), p. 172-187 (abstract).*
Author: Arain, T. et al., Title: Bioluminescence Screening in Vitro (Bio-Siv) Assays for High-Volume Antimycobacterial Drug Discovery, Publ: *Antimicrobial Agents and Chemotherapy*, vol./Iss: 40(6), pp. 1536-1541, Date: Jan. 1, 1996.
Author: Barry, C. et al., Title: Use of Genomics and Combinatorial Chemistry in the Development of New Antimycobacterial Drugs, Publ: *Biochemical Pharmacology*, vol./Iss: 59, pp. 221-231, Date: Jan. 1, 2000.
Author: Bass, J. et al., Title: Treatment of Tuberculosis and Tuberculosis Infection in Adults and Children, Publ: *American Journal of Resiratory and Critical Care Medicine*, vol./Iss: 149, pp.1359-1374, Date: Jan. 1, 1994.

(Continued)

*Primary Examiner*—Brian J Davis
(74) *Attorney, Agent, or Firm*—King & Spalding LLP

(57) ABSTRACT

Methods and compositions for treating disease caused by infectious agents, particularly tuberculosis. In particular, methods and compositions comprising substituted ethylene diamines for the treatment of infectious diseases are provided. In one embodiment, these methods and compositions are used for the treatment of mycobacterial infections, including, but not limited to, tuberculosis.

27 Claims, 109 Drawing Sheets

OTHER PUBLICATIONS

Author: Belanger, A et al., Title: The EmbAB Genes of Mycobacterium Avium Encode an Arabinosyl Transferase Involved in Cell Wall Arabinan Biosynthesis that is the Target for the Antimycobacterial Drug Ethambutol, Publ: *Proceedings of the National Academy of Science*, vol./Iss. 93, pp. 11919-11924, Date: Jan. 1, 1996.

Author: Brown, D. et al. Title: Merrified Alpha-Methoxyphenyl (MAMP) Resin: A New Versatile Solid Support for the Synthesis of Secondary Amines, Publ: *Tetrahedron Letters*, vol./Iss. 39, pp. 8533-8536, Date: Jan. 1, 1998.

Chan-Tack, K., Title: Antituberculosis-Drug Resistance, Publ: *New England Journal of Medicine*, vol./Iss. 339(15), pp. 1079, Date: Jan. 1, 1998.

Author: Cole, S. et al., Title: Deciphering the Biology of Mycobacterium Tuberculosis from the Complete Genome Sequence, Publ: *Nature*, vol./Iss: 393, pp. 537-544, Date: Jan. 1, 1998.

Author: Cuervo, J. et al., Title: Polyalkylamine Chemical Combinatorial Libraries, Publ: *Peptides 1994: Proceedings of the European Peptide Symposium*, pp. 465-466, Date: Jan. 1, 1995.

Author: Cymerman-Craig, J. et al., Title: Chemical Constitution and Anti-Tuberculous Activity: Part II: Bases Possessing the Diphenyl Structure, Publ: *British Journal of Experimental Pathology*, vol./Iss: 36, pp. 254-260, Date: Jan. 1, 1955.

Author: Cynamon et al., Title: Activities of Several Novel Oxazolidinones Against Mycobacterium Tuberculosis in a Murine Model, Publ: *Antimicrobial Agents and Chemotherapy*, vol./Iss: 43(5), pp. 1189-1191, Date: May 1, 1999.

Author: Deng, I. et al., Title: Recognition of Multiple Effects of Ethambutol on Metabolism of Mycobacterial Cell Envelope, Publ: *Antimicrobial Agents and Chemotherapy*, vol./Iss: 39(3), pp. 694-701, Date: Jan. 1, 1995.

Author: Dye, C. et al., Title: Global Burden of Tuberculosis: Estimated Incidence, Prevalence and Mortality by Country, Publ: *Journal of the American Medical Association*, vol./Iss: 282(7), pp. 677-686, Date: Jan. 1, 1999.

Author: Farmer, P. et al., Title: The Dilemma of MDR-TB in the Global Era, Publ: *International Journal of Tuberculosis and Lung Disease*, vol./Iss: 2(11), pp. 869-876, Date: Jan. 1, 1998.

Author: Garigipati, R., Title: Reagents for Combinatorial Organic Synthesis: Preparation and Uses of Rink-Chloride, Publ: *Tetrahedron Letters*, vol./Iss: 38(39), pp. 6807-6810, Date: Jan. 1, 1997.

Author: Gordon, D., Title: Reductive Alkylation on a Solid Phase: Synthesis of Piperazinedione Combinatorial Library, Publ: *Bioorganic & Medicinal Chemistry Letters*, vol./Iss: 5(1), pp. 47-50, Date: Jan. 1, 1995.

Author: Gustafson, G., Title: Incorporation of Carbohydrates and Peptides into Large Triazine-Based Screening Libraries Using Automated Parallel Synthesis, Publ: *Tetrahedron*, vol./Iss: 54, pp. 4051-4065, Date: Jan. 1, 1998.

Author: Hamilton-Miller, J.M., Title: Inhibition of *Candida* by Compounds which Inhibit Cholesterol Biosynthesis, Publ: *Chemotherapy*, vol./Iss: 18, pp. 154-161, Date: Jan. 1, 1973.

Author: Hausler, H. et al., Title: Ethambutol Analogues as Potential Antimycobacterial Agents, Publ: *Bioorganic & Medicinal Chemistry Letters*, vol./Iss: 11, pp. 1678-1681, Date: Jan. 1, 2001.

Author: Lee, M. et al., Title: Site-Specific Integration of Mycobacteriophage L5: Integration-Proficient Vectors for Mycobacterium smegmatis, Mycobacterium tuberculosis, and bacilli Calmette-Guerin, Publ: *Proceedings of the National Academy of Science*, vol./Iss: 88, pp. 3111-3115, Date: Jan. 1, 1991.

Author: Lee, R., Title: Combinatorial Lead Optimization of [1,2]-Diamines Based on Ethambutol as Potential Antituberculosis Preclinical Candidates, Publ: *Journal of Combinatorial Chemistry*, vol./Iss: 5, pp. 172-187, Date: Jan. 1, 2003.

Author: Lee, R. et al., Title: Synthesis of the Mycobacterial Arabinose Donor β-D-Arabinofuranosyl-1-monophosphoryldecaprenol, Development of a Basic Arabinosyl-Transferase Assay, and Identification of Ethambutol as an Arabinosyl Transferase Inhibitor, Publ: *Journal of the American Chemical Society*, vol./Iss: 117, pp. 11829-11832, Date: Jan. 1, 1995.

Author: Liu, G. et al., Title: A General Solid-Phase Syntheses Strategy for the Preparation of 2-Pyrrolidinemethanol Ligands, Publ: *Journal of Organic Chemistry*, vol./Iss: 60, pp. 7712-7713, Date: Jan. 1, 1995.

Author: March, J., Title: Advanced Organic Chemistry: Reactions, Mechanisms and Structure, 3rd edition; Publisher: John Wiley and Sons, New York, pp. 916, Date: Jan. 1, 1985.

Author: O'Brien, R., Title: Scientific Blueprint for Tuberculosis Drug Development; Publisher: the Global Alliance for TB Drug Development, Inc., Date: Jan. 1, 2001.

Author: Pablos-Mendez, A. et al., Title: Global Surveillance for Antituberculosis Drug Resistance 1994-1997, Publ: *New England Journal of Medicine*, vol./Iss: 338(23), pp. 1641-1649, Date: Jan. 1, 1998.

Author: Rink, H., Title: Solid-Phase Synthesis of Protected Peptide Fragments Using a Trialkoxy-Diphenyl-Methylester Resin, Publ: *Tetrahedron Letters*, vol./Iss: 28(33), pp. 3787-3790, Date: Jan. 1, 1987.

Author: Roark, W. et al., Title: Bioisosterism in Drug Design: Identification of and Structure-Activity Relationships in a Series of Glycine Anilide ACAT Inhibitors, Publ: *Bioorganic & Medicinal Chemistry Letters*, vol./Iss: 3 (1), pp. 29-39, Date: Jan. 1, 1995.

Author: S/ Budavari, ed., Publ: *the Merck Index 12th Edition*, pp. 646, entry No., Date: Jan. 1, 1996.

Author: Shawar, R. et al., Title: Rapid Screening of Natural Products for Antimycobacterial Activity by Using Luciferase-Expressing Strains of Mycobacterium bovis BCG and Mycobacterium intracellular, Publ: *Antimicrobial Agents and Chemotherapy*, vol./Iss: 41(3), pp. 570-574, Date: Jan. 1, 1997.

Author: Shepherd, R. et al., Title: Structure-Activity Studies Leading to Ethambutol, a New Type of Antituberculosis Compound. Publ: *Annals of the New York Academy of Science*, vol./Iss: 134, pp. 686-710, Date: Jan. 1, 1966.

Author: Silen, J. et al. Title: Screening for Novel Antimicrobials from Encoded Combinatorial Libraries by Using a Two-Dimensional Agar Format, Publ: *Antimicrobial Agents and Chemotherapy*, vol./Iss: 42(6), pp. 1447-1453, Date: Jan. 1, 1999.

Author: Sterling, T., Title: Relapse Rates After Short-Course (6-month) Treatment of Tuberculosis in HIV-Infected and Uninfected Persons, Publ: *AIDS*, vol./Iss: 13(14), pp. 1899-1904, Date: Jan. 1, 1999.

Author: Telenti, A. et al., Title: The Emb Operon, a Gene Cluster of Mycobacterium Tubeculosis Involved in Resistance to Ethambutol, Publ: *Natural Medicine*, vol./Iss: 3(5), pp. 567-570, Date: Jan. 1, 1997.

Author: Zuckermann, R. et al., Title: Efficient Method for the Preparation of Peptoids [Oligo(N-substituted glycines)] by Submonomer Solid-Phase Synthesis, Publ: *Journal of the American Chemical Society*, vol./Iss: 114, pp. 10646-10647, Date: Jan. 1, 1992.

Author: Forbes et al., Title: Studies on the Mode of Action of Ehtambutol, Publ: *Med International Congress of Chemotherapy*, vol./Iss: 1, pp. 174-177, Jan. 1, 1964.

\* cited by examiner

Primary Amines 1. 4-Methylbenzylamine
2. Cyclopentylamine
3. 2-(Aminomethylo)pyridine
6. Furfurylamine
7. 3,4,5-Trimethoxybenzylamine
8. 1-Methyl-3-phenylproplyamine
9. Cyclobutylamine
10. 1,2,3,4-Trimethoxybenzylamine 11. 2,3-Dimethylcyclohexylamine 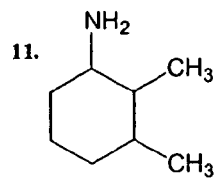
12. Tyramine 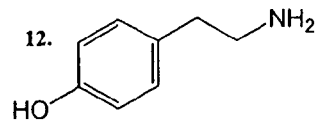
13. 2-Fluorobenzylamine 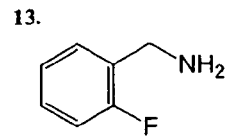
16. (R)-2-Amino-1-butanol 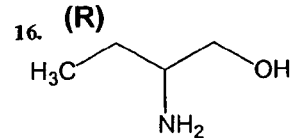
17. 3,4-Dimethoxyphenethylamine 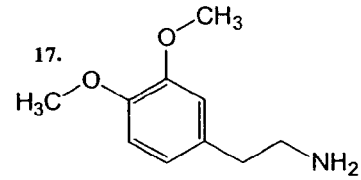
18. 3,3-Diphenylpropylamine 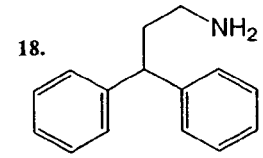
19. Propylamine 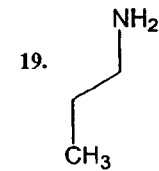
21. 1-(2-Aminoethyl)piperidine 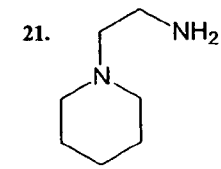
FIGURE 2(b)

| | | |
|---|---|---|
| 22. | Phenethylamine | 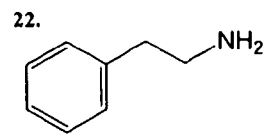 |
| 23. | 4-(2-Aminoethyl)morpholine | 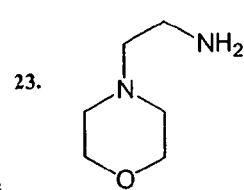 |
| 24. | (S)-Phenylglycinol | 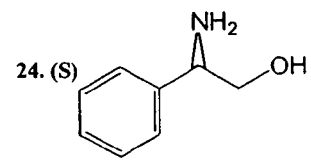 |
| 25. | Tryptamine | 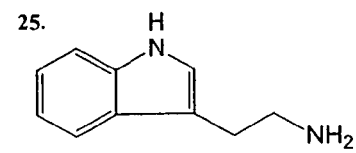 |
| 27. | Cyclohexylamine | 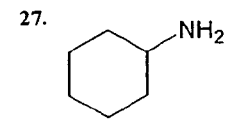 |
| 28a. | (+)-Isopinocampheylamine | 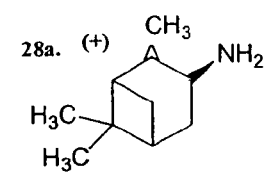 |
| 29. | Benzylamine | 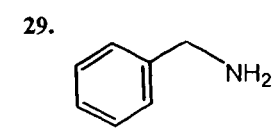 |
| 30. | 3-Amino-1-propanol | 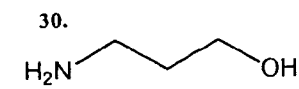 |
| 31. | 2-Fluorophenethylamine | 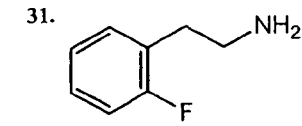 |
FIGURE 2(c)

| # | Name | Structure |
|---|------|-----------|
| 33. | b-Methylphenethylamine | 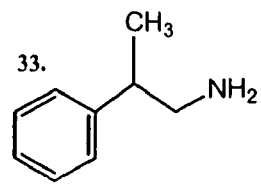 |
| 34. | 4-Methoxyphenethylamine | 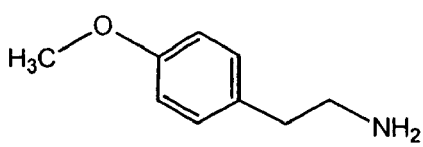 |
| 35. | N,N-Dimethylethylenediamine | 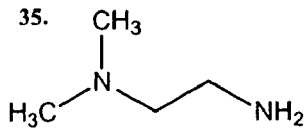 |
| 36. | L-Methioninol | 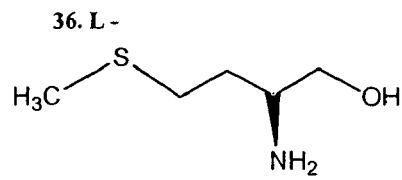 |
| 37. | Tetrahydrofurfurylamine | 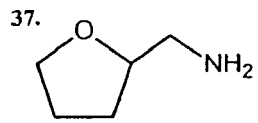 |
| 38. | Amylamine | 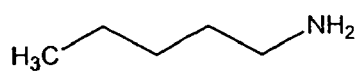 |
| 39. | Aminomethylcyclopropane |  |
| 41. | 1-(2-Aminoethyl)piperazine | 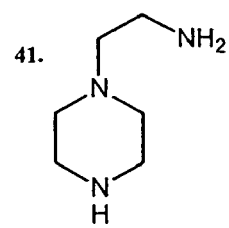 |
FIGURE 2(d)

| | |
|---|---|
| 42a. | (+)-Bornylamine |
| 43. | tert-Octylamine |
| 44. | 1-Adamantanemethylamine |
| 45. | 2-Amino-1-propanol, d,l |
| 46. | 3-Phenyl-1-propylamine |
| 47. | 2,2-Diphenylamine |
| 48. | 1-(3-Aminopropyl)-2-pyrrolidinone (tech) |

| | | |
|---|---|---|
| 49. | 4-(Trifluoromethyl)benzylamine | 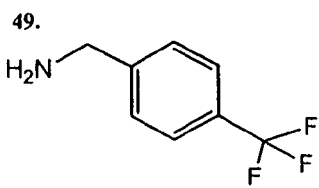 |
| 50. | 1-(2-Aminoehtyl)-pyrrolidine | 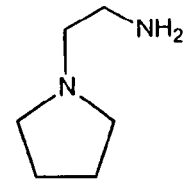 |
| 51. | Veratryl amine | 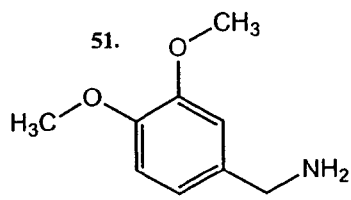 |
| 52. | 5-Amino-1-pentanol | 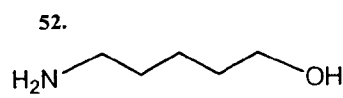 |
| 53. | 2-(1-Cylcohexenyl)ethylamine | 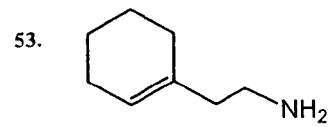 |
| 54. | 5-Aminoquinoline | 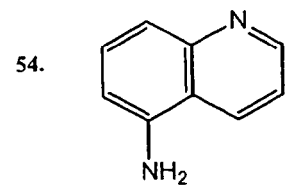 |
| 55. | 1-Aminomethyl-1-cylcohexanol, HCl | 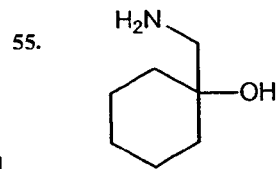 |
| 56. | 1-Aminopiperidine | 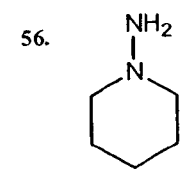 |
FIGURE 2(f)

| | | |
|---|---|---|
| 57. | 3-Fluorobenzylamine | 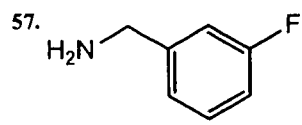 |
| 59. | (1S,2R)-cis-1-Amino-2-indanol | 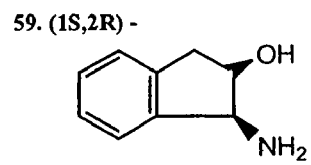 |
| 61. | 4-Amino-1-butanol | 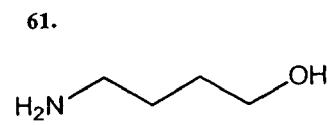 |
| 63. | (S)-2-Amino-1-butanol | 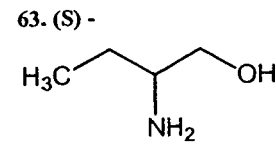 |
| 66. | 2,4-Dimethoxybenzylamine | 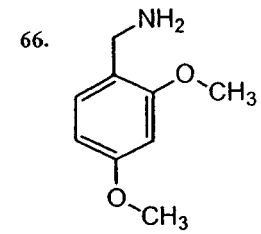 |
| 68. | 1-(1-Naphthyl)ethylamine | 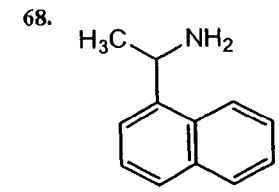 |
| 69. | 2-(2-Aminoethyoxy)ethanol | 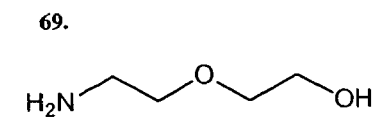 |
| 70. | 3-Amino-1,2,4-triazine | 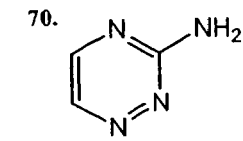 |
FIGURE 2(g)

71. 2-Ethoxybenzylamine 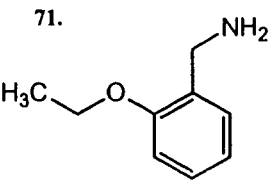
72. 4-(3-Aminopropyl)morpholine 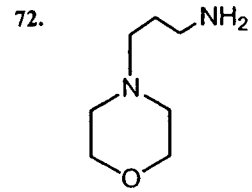
73. 2-Amino-1-methoxypropane 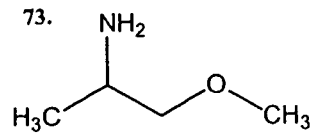
74a. cis-(-)-Myrtanylamine 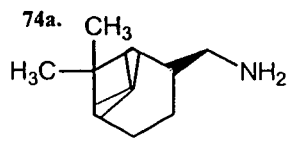
77a. Cyclooctylamine 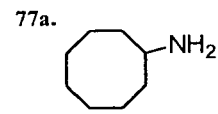
78a. 2-Adamantamine, HCl 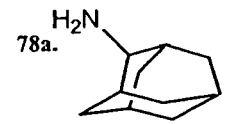
79. trans-2-Aminocyclohexanol, HCl 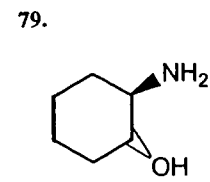
80. 3,Amino-5-phenyl pyrazole 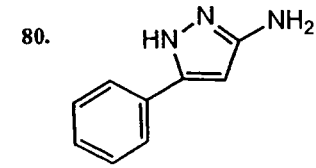
FIGURE 2(h)

| | | |
|---|---|---|
| 82. | 2,3-Dimethoxybenzylamine | 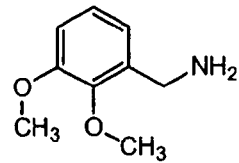 |
| 83a. | Noradamantamine, HCl |  |
| 84. | 4-Amino-1-benzylpiperidine | 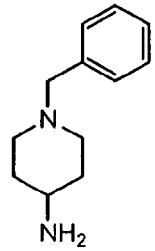 |
| 85. | 4-Methylcyclohexylamine | 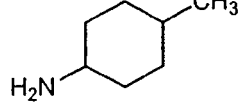 |
| 86. | (1R,2S)-1-Amino-2-indanol | 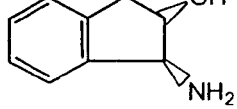 |
| 87. | 3-Aminopyrazole | 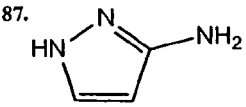 |
| 88. | 4-Fluorobenzylamine | 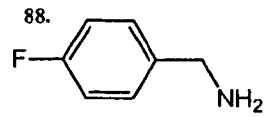 |
| 90a. | trans-2-Phenylcyclopropylamine, HCl | 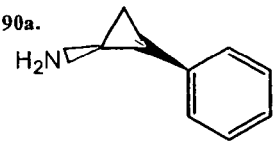 |
FIGURE 2(i)

| | | |
|---|---|---|
| 91. | 1-(3-Aminopropyl)pipecoline | |
| 92. | 2-Amino-1,3-propanediol | |
| 93. | Thiomicamine | |
| 94. | (R)-1-Amino-2-propanol | |
| 95. | (S)-2-Amino-3-cyclohexyl-1-propanol, HCl | |
| 97. | 1-Amino-1-cyclopentane methanol | |
| 98. | (S)-Isoleucinol | |
| 99. | 4-Clorophenyl alaniol | |

100. l-Leucinol 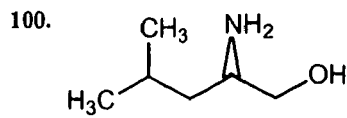
101. (1S,2S)-(+)-2-Amino-1-phenyl-1,3-propanediol 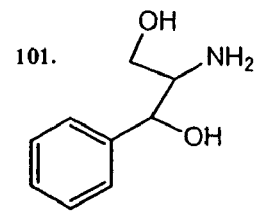
102. (S)-(+)-1-Amino-2-propanol 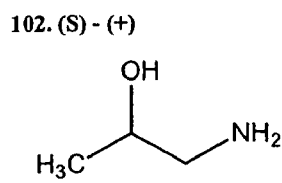
103. 2-Amino-2-methyl-1,3-propanediol 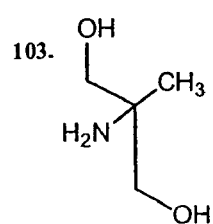
104. d,l-Serine methyl ester, HCl 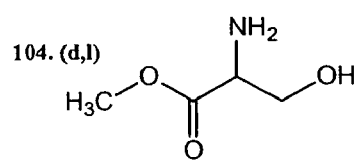
105a. (-)-Isopinocampheylamine 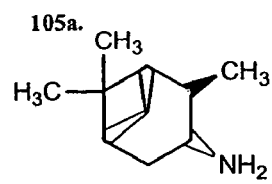
107. Histidinol 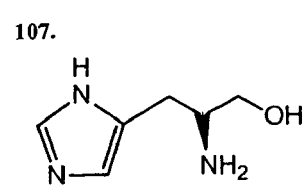
FIGURE 2(k)

| | | |
|---|---|---|
| 108. | 2-Amino-5-cyclopropyl-1,3,4-thiadiazol | 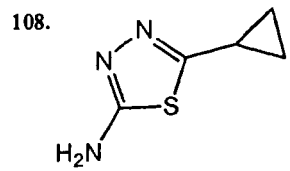 |
| 109. | 2-Amino-2-methyl-1-propanol | 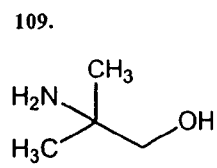 |
| 111. | Allylamine | 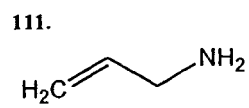 |
| 112. | 3-Amino-1,2-propanediol | 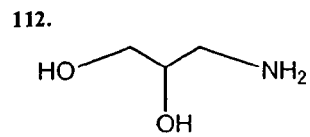 |
| 115. | Hexamethyleimine | 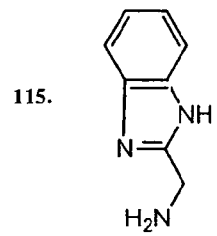 |
| 117. | 3-Aminorhodamine | 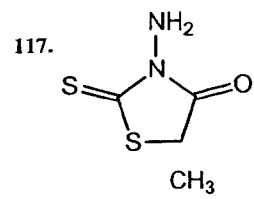 |
| 119. | (R)-(-)-2-Phenylglycinol | 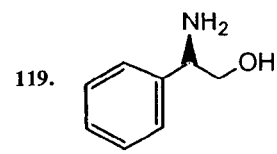 |
| 126. | Methyl-3-aminocrotonate | 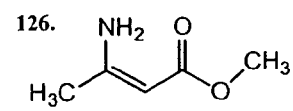 |
FIGURE 2(l)

129. d,1-Homocysteine, thiolactone, HCl 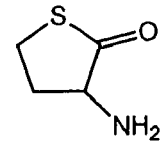
137. 2-Amino-5trifluoromethyl-1,3,4-thiadiazol 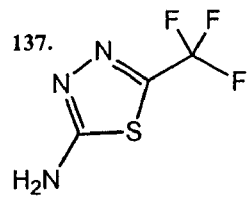
138. d,1-2-Amino-1-butanol (test, making EMB) 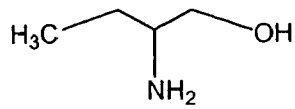
138. Racemic; "test" well
140. 3-Etoxypropylamine 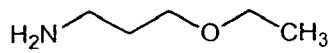
141. sec-Butylamine 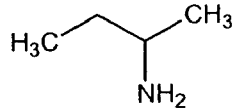
142. 2-Aminoheptane 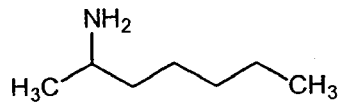
143. 2-Amino-2-methyl-1-propanol** 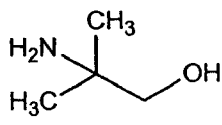
144. (S)-1-Amino-2-(Methoxymethyl)pyrrolidine 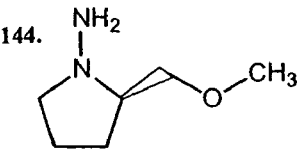
FIGURE 2(m)

145a. trans-1,2-Diaminocyclohexane 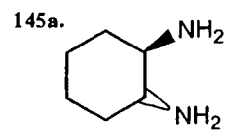
147. 3-Amino-2-methoxydibenzofuran 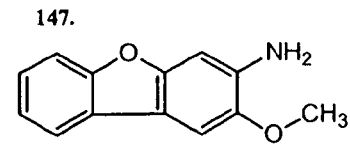
148. 2-Amino-4-methoxybenzothiazole 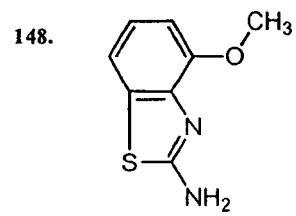
149. 1-Aminohomopiperidine 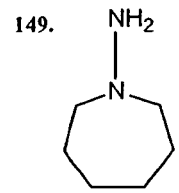
150. 2-Amino-3-hydroxypyridine 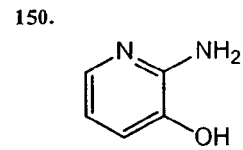
151. 1-Aminopyrrolidine, HCl 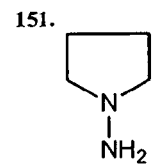
152. d,1-2-Amino-1-pentanol 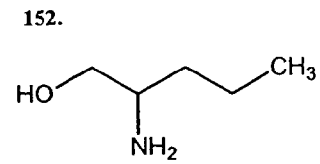
154. Ethanolamine 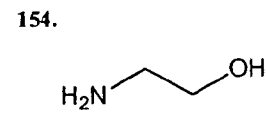
FIGURE 2(n)

| | | |
|---|---|---|
| 155. | 3-Methylbenzylamine | 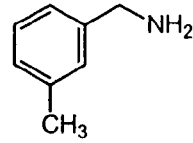 |
| 156. | 3-(Dibutylamino)propylamine | 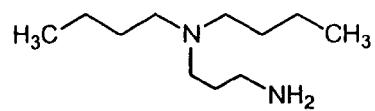 |
| 157. | Norephedrine, HCl | 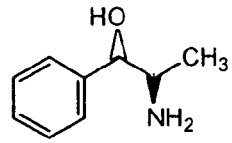 |
| 158. | Piperonylamine | 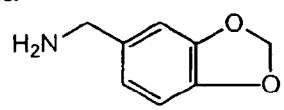 |
| 159. | 2-Methoxyethylamine | 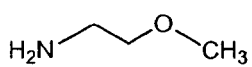 |
| 160. | 1-Ethylpropylamine | 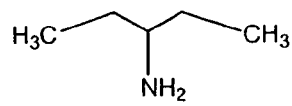 |
| 161. | 1-(3-Aminopropyl)imidazol | 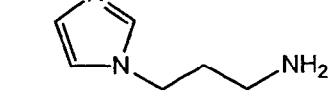 |
| 162. | 1-Aminoadamantamine |  |
| 164. | Dimethyl aminomalonate, HCl | 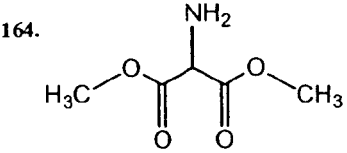 |
FIGURE 2(o)

| | | |
|---|---|---|
| 166. | Isopropylamine | 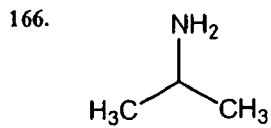 |
| 167. | 3-(Dimethylamino)propylamine | 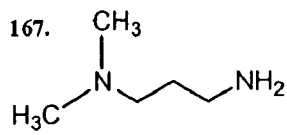 |
| 169. | 4-Fluorophenethylamine | 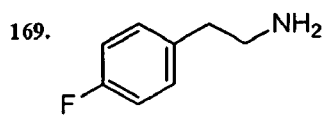 |
| 170. | 2-(4-Aminophenyl)ethylamine | 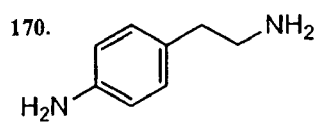 |
| 171. | 3-Aminoisoxazole | 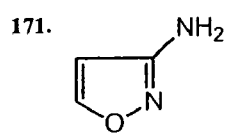 |
| 172. | 1,2-Diaminopropane | 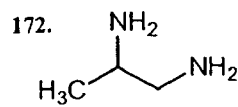 |
| 173. | d,l-Tryptophan methyl ester, HCl | 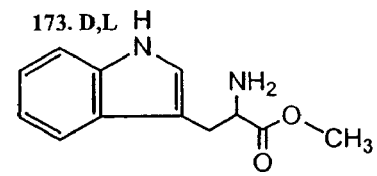 |
| 174. | d-Aspartic acid, dimethyl ester, HCl | 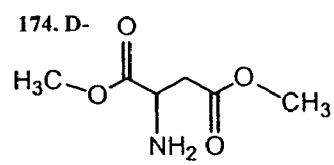 |
| 175. | l-Leucine ethyl ester, HCl | 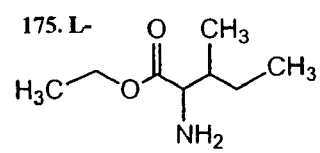 |
FIGURE 2(p)

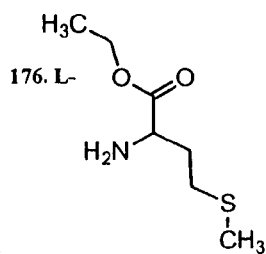
176. l-Methionine ethyl ester, HCl
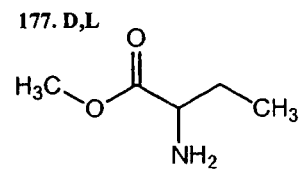
177. d,l-a-Amino-n-butyric acid methyl ester, HCI
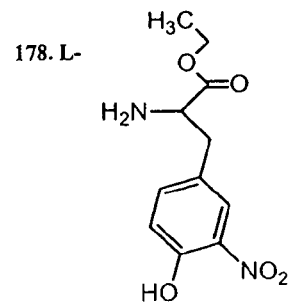
178. 3-Mnitro-l-tyrosine ethyl ester, HCI
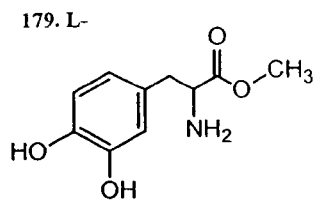
179. l-3,4-Dihydroxyphenylalanine methyl ester, HCl
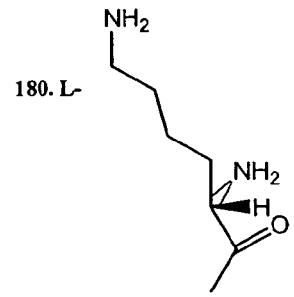
180. l-Lysine methyl ester, HCl
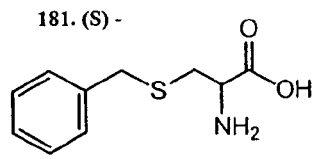
181. (S)-Benzyl-l-cysteine ethyle ester, HCl
FIGURE 2(q)

182. L-
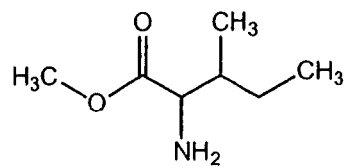
182. l-Isoleucine methyl ester, HCl
183. L-
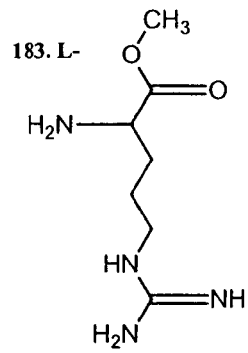
183. l-Arginine methyl ester, HCl
184. D,L
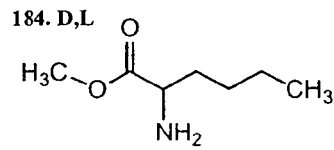
184. d,l-Norleucine methyl ester, HCl
185.
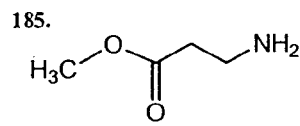
185. b-Alanine ethyle ester, HCl
186. L-
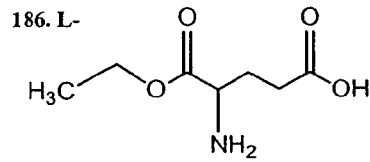
186. l-Glutamic acid ethyl ester, HCl
187. L-
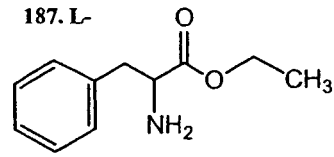
187. l-Phenylalanine ethyl ester, HCl
188. D,L-
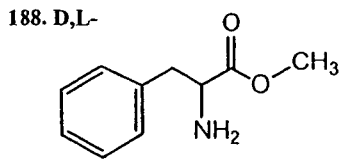
188. d,l-Phenylalanin methyl ester, HCl
FIGURE 2(r)

189. l-Histidine methyl ester, HCl 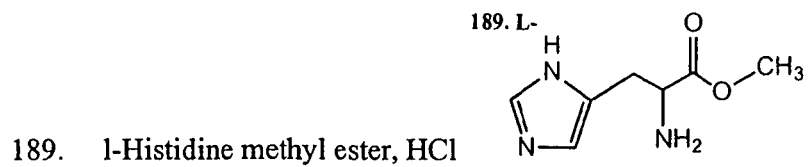
190. d,l-Alanine ethyl ester, HCl 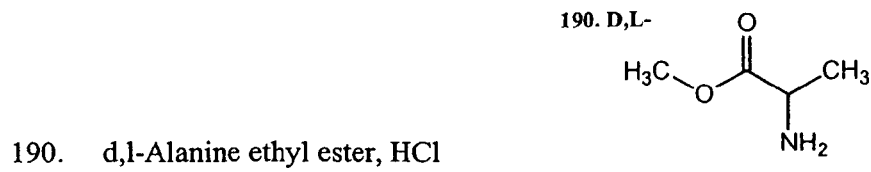
191. Tyrosine ethyl ester, HCl 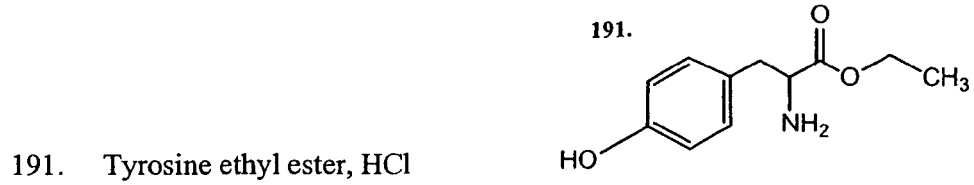
192. l-Valine ethyl ester, HCl 
193. tert-Amylamine 
194. tert-Butylamine 
197. S-Benzyl-L-cysteinol 
198. N-Phenylethyldiamine 
FIGURE 2(s)

201. N,N,2,2-Tetramethyl-1,3-propanediamine 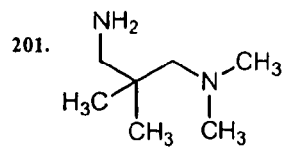
202. Isonipecotamide 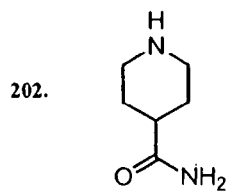
203. Isobutylamine 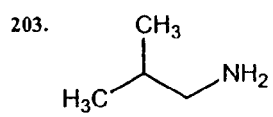
204. Hexetidine (mixture of stereosiomers) 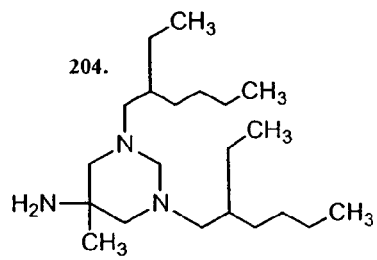
206. exo-Aminonorbornane 
207. Ehtyl 4-amino-1-piperidinecarboxylate 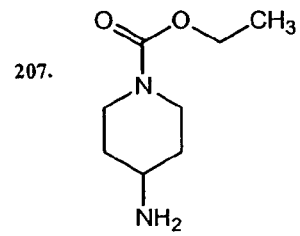
211. D-Glucosamine, HCl 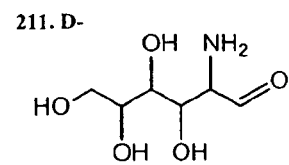
FIGURE 2(t)

| | | |
|---|---|---|
| 214. | Aminodiphenylmethane | 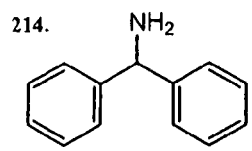 |
| 215. | alpha-Methyltryptamine | 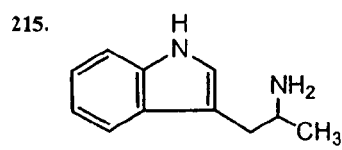 |
| 216. | 9-Aminofluorene, HCl | 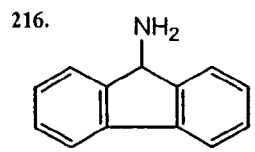 |
| 219. | 4-Phenylbutylamine | 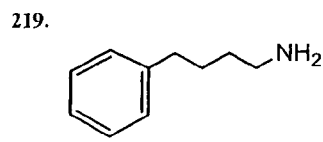 |
| 221. | 4-Chloroamphetamine, HCl | 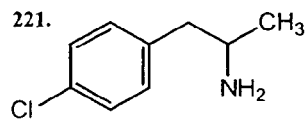 |
| 222. | 4-Amino-2,2,6,6-tetramethylpiperidine | 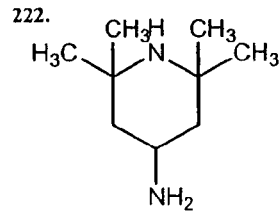 |
| 223. | 4-(Hexacylamino)benzylamine | |
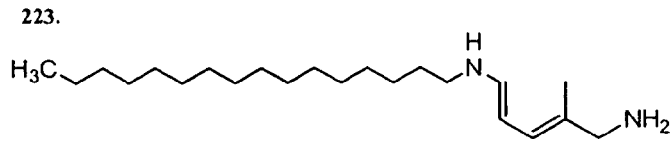
FIGURE 2(u)

225. 3-o-Methyldopamine, HCl 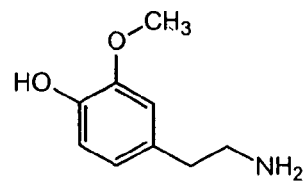
226. 3-Fluorophenethylamine 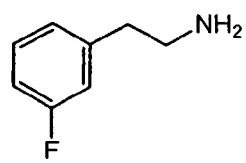
227. 3-Aminopyrrolidine, diHCl 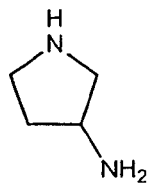
229. 2-Thiopheneethylamine 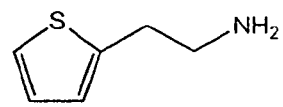
230. 2-Methylcyclohexylamine 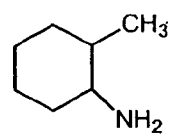
230. mix of cis/trans
231. 2-Methoxyphenethylamine 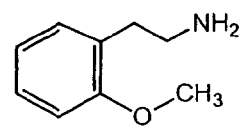
232. 2-Fluoroethylamine, HCl 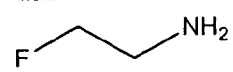
FIGURE 2(v)

233. 2-Chlorobenzylamine 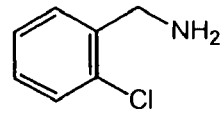
234. 2-Aminoindan, HCl 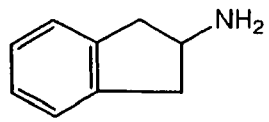
235. 2-Amino-4-phenyl-5-tetradecylthiazole
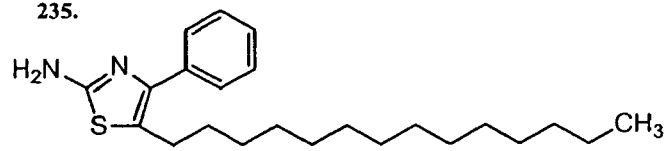
236. 2-Amino-1-phenylethanol 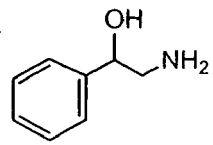
238. 2,5-Dimethoxyphenethylamine 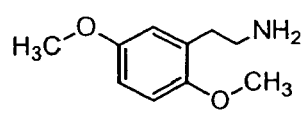
240. 2,4-Dichlorophenethylamine 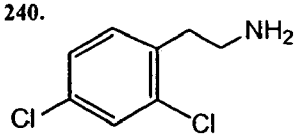
241. 2,2,2-Trifluoroethylamine 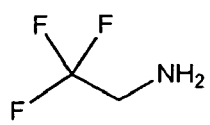
FIGURE 2(w)

242. 2-(2-Chlorophenyl)ethylamine 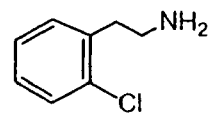
243. 2-(2-Aminomethyl)phenylthio)benzyl alcohol 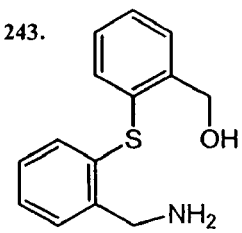
245. 1-Aminoindan 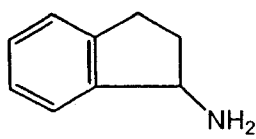
246. 1-Amino-4-(2-hydroxyethyl)piperazine 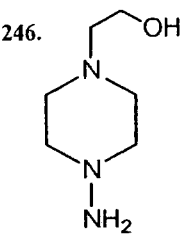
247. 1,3-Dimethylbutylamine 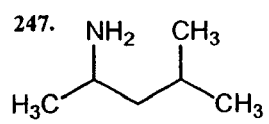
249. 1,2-Dimethylbutylamine 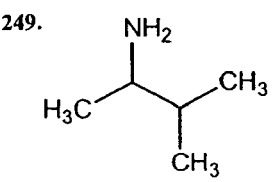
FIGURE 2(x)

253. 1-(1-Adamantyl)ethylamine, HCl 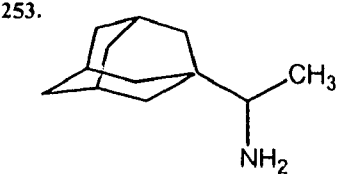
254. (S)-(+)-2-(Aminomethyl)pyrrolidine 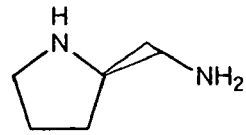
255. (S)-(-)-2-Cyclohexylethylamine 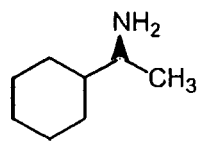
256. (S)-(-)-2-Amino-3-phenyl-1-propanol 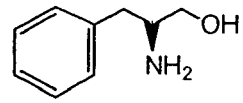
257. (R)-(-)-Cyclohexylethylamine 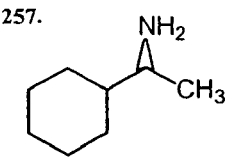
259. (1S,2S)-(+)-2-Amino-3-methoxy-1-phenyl-1-propanol 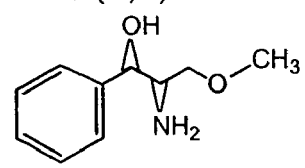
FIGURE 2(y)

260. (1R,2S)-(-)-2-Amino-1,2-diphenylethanol 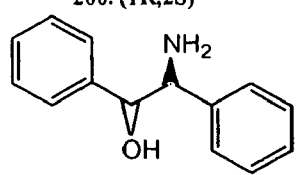
261. (-)-3,4-Dihydroxynorephedrine 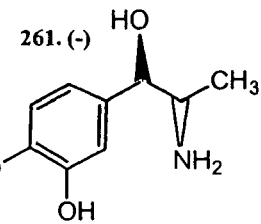
262. (1S,2R)-(+)-2-Amino-1,2-diphenylethanol 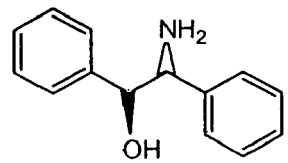
263. Octadecylamine 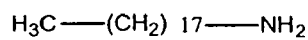
264. 3-Aminoquinonuclidine, diHCl 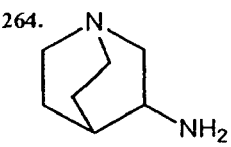
265. (R)-Cycloserine 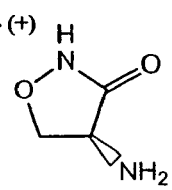
266. Undecylamine 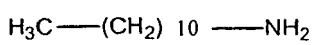
FIGURE 2(z)

267. 3,4-Dihydroxynorephedrine 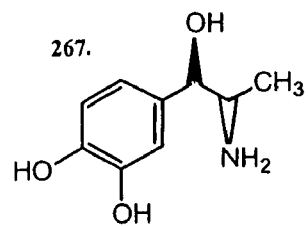
268. 3-Hydroxytyramine 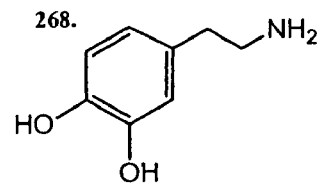
269. 4-(Trifluoromethoxy)benzylamine 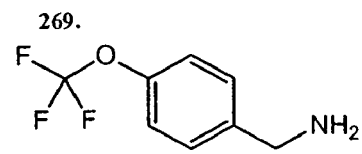
272. Geranylamine 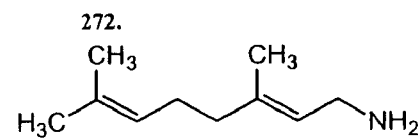
275. 5-Methoxytryptamine 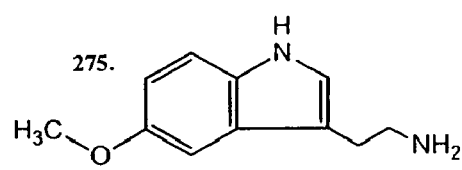
276. 6-Amino-2-methyl-2-heptanol, HCl 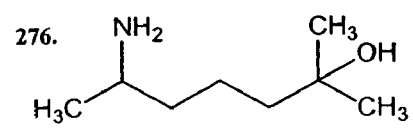
277. 6-Amino-1-hexanol 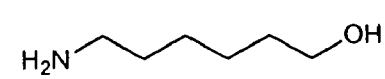
FIGURE 2(aa)

278. Dehydroabietylamine 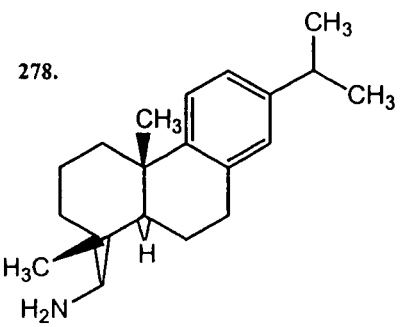
279. 1-(1-Naphthyl)ethylamine 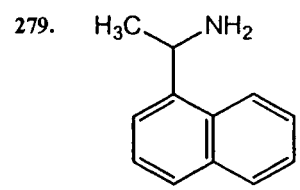
281. 2-(2-Aminoethyl)-1-methylpyrrolidine 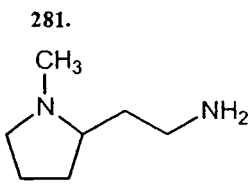
282. d,1-Valinol 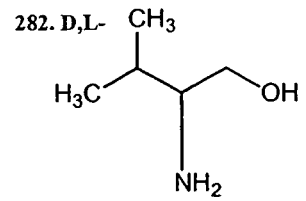
283. d,1-2-Amino-1-hexanol 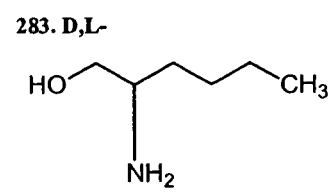
284. trans-2-Aminocyclohexanol, HCl 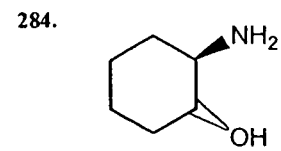
FIGURE 2(ab)

285. S-Benzylcysteamine, HCl    285. (S)- 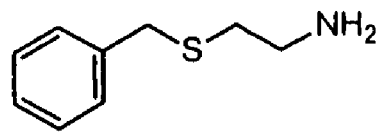
288. 4-Fluoro-a-methylbenzylamine    288. 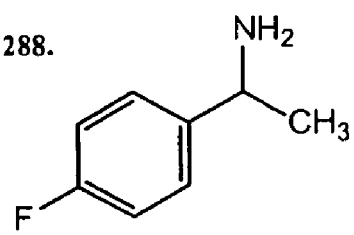
FIGURE 2(ac)

Acyclic Secondary Amines
4. N-Propylcyclopropanemethylamine 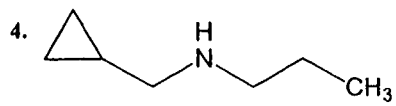
15. 2-(Ethylamino)ethanol 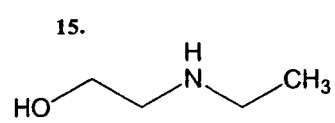
20. N-Methyl-iso-propylamine 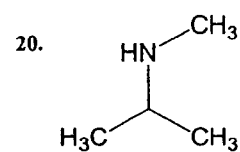
60. N-Methylpropylamine 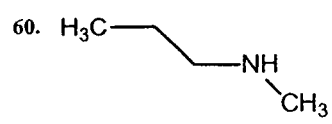
62. 2-Methylaminomethyl 1,3-dioxolane 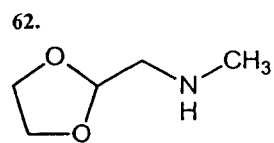
64. Dibenzylamine 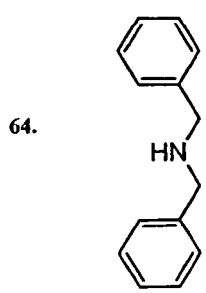
65. N-Butylbenzylamine 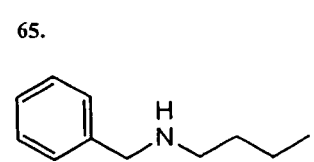
FIGURE 3(a)

67. N-Benzylethylamine 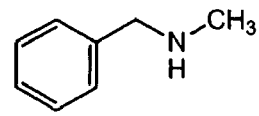
76. (Methylaminomethyl)benzyl alcohol 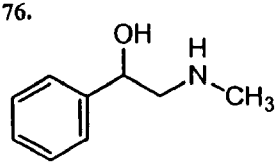
81. N-Benzyl-2-phenethylamine 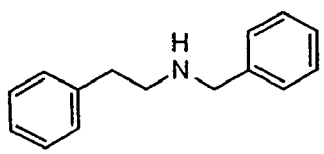
89. Pseudoephedrine 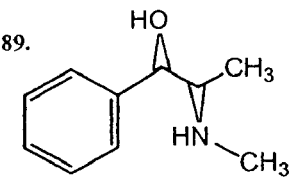
110. (1R,2S)-(-)-Ephedrine 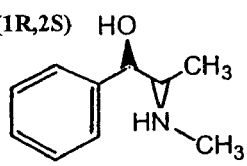
113. Diethanolamine 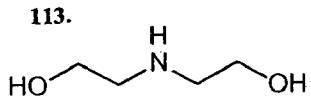
118. N-Benzylethanolamine 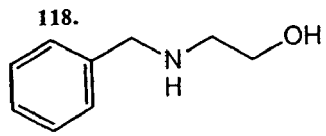
FIGURE 3(b)

| | | |
|---|---|---|
| 120. | 2-(Propylamine)-ethanol | 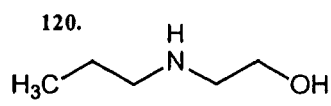 |
| 121. | N-methylbutylamine | 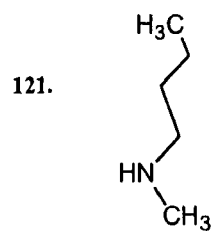 |
| 127. | N-Benzyl-n,N-dimethylethylenediamine | 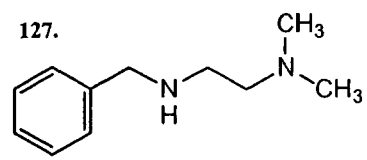 |
| 131. | N-Methylphenethylamine | 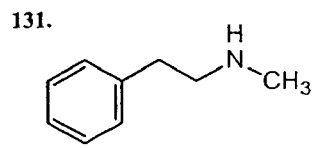 |
| 132. | N-Ethylcyclohexylamine | 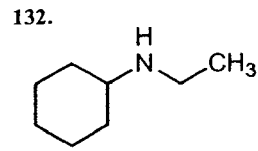 |
| 136. | 4-(Ethylaminomethyl)pyridine | 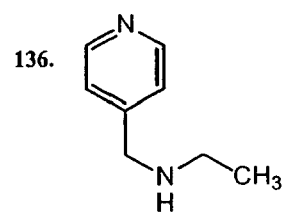 |
| 163. | Bis(2-methoxyethyl)amiane | 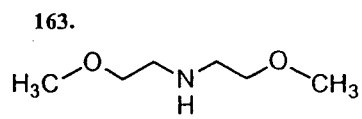 |
FIGURE 3(c)

183. l-Arginine methyl ester, HCl 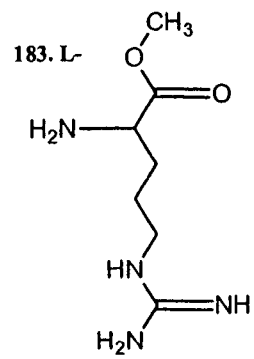
196. Synephrine 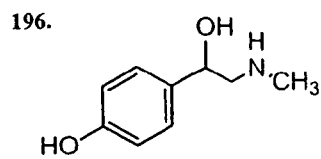
198. N-Phenylethyldiamine 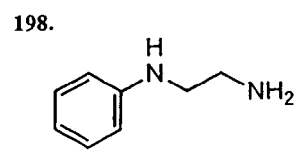
199. N-Methylhomoveratrylamine 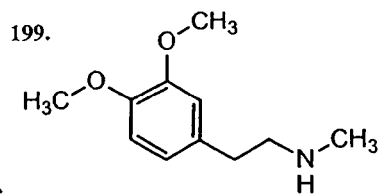
200. N-Allylcyclopentylamine 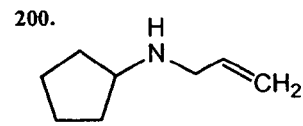
208. Epinephrine 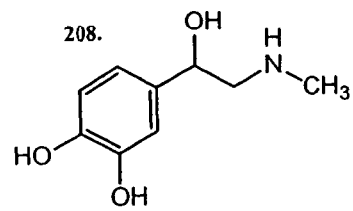
FIGURE 3(d)

209. Di-sec-butylamine (mix of (+), (-) and meso)
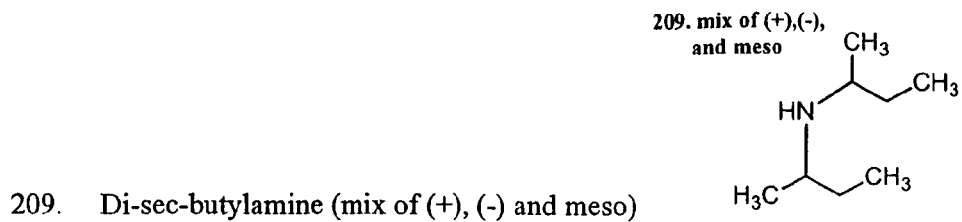
210. Diisopropylamine
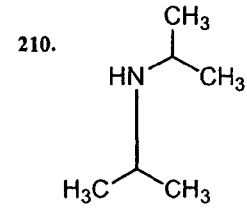
212. cis-(1S,2R)-(-)-2-(Benzylamino)cyclohexanemethanol
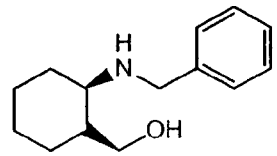
213. cis-(1R,2S)—(+)-2-(Benzylamino)cyclohexanemethanol
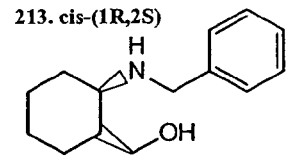
223. 4-(Hexacylamino)benzylamine
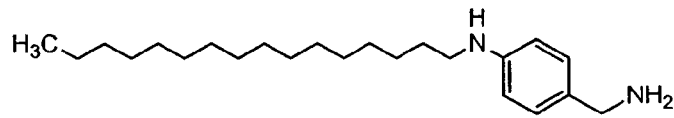
258. (3S(3a,4Ab),8A b)-N-t-butyl-D-ecahydro-3-isoquinolinecarboxamide
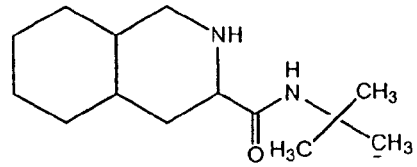
FIGURE 3(e)

274. Allylcyclohexyamine

Cyclic Secondary Amines
5. 4-Benzylpiperidine 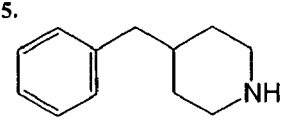
14. 3-Piperidinemethanol 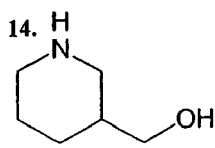
25. Tryptamine 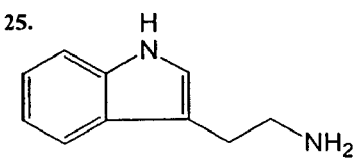
26. Morpholine 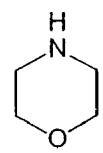
32. 4-Piperidinopiperidine 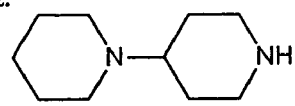
40. Ethyl 1-piperazine carboxylate 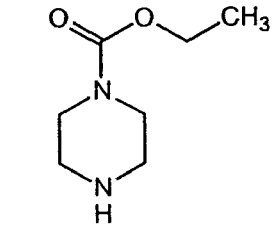
FIGURE 4(a)

| | | |
|---|---|---|
| 41. | 1-(2-Aminoethyl)piperazine | 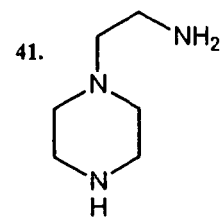 |
| 58. | Decahydroquinoline | 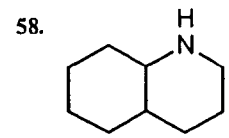 |
| 75. | 1,2,3,4-Tetrahydropyridoindole | 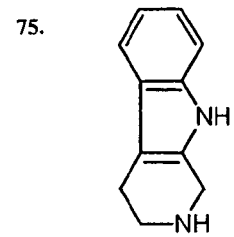 |
| 80. | 3-Amino-5-phenyl pyrazole | 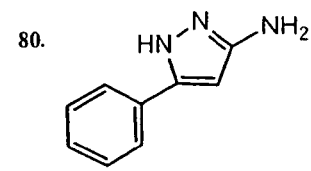 |
| 87. | 3-Aminopyrazole | 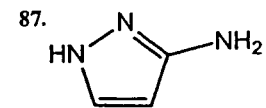 |
| 96a. | 1-(2-Fluorophenyl)piperazine | 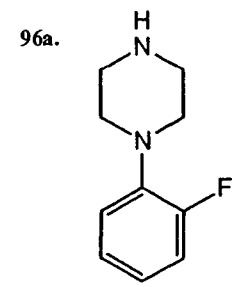 |
FIGURE 4(b)

| | | |
|---|---|---|
| 106. | 1-Proline methyl ester | 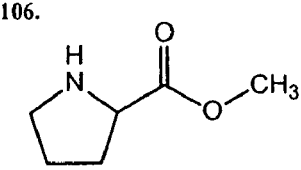 |
| 107. | Histidinol | 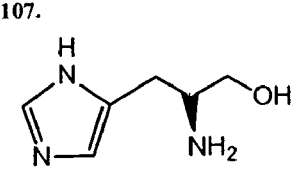 |
| 114. | 1-Piperonylpiperazine | 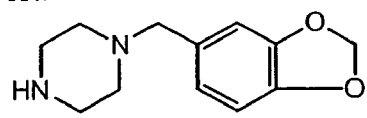 |
| 115. | Hexamethyleimine | 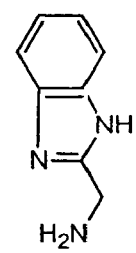 |
| 122. | 4-Hydroxypiperidine | 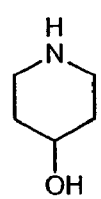 |
| 123. | 2-Piperidinemethanol | 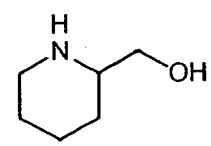 |
FIGURE 4(c)

124. 1,3,3-Trimethyl-6-azabicyclo[3.2.1]octane 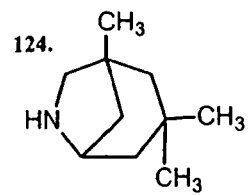
125. 3-Pyrrolidinol 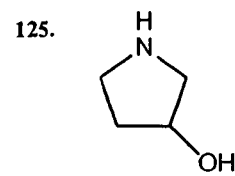
128. 1-Methylpiperazine 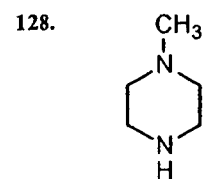
130. (S)-(+)-(2-Pyrolidinylmethyl)pyrrolidine 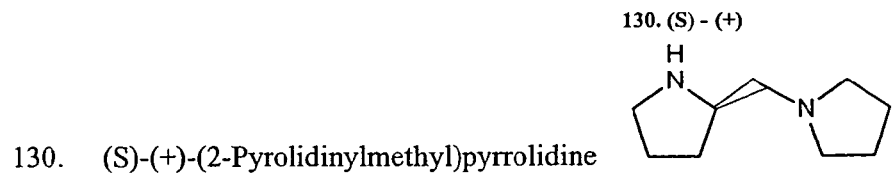
133. 1-Methylhomopiperazine 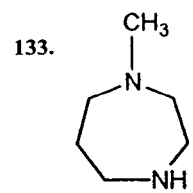
135. Methyl pipecolinate, HCl 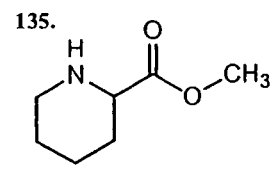
139. 2-Ethylpiperidine 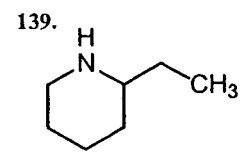
FIGURE 4(d)

153. 1,2,3,4-Tetrahydroisoquinoline 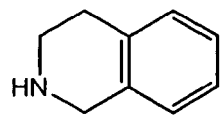
165. Piperidine 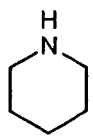
168. 1-(4-Fluorophenyl)piperazine 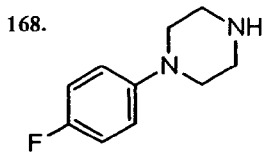
173. d,l-Tryptophan methyl ester, HCl 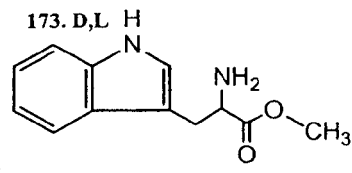
189. l-Histidine methyl ester, HCl 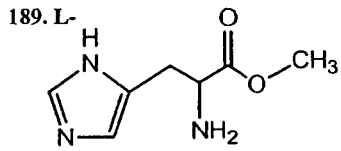
195. tert-Butyl (1S,4S)-(-)-2,5-diazabicyclo[2.2.1]heptane-2-carboxylate
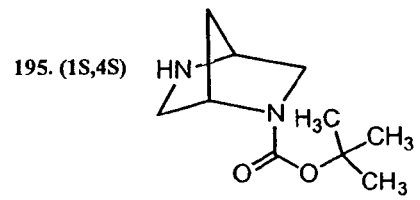
202. Isonipecotamide 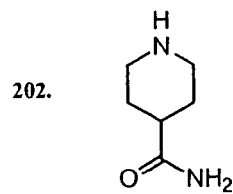
FIGURE 4(e)

205. Heptamethyleneimine 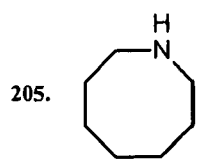
215. alpha-Methyltryptamine 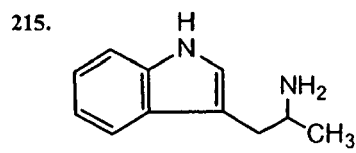
217. 6-Fluoro-1,2,3,4-tetrahydro-2-methylquinoline 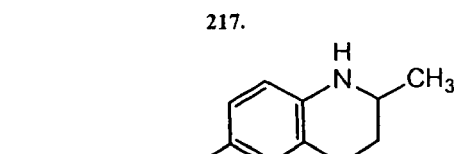
218. 6,7-Dimethoxy 1,2,3,4-tetrahydroisoquinoline, HCl
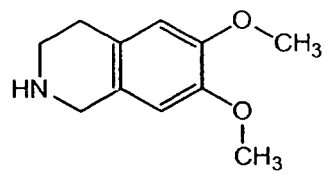
222. 4-Amino-2,2,6,6-tetramethylpiperidine 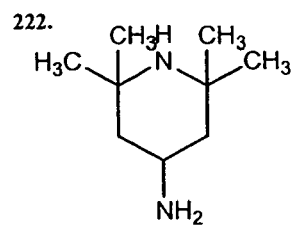
224. 4-(-4-Chlorophenyl)-4-hydroxypiperidine 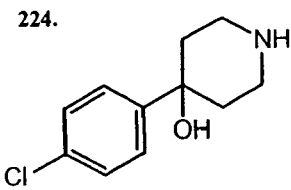
FIGURE 4(f)

227. 3-Aminopyrrolidine, diHCl 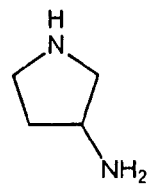
228. 3,5-Dimethylpiperidine (cis-and trans-) 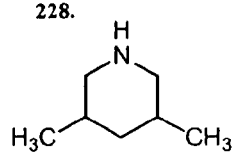
237. 2,6-Dimethylmorpholine 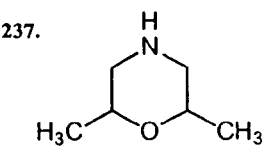
239. 1,4-Dioxo-8-azaspiro[4.5]decane 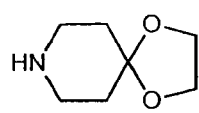
244. 1-Methyl-6,7-dihydroxy-1,2,3,4-tetrahydroisoquinoline, HBr 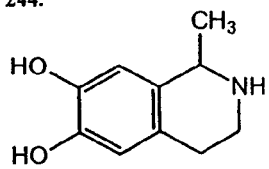
248. 1,3,4,6,7,8-Hexahydro-2H-pyrido(1,2-A)pyrimidine 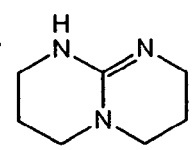
250. 1,2,3,4-Tetrahydroquinoline 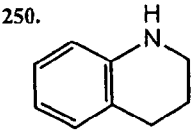
FIGURE 4(g)

251. 1-(2-Methoxyphenyl)piperazine 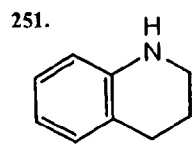
252. 1-(2-(2-Hydroxyethoxy)ethyl)piperazine 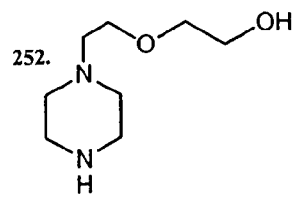
254. (S)-(+)-2-(Aminomethyl)pyrrolidine 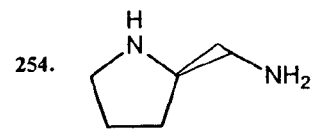
258. (3S(3a,4Ab),8A b)-N-t-butyl-D-ecahydro-3-isoquinolinecarboxamide
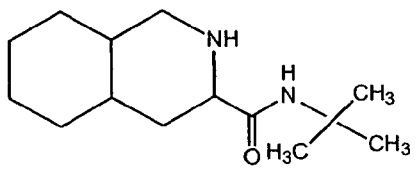
265. 3-Aminoquinonuclidine, diHCl 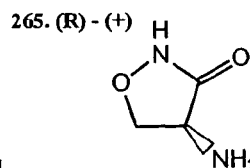
270. Homopiperazine 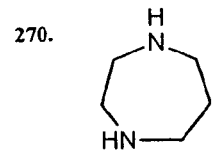
FIGURE 4(h)

271. 2,6-Dimethylpiperazine 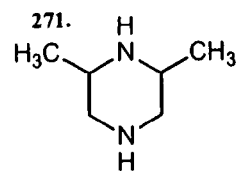
273. Iminodibenzyl 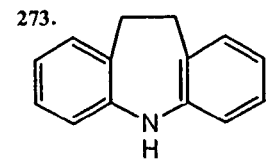
275. 5-Methoxytryptamine 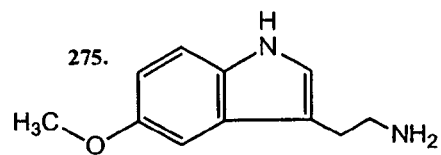
280. 4,4'-Bipiperidine, HCl 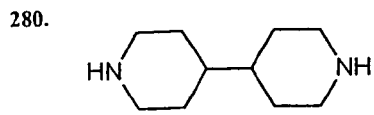
286. 1-(2-Hydroxyethyl)piperazine 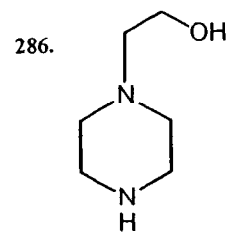
287. 4-Methylpiperidine 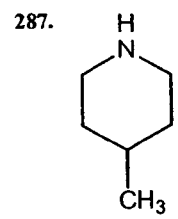
FIGURE 4(i)

compound 58 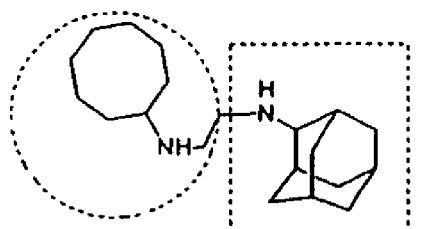
compound 59 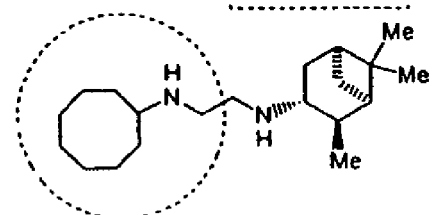
compound 109 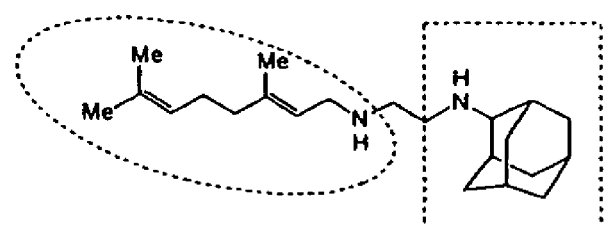
compound 73 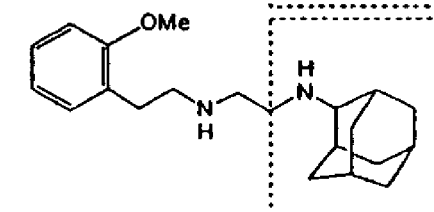
compound 111 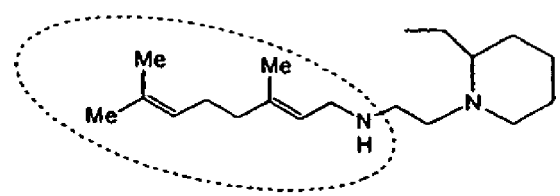
FIGURE 22

Table 22
Binding Assays - Summary Results

| Assay | Cerep Compound I.D. | Client Compound I.D. | Test Concentration (M) | % Inhibition of Control Specific Binding |
|---|---|---|---|---|
| $A_1$ (h) | 6826-1 | SQ109 | 1.0E-05 | 26 |
| $A_{2A}$ (h) | 6826-1 | SQ109 | 1.0E-05 | -5 |
| $\alpha_1$ (non-selective) | 6826-1 | SQ109 | 1.0E-05 | 37 |
| $\alpha_2$ (non-selective) | 6826-1 | SQ109 | 1.0E-05 | 36 |
| $\beta_1$ (h) | 6826-1 | SQ109 | 1.0E-05 | 31 |
| $AT_1$ (h) | 6826-1 | SQ109 | 1.0E-05 | 24 |
| BZD (central) | 6826-1 | SQ109 | 1.0E-05 | 22 |
| $B_2$ (h) | 6826-1 | SQ109 | 1.0E-05 | -15 |
| $CCK_A$ (h) ($CCK_1$) | 6826-1 | SQ109 | 1.0E-05 | 2 |
| D1 (h) | 6826-1 | SQ109 | 1.0E-05 | 51 |
| D2S (h) | 6826-1 | SQ109 | 1.0E-05 | 73 |
| $ET_A$ (h) | 6826-1 | SQ109 | 1.0E-05 | 4 |
| GABA (non-selective) | 6826-1 | SQ109 | 1.0E-05 | 10 |
| NMDA | 6826-1 | SQ109 | 1.0E-05 | 3 |
| $H_1$ (central) | 6826-1 | SQ109 | 1.0E-05 | 2 |
| $MC_4$ (h) | 6826-1 | SQ109 | 1.0E-05 | 90 |
| M (non-selective) | 6826-1 | SQ109 | 1.0E-05 | 96 |
| $NK_1$ (h) | 6826-1 | SQ109 | 1.0E-05 | 41 |
| Y (non-selective) | 6826-1 | SQ109 | 1.0E-05 | -3 |
| N (neuronal) ($\alpha$-BGTX-insensitive) | 6826-1 | SQ109 | 1.0E-05 | -10 |
| Opiate (non-selective) | 6826-1 | SQ109 | 1.0E-05 | 58 |
| ORL1 (h) (NOP) | 6826-1 | SQ109 | 1.0E-05 | 39 |
| PCP | 6826-1 | SQ109 | 1.0E-05 | 5 |
| 5-HT (non-selective) | 6826-1 | SQ109 | 1.0E-05 | 33 |
| $\sigma$ (non-selective) | 6826-1 | SQ109 | 1.0E-05 | 106 |
| Glucocorticoid (h) (GR) | 6826-1 | SQ109 | 1.0E-05 | 3 |
| $V_{1a}$ (h) | 6826-1 | SQ109 | 1.0E-05 | 15 |
| NE transporter (h) | 6826-1 | SQ109 | 1.0E-05 | 87 |
| DA transporter | 6826-1 | SQ109 | 1.0E-05 | 63 |
| 5-HT transporter (h) | 6826-1 | SQ109 | 1.0E-05 | 95 |

FIGURE 38

Table 23
Binding Assays - Reference Compound Data

| Assay | Reference Compound | $IC_{50}$ (M) | $K_i$ (M) | $n_H$ |
|---|---|---|---|---|
| $A_1$ (h) | DPCPX | 4.7E-08 | 2.9E-08 | 1.3 |
| $A_{2A}$ (h) | NECA | 3.2E-08 | 2.6E-08 | 0.6 |
| $\alpha_1$ (non-selective) | prazosin | 4.4E-10 | 1.2E-10 | 1.7 |
| $\alpha_2$ (non-selective) | yohimbine | 6.3E-08 | 2.7E-08 | 1.0 |
| $\beta_1$ (h) | atenolol | 9.7E-07 | 5.0E-07 | 0.7 |
| $AT_1$ (h) | saralasin | 1.8E-09 | 1.3E-09 | 1.1 |
| BZD (central) | diazepam | 1.7E-08 | 1.4E-08 | 1.0 |
| $B_2$ (h) | NPC 567 | 4.1E-09 | 1.9E-09 | 0.8 |
| $CCK_A$ (h) ($CCK_1$) | SR27897B | 8.3E-08 | 3.6E-08 | 0.7 |
| D1 (h) | SCH 23390 | 3.9E-10 | 1.4E-10 | 1.0 |
| D2S (h) | (+)butaclamol | 8.7E-09 | 3.2E-09 | 1.1 |
| $ET_A$ (h) | endothelin-1 | 8.4E-11 | 7.3E-11 | 0.9 |
| GABA (non-selective) | GABA | 3.9E-08 | 2.3E-08 | 0.9 |
| NMDA | CGS 19755 | 3.7E-07 | 3.0E-07 | 1.1 |
| $H_1$ (central) | pyrilamine | 2.8E-09 | 1.2E-09 | 1.2 |
| $MC_4$ (h) | NDP-$\alpha$-MSH | 2.8E-10 | 2.1E-10 | 1.0 |
| M (non-selective) | atropine | 2.8E-10 | 4.6E-11 | 1.1 |
| $NK_1$ (h) | [Sar$^9$,Met($O_2$)$^{11}$]-SP | 1.9E-09 | 3.2E-10 | 0.8 |
| Y (non-selective) | NPY | 2.0E-09 | 1.5E-09 | 1.0 |
| N (neuronal) ($\alpha$-BGTX-insensitive) | nicotine | 7.4E-09 | 4.0E-09 | 1.0 |
| Opiate (non-selective) | naloxone | 1.3E-09 | 9.7E-10 | 1.0 |
| ORL1 (h) (NOP) | nociceptin | 2.9E-09 | 1.8E-09 | 1.3 |
| PCP | MK 801 | 4.9E-09 | 4.6E-09 | 1.1 |
| 5-HT (non-selective) | serotonin | 3.1E-09 | 1.7E-09 | 0.9 |
| $\sigma$ (non-selective) | haloperidol | 2.9E-08 | 2.3E-08 | 0.7 |
| Glucocorticoid (h) (GR) | dexamethasone | 4.7E-09 | 2.4E-09 | 1.0 |
| $V_{1a}$ (h) | [d($CH_2$)$_5^1$,Tyr(Me)$_2$]-AVP | 1.6E-09 | 4.5E-10 | 2.1 |
| NE transporter (h) | protriptyline | 3.0E-08 | 2.8E-08 | 1.6 |
| DA transporter | GBR 12909 | 1.4E-08 | 7.2E-09 | 2.1 |
| 5-HT transporter (h) | imipramine | 6.9E-09 | 2.9E-09 | 1.1 |

FIGURE 39

Table 24(a) - Data Summary

Summary of the results of the test compound, as assayed in this study

| Cerep Compound I.D. | Client Compound I.D. | Solubility PBS pH 7.4 (µM) | Permeability A to B TC 7 Cells (10⁻⁶ cm/s) | Human Microsomal Stability (% remaining) | CYP1A2 (CEC) (% inhibition) | CYP2C9 (MFC) (% inhibition) | CYP2C19 (CEC) (% inhibition) | CYP2D6 (AMMC) (% inhibition) | CYP3A4 (BFC) (% inhibition) |
|---|---|---|---|---|---|---|---|---|---|
| | Test Concentration (µM) | 200 | 50 | 1 | 10 | 10 | 10 | 10 | 10 |
| 6826-1 | SQ109 | 160 | 13.14 | 1.5 | 9 | 27 | 25 | 99 | 31 |

FIGURE 40

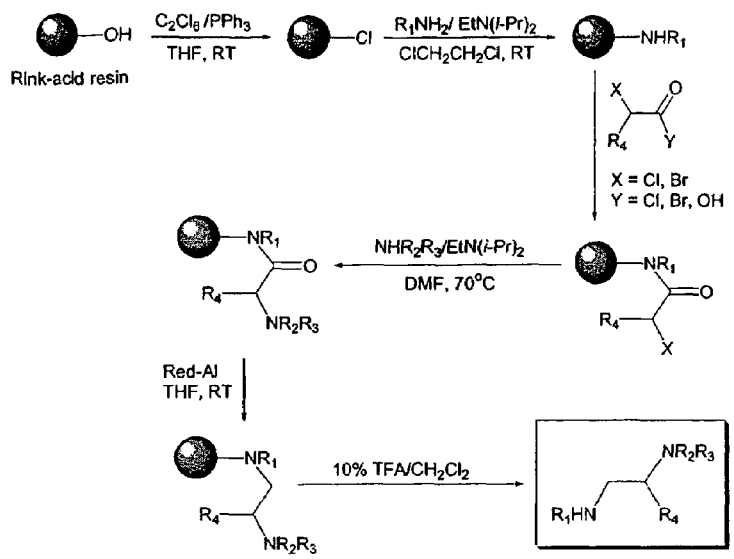
Scheme 1.
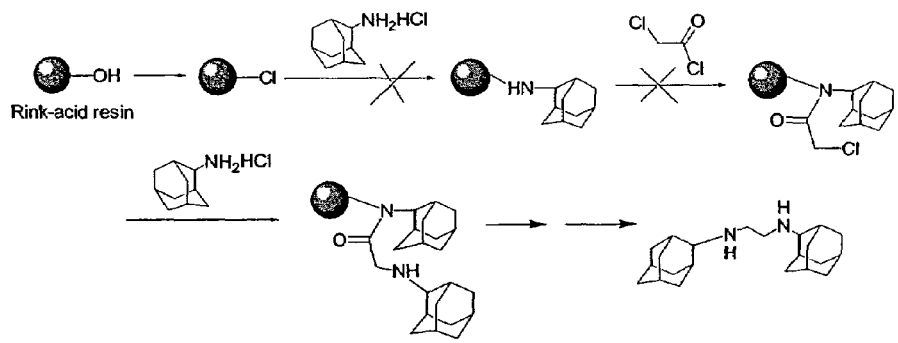
Scheme 2.
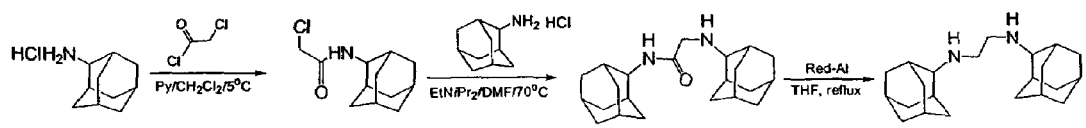
Scheme 3.
FIGURE 41

Figure 43

Table 25.

| Linker | Plate # | Yield, % | Active mixtures Based on MICs<12.5 | Active mixtures Based on Lux>1.5 | Number of active mixtures | Number of hits |
|---|---|---|---|---|---|---|
| Acid chlorides | | | | | | |
| 4-Chlorobutyryl chloride | 12-017 | <5 | | | dropped | |
| 4-Chlorobutyryl chloride | 12-032 | 0 | | | dropped | |
| 3-(Chloromethyl)benzoyl chloride | 12-019 | 12 | | | dropped | |
| Amino acids | | | | | | |
| Phe-OH | 12-056 | 60 | 16 | 0 | 16 | 1 |
| Phe-OH | 12-089 | 50 | 16 | 1 | 8 | 0 |
| Phe-OH | 12-099 | 33-42 | 9 | 1 | 8 | 0 |
| Phe-OH | 12-107 | 17 | 0 | not run | 0 | 0 |
| Pro-OH | 12-065 | 5 | | | dropped | |
| Trp-OH | 12-119 | 0 | | | dropped | |
| Ile-OH | 12-066 | 11 | 0 | 0 | 0 | 0 |
| Ile-OH | 12-118 | 28 | 8 | 2 | 8 | 0 |
| Leu-OH | 12-057 | 30 | 9 | 0 | 8 | 11 |
| Ser-OH | 12-098 | 23 | 21 | 17 | 16 | 0 |
| Ser-OH | 12-117 | 34 | 0 | 1 | 0 | 0 |
| Ser-OH | 12-108 | 17 | 0 | not run | 0 | 0 |
| Thi | 12-105 | 30 | 16 | 3 | 16 | 0 |
| Thi | 12-123 | 30-33% | 10 | 2 | 10 | 1 |
| Cha | 12-094 | 23 | 0 | 0 | 0 | 0 |
| Met | 12-097 | 20 | 6 | 2 | 8 | 6 |
| Amc | 12-091 | no res. | | | dropped | |
| Arg | 12-092 | no res. | | | dropped | |
| Cyclohexane carb. Acid | 12-090 | no res. | | | dropped | |
| Inp | 12-095 | 7 | | | dropped | |
| His | 12-096 | no res. | | | dropped | |
| The number of the plates | 23 | | | | | |
| *Total actives* | | | | | 98 | 19 |

SCHEME 5

$R_3$ = H or alkyl or aryl

FIGURE 47
TABLE 26

Phenylalanine
Leucine
Isoleucine
Tryptophan
Serine
Cyclohexylalanine
Methionine
Arginine
Histidine
Isonipecotic acid
4-Aminomethyl cyclohexane carboxylic acid
Tetrahydroisoquinoline-3-carboxylic acid
2-Chlorophenylalanine
Thiazoline carboxylic acid
Proline
Thienylalanine

| Position on Plate | Reagent # | Acids | F.W. |
|---|---|---|---|
| | | Name | |
| a1 | 1 | 1-Adamantanecarboxylic acid | 180.25 |
| a2 | 2 | Cyclohexanecarboxylic acid | 128.17 |
| a3 | 3 | Cyclopentanecarboxylic acid | 114.14 |
| a4 | 4 | 1-Cyclopentene-1-carboxylic acid | 112.13 |
| a5 | 5 | Cyclopropanecarboxylic acid | 86.09 |
| a6 | 6 | 3-Methoxycyclohexanecarboxylic acid | 158.20 |
| a7 | 7 | 2-(2-Methoxyethoxy)acetic acid | 134.13 |
| a8 | 8 | 2-Methylbutyric acid | 102.13 |
| a9 | 9 | 4-Methyl-1-cyclohexanecarboxylic acid | 142.20 |
| a10 | 10 | Propionic acid | 74.08 |
| a11 | 11 | Tetrahydro-2-furoic acid | 116.12 |
| a12 | 12 | Tetrahydro-3-furoic acid | 116.12 |

| Position on Plate | Reagent # | Ketones | F.W. |
|---|---|---|---|
| | | Name | |
| b1 | 97 | 3-Acetyl-1-propanol | 102 |
| b2 | 98 | 2-Adamantanone | 150.22 |
| b3 | 99 | 1-Adamantyl methyl ketone | 178.28 |
| b4 | 100 | Cyclobutanone | 70.09 |
| b5 | 101 | 1,4-Cyclohexanedione monoethylene ketal | 156.18 |
| b6 | 102 | 2-Decalone | 152.24 |
| b7 | 103 | (4-Fluorophenyl)acetone | 152.17 |
| b8 | 104 | Geranylacetone | 194.32 |
| b9 | 105 | 5-Hydroxy-2-adamantanone | 166.22 |
| b10 | 106 | 3-Hydroxy-2-butanone | 88.11 |
| b11 | 107 | 4-(4-Hydroxyphenyl)-2-butanone | 164.20 |
| b12 | 108 | 4-Methylcyclohexanone | 112.17 |

| Position on Plate | Reagent # | Aldehydes + Ketones | F.W. |
|---|---|---|---|
| | | Name | |
| c1 | 25 | 1,4-Benzodioxan-6-carboxaldehyde | 164.16 |
| c2 | 26 | 4-Benzyloxybenzaldehyde | 212.25 |
| c3 | 27 | Benzyloxyacetaldehyde | 150.18 |
| c4 | 28 | 2-Chlorobenzaldehyde | 140.57 |
| c5 | 29 | 4-Chlorobenzaldehyde | 140.57 |

CARBONYL COMPOUNDS USED IN MASTERPLATE

TABLE 27.

Figure 49 (a)

| | | | |
|---|---|---|---|
| c6 | 109 | 1-Methyl-4-piperidone | 113.16 |
| c7 | 31 | 2-Chloro-4-fluorobenzaldehyde | 158.56 |
| c8 | 32 | 3-(4-Chlorophenoxy)-benzaldehyde | 232.67 |
| c9 | 33 | 5-(4-Chlorophenyl)furfural | 206.63 |
| c10 | 34 | trans-Cinnamaldehyde | 132.16 |
| c11 | 35 | (S)-(-)-Citronellal | 154.25 |
| c12 | 36 | Cyclohexanecarboxaldehyde | 112.17 |

| | | | |
|---|---|---|---|
| d1 | 37 | Cyclopropanecarboxaldehyde | 70.09 |
| d2 | 38 | 2,4-Dichlorobenzaldehyde | 175.01 |
| d3 | 39 | 2,4-Difluorobenzaldehyde | 142.11 |
| d4 | 40 | 2,5-Difluorobenzaldehyde | 142.11 |
| d5 | 41 | 2,3-Dihydroxybenzaldehyde | 138.12 |
| d6 | 42 | 2,4-Dihydroxybenzaldehyde | 138.12 |
| d7 | 43 | 2,5-Dimethoxy-3-tetrahydrofurancarboxaldehyde | 160.17 |
| d8 | 44 | 4-(Dimethylamino)benzaldehyde | 149.19 |
| d9 | 45 | 2,5-Dimethylbenzaldehyde | 134.18 |
| d10 | 110 | Nerylacetone (Geranylacetone ~ 35% Neryacetone) | 194.32 |
| d11 | 47 | Diphenylacetaldehyde | 196.25 |
| d12 | 48 | 2-Ethoxybenzaldehyde | 150.18 |

| | | | |
|---|---|---|---|
| e1 | 49 | 4-Ethoxybenzaldehyde | 150.18 |
| e2 | 50 | 3-Ethoxysalicylaldehyde | 166.18 |
| e3 | 111 | (1R)-(+)-Nopinone | 138.21 |
| e4 | 52 | 3-Fluoro-p-anisaldehyde | 154.14 |
| e5 | 53 | 2-Fluorobenzaldehyde | 124.11 |
| e6 | 54 | 4-Fluorobenzaldehyde | 124.11 |
| e7 | 55 | 3-Fluorosalicylaldehyde | 140.11 |
| e8 | 56 | 2-Furaldehyde | 96.09 |
| e9 | 112 | Norcamphor | 110.16 |
| e10 | 113 | 2-Phenylcycloheptanone | 188.27 |
| e11 | 59 | Hydrocinnamaldehyde | 134.18 |
| e12 | 60 | 3-Hydroxybenzaldehyde | 122.12 |

| | | | |
|---|---|---|---|
| f1 | 61 | 4-Hydroxybenzaldehyde | 122.12 |
| f2 | 62 | 2-Hydroxy-4-methoxybenzaldehyde | 152.15 |
| f3 | 63 | 5-(Hydroxymethyl)furfural | 126.11 |
| f4 | 64 | 4-Hydroxy-3-nitrobenzaldehyde | 167.12 |
| f5 | 65 | Cyclooctanone | 126 |
| f6 | 66 | Indole-3-carboxaldehyde | 145.16 |
| f7 | 67 | Isobutyraldehyde | 72.11 |
| f8 | 68 | 4-Isopropylbenzaldehyde | 148.21 |
| f9 | 69 | Isovaleraldehyde | 86.13 |
| f10 | 70 | 2-Methoxycinnamaldehyde | 162.19 |
| f11 | 71 | 2-Methoxy-1-naphthaldehyde | 186.21 |
| f12 | 114 | 3-Quinuclidinone hydrochloride | 161.63 |

Figure 49 (b)

| g1 | 73 | 2,3-(Methylenedioxy)benzaldehyde | 150.13 |
|---|---|---|---|
| g2 | 74 | 4-Methyl-5-imidazolecarboxaldehyde | 110.12 |
| g3 | 75 | 1-Methylindole-3-carboxaldehyde | 159.19 |
| g4 | 76 | 1-Methyl-2-pyrrolecarboxaldehyde | 109.13 |
| g5 | 77 | 4-(Methylthio)benzaldehyde | 152.22 |
| g6 | 78 | 3-Methyl-2-thiophenecarboxaldehyde | 126.18 |
| g7 | 79 | (1R)-(-)-Myrtenal | 150.22 |
| g8 | 115 | Tetrahydro-4H-pyran-4-one | 100.12 |
| g9 | 81 | 2-Naphthaldehyde | 156.18 |
| g10 | 82 | 2-Nitrobenzaldehyde | 151.12 |
| g11 | 83 | 5-Norbornene-2-carboxaldehyde | 122.17 |
| g12 | 84 | (S)-(-)-Perillaldehyde | 150.22 |

| h1 | 116 | β-Tetralone | 146.19 |
|---|---|---|---|
| h2 | 86 | Trimethylacetaldehyde | 86.13 |
| h3 | 87 | 2-Pyridinecarboxaldehyde | 107.11 |
| h4 | 88 | 3-Pyridinecarboxaldehyde | 107.11 |
| h5 | 89 | 4-Pyridinecarboxaldehyde | 107.11 |
| h6 | 90 | Pyrrole-2-carboxaldehyde | 95.10 |
| h7 | 91 | 4-Quinolinecarboxaldehyde | 157.17 |
| h8 | 92 | 1,2,3,6-Tetrahydrobenzaldehyde | 110.16 |
| h9 | 93 | 2-Thiophenecarboxaldehyde | 112.15 |
| h10 | 94 | α,α,α-Trifluoro-p-tolualdehyde | 174.12 |
| h11 | 95 | 2,3,4-Trimethoxybenzaldehyde | 196.20 |
| h12 | 117 | o-Anisaldehyde | 136.15 |

Figure 49 (c)

| A1 | A2 | A3 | A4 | A5 | A6 | A7 | A8 | A9 | A10 | Selected carb comp added to A1-A10 |
|---|---|---|---|---|---|---|---|---|---|---|
| B1 | B2 | B3 | B4 | B5 | B6 | B7 | B8 | B9 | B10 | Selected carb comp, added to B1-B10 |
| C1 | C2 | C3 | C4 | C5 | C6 | C7 | C8 | C9 | C10 | Selected carb comp, added to C1-C10 |
| D1 | D2 | D3 | D4 | D5 | D6 | D7 | D8 | D9 | D10 | Selected carb comp, added to D1-D10 |
| E1 | E2 | E3 | E4 | E5 | E6 | E7 | E8 | E9 | E10 | Selected carb comp, added to E1-E10 |
| F1 | F2 | F3 | F4 | F5 | F6 | F7 | F8 | F9 | F10 | Selected carb comp, added to F1-F10 |
| G1 | G2 | G3 | G4 | G5 | G6 | G7 | G8 | G9 | G10 | Selected carb comp, added to G1-G10 |
| H1 | H2 | H3 | H4 | H5 | H6 | H7 | H8 | H9 | H10 | Selected carb comp, added to H1-H10 |
| Resin #1 | Resin #2 | Resin #3 | Resin #4 | Resin #5 | Resin #6 | Resin #7 | Resin #8 | Resin #9 | Resin #10 | "X" selected carbonyl compounds to be added on the step 4<br><br>Individual resins ##1 through 10, pre-loaded with proper amine N1 |

Table 28

Figure 52

| # | Structure | MIC | MIC exper. | LD50 (uM) | SI | Lux | LogP | TPSA | Frag. #2 | Original plate # |
|---|---|---|---|---|---|---|---|---|---|---|
| | Rink | | | | | | | | | |
| 673 | 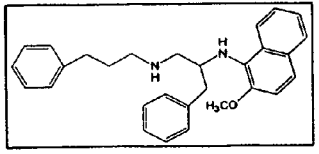 | 12.5 | | | | | | | | 12-056-2 H6 |
| 674 | 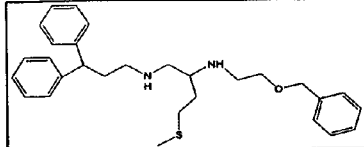 | 12.5 | | | | | | | | 12-097-1 A1 |
| 675 | 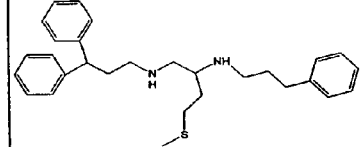 | 12.5 | | | | | | | | 12-097-1 F1 |
| 676 | 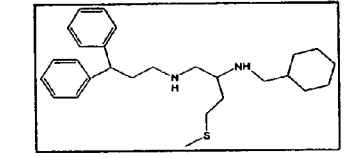 | 12.5 | | | | | | | | 12-097-1 G1 |
| 677 | 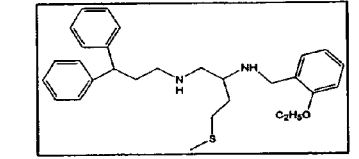 | 12.5 | | | | | | | | 12-097-1 H1 |
| 678 | 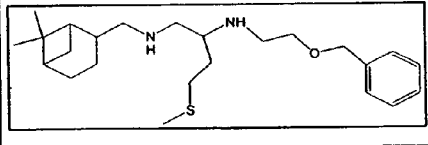 | 12.5 | | | | | | | | 12-097-1 A5 |
| 679 | 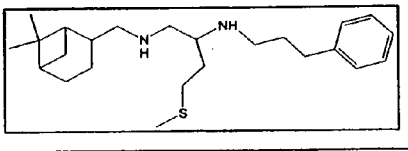 | 12.5 | | | | | | | | 12-097-1 F5 |
| 680 | 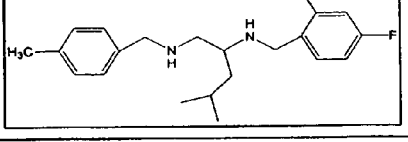 | 12.5 | | | | | | | | 12-057-1 B1 |
| 681 | 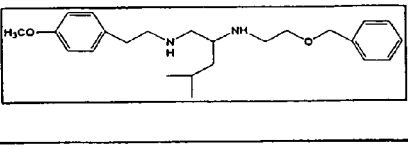 | 12.5 | | | | | | | | 12-057-1 A4 |
Table 30    Figure 53 (a)

| # | Structure | MIC | MIC exper. | LD50 (uM) | SI | Lux | LogP | TPSA | Frag. #2 | Original plate # |
|---|---|---|---|---|---|---|---|---|---|---|
| | Rink | | | | | | | | | |
| 682 | 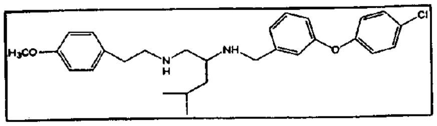 | 6.25 | | | | | | | | 12-057-1 C4 |
| 683 | 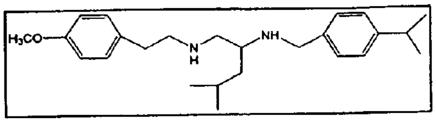 | 6.25 | | | | | | | | 12-057-1 D4 |
| 684 | 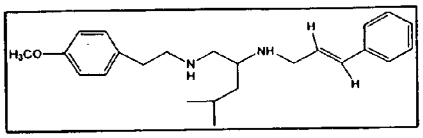 | 12.5 | | | | | | | | 12-057-1 G4 |
| 685 | 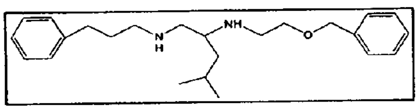 | 12.5 | | | | | | | | 12-057-1 A5 |
| 686 | 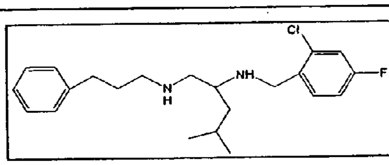 | 12.5 | | | | | | | | 12-057-1 B5 |
| 687 | 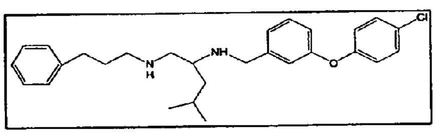 | 12.5 | | | | | | | | 12-057-1 C5 |
| 688 | 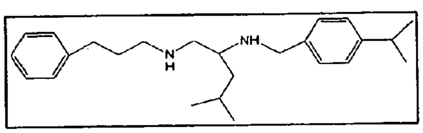 | 6.25 | | | | | | | | 12-057-1 D5 |
| 689 | 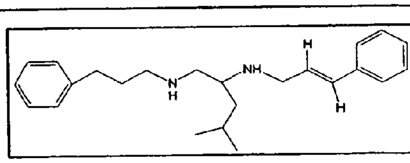 | 12.5 | | | | | | | | 12-057-1 G5 |
| 690 | 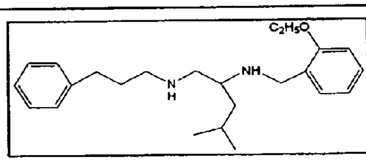 | 12.5 | | | | | | | | 12-057-1 H5 |

Figure 53 (b)

*In vitro* activity of Rif in combination with SQ109 and INH.

*In vivo* studies in mice. Rapid model.

SQ109 in combination with Rifampin (Rif), Isoniazid (INH), Ethambutol (EMB), Pyrazinamide (PZA), and Moxifloxacin (Moxi).

Dynamics in body weight (left) and the mortality data (right) of H37Rv infected animals treated with SQ109, Rif, and SQ109-Rif combination, and of the placebo (infected non-treated) in the rapid model.

Dynamics of body weight of mice treated with combination Rif-EMB.

*In vivo* efficacy studies of SQ109-Rif combination in the mouse model of chronic TB infection.

SQ109 in multi-drug intensive-phase regimen (in combination with Rif and INH). Chronic mouse model.

Figure 60.

| Assay | % of Control Specific Binding (mean value) | Assay | % of Control Specific Binding (mean value) |
|---|---|---|---|
| $A_1$ (h) | 74.4 | $MC_4$ (h) | 9.5 |
| $A_{2A}$ (h) | 105.4 | M (non-selective) | 4.4 |
| $\alpha_1$ (non-selective) | 62.9 | $NK_1$ (h) | 58.9 |
| $\alpha_2$ (non-selective) | 64 | Y (non-selective) | 102.9 |
| $\beta_1$ (h) | 69.4 | N (neuronal) ($\alpha$-BGTX-insensive) | 109.7 |
| $AT_1$ (h) | 76.2 | Opiate (non-selective) | 42.3 |
| BZD (central) | 78 | ORL1 (h) (NOP) | 60.9 |
| $B_2$ (h) | 115.3 | PCP | 95.1 |
| $CCK_A$ (h) ($CCK_1$) | 98 | 5-HT (non-selective) | 67.3 |
| D1 (h) | 49.2 | σ (non-selective) | -5.9 |
| D2S (h) | 27.3 | Glucocorticoid (h) (GR) | 96.7 |
| $ET_A$ (h) | 96.4 | $V_{1a}$ (h) | 85.4 |
| GABA (non-selective) | 89.8 | NE-transporter (h) | 13.3 |
| NMDA | 97.5 | DA transporter | 37.4 |
| $H_1$ (central) | 97.5 | 5-HT transporter | 4.6 |

Table 31. Mean values for the effects of SQ109 on receptors and transporters (data by Cerep).

Figure 61.

| Assay | % Inhibition of Control Specific Binding | Assay | % Inhibition of Control Specific Binding |
|---|---|---|---|
| $A_1$ (h) | 26 | MC$_4$ (h) | 90 |
| $A_{2A}$ (h) | -5 | M (non-selective) | 96 |
| $\alpha_1$ (non-selective) | 37 | NK$_1$ (h) | 41 |
| $\alpha_2$ (non-selective) | 36 | Y (non-selective) | -3 |
| $\beta_1$ (h) | 31 | N (neuronal) ($\alpha$-BGTX-insensive) | -10 |
| AT$_1$ (h) | 24 | Opiate (non-selective) | 58 |
| BZD (central) | 22 | ORL1 (h) (NOP) | 39 |
| B$_2$ (h) | -15 | PCP | 5 |
| CCK$_A$ (h) (CCK$_1$) | 2 | 5-HT (non-selective) | 33 |
| D1 (h) | 51 | σ (non-selective) | 106 |
| D2S (h) | 73 | Glucocorticoid (h) (GR) | 3 |
| ET$_A$ (h) | 4 | V$_{1a}$ (h) | 15 |
| GABA (non-selective) | 10 | NE-transporter (h) | 87 |
| NMDA | 3 | DA transporter | 63 |
| H$_1$ (central) | 2 | 5-HT transporter | 95 |

Table 32. Inhibition activity of SQ109 on control specific binding for tested receptors and transporters (data by Cerep).

Figure 62

Table 33. MIC Results for All Gram-Positive Organisms Tested Against SQ-109

| Organism | Geographic Location | Date of Isolation | Patient Age | Specimen Source | MIC (ug/ml) SQ-109 |
|---|---|---|---|---|---|
| Enterococci | | | | | |
| Enterococcus faecalis | EAST SOUTH CENTRAL | 04/22/04 | 56 | Blood | 32 |
| Enterococcus faecalis | EAST SOUTH CENTRAL | 04/30/04 | 76 | Blood | 32 |
| Enterococcus faecalis | EAST SOUTH CENTRAL | 04/30/04 | 74 | Blood | 32 |
| Enterococcus faecium | MID ATLANTIC | 04/11/04 | 73 | Blood | 64 |
| Enterococcus faecium | EAST SOUTH CENTRAL | 03/13/04 | 38 | Blood | 16 |
| Enterococcus faecium | EAST NORTH CENTRAL | 03/20/04 | 66 | Urine: Unknown | 16 |
| Enterococcus species | NEW ENGLAND | 09/08/00 | 21 | Urine: Unknown | 32 |
| Enterococcus species | MID ATLANTIC | 10/22/00 | 71 | Blood | 16 |
| Enterococcus species | EAST NORTH CENTRAL | 02/06/01 | 68 | Deep wound | 32 |
| Staphylococci | | | | | |
| Staphylococcus aureus | NEW ENGLAND | 01/06/04 | 53 | Sputum | 32 |
| Staphylococcus aureus | NEW ENGLAND | 04/15/04 | 81 | Blood | 32 |
| Staphylococcus aureus | NEW ENGLAND | 06/21/04 | 71 | Sputum | 32 |
| Staphylococcus epidermidis | EAST NORTH CENTRAL | 04/19/04 | 53 | Wound | 16 |
| Staphylococcus epidermidis | WEST SOUTH CENTRAL | 07/03/04 | 61 | Blood | 16 |
| Staphylococcus epidermidis | NEW ENGLAND | 05/04/04 | 75 | Blood | 16 |
| Staphylococcus haemolyticus | WEST NORTH CENTRAL | 04/01/04 | 24 | Blood | 16 |
| Staphylococcus hominis | NEW ENGLAND | 03/25/04 | 73 | Blood | 16 |
| Staphylococcus saprophyticus | PACIFIC | 07/25/04 | Unknown | Blood | 16 |
| Streptococci | | | | | |
| Streptococcus agalactiae | NEW ENGLAND | 03/29/04 | 90 | Blood | 32 |
| Streptococcus agalactiae | SOUTH ATLANTIC | 04/03/04 | Unknown | Blood | 32 |
| Streptococcus agalactiae | EAST SOUTH CENTRAL | 03/21/04 | 39 | Blood | 16 |
| Streptococcus pneumoniae | EAST NORTH CENTRAL | 04/16/04 | 55 | Sinus | 4 |
| Streptococcus pneumoniae | EAST NORTH CENTRAL | 04/17/04 | 1 | Blood | 4 |
| Streptococcus pneumoniae | MOUNTAIN | 04/15/04 | 47 | Bronchial Washings/BAL | 8 |

Figure 63A.

Table 34. MIC Results for All Gram-Negative Organisms Tested Against SQ-109

| Organism | Geographic Location | Date of Isolation | Patient Age | Specimen Source | MIC (ug/ml) SQ-109 |
|---|---|---|---|---|---|
| Enterobacteriaceae | | | | | |
| Escherichia coli | NEW ENGLAND | 1/6/2004 | 32 | Urine: Clean Catch | 32 |
| Escherichia coli | NEW ENGLAND | 1/2/2004 | 77 | Urine: Clean Catch | 32 |
| Escherichia coli | NEW ENGLAND | 1/4/2004 | 19 | Urine: Clean Catch | 32 |
| Citrobacter freundii | NEW ENGLAND | 2/25/2004 | 34 | Urine: Clean Catch | 64 |
| Citrobacter freundii | NEW ENGLAND | 3/1/2004 | 82 | Urine: Clean Catch | 32 |
| Citrobacter freundii | MID ATLANTIC | 1/10/2004 | 44 | Urine: Clean Catch | 64 |
| Citrobacter koseri (diversus) | FRANCE MISC1 | 2/17/2003 | 86 | Blood | 64 |
| Citrobacter koseri (diversus) | FRANCE MISC1 | 1/25/2003 | 79 | Blood | 64 |
| Citrobacter koseri (diversus) | GERMANY | 2/10/2003 | 71 | Tracheal Aspirate | 32 |
| Enterobacter cloacae | NEW ENGLAND | 1/8/2004 | 84 | Urine: Clean Catch | >64 |
| Enterobacter cloacae | NEW ENGLAND | 1/25/2004 | 82 | Urine: Clean Catch | 64 |
| Enterobacter cloacae | NEW ENGLAND | 2/24/2004 | 1 | Sputum | >64 |
| Enterobacter aerogenes | PACIFIC | Unknown | Unknown | Unknown | 64 |
| Enterobacter aerogenes | PACIFIC | Unknown | Unknown | Unknown | >64 |
| Enterobacter aerogenes | PACIFIC | Unknown | Unknown | Unknown | 64 |
| Klebsiella pneumoniae | NEW ENGLAND | 1/6/2004 | 63 | Urine: Clean Catch | 64 |
| Klebsiella pneumoniae | NEW ENGLAND | 1/3/2004 | 79 | Urine: Clean Catch | 64 |
| Klebsiella pneumoniae | NEW ENGLAND | 1/16/2004 | 76 | Urine: Clean Catch | 64 |
| Klebsiella oxytoca | PACIFIC | Unknown | Unknown | Unknown | 64 |
| Klebsiella oxytoca | PACIFIC | Unknown | Unknown | Unknown | 64 |
| Klebsiella oxytoca | PACIFIC | Unknown | Unknown | Unknown | 64 |
| Morganella morganii | FRANCE MISC1 | 9/25/2003 | 77 | Urine: Unknown | >64 |
| Morganella morganii | PACIFIC | Unknown | Unknown | Unknown | >64 |
| Morganella morganii | PACIFIC | Unknown | Unknown | Unknown | >64 |
| Proteus mirabilis | NEW ENGLAND | 1/5/2004 | 72 | Urine: Clean Catch | >64 |
| Proteus mirabilis | NEW ENGLAND | 1/28/2004 | 59 | Urine: Clean Catch | >64 |
| Proteus mirabilis | NEW ENGLAND | 2/28/2004 | 69 | Urine: Clean Catch | >64 |
| Proteus vulgaris | PACIFIC | Unknown | Unknown | Unknown | >64 |
| Proteus vulgaris | PACIFIC | Unknown | Unknown | Unknown | >64 |
| Proteus vulgaris | PACIFIC | Unknown | Unknown | Unknown | >64 |
| Providencia stuartii | FRANCE | 6/10/2003 | 83 | Urine: Unknown | >64 |
| Providencia stuartii | FRANCE | 1/29/2003 | 76 | Other | >64 |
| Providencia stuartii | ITALY | 1/9/2003 | 35 | Tracheal Aspirate | >64 |
| Serratia marcescens | NEW ENGLAND | 1/4/2004 | 56 | Sputum | >64 |
| Serratia marcescens | NEW ENGLAND | 2/25/2004 | 47 | Wound | >64 |
| Serratia marcescens | NEW ENGLAND | 1/12/2004 | 81 | Urine: Catheter | >64 |
| Non-Enterobacteriaceae | | | | | |
| Acinetobacter baumannii | FRANCE | 1/24/2003 | 64 | Urine: Cystoscopic | 16 |
| Acinetobacter baumannii | FRANCE | 1/17/2003 | 75 | Blood | 16 |
| Acinetobacter baumannii | SPAIN | 3/25/2003 | 68 | Sputum | 32 |
| Acinetobacter calcoaceticus | SPAIN | 1/17/2003 | 73 | Bronchial Washings/BAL | 32 |
| Acinetobacter calcoaceticus | SPAIN | 2/18/2003 | 56 | Tracheal Aspirate | 32 |
| Acinetobacter species | PACIFIC | Unknown | Unknown | Unknown | 16 |
| Pseudomonas aeruginosa | NEW ENGLAND | 1/3/2004 | 77 | Urine: Clean Catch | >64 |
| Pseudomonas aeruginosa | NEW ENGLAND | 1/8/2004 | 63 | Sputum | 64 |
| Pseudomonas aeruginosa | MID ATLANTIC | 1/9/2004 | 75 | Sputum | 64 |
| Stenotrophomonas maltophilia | MID ATLANTIC | 1/7/2004 | 35 | Blood | 32 |
| Stenotrophomonas maltophilia | SOUTH ATLANTIC | 2/6/2004 | 34 | Bronchial Washings/BAL | 16 |
| Stenotrophomonas maltophilia | WEST NORTH CENTRAL | 1/17/2004 | 83 | Skin | 16 |

Figure 63B.

Table 34 cont. MIC Results for All Gram-Negative Organisms Tested Against SQ-109

| Organism | Geographic Location | Date of Isolation | Patient Age | Specimen Source | MIC (ug/ml) SQ-109 |
|---|---|---|---|---|---|
| Miscellaneous | | | | | |
| Haemophilus influenzae | PACIFIC | 1/7/2004 | 69 | Ear | 1 |
| Haemophilus influenzae | NEW ENGLAND | 1/15/2004 | 46 | Sputum | 32 |
| Haemophilus influenzae | EAST NORTH CENTRAL | 10/1/2002 | 18 | Nasopharynx/Throat/Nose | 8 |
| Helicobacter pylori | SOUTH ATLANTIC | Unknown | Unknown | Unknown | 4 |
| Helicobacter pylori | SOUTH ATLANTIC | Unknown | Unknown | Unknown | 4 |
| Helicobacter pylori | SOUTH ATLANTIC | Unknown | Unknown | Unknown | 4 |

Figure 64.

Table 35. MIC Results for All Anaerobes Tested Against SQ-109

| Organism | Geographic Location | MIC (ug/ml) SQ-109 | CLINDAMYCIN |
|---|---|---|---|
| Bacteroides fragilis | PACIFIC | 64 | 1 |
| Bacteroides fragilis | PACIFIC | 64 | 8 |
| Bacteroides fragilis | PACIFIC | 64 | 0.5 |
| Clostridium difficile | SOUTH ATLANTIC | 32 | 8 |
| Clostridium difficile | SOUTH ATLANTIC | 32 | 8 |
| Clostridium difficile | SOUTH ATLANTIC | 16 | 8 |
| Propionibacterium acnes | SOUTH ATLANTIC | 16 | 0.25 |
| Propionibacterium acnes | SOUTH ATLANTIC | 16 | 0.25 |
| Propionibacterium acnes | SOUTH ATLANTIC | 32 | 0.25 |

Figure 65.

Spectrum of Activity Testing – Fungi

Table 36. MIC Results for All Fungi Tested Against SQ-109

| Organism/Isolate ID | MIC (ug/ml) | |
|---|---|---|
| | SQ-109 | Amphotericin B |
| Candida albicans | 8 | NT |
| Candida albicans | 8 | NT |
| Candida albicans | 4 | NT |
| Aspergillus fumigatus 10199A | 16 | 1 |
| Aspergillus fumigatus 11168A | 16 | 0.5 |
| Aspergillus fumigatus 11166A | 16 | 0.5 |

Figure 66.

Spectrum of Activity Testing - Mycobacteria

Table 37. MIC Results for Members of the MTB Complex (MTBC) Tested Against SQ-109

| Organism/Isolate ID | Phenotype | MIC (ug/ml) | | | |
|---|---|---|---|---|---|
| | | SQ-109 | INH (0.1) | RIF (5.0) | EMB (5.0) |
| M. tuberculosis H37Rv (ATCC 27294) | SM/INH/RIF/EMB-S[1] | 0.5 | Susceptible | Susceptible | Susceptible |
| M. tuberculosis (msi 04-0895) | INH-R[1] | 0.25 | Resistant | NT | NT |
| M. tuberculosis (msi 04-8906) | EMB-R[1] | 0.5 | NT | NT | Resistant |
| M. bovis (msi 04-3981) | Unknown | 0.25 | NT | NT | Susceptible |
| M. bovis (msi 02-12548) | Unknown | 0.25 | NT | NT | Susceptible |
| M. bovis BCG (Tokyo) | Unknown | 0.5 | NT | NT | Susceptible |
| M. bovis BCG (Copenhagen) | Unknown | 0.5 | NT | NT | Susceptible |

NT = Not Tested
[1] Phenotypes confirmed for MTB: SM = Streptomycin, INH = Isoniazid, RIF = Rifampin, EMB = Ethambutol, (S) = Susceptible, (R) = Resistant Table 38. MIC Results for Mycobacteria-other-than-TB (MOTT) Tested Against SQ-109

| Organism/Isolate ID | Phenotype | MIC (ug/ml) | | | | |
|---|---|---|---|---|---|---|
| | | SQ-109 | INH (0.2) | INH (1.0) | RIF (1.0) | EMB (5.0) |
| M. avium complex (ATCC 700898) | SM/INH/RIF/EMB-R[2] | 32 | Resistant | Resistant | Susceptible | Resistant |
| M. avium complex (msi 04-11290) | SM/INH/RIF/EMB-R[2] | 8 | Resistant | Resistant | Resistant | Resistant |
| M. avium complex (msi 04-10846) | SM/INH/RIF/EMB-R[2] | 16 | Resistant | Resistant | Resistant | Resistant |
| M. marinum (ATCC 927) | Unknown | 8 | NT | NT | Susceptible | Intermediate |
| M. marinum (msi 04-3560) | Unknown | 8 | NT | NT | Susceptible | Resistant |
| M. marinum (msi 03-15428) | Unknown | 8 | NT | NT | Susceptible | Intermediate |
| M. kansasii (ATCC 12478) | Unknown | 16 | Resistant | Susceptible | Susceptible | Resistant |
| M. kansasii (msi 04-3979) | Unknown | 16 | Resistant | Susceptible | Susceptible | Resistant |
| M. kansasii (msi 04-684) | Unknown | 16 | Resistant | Susceptible | Susceptible | Resistant |

NT = Not Tested
[2] Members of the M. avium complex are intrinsically resistant to most of the first-line anti-mycobacterial drugs and therefore not tested against t Table 39. MIC Results for Rapid-Growers Tested Against SQ-109

| Organism/Isolate ID | Phenotype | MIC (ug/ml) | |
|---|---|---|---|
| | | SQ-109 | EMB (5.0) |
| M. chelonae (msi 04-297) | Unknown | 16 | Resistant |
| M. chelonae (msi 04-298) | Unknown | 16 | Resistant |
| M. abscessus (msi 04-10998) | Unknown | 16 | Resistant |
| M. fortuitum (msi 04-7174) | Unknown | 1 | Susceptible |
| M. fortuitum (msi 04-6759) | Unknown | 1 | Susceptible |
| M. fortuitum (msi 04-6097) | Unknown | 1 | Susceptible |

ANTI TUBERCULAR DRUG: COMPOSITIONS AND METHODS

CROSS REFERENCE TO RELATED PATENT APPLICATIONS

The present application is a continuation-in-part application of pending U.S. patent application Ser. No. 11/145,499, filed Jun. 3, 2005, which is a continuation of U.S. patent application Ser. No. 10/441,146, filed May 19, 2003, now abandoned, which is a continuation-in-part application of pending U.S. patent application Ser. No. 10/147,587 filed May 17, 2002, now U.S. Pat. No. 6,951,961. The present application also claims priority to U.S. Provisional Patent Application Ser. No. 60/381,220 filed May 17, 2002.

FIELD OF INVENTION

The present invention relates to methods and compositions for treating infectious disease and disease caused by microorganisms, particularly tuberculosis. The present invention also relates to methods and compositions having improved anti-mycobacterial activity, namely compositions comprising novel substituted ethylene diamine compounds.

BACKGROUND OF THE INVENTION

Mycobacterial infections often manifest as diseases such as tuberculosis. Human infections caused by mycobacteria have been widespread since ancient times, and tuberculosis remains a leading cause of death today. Although the incidence of the disease declined, in parallel with advancing standards of living, since the mid-nineteenth century, mycobacterial diseases still constitute a leading cause of morbidity and mortality in countries with limited medical resources. Additionally, mycobacterial diseases can cause overwhelming, disseminated disease in immunocompromised patients. In spite of the efforts of numerous health organizations worldwide, the eradication of mycobacterial diseases has never been achieved, nor is eradication imminent. Nearly one third of the world's population is infected with *mycobacterium tuberculosis* complex, commonly referred to as tuberculosis (TB), with approximately 8 million new cases, and two to three million deaths attributable to TB yearly. Tuberculosis (TB) is the cause of the largest number of human deaths attributable to a single etiologic agent (see Dye et al., J. Am. Med. Association, 282, 677-686, (1999); and 2000 WHO/OMS Press Release).

After decades of decline, TB is now on the rise. In the United States, up to 10 million individuals are believed to be infected. Almost 28,000 new cases were reported in 1990, constituting a 9.4 percent increase over 1989. A sixteen percent increase in TB cases was observed from 1985 to 1990. Overcrowded living conditions and shared air spaces are especially conducive to the spread of TB, contributing to the increase in instances that have been observed among prison inmates, and among the homeless in larger U.S. cities. Approximately half of all patients with "Acquired Immune Deficiency Syndrome" (AIDS) will acquire a mycobacterial infection, with TB being an especially devastating complication. AIDS patients are at higher risks of developing clinical TB, and anti-TB treatment seems to be less effective than in non-AIDS patients. Consequently, the infection often progresses to a fatal disseminated disease.

Mycobacteria other than *M. tuberculosis* are increasingly found in opportunistic infections that plague the AIDS patient. Organisms from the *M. avium-intracellulare* complex (MAC), especially serotypes four and eight, account for 68% of the mycobacterial isolates from AIDS patients. Enormous numbers of MAC are found (up to $10^{10}$ acid-fast bacilli per gram of tissue), and consequently, the prognosis for the infected AIDS patient is poor.

The World Health Organization (WHO) continues to encourage the battle against TB, recommending prevention initiatives such as the "Expanded Program on Immunization" (EPI), and therapeutic compliance initiatives such as "Directly Observed Treatment Short-Course" (DOTS). For the eradication of TB, diagnosis, treatment, and prevention are equally important. Rapid detection of active TB patients will lead to early treatment by which about 90% cure is expected. Therefore, early diagnosis is critical for the battle against TB. In addition, therapeutic compliance will ensure not only elimination of infection, but also reduction in the emergence of drug-resistance strains.

The emergence of drug-resistant *M. tuberculosis* is an extremely disturbing phenomenon. The rate of new TB cases proven resistant to at least one standard drug increased from 10 percent in the early 1980's to 23 percent in 1991. Compliance with therapeutic regimens, therefore, is also a crucial component in efforts to eliminate TB and prevent the emergence of drug resistant strains. Equally important is the development of new therapeutic agents that are effective as vaccines, and as treatments, for disease caused by drug resistant strains of mycobacteria.

Multidrug-resistant tuberculosis (MDR TB) is a form of tuberculosis that is resistant to two or more of the primary drugs used for the treatment of tuberculosis. Resistance to one or several forms of treatment occurs when bacteria develop the ability to withstand antibiotic attack and relay that ability to their progeny. Since an entire strain of bacteria inherit this capacity to resist the effects of various treatments, resistance can spread from one person to another.

The World Health Organization estimates that up to 50 million persons worldwide may be infected with drug resistant strains of tuberculosis. Also, 300,000 new cases of MDR-TB are diagnosed around the world each year and 79 percent of the MDR-TB cases now show resistance to three or more drugs routinely used to treat tuberculosis.

In 2003, the Centre for Disease control (CDC) reported that 7.7 percent of tuberculosis cases in the U.S. were resistant to isoniazid, a first line drug used to treat Tuberculosis. The CDC also reported that 1.3 percent of tuberculosis cases in the U.S. were resistant to both isoniazid and rifampin. Rifampin is the drug most commonly used with isoniazid.

Clearly, the possibility of drug resistant strains of tuberculosis that develop during or before treatment are a major concern to health organizations and heath care practitioners. Drugs used in the treatment of tuberculosis include, but are not limted to, Ethambutol, Pyrazinamide, Streptomycin, Isoniazid, Moxifloxacin and Rifampin. The exact course and duration of treatment can be tailored to a specific individual, however several strategies are well known to those skilled in the art.

Although over 37 species of mycobacteria have been identified, more than 95% of all human infections are caused by six species of mycobacteria: *M. tuberculosis, M. avium intracellulare, M. kansasii, M. fortuitum, M. chelonae*, and *M. leprae*. The most prevalent mycobacterial disease in humans is tuberculosis (TB) which is predominantly caused by mycobacterial species comprising *M. tuberculosis, M. bovis*, or *M. africanum* (Merck Manual 1992). Infection is typically initiated by the inhalation of infectious particles which are able to reach the terminal pathways in lungs. Following engulfment by alveolar macrophages, the bacilli are able to replicate freely, with eventual destruction of the phagocytic cells. A cascade effect ensues wherein destruction of the phagocytic cells causes additional macrophages and lymphocytes to migrate to the site of infection, where they too are ultimately eliminated. The disease is further disseminated during the initial stages by the infected macrophages which travel to local lymph nodes, as well as into the blood stream and other tissues such as the bone marrow, spleen, kidneys, bone and central nervous system. (See Murray et al. *Medical Microbiology*, The C.V. Mosby Company 219-230 (1990)).

There is still no clear understanding of the factors which contribute to the virulence of mycobacteria. Many investigators have implicated lipids of the cell wall and bacterial surface as contributors to colony morphology and virulence. Evidence suggests that C-mycosides, on the surface of certain mycobacterial cells, are important in facilitating survival of the organism within macrophages. Trehalose 6,6' dimycolate, a cord factor, has been implicated for other mycobacteria.

The interrelationship of colony morphology and virulence is particularly pronounced in *M. avium. M. avium* bacilli occur in several distinct colony forms. Bacilli which grow as transparent, or rough, colonies on conventional laboratory media are multiplicable within macrophages in tissue culture, are virulent when injected into susceptible mice, and are resistant to antibiotics. Rough or transparent bacilli, which are maintained on laboratory culture media, often spontaneously assume an opaque R colony morphology, at which time they are not multiplicable in macrophages, are avirulent in mice, and are highly susceptible to antibiotics. The differences in colony morphology between the transparent, rough and opaque strains of *M. avium* are almost certainly due to the presence of a glycolipid coating on the surface of transparent and rough organisms which acts as a protective capsule. This capsule, or coating, is composed primarily of C-mycosides which apparently shield the virulent *M. avium* organisms from lysosomal enzymes and antibiotics. By contrast, the non-virulent opaque forms of *M. avium* have very little C-mycoside on their surface. Both the resistance to antibiotics and the resistance to killing by macrophages have been attributed to the glycolipid barrier on the surface of *M. avium.*

Diagnosis of mycobacterial infection is confirmed by the isolation and identification of the pathogen, although conventional diagnosis is based on sputum smears, chest X-ray examination (CXR), and clinical symptoms. Isolation of mycobacteria on a medium takes as long as four to eight weeks. Species identification takes a further two weeks. There are several other techniques for detecting mycobacteria such as the polymerase chain reaction (PCR), *mycobacterium tuberculosis* direct test, or amplified *mycobacterium tuberculosis* direct test (MTD), and detection assays that utilize radioactive labels.

One diagnostic test that is widely used for detecting infections caused by *M. tuberculosis* is the tuberculin skin test. Although numerous versions of the skin test are available, typically one of two preparations of tuberculin antigens are used: old tuberculin (OT), or purified protein derivative (PPD). The antigen preparation is either injected into the skin intradermally, or is topically applied and is then invasively transported into the skin with the use of a multiprong inoculator (Tine test). Several problems exist with the skin test diagnosis method. For example, the Tine test is not generally recommended because the amount of antigen injected into the intradermal layer cannot be accurately controlled. (See Murray et al. *Medical Microbiology*, The C.V. Mosby Company 219-230 (1990)).

Although the tuberculin skin tests are widely used, they typically require two to three days to generate results, and many times, the results are inaccurate since false positives are sometimes seen in subjects who have been exposed to mycobacteria, but are healthy. In addition, instances of mis-diagnosis are frequent since a positive result is observed not only in active TB patients, but also in persons vaccinated with Bacille Calmette-Guerin (BCG), and those who had been infected with mycobacteria, but have not developed the disease. It is hard therefore, to distinguish active TB patients from the others, such as household TB contacts, by the tuberculin skin test. Additionally, the tuberculin test often produces a cross-reaction in those individuals who were infected with mycobacteria other than *M. tuberculosis* (MOTT). Therefore, diagnosis using the skin tests currently available is frequently subject to error and inaccuracies.

The standard treatment for tuberculosis caused by drug-sensitive organisms is a six-month regimen consisting of four drugs given for two months, followed by two drugs given for four months. The two most important drugs, given throughout the six-month course of therapy, are isoniazid and rifampin. Although the regimen is relatively simple, its administration is quite complicated. Daily ingestion of eight or nine pills is often required during the first phase of therapy; a daunting and confusing prospect. Even severely ill patients are often symptom free within a few weeks, and nearly all appear to be cured within a few months. If the treatment is not continued to completion, however, the patient may experience a relapse, and the relapse rate for patients who do not continue treatment to completion is high. A variety of forms of patient-centered care are used to promote adherence with therapy. The most effective way of ensuring that patients are taking their medication is to use directly observed therapy, which involves having a member of the health care team observe the patient take each dose of each drug. Directly observed therapy can be provided in the clinic, the patient's residence, or any mutually agreed upon site. Nearly all patients who have tuberculosis caused by drug-sensitive organisms, and who complete therapy will be cured, and the risk of relapse is very low ("Ending Neglect: The Elimination of Tuberculosis in the United States" ed. L. Geiter Committee on the Elimination of Tuberculosis in the United States Division of Health Promotion and Disease Prevention, Institute of Medicine. Unpublished.)

Although the FDA approved a medication that combines the three main drugs (isoniazid, rifampin, and pyrazinamide) used to treat tuberculosis into one pill. Thereby reducing the number of pills a patient has to take each day and making it impossible for the patient to take only one of the three medications, a common path to the development of MDR-TB, there is still a need in the art to treat tuberculosis, especially in those cases wherein the tuberculosis strain is drug resistant.

What is needed are effective therapeutic regimens that include improved vaccination and treatment protocols. Currently available therapeutics are no longer consistently effective as a result of the problems with treatment compliance, and these compliance problems contribute to the development of drug resistant mycobacterial strains.

Furthermore, there is a need in the art for novel compositions and methods that are effective against infectious disease. More particularly, there is a need for novel compositions and methods for the effective treatment of Mycobacterial disease.

Ethambutol (EMB) is a widely used antibiotic for the treatment of TB, with over 300 million doses delivered for tuberculosis therapy in 1988.

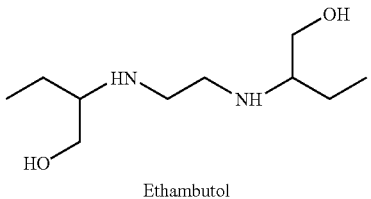

Ethambutol

Ethambutol, developed by Lederle Laboratories in the 1950s, has low toxicity and is a good pharmacokinetic. However, ethambutol has a relatively high Minimum Inhibition Concentration (MIC) of about 5 μg/ml, and can cause optic neuritis. Thus, there is an increasing need for new, and more effective, therapeutic compositions (See for example, U.S. Pat. Nos. 3,176,040; 4,262,122; 4,006,234; 3,931,157; 3,931,152; U.S. Re 29,358; and Häusler et al., Bioorganic & Medicinal Chemistry Letters 11 (2001) 1679-1681). In the decoder years since the discovery of the beneficial effects of ethambutol, few pharmacological advances in TB treatment have been developed. Moreover, with the combined emergence of drug resistant strains, and the more prevalent spread of mycobacterial disease, it is becoming seriously apparent that new therapeutic compositions are crucial in the fight against tuberculosis.

Clearly effective therapeutic regimens that include improved vaccination and treatment protocols are needed. A therapeutic vaccine that would prevent the onset of tuberculosis, and therefore eliminate the need for therapy is desirable. Although currently available therapeutics such as ethambutol are effective, the emergence of drug resistant strains has necessitated new formulations and compositions that are more versatile than ethambutol. Currently available therapeutics are no longer consistently effective as a result of the problems with treatment compliance, lending to the development of drug resistant mycobacterial strains. What is needed are new anti-tubercular drugs that provide highly effective treatment, and shorten or simplify tuberculosis chemotherapy.

SUMMARY OF THE INVENTION

The present invention comprises methods and compositions comprising ethylene diamine compounds effective for the treatment of infectious disease. The present invention also provides methods and compositions comprising substituted ethylene diamines having improved anti-mycobacterial activity, including substituted ethylene diamines having improved anti-tuberculosis activity.

The present invention contemplates substituted ethylene diamines, which can derive from a variety of amine compounds. In the present invention, the substituted ethylene diamines are based on the following structure.

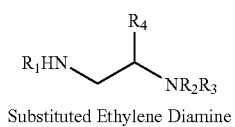

Substituted Ethylene Diamine

The substituted ethylene diamine compounds described herein are synthesized and screened for activity as follows. A chemical library of substituted ethylene diamines is prepared on a solid polystyrene support using split and pool technologies. This technique allows for the synthesis of a diverse set of substituted ethylene diamines. These diamines are screened for anti-TB activity using in vitro, biological assays, including a High-Throughput Screening (HTS) assay, based on the recently completed genomic sequence of M. tuberculosis, and a Minimum Inhibition Concentration (MIC) assay.

The methods and compositions described herein comprise substituted ethylene diamines that are effective against disease caused by infectious organisms, including, but not limited to, bacteria and viruses. One embodiment of the invention provides methods and compositions comprising substituted ethylene diamines that are effective against mycobacterial disease. Another embodiment of the invention provides methods and compositions comprising substituted ethylene diamines that have MIC of 50 μM or lower for mycobacterial disease. Another embodiment of the present invention comprises substituted ethylene diamines that have an MIC of 25 μM or lower for mycobacterial disease. Yet another embodiment of the present invention comprises substituted ethylene diamines that have an MIC of 12.5 μM or lower for mycobacterial disease. Another embodiment of the present invention comprises substituted ethylene diamines that have an MIC of 5 μM or lower for mycobacterial disease In another embodiment of the present invention, the methods and compositions comprise substituted ethylene diamines with HTS Luc activity of 10% or greater. In yet another embodiment of the present invention, the methods and compositions comprise substituted ethylene diamines, wherein one amine group is derived from a primary amine, and wherein the other amine group is derived from a primary or secondary amine. In another embodiment of the present invention, the methods and compositions comprise substituted ethylene diamines, wherein one amine is derived from cis-(−)myrtanylamine, cyclooctylamine, 2,2-diphenylethylamine, 3,3-diphenylpropylamine, (+)-bornylamine, 1-adamantanemethylamine, (+)-isopinocampheylamine; or (−)-isopinocampheylamine.

The present invention contemplates various salt complexes and other substituted derivatives of the substituted ethylene diamines. The present invention also contemplates enantiomers and other stereoisomers of the substituted ethylene diamines and their substituted derivatives. The present invention further contemplates treatment for animals, including, but not limited to, humans.

Accordingly, it is an object of the present invention to provide methods and compositions for the treatment and prevention of diseases caused by microorganisms Accordingly, it is an object of the present invention to provide methods and compositions for the treatment and prevention of infectious diseases.

Another object of the present invention is to provide methods and compositions for the treatment and prevention of mycobacterial disease, including but not limited to, tuberculosis.

Yet another object of the present invention is to provide methods and compositions for the treatment and prevention of infectious diseases using compositions comprising substituted ethylene diamines.

Another object of the present invention is to provide methods and compositions for the treatment and prevention of mycobacterial disease using compositions comprising substituted ethylene diamines.

Still another object of the present invention is to provide methods and compositions for the treatment and prevention of tuberculosis using compositions comprising substituted ethylene diamines.

Another object of the present invention is to provide methods and compositions for the treatment and prevention of tuberculosis using compositions comprising substituted ethylene diamines, wherein the diamine has an MIC of 50 µM, or less.

Another object of the present invention is to provide methods and compositions for the treatment and prevention of tuberculosis using compositions comprising substituted ethylene diamines, wherein the diamine has an MIC of 25 µM, or less.

Another object of the present invention is to provide methods and compositions for the treatment and prevention of tuberculosis using compositions comprising substituted ethylene diamines, wherein the diamine has an MIC of 12.5 µM, or less.

Yet another object of the present invention is to provide methods and compositions for the treatment and prevention of tuberculosis using compositions comprising substituted ethylene diamines, wherein the diamine has an MIC of 5 µM, or less.

Yet another object of the present invention is to provide methods and compositions for the treatment and prevention of tuberculosis using compositions comprising substituted ethylene diamines, wherein the diamine has HTS/Luc activity of 10% or greater.

Another object of the present invention is to provide methods and compositions for the treatment and prevention of tuberculosis using compositions comprising substituted ethylene diamines, wherein one amine group is derived from a primary amine, and the other amine group is derived from a primary or secondary amine.

Yet another object of the present invention is to provide methods and compositions for the treatment and/or prevention of tuberculosis using compositions comprising substituted ethylene diamines, wherein one amine is derived from cis-(−)myrtanylamine, cyclooctylamine, 2,2-diphenylethylamine, 3,3-diphenylpropylamine, (+)-bornylamine, 1-adamantanemethylamine, (+)-isopinocampheylamine; or (−)-isopinocampheylamine.

Yet another object of the present invention is to provide composition for the therapeutic formulation for the treatment and prevention of mycobacterial disease.

Another object of the present invention is to provide compositions for therapeutic formulations for the treatment and prevention of mycobacterial disease caused by mycobacterial species comprising *M. tuberculosis* complex, *M. avium intracellulare, M. kansarii, M. fortuitum, M. chelonoe, M. leprae, M. africanum, M. microti, M. bovis* BCG or *M. bovis*.

Still another object of the present invention is to provide compositions and methods for the treatment or prevention of infectious disease caused by *Mycobacterium-fortuitum, Mycobacterium marinum, Helicobacter pylori, Streptococcus pneumoniae* and *Candida albicans*.

Another object of the instant invention is to provide one or more novel compounds in a combination therapy to provide a synergistic effect that is active against mycobacterial disease.

Yet another object of the instant invention is to provide one or more novel compounds in combination with a drug to provide a synergistic effect active against mycobacterial disease.

Another object of the instant invention is to provide one or more novel compounds in combination with a standard tuberculosis drug to provide a synergistic effect active against mycobacterial disease.

It is a further objective that the instant invention provide novel methods of treatment wherein one or more novel compounds are used in combination with at least one known drug to provide a synergistic effect, by which to treat or prevent infectious disease.

These and other objects, features and advantages of the present invention will become apparent after a review of the following detailed description of the disclosed embodiments and the appended claims.

BRIEF DESCRIPTION OF THE FIGURES

FIGS. 3(a)-3(f) provide chemical structures of a variety of acyclic secondary amines.

FIGS. 4(a)-4(i) provide chemical structures of a variety of cyclic secondary amines.

FIG. 22 provides the compounds tested for in vivo efficacy.

FIG. 38. Binding assays for compound 109.

FIG. 39. Binding assays for reference compound.

FIG. 40. Data summary for compound 109

FIG. 41. Scheme 1. Synthesis of 100,000 compound library of ethambutol analogues on solid support.

FIG. 41. Scheme 2. Attempts to synthesize SQBisAd on solid support.

FIG. 43 provides Table 25 summarizing data for synthesized plates of diamines for the prepared library of targeted 20,000 ethambutol analogs.

FIG. 47 provides Table 26 listing the amino acids that were used in the prepartion of the diamine library.

FIG. 49 provides Table 27 showing carbonyl compounds used in the masterplate for the synthesis of the diamine library.

FIG. 52 provides the layout of a representative 96-well deconvolution plate.

FIG. 53 provides a list of compound hits and structures for the modified linker diamine library.

FIG. 60 provides results of binding assay as % of Control Specific Binding for compound 109.

FIG. 61 provides results of binding assay as % inhibition of Control Specific Binding for compound 109.

FIG. 62 provide MIC results of Gram-Positive Organisms Tested Against SQ-109.

FIGS. 63A and 63B provide MIC results of Gram-Negative Organisms Tested Against SQ-109.

FIG. 64 provides MIC results of Anaerobes Tested Against SQ-109.

FIG. 65 provides MIC results of Fungi Tested Against SQ-109.

FIG. 66 provides MIC results of *Mycobacteria* Tested Against SQ-109.

DETAILED DESCRIPTION

Figure 1:
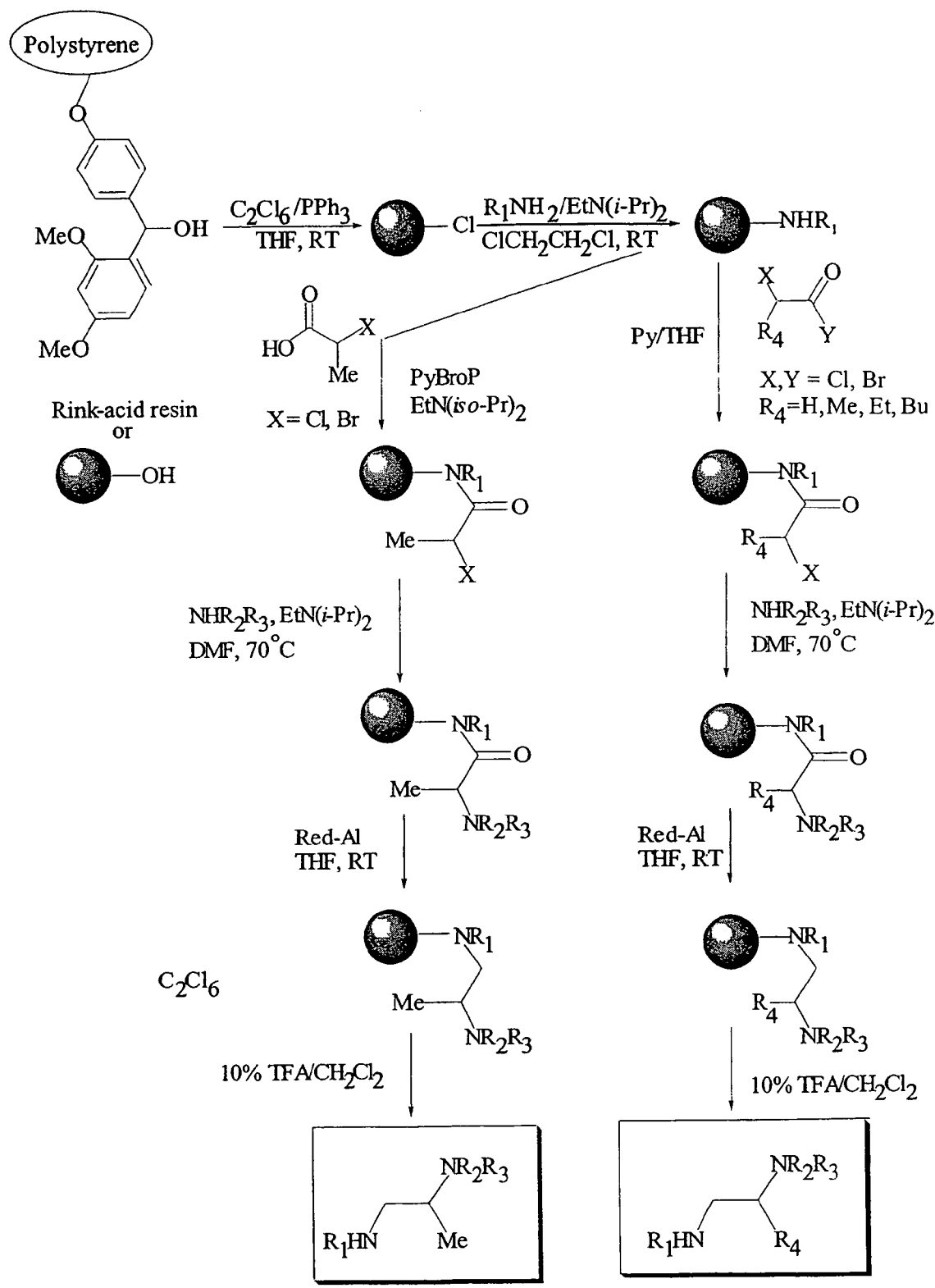
FIG. 1 represents a flow chart schematic showing various solid support syntheses used to prepare substituted ethylene diamines.

The present invention may be understood more readily by reference to the following detailed description of the specific embodiments included herein. However, although the present invention has been described with reference to specific details of certain embodiments thereof, it is not intended that such details should be regarded as limitations upon the scope of the invention. The entire text of the references mentioned herein are hereby incorporated in their entireties by reference including U.S. patent application Ser. No. 11/145,499, filed Jun. 3, 2005, U.S. patent application Ser. No. 10/147,587 filed May 17, 2002, and U.S. Provisional Patent Application Ser. No. 60/381,220 filed May 17, 2002.

Mycobacterial infections, such as those causing tuberculosis, once thought to be declining in occurrence, have rebounded, and again constitute a serious health threat. Tuberculosis (TB) is the cause of the largest number of human deaths attributed to a single etiologic agent with two to three million people infected with tuberculosis dying each year. Areas where humans are crowded together, or living in substandard housing, are increasingly found to have persons affected with mycobacteria. Individuals who are immunocompromised are at great risk of being infected with mycobacteria and dying from such infection. In addition, the emergence of drug-resistant strains of mycobacteria has led to treatment problems of such infected persons Many people who are infected with mycobacteria are poor, or live in areas with inadequate healthcare facilities. As a result of various obstacles (economical, education levels, etc.), many of these individuals are unable to comply with the prescribed therapeutic regimens. Ultimately, persistent non-compliance by these and other individuals results in the prevalence of disease. This noncompliance is frequently compounded by the emergence of drug-resistant strains of mycobacteria. Effective compositions and vaccines that target various strains of mycobacteria are necessary to bring the increasing number of tuberculosis cases under control.

Chemotherapy is a standard treatment for tuberculosis. Some current chemotherapy treatments require the use of three or four drugs, in combination, administered daily for two months, or administered biweekly for four to twelve months. Table 1 lists several treatment schedules for standard tuberculosis drug regimens.

TABLE 1

Treatment Schedules for Standard TB Drug Regimens.

| STANDARD DRUG REGIMEN | INDUCTION PHASE Dosing Schedule | DURATION | DRUG | CONTINUATION PHASE Dosing Schedule | DURATION |
|---|---|---|---|---|---|
| Isoniazid | Daily, DOT | 8 weeks | Isoniazid | 2/week, DOT | 16 weeks |
| Rifampicin | Daily, DOT | 8 weeks | Rifampicn | 2/week, DOT | 16 weeks |
| Pyrazinamide | Daily, DOT | 8 weeks | | | |
| Ethambutol or Streptomycin | Daily, DOT | 8 weeks | | | |

Decades of misuse of existing antibiotics and poor compliance with prolong and complex therapeutic regimens has led to mutations of the *mycobacterium tuberculosis* and has created an epidemic of drug resistance that threatens tuberculosis control world wide. The vast majority of currently prescribed drugs, including the front line drugs, such as isoniazid, rifampin, pyrazinamide, ethambutol and streptomycin were developed from the 1950s to the 1970s. Thus, this earlier development of tuberculosis chemotherapy did not have at its disposal the implications of the genome sequence of *Mycobacterium tuberculosis*, the revolution in pharmaceutical drug discovery of the last decades, and the use of national drug testing and combinational chemistry.

Consequently, the treatments of drug-resistant *M. tuberculosis* strains, and latent tuberculosis infections, require new anti-tuberculosis drugs that provide highly effective treatments, and shortened and simplified tuberculosis chemotherapies. Moreover, it is desirable that these drugs be prepared by a low-cost synthesis, since the demographics of the disease dictate that cost is a significant factor.

The present invention provides methods and compositions comprising a class of substituted ethylene diamine compounds effective in treatment and prevention of disease caused by microorganisms including, but not limited to, bacteria. In particular, the methods and compositions of the present invention are effective in inhibiting the growth of the microorganism, *M. tuberculosis*. The methods and compositions of the present invention are intended for the treatment of mycobacteria infections in human, as well as other animals. For example, the present invention may be particularly useful for the treatment of cows infected by *M. bovis*.

As used herein, the term "tuberculosis" comprises disease states usually associated with infections caused by mycobacteria species comprising *M. tuberculosis* complex. The term "tuberculosis" is also associated with mycobacterial infections caused by mycobacteria other than *M. tuberculosis* (MOTT). Other mycobacterial species include *M. avium-intracellulare*, *M. kansari*, *M. fortuitum*, *M. chelonae*, *M. leprae*, *M. africanum*, and *M. microti*, *M. avium paratuberculosis*, *M. intracellulare*, *M. scrofulaceum*, *M. xenopi*, *M. marinum*, *M. ulcerans*.

The present invention further comprises methods and compositions effective for the treatment of infectious disease, including but not limited to those caused by bacterial, mycological, parasitic, and viral agents. Examples of such infectious agents include the following: *staphylococcus*, streptococcaceae, neisseriaaceae, cocci, enterobacteriaceae, pseudomonadaceae, vibrionaceae, *campylobacter*, pasteurellaceae, *bordetella, francisella, brucella*, legionellaceae, bacteroidaceae, gram-negative bacilli, *clostridium, corynebacterium, propionibacterium*, gram-positive bacilli, anthrax, *actinomyces, nocardia, mycobacterium, Helicobacter pylori, Streptococcus pneumoniae, Candida albicans, treponema, borrelia, leptospira, mycoplasma, ureaplasma, rickettsia*, chlamydiae, systemic mycoses, opportunistic mycoses, protozoa, nematodes, trematodes, cestodes, adenoviruses, herpesviruses, poxviruses, papovaviruses, hepatitis viruses, orthomyxoviruses, paramyxoviruses, coronaviruses, picomaviruses, reoviruses, togaviruses, flaviviruses, bunyaviridae, rhabdoviruses, human immunodeficiency virus and retroviruses.

The present invention further provides methods and compositions useful for the treatment of infectious disease, including by not limited to, tuberculosis, leprosy, Crohn's Disease, acquired immunodeficiency syndrome, lyme disease, cat-scratch disease, Rocky Mountain Spotted Fever and influenza.

The anti-infective methods and compositions of the present invention contain one or more substituted ethylene diamine compounds. In particular, these compounds encompass a wide range of substituted ethylene diamine compounds having the following general formula:

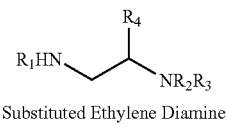

Figure 2A:
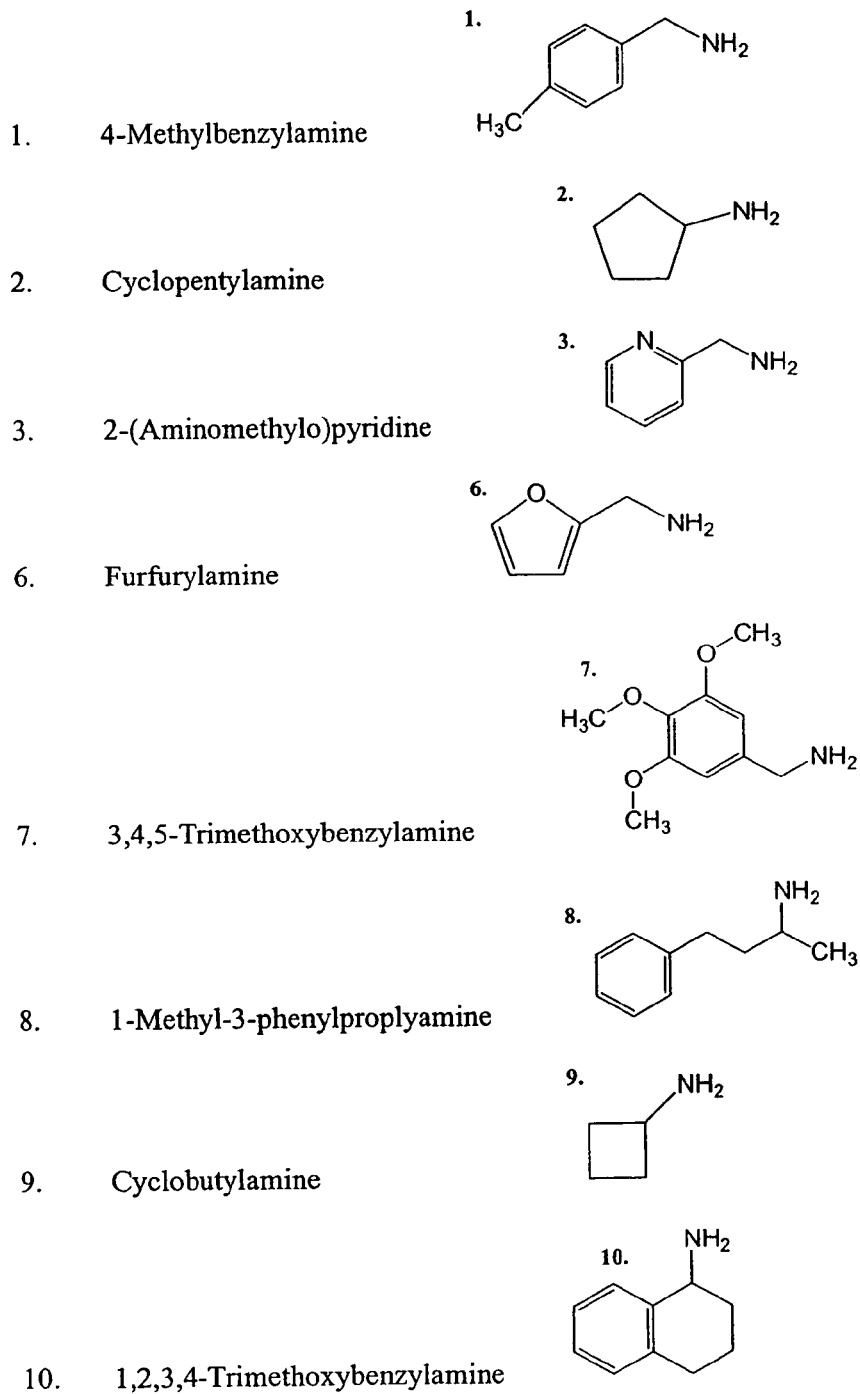
FIGS. 2(a)-2(ac) provide chemical structures of a variety of primary amines.
Figure 2E:
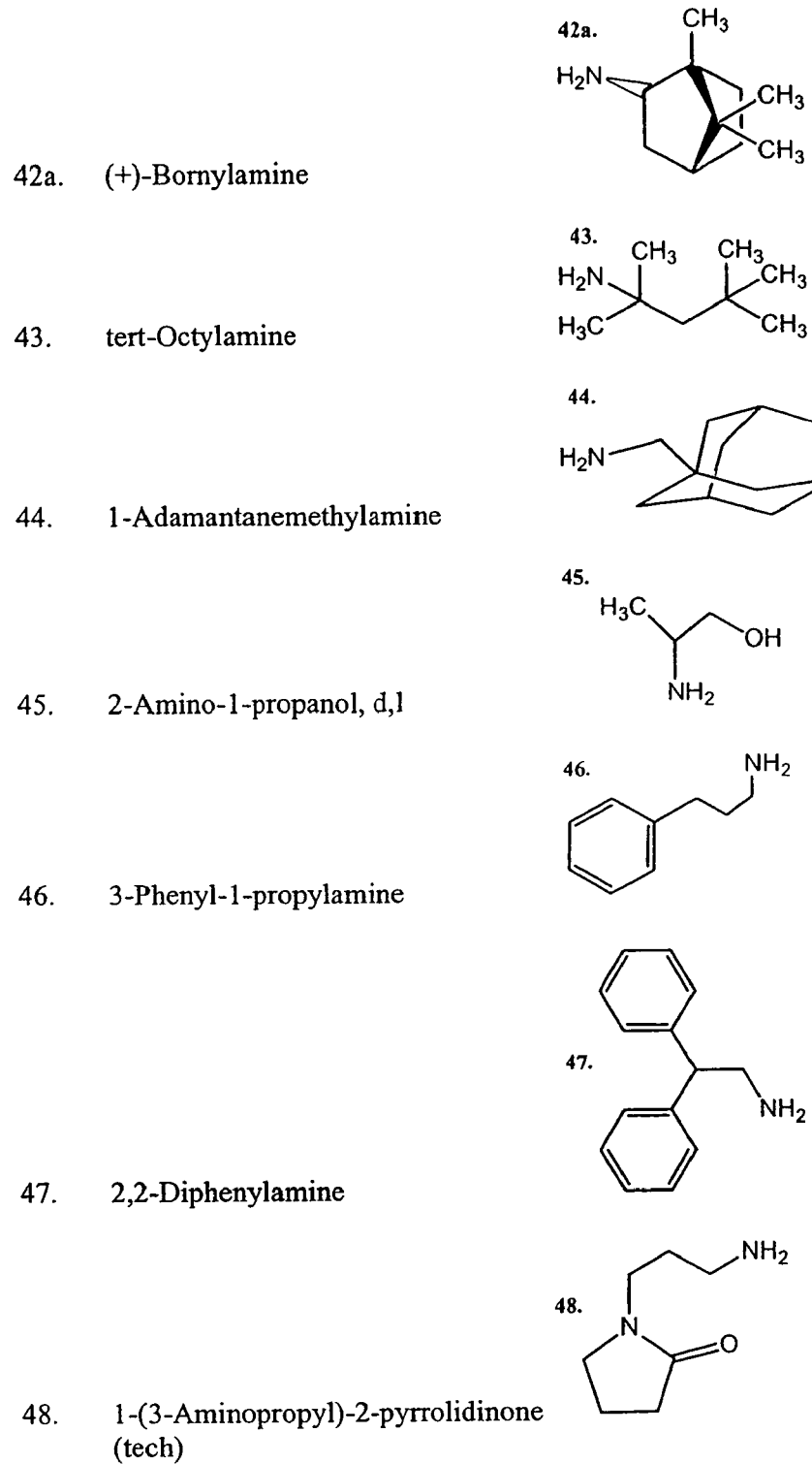
Figure 2J:
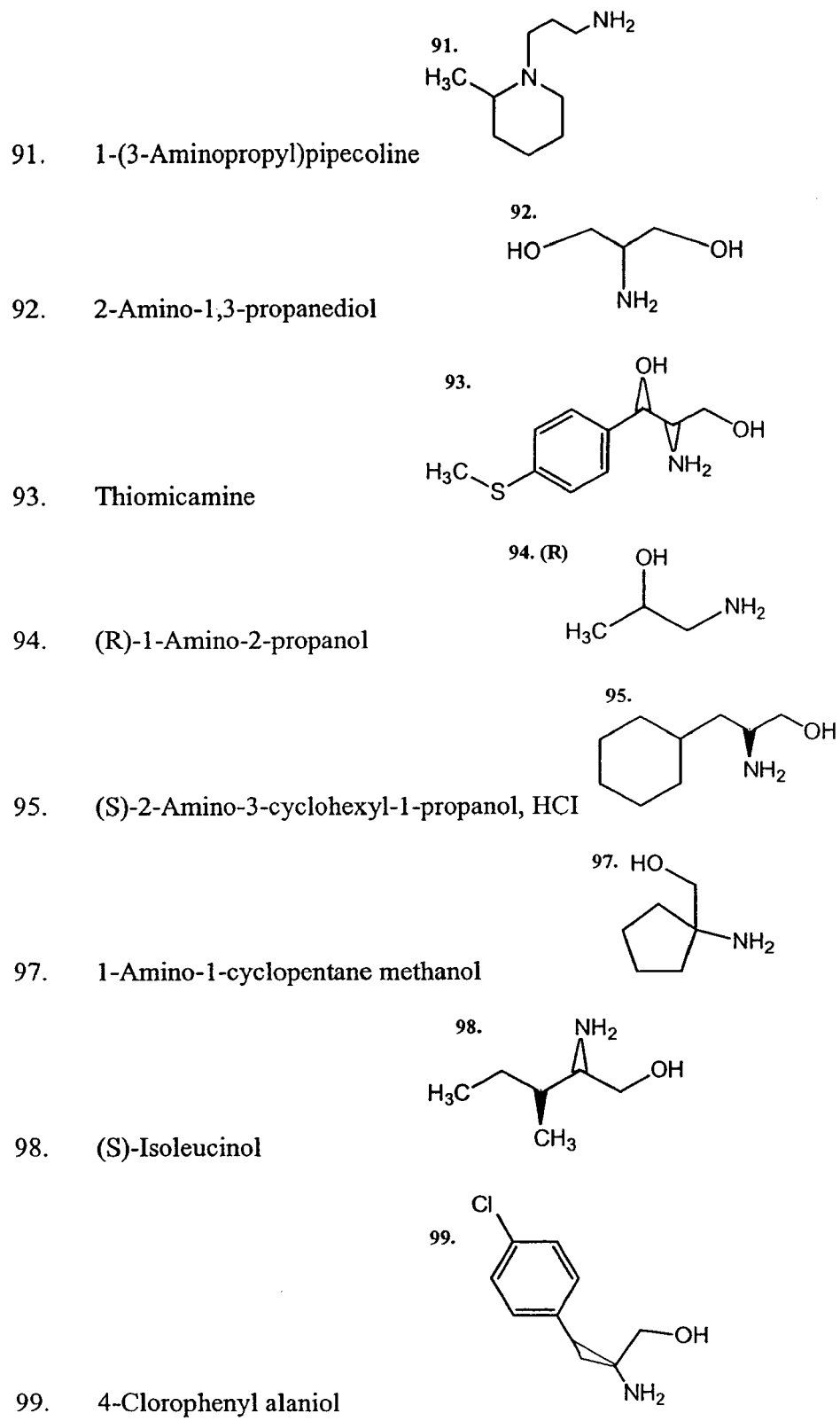
Figure 3F:
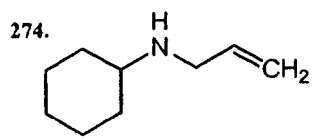

Substituted Ethylene Diamine where "$R_1NH$" is typically derived from a primary amine, and "$R_2R_3N$" is typically derived from a primary or secondary amine. The ethylene diamines of the present invention are prepared by a modular approach using primary and secondary amines as building blocks, and coupling the amine moieties with an ethylene linker building block. Representative primary amines, acyclic secondary amines, and cyclic secondary amines are shown in FIGS. 2, 3, and 4, respectively.

Generally, chemical moieties $R_1$, $R_2$, and $R_3$ of the ethylene diamine compounds of the present invention are independently selected from H, alkyl; aryl; alkenyl; alkynyl; aralkyl; aralkenyl; aralkynyl; cycloalkyl; cycloalkenyl; heteroalkyl; heteroaryl; halide; alkoxy; aryloxy; alkylthio; arylthio; silyl; siloxy; a disulfide group; a urea group; amino; and the like, including straight or branched chain derivatives thereof, cyclic derivatives thereof, substituted derivatives thereof, heteroatom derivatives thereof, heterocyclic derivatives thereof, functionalized derivatives thereof, salts thereof, such salts including, but not limited to hydrochlorides and acetates, isomers thereof, or combinations thereof. For example, nitrogen-containing heterocyclic moieties include, but are not limited to, groups such as pyridinyl (derived from pyridine, and bonded through a ring carbon), piperidinyl (derived from piperidine and bonded through the ring nitrogen atom or a ring carbon), and pyrrolidinyl (derived from pyrrolidine and bonded through the ring nitrogen atom or a ring carbon). Examples of substituted, or functionalized, derivatives of $R_1$, $R_2$, and $R_3$ include, but are not limited to, moieties containing substituents such as acyl, formyl, hydroxy, acyl halide, amide, amino, azido, acid, alkoxy, aryloxy, halide, carbonyl, ether, ester, thioether, thioester, nitrile, alkylthio, arythio, sulfonic acid and salts thereof, thiol, alkenyl, alkynyl, nitro, imine, imide, alkyl, aryl, combinations thereof, and the like. Moreover, in the case of alkylated derivatives of the recited moieties, the alkyl substituent may be pendant to the recited chemical moiety, or used for bonding to the amine nitrogen through the alkyl substituent.

Examples of chemical moieties $R_1$, $R_2$, and $R_3$ of the present invention include, but are not limited to: H; methyl; ethyl; propyl; butyl; pentyl; hexyl; heptyl; octyl; ethenyl; propenyl; butenyl; ethynyl; propynyl; butynyl; cyclopropyl; cyclobutyl; cyclopentyl; cyclohexyl; cyclooctyl cyclobutenyl; cyclopentenyl; cyclohexenyl; phenyl; tolyl; xylyl; benzyl; naphthyl; pyridinyl; furanyl; tetrahydro-1-napthyl; piperidinyl; indolyl; indolinyl; pyrrolidinyl; 2-(methoxymethyl) pyrrolidinyl; piperazinyl; quinolinyl; quinolyl; alkylated-1,3-dioxolane; triazinyl; morpholinyl; phenyl pyrazolyl; indanyl; indonyl; pyrazolyl; thiadiazolyl; rhodaninyl; thiolactonyl; dibenzofuranyl; benzothiazolyl; homopiperidinyl; thiazolyl; quinonuclidinyl; isoxazolidinonyl; any isomers, derivatives, or substituted analogs thereof; or any substituted or unsubstituted chemical species such as alcohol, ether, thiol, thioether, tertiary amine, secondary amine, primary amine, ester, thioester, carboxylic acid, diol, diester, acrylic acid, acrylic ester, methionine ethyl ester, benzyl-1-cysteine ethyl ester, imine, aldehyde, ketone, amide, or diene. Further examples of chemical moieties $R_1$, $R_2$, and $R_3$ of the present invention include, but are not limited to, the following species or substituted or alkylated derivatives of the following species, covalently bonded to the amine nitrogen: furan; tetrahydrofuran; indole; piperazine; pyrrolidine; pyrrolidinone; pyridine; quinoline; anthracene; tetrahydroquinoline; naphthalene; pyrazole; imidazole; thiophene; pyrrolidine; morpholine; and the like. One feature of the recited species or substituted or alkylated derivatives of these species, is that they may be covalently bonded to the amine nitrogen in any fashion, including through the pendant substituent or alkyl group, through the heteroatom as appropriate, or through a ring atom as appropriate, as understood by one of ordinary skill in the art.

The chemical moieties $R_1$, $R_2$, and $R_3$ of the present invention also include, but are not limited to, cyclic alkanes and cyclic alkenes, and include bridged and non-bridged rings. Examples of bridged rings include, but are not limited to, the following groups: isopinocamphenyl; bornyl; norbornyl; adamantanetetyl; cis-(–)myrtanyl; adamantyl; noradamantyl; 6-azabicyclo[3.2.1]octane; exo-norbornane; and the like.

In one embodiment of the present invention, $NR_2R_3$ is derived from a cyclic secondary amine. Examples of a cyclic chemical moiety, $NR_2R_3$, of the present invention include, but are not limited to, 4-benzyl-piperidine; 3-piperidinemethanol; piperidine; tryptamine; moropholine; 4-piperidinopiperidine; ethyl 1-piperazine carboxylate; 1-(2-amino-ethyl)-piperazine; decahydroquinoline; 1,2,3,4-tetrahydropyridoindole (reaction at either amine); 3-amino-5-phenyl pyrazole; 3-aminopyrazole; 1-(2-fluorophenyl) piperazine; 1-proline methyl ester; histidinol; 1-piperonyl-piperazine; hexamethyleimine; 4-hydroxypiperidine; 2-piperidinemethanol; 1,3,3-trimethyl-6-azabicyclo[3.2.1]octane; 3-pyrrolidinol; 1-methylpiperazine; (S)-(+)-(2-pyrolidinylmethyl) pyrrolidine; 1-methylhomopiperazine; 2-ethyl-piperidine; 1,2,3,4-tetrahydroisoquinoline; 1-(4-fluorophenyl) piperazine; d,l-tryptophan methyl ester; tert-butyl (15, 45)-(–)-2,5-diazabiclyclo[2.2.1] heptane-2-carboxylate; isonipecotamide; heptamethyleneimine; alpha-methyltryptamine; 6,7-dimethoxy-1,2,3,4-tetrahydroisoquinoline; 3-aminopyrrolidine; 3,5-dimethylpiperidine; 2,6-dimethylmorpholine; 1,4-dioxo-8-azaspiro[4.5]decane; 1-methol-6,7-dihydroxy-1,2,3,4-tetrahydroisoquinoline; 1, 3, 4, 6, 7,8-hexahydro-2H-pyrido (1,2-A) pyrimidine; 1,2,3,4-tetrahydroquinoline; 1-(2-methoxyphenyl) piperazine; 1-(2-(2-hydroxyethoxy)ethyl) piperazine; (S)-(+)-2-(aminomethyl) pyrrolidine; (3S(3a,4Ab), 8Ab)-N-t-butyl-D-ecahydro-3-isoquino-linecarboxamide; (R)-cycloserine; homopiperazine; 2,6-dimethylpiperazine (reaction at either amine); iminodibenzyl; 5-methoxytryptamine; 4,4'-bipiperidine; 1-(2-hydroxyethyl) piperazine; 4-methylpiperidine; 1-histidine methyl ester; or methyl pipecoliate.

The $R_1HN$ substituent is derived from a primary amine. The $R_2R_3N$ substituent is typically derived from a primary or secondary amine, but may also arise from an amino acid, or an amino acid precursor. The amino acid can transform into an amino alcohol. When an amino acid is employed as the source of the $R_2R_3N$ moiety, the precursor compound may be selected from, among others, the following compounds and their derivatives: d,l-tryptophan methyl ester; 1-methionine ethyl ester; 1-lysine methyl ester (via reaction at either primary amine); (S)-benzyl-1-cysteine ethyl ester; 1-arginine methyl ester (via reaction at either primary amine); 1-glutamic acid ethyl ester; 1-histidine methyl ester; or (3S (3a,4Ab), 8A b)-N-t-butyl-D-ecahydro-3-iso-quino linecarboxamide.

The $R_4$ moiety of the substituted ethylene diamine compounds of the present invention is typically selected from H, alkyl or aryl, but $R_4$ can also constitute alkenyl, alkynyl, aralkyl, aralkenyl, aralkynyl, cycloalkyl, cycloalkenyl, and the like. Examples of the $R_4$ chemical moiety include, but are not limited to: H; methyl; ethyl; propyl; butyl; pentyl; hexyl; heptyl; octyl; ethenyl; propenyl; butenyl; ethynyl; propynyl; butynyl; cyclobutyl; cyclopentyl; cyclohexyl; cyclobutenyl; cyclopentenyl; cyclohexenyl; phenyl; tolyl; xylyl; benzyl; naphthyl; straight or branched chain derivatives thereof; cyclic derivatives thereof; substituted, functionalized, and heteroatom derivatives thereof; and heterocyclic derivatives thereof, and the like. Typically, $R_4$ is selected from H, methyl, ethyl, butyl or phenyl. However, when $R_4$ is "H" the ethylene diamine does not contain ethambutol.

A majority of the ethylene diamine compounds described hrein are preferably prepared using a solid support synthesis, as set forth in one of the representative reaction schemes shown in FIG. 1. However, when $R_4$ is H, the reaction does not proceed well when sterically hindered amines are used for $R_1NH_2$, or when diamines, such as amino alkylenemorpholine, or aminoalkylene-piperidines, are used for $R_1NH_2$. When $R_4$ is methyl, or phenyl, sterically hindered amines used for $R_3R_2NH$ do not work well due to steric hindrance at the reaction site. In this case, a competing hydrolysis reaction producing the corresponding amino alcohols, and incomplete reduction of the amidoethyleneamines, interfere with the reaction scheme. As a result, the desired diamine products form in low yields.

The preparation of the ethylene diamines is preferably accomplished in six steps, using a rink-acid resin. The first step of the synthesis is converting the rink-acid resin to rink-chloride by treatment with triphenylphosphine and hexachloroethane in tetrahydrofuran (THF). This step is followed by addition of the primary amine in the presence of Hunig's base (EtN(i-Pr)$_2$) in dichloroethane. The third step is the acylation of the resin-attached amine using either one of the two acylation routes shown in FIG. 1. The acylation step is preferably accomplished using either α-chloroacetyl chloride, α-bromo-α-methyl acetylbromide, α-bromo-α-ethylacetyl bromide, α-bromo-α-butyl acetylbromide, or α-chloro-α-phenyl-acetylchloride, each in the presence of pyridine in THF. Other acylation reagents known to those skilled in the art may also be used, however, the α-bromoacetyl halides result in low product yields, which may be attributed to HBr elimination. The acylation may also be accomplished via a peptide coupling mechanism using α-bromo-α-methylacetic acid, or α-chloro-α-methylacetic acid, in the presence of benzotriazole-1-yl-oxy-tris-pyrrolidino-phosphonium hexafluorophosphate (PyBrop) and $N_1N$-diisopropylethyl amine (EtN(i-Pr)$_2$) in dichloromethane (DCM) and dimethylformamide (DMF). Again, other acylation reagents known to those skilled in the art may also be used. The acylation step is preferably performed twice to achieve better acylated product yields.

Introduction of the second nitrogen moiety is preferably achieved in the presence of Hunig's base in dimethylformamide (DMF). Reduction of the intermediate amine-amide is carried out using Red-Al (3.4M solution of sodium bis (2-methoxyethoxy) aluminum hydride in toluene). The final product is cleaved from the resin support using a 10% solution (by volume) of trifluoroacetic acid (TFA) in dichloromethane (DCM). The solvent is evaporated, and the TFA salts of the final diamine products are analyzed by mass spec, and screened against *M. tuberculosis* for effectiveness. Some of the substituted ethylene diamines, prepared using the above-described solid-support synthesis, are also prepared using a solution phase synthesis described below.

Formation of the Substituted Ethylene Diamine Library

The solid support syntheses, shown in FIG. 1, are preferably used to prepare a substituted ethylene diamine library. Solid phase synthesis offers at least three principal advantages: (i) a reduced need for chromatographic procedures, (ii) the use of excess reagents to drive a reaction forward in high yields, and (iii) the use of split and pool technologies for the synthesis of a large number of compounds. Solid support syntheses of 1,2-diamine libraries have previously been accomplished by the reduction of short peptides (Cuervo et al., Peptides 1994: Proceedings of the European Peptide Symposium; Maia HSL Ed., Esom: Leiden, 1995, 465-466). However, as described herein, an ethylene diamine library is created using amines, rather than simple amino acids, to allow for greater diversity in the building-block monomers. The first three steps of each support synthesis: the activation of the Rink-acid resin, the addition of the first amine, and the acylation step are carried out in 10 ml tubes on a QUEST® 210 Synthesizer manufactured by ARGONAUT TECHNOLOGIES®, Inc., Foster City, Calif. The synthesizer handles up to twenty simultaneous reactions in 5 ml or 10 ml reaction vessels to allow for rapid synthesis of target compounds. The synthesizer provides programmable temperature control and agitation, and the automated delivery of solvents into the reaction vessels. The addition of the second amine, the reduction with Red-Al, and the cleavage from the solid support are carried out in 2 ml wells in a 96-well, chemically resistant plate.

Figure 5:
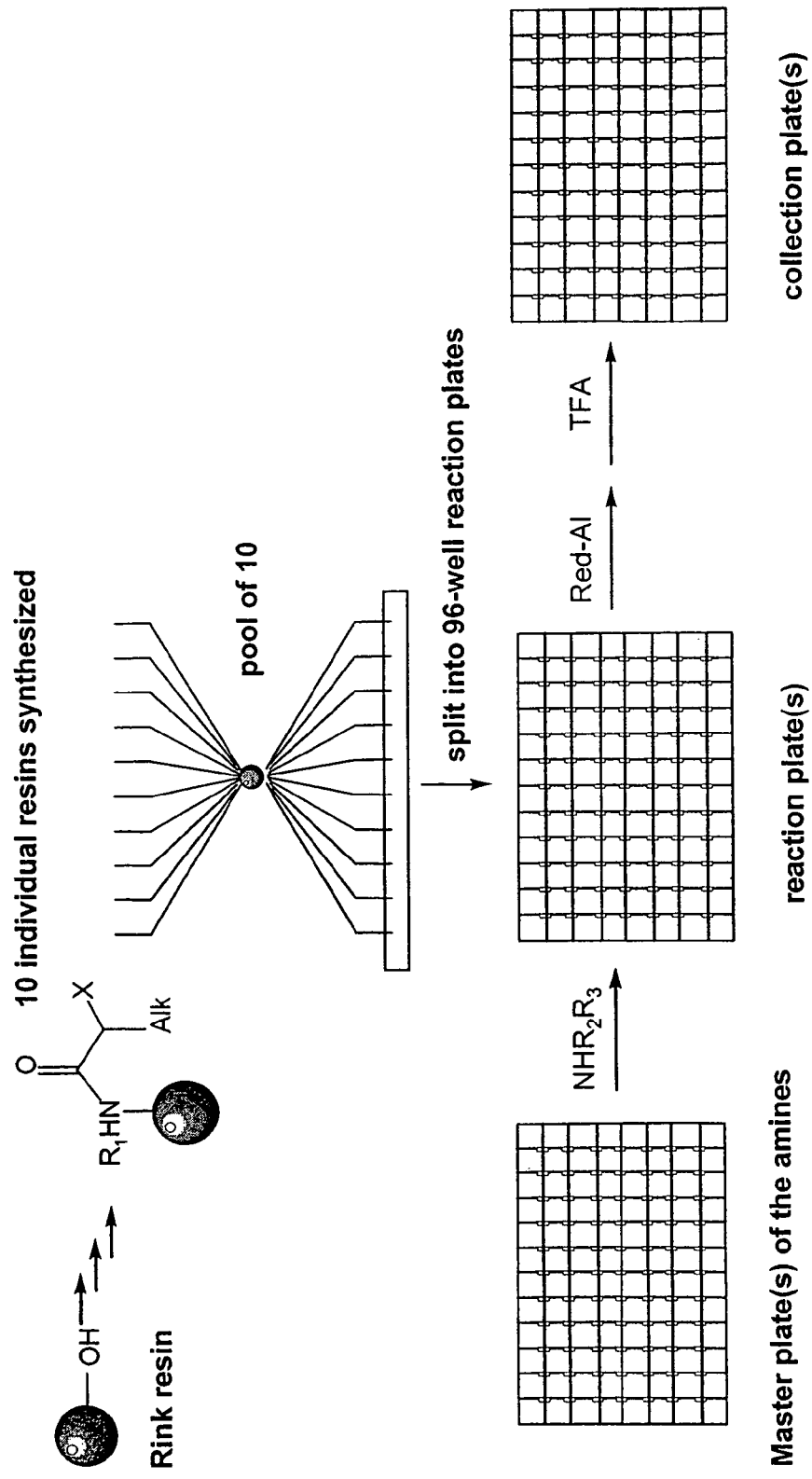
FIG. 5 represents a flow schematic for a representative reaction pool of ten substituted ethylene diamines.

Prior to the solid support synthesis, each amine, within numbers 1 to 288, as shown in FIGS. 2, 3, and 4, is dissolved in DMF as a one molar solution, and organized in three, 96-well plates (one amine per well), to yield three master plates of these amines. An individual haloacetyl amide from each primary amine and a particular $R_4$ group, is formed in the first three steps of the support synthesis. Individual haloacetyl amides are then pooled into groups of ten or thirty. A suspension of the pooled resins in a 2:1 mixture of DCM/THF is evenly distributed into one, two or three reaction plates to assure 15-20 mg of the suspension per well. The number of reaction plates used is based on the amount of suspension available. Each well of pooled resins is reacted with a corresponding amine from the master plates. FIG. 5 provides a flow schematic for a representative pool. Each reaction occurs in a separate well, in the presence of Hunig's base in DMF at 70-75° C. for 16-20 hours. Each resulting amine-amide is reduced using 65+w % Red-Al at room temperature. The reduction is followed by cleavage with 10% vol. TFA in DCM. The solvents in each reaction well are evaporated, and the TFA salts of the diamines analyzed (mass spec), and screened against *M. tuberculosis*. One plate of pooled diamines are screened against *M. smegmatis*. Two randomly selected rows in each plate; i.e., 24 samples per 96-well plate, or 25% of the library, are examined by mass spectroscopy. Specific protocols and detailed methods are provided below in the Examples.

Screening against *M. tuberculosis*

An entire library of synthesized substituted ethylene diamines (targeted number of compounds about 100,000), prepared as described above, was screened, in vitro, against *M. tuberculosis* in ethambutol (EMB) sensitive Luc-assay. The MIC (Minimum Inhibition Concentration) was also determined. The MIC is the minimum concentration of a growth inhibitor, here the substituted ethylene diamine, where there is no multiplication of the microorganism under examination. Screening was done using a High-Throughout Screening (HTS) Luc assay with recombinant mycobacteria containing a promoter fusion of a luciferase to the EB-inducible gene (Luc assay). The Luc-assay and MIC assay are described in detail below. These assays are well known to those skilled in the art. Based on this initial screening, 300+ compound mixtures showed anti-TB activity. FIG. 6 represents typical assay data in a luciferase reporter strain containing an Rv0341 EMB-inducible promoter. FIG. 6 represents percent maximum Luminescense Count per Second (% Max. LCPS) for pooled compound mixtures in one row (row D) in one of the 96-well plates.

Deconvolution of the Reactive Wells

The *M. tuberculosis* screening revealed approximately 300 active compounds mixtures that were selected for deconvolution. In particular, wells possessing activity of approximately <12.5 μM in the HTS Luc assay, and/or an MIC of approximately <12.5 μM, were selected for a total of 336 wells.

Deconvolutions were performed by discrete re-synthesis of each substituted ethylene diamine compound in each active compound pool. The pooled compounds in each active well were individually synthesized, and screened. Syntheses of the targeted diamine compounds in each active pool were done in the 96-well plates using stored archived α-haloacetyl amides (resin attached haloacetyl amides), according to the previously described reaction steps (the addition of the second amine, the reduction with Red-Al, and the cleavage from the solid support). The archived resins were stored as individual compounds at 4° C. The 96-well plates were used for the remaining synthesis steps as previously described.

The same screening tests, MIC and HTS Luc assay, were performed on each deconvoluted compound. Representative Luminescence data for deconvoluted compounds are shown in FIGS. 7 and 8. FIGS. 7 and 8 represent the Luminescence Count per Second (LCPS) for individual compounds.

Summary of Screening Results

Overall, the deconvolution screening results revealed about 2,000 ethylene diamine compounds with inhibitory activity against *M. tuberculosis*. More than 150 of these compounds exhibited MICs equal to or lower than approximately 12.5 μM. FIG. 9 summarizes the MIC data for all synthesized discrete compounds with an MIC of 50 μM or less. FIG. 10 summarizes Luc assay data for all compounds that exhibit at least 10% activity at each concentration (the results are not cumulative). The MIC and Luc activities were obtained for non-purified samples, with chemical yields of approximately 20%, based on an assumed 80% yield at each reaction step. In the Luc assay, 32 compounds exhibited activity at 1.56 μM, and in the MIC assay, at least 11 compounds had an MIC of 3.13 μM.

The total frequency of the top thirteen amines that contributed to the activity of the substituted ethylene diamines are shown in FIG. 11, with each amine represented by its numerical designation. These amines include the following:

11 2,3-Dimethylcylochexy amines
18 3,3-Diphenylpropylamine
44 1-Adamantanemethylamine
47 2,2-Diphenylethylamine
63 (S)-2-Amino-1-butanol
74.1 (−)-cis-Myrtanylamine
77.1 Cyclooctylamine
78.1 2-Adamantamine
105a (1R,2R,3R,5 S)-(−)-Isopinocampheylamine

231 2-Methoxyphenethylamine
255 (S)-Cylcohexylethylamine
266 Undecylamine
272 Geranylamine Other amines that contributed to the activity of the substituted ethylene diamines are shown in Table 2. The compounds in Table 2 are sorted by their MIC results. Some compounds, synthesized in larger quantities (2-60 mg) on the Quest® Synthesizer, and purified by HPLC using semi-preparative C18-column, are shown in Table 3. Generally, the final purity of each compound in Table 3 was at least 90%.

In one embodiment, the present invention comprises a composition comprising compound 109 and compound 73.

In another embodiment, the present invention comprises a composition comprising compound 109 and compound 73 and a standard tuberculosis drug.

In yet another embodiment, the present invention comprises a method of treating disease caused by an infectious agent comprising administering an effective amount of compound 109.

Still a further embodiment, the present invention comprises a method of treating disease caused by an infectious agent comprising administering an effective amount of compound 109 and compound 73.

In yet another embodiment, the present invention comprises a method of treating disease caused by an infectious agent comprising administering an effective amount of compound 109 and compound 73 and a standard tuberculosis drug. In another embodiment, the present invention comprises a method of treating disease caused by an infectious agent comprising administering an effective amount of compound 109 and compound 73 and a pharmaceutical carrier.

TABLE 2

Synthetic Substituted Diethylene Diamines Sorted by Minimum Inhibition Concentration

| N1 | N2 | R4 | MIC (uM) | % Induction |
|---|---|---|---|---|
| 3,3-Diphenylpropylamine | exo-Aminonorbornane | Hydrogen | 3.13 | 53.70 |
| 2,2-Diphenylamine | (+)-Isopinocampheylamine | Hydrogen | 3.13 | 93.94 |
| 2,2-Diphenylamine | cis-(−)-Myrtanylamine | Hydrogen | 3.13 | 64.49 |
| 2,2-Diphenylamine | Cyclooctylamine | Hydrogen | 3.13 | 63.44 |
| 2,2-Diphenylamine | 3,4-Dihydroxynorephedrine | Hydrogen | 3.13 | 42.80 |
| 5-Aminoquinoline | Cyclohexylamine | Hydrogen | 3.13 | 18.33 |
| 5-Aminoquinoline | tert-Octylamine | Hydrogen | 3.13 | 20.85 |
| 5-Aminoquinoline | 4-Methylcyclohexylamine | Hydrogen | 3.13 | 26.33 |
| cis-(−)-Myrtanylamine | (+)-Bornylamine | Hydrogen | 3.13 | 100.00 |
| cis-(−)-Myrtanylamine | 1-Adamantanemethylamine | Hydrogen | 3.13 | 85.20 |
| cis-(−)-Myrtanylamine | (−)-Isopinocampheylamine | Hydrogen | 3.13 | 60.94 |
| 1-Adamantanemethylamine | tert-Octylamine | Hydrogen | 4.7 | 9.81 |
| 3,4-Dimethoxyphenethylamine | 1-Adamantanemethylamine | Hydrogen | 6.25 | 11.45 |
| 3,4-Dimethoxyphenethylamine | Hexetidine (mixture of isomers) | Hydrogen | 6.25 | 0 |
| 3,4-Dimethoxyphenethylamine | Dehydroabietylamine | Hydrogen | 6.25 | 0 |
| 3,3-Diphenylpropylamine | 1-Adamantanemethylamine | Hydrogen | 6.25 | 9.53 |
| 3,3-Diphenylpropylamine | 2-Methylcyclohexylamine (mix of cis and trans) | Hydrogen | 6.25 | 50.08 |
| 3,3-Diphenylpropylamine | 1,3-Dimethylbutylamine | Hydrogen | 6.25 | 39.40 |
| 3,3-Diphenylpropylamine | 1-(1-Adamantyl)ethylamine, HCl | Hydrogen | 6.25 | 45.14 |
| 3,3-Diphenylpropylamine | (S)-(−)-Cyclohexylethylamine | Hydrogen | 6.25 | 43.49 |
| 3,3-Diphenylpropylamine | (R)-(−)-Cyclohexylethylamine | Hydrogen | 6.25 | 34.54 |
| 3,3-Diphenylpropylamine | 1-Adamantanemethylamine | Methyl | 6.25 | 16.14 |
| Propylamine | Hexetidine (mixture of isomers) | Hydrogen | 6.25 | 0 |
| Phenethylamine | Hexetidine (mixture of isomers) | Hydrogen | 6.25 | 0 |
| b-Methylphenethylamine | Hexetidine (mixture of isomers) | Hydrogen | 6.25 | 0 |
| b-Methylphenethylamine | Undecylamine | Hydrogen | 6.25 | 0 |
| 2,2-Diphenylamine | (+)-Bornylamine | Hydrogen | 6.25 | 87.86 |
| 2,2-Diphenylamine | (−)-Isopinocampheylamine | Hydrogen | 6.25 | 77.80 |
| 2,2-Diphenylamine | alpha-Methyltryptamine | Hydrogen | 6.25 | 55.07 |
| 2,2-Diphenylamine | alpha-Methyltryptamine | Hydrogen | 6.25 | 23.08 |
| 2,2-Diphenylamine | 4-Phenylbutylamine | Hydrogen | 6.25 | |
| 2,2-Diphenylamine | 2,5-Dimethoxyphenethylamine | Hydrogen | 6.25 | |
| 2,2-Diphenylamine | 2,4-Dichlorophenethylamine | Hydrogen | 6.25 | |
| 2,2-Diphenylamine | 2-(2-Aminomethyl)phenylthio)benzyl alcohol | Hydrogen | 6.25 | |
| 2,2-Diphenylamine | 1-(1-Naphthyl)ethylamine | Hydrogen | 6.25 | 7.20 |
| Veratryl amine | 2,5-Dimethoxyphenethylamine | Hydrogen | 6.25 | |
| Veratryl amine | 2-(2-Aminomethyl)phenylthio)benzyl alcohol | Hydrogen | 6.25 | |
| 5-Aminoquinoline | 2-Aminoheptane | Hydrogen | 6.25 | 26.22 |
| 5-Aminoquinoline | 1-Adamantanamine | Hydrogen | 6.25 | 18.91 |
| 1-Aminomethyl-1-cyclohexanol, HCl | Hexetidine (mixture of isomers) | Hydrogen | 6.25 | |
| cis-(−)-Myrtanylamine | 2,3-Dimethylcyclohexylamine | Hydrogen | 6.25 | 100.00 |
| cis-(−)-Myrtanylamine | 3,3-Diphenylpropylamine | Hydrogen | 6.25 | 87.78 |
| cis-(−)-Myrtanylamine | (+)-Isopinocampheylamine | Hydrogen | 6.25 | 93.10 |
| cis-(−)-Myrtanylamine | 2,2-Diphenylamine | Hydrogen | 6.25 | 81.84 |
| cis-(−)-Myrtanylamine | cis-(−)-Myrtanylamine | Hydrogen | 6.25 | 68.24 |
| cis-(−)-Myrtanylamine | 1,3,3-Trimethyl-6-azabicyclo[3.2.1]octane | Hydrogen | 6.25 | 68.18 |

TABLE 2-continued

Synthetic Substituted Diethylene Diamines Sorted by Minimum Inhibition Concentration

| N1 | N2 | R4 | MIC (uM) | % Induction |
|---|---|---|---|---|
| cis-(−)-Myrtanylamine | 1-Adamantanemethylamine | Methyl | 6.25 | 24.22 |
| cis-(−)-Myrtanylamine | cis-(−)-Myrtanylamine | Methyl | 6.25 | 44.14 |
| Cyclooctylamine | 3,3-Diphenylpropylamine | Hydrogen | 6.25 | 100.00 |
| Cyclooctylamine | (−)-Isopinocampheylamine | Hydrogen | 6.25 | 59.13 |
| sec-Butylamine | Hexetidine (mixture of isomers) | Hydrogen | 6.25 | |
| 3-Methylbenzylamine | Hexetidine (mixture of isomers) | Hydrogen | 6.25 | |
| 3-Methylbenzylamine | Undecylamine | Hydrogen | 6.25 | |
| 2-Methoxyethylamine | Hexetidine (mixture of isomers) | Hydrogen | 6.25 | |
| Geranylamine | 2-Adamantanamine, HCl | Hydrogen | 6.25 | 25.66 |
| 1-Adamantanemethylamine | 4-Benzylpiperidine | Hydrogen | 9.4 | 0 |
| 1-Adamantanemethylamine | 2,3-Dimethylcyclohexylamine | Hydrogen | 9.4 | 0 |
| 1-Adamantanemethylamine | 3,3-Diphenylpropylamine | Hydrogen | 9.4 | 40.06 |
| 1-Adamantanemethylamine | 1-Adamantanemethylamine | Hydrogen | 9.4 | 15.25 |
| 1-Adamantanemethylamine | 2,2-Diphenylamine | Hydrogen | 9.4 | 0 |
| 1-Adamantanemethylamine | 1,3,3-Trimethyl-6-azabicyclo[3.2.1]octane | Hydrogen | 9.4 | 0 |
| 1-Adamantanemethylamine | 138 | Hydrogen | 9.4 | 0 |
| 3-Phenyl-1-propylamine | 138 | Hydrogen | 9.4 | |
| 2,2-Diphenylamine | 1-Adamantanemethylamine | Hydrogen | 9.4 | 65.89 |
| 2,2-Diphenylamine | 138 | Hydrogen | 9.4 | |
| Furfurylamine | Hexetidine (mixture of isomers) | Hydrogen | 12.5 | 0 |
| 3,4,5-Trimethoxybenzylamine | Hexetidine (mixture of isomers) | Hydrogen | 12.5 | 0 |
| 1-Methyl-3-phenylpropylamine | Dehydroabietylamine | Hydrogen | 12.5 | 0 |
| Cyclobutylamine | Hexetidine (mixture of isomers) | Hydrogen | 12.5 | 0 |
| 2-Fluorobenzylamine | Hexetidine (mixture of isomers) | Hydrogen | 12.5 | 0 |
| 2-Fluorobenzylamine | Dehydroabietylamine | Hydrogen | 12.5 | 0 |
| 3,4-Dimethoxyphenethylamine | Undecylamine | Hydrogen | 12.5 | 0 |
| 3,3-Diphenylpropylamine | exo-Aminonorbornane | Hydrogen | 12.5 | 14.38 |
| 3,3-Diphenylpropylamine | Decahydroquinoline | Hydrogen | 12.5 | 22.52 |
| 3,3-Diphenylpropylamine | Hexetidine (mixture of isomers) | Hydrogen | 12.5 | 0 |
| 3,3-Diphenylpropylamine | 4-Phenylbutylamine | Hydrogen | 12.5 | 0 |
| 3,3-Diphenylpropylamine | 2-Methoxyphenethylamine | Hydrogen | 12.5 | 6.82 |
| 3,3-Diphenylpropylamine | 2,4-Dichlorophenethylamine | Hydrogen | 12.5 | 0 |
| 3,3-Diphenylpropylamine | 1-Aminoindan | Hydrogen | 12.5 | 18.05 |
| 3,3-Diphenylpropylamine | Undecylamine | Hydrogen | 12.5 | 0 |
| 3,3-Diphenylpropylamine | Dehydroabietylamine | Hydrogen | 12.5 | 0 |
| 3,3-Diphenylpropylamine | 2-(1-Cyclohexenyl)ethylamine | Methyl | 12.5 | 9.5 |
| 3,3-Diphenylpropylamine | cis-(−)-Myrtanylamine | Methyl | 12.5 | 18.41 |
| 3,3-Diphenylpropylamine | Cyclooctylamine | Methyl | 12.5 | 20.84 |
| Propylamine | Dehydroabietylamine | Hydrogen | 12.5 | 0 |
| Phenethylamine | Dehydroabietylamine | Hydrogen | 12.5 | 0 |
| Cyclohexylamine | Hexetidine (mixture of isomers) | Hydrogen | 12.5 | 0 |
| 3-Amino-1-propanol | Hexetidine (mixture of isomers) | Hydrogen | 12.5 | 0 |
| b-Methylphenethylamine | Dehydroabietylamine | Hydrogen | 12.5 | 0 |
| 4-Methoxyphenethylamine | 2-Fluorophenethylamine | Hydrogen | 12.5 | 0 |
| 4-Methoxyphenethylamine | 2-(1-Cyclohexenyl)ethylamine | Hydrogen | 12.5 | 0 |
| 4-Methoxyphenethylamine | 2,4-Dimethoxybenzylamine | Hydrogen | 12.5 | 0 |
| 4-Methoxyphenethylamine | 4-Fluorophenethylamine | Hydrogen | 12.5 | 16.78 |
| 4-Methoxyphenethylamine | Hexetidine (mixture of isomers) | Hydrogen | 12.5 | 0 |
| Tetrahydrofurfurylamine | Hexetidine (mixture of isomers) | Hydrogen | 12.5 | 0 |
| Amylamine | 4-Fluorophenethylamine | Hydrogen | 12.5 | 0 |
| 3-Phenyl-1-propylamine | 2-(1-Cyclohexenyl)ethylamine | Hydrogen | 12.5 | |
| 3-Phenyl-1-propylamine | 4-Fluorophenethylamine | Hydrogen | 12.5 | 12.94 |
| 2,2-Diphenylamine | tert-Amylamine | Hydrogen | 12.5 | 9.05 |
| 2,2-Diphenylamine | Undecylamine | Hydrogen | 12.5 | |
| 2,2-Diphenylamine | Dehydroabietylamine | Hydrogen | 12.5 | |
| 2,2-Diphenylamine | cis-(−)-Myrtanylamine | Methyl | 12.5 | 45.18 |
| 1-(3-Aminopropyl)-2-pyrrolidinone (tech) | 2,5-Dimethoxyphenethylamine | Hydrogen | 12.5 | |
| 1-(3-Aminopropyl)-2-pyrrolidinone (tech) | 2-(2-Aminomethyl)phenylthio)benzyl alcohol | Hydrogen | 12.5 | |
| 4-(Trifluoromethyl)benzylamine | 2,5-Dimethoxyphenethylamine | Hydrogen | 12.5 | |
| 4-(Trifluoromethyl)benzylamine | 1-(1-Naphthyl)ethylamine | Hydrogen | 12.5 | |
| Veratryl amine | 4-Phenylbutylamine | Hydrogen | 12.5 | |
| 5-Amino-1-pentanol | 2,5-Dimethoxyphenethylamine | Hydrogen | 12.5 | |
| 5-Amino-1-pentanol | 2-(2-Aminomethyl)phenylthio)benzyl alcohol | Hydrogen | 12.5 | |
| 2-(1-Cyclohexenyl)ethylamine | 2-(1-Cyclohexenyl)ethylamine | Hydrogen | 12.5 | |
| 2-(1-Cyclohexenyl)ethylamine | 4-Fluorophenethylamine | Hydrogen | 12.5 | |
| 2-(1-Cyclohexenyl)ethylamine | 4-Phenylbutylamine | Hydrogen | 12.5 | |
| 2-(1-Cyclohexenyl)ethylamine | 2,5-Dimethoxyphenethylamine | Hydrogen | 12.5 | |

TABLE 2-continued

Synthetic Substituted Diethylene Diamines Sorted by Minimum Inhibition Concentration

| N1 | N2 | R4 | MIC (uM) | % Induction |
|---|---|---|---|---|
| 2-(1-Cyclohexenyl)ethylamine | 2-(2-Aminomethyl)phenylthio)benzyl alcohol | Hydrogen | 12.5 | |
| 1-Aminomethyl-1-cyclohexanol, HCl | 2,5-Dimethoxyphenethylamine | Hydrogen | 12.5 | |
| 3-Fluorobenzylamine | 2,5-Dimethoxyphenethylamine | Hydrogen | 12.5 | |
| 4-Amino-1-butanol | Hexetidine (mixture of isomers) | Hydrogen | 12.5 | |
| 2-Ethoxybenzylamine | Hexetidine (mixture of isomers) | Hydrogen | 12.5 | |
| cis-(−)-Myrtanylamine | Cyclooctylamine | Hydrogen | 12.5 | 67.73 |
| cis-(−)-Myrtanylamine | 4-Methylcyclohexylamine | Hydrogen | 12.5 | 18.39 |
| cis-(−)-Myrtanylamine | 1-Adamantanamine | Hydrogen | 12.5 | 60.16 |
| cis-(−)-Myrtanylamine | 3,3-Diphenylpropylamine | Methyl | 12.5 | 22.32 |
| Cyclooctylamine | (+)-Isopinocampheylamine | Hydrogen | 12.5 | 57.83 |
| Cyclooctylamine | (+)-Bornylamine | Hydrogen | 12.5 | 100.00 |
| Cyclooctylamine | 1-Adamantanemethylamine | Hydrogen | 12.5 | 52.95 |
| Cyclooctylamine | 2,2-Diphenylamine | Hydrogen | 12.5 | 71.43 |
| Cyclooctylamine | cis-(−)-Myrtanylamine | Hydrogen | 12.5 | 84.56 |
| Cyclooctylamine | Cyclooctylamine | Hydrogen | 12.5 | 59.21 |
| Cyclooctylamine | Hexetidine (mixture of isomers) | Hydrogen | 12.5 | |
| Cyclooctylamine | Aminodiphenylmethane | Hydrogen | 12.5 | |
| Cyclooctylamine | Undecylamine | Hydrogen | 12.5 | 5.61 |
| Cyclooctylamine | 3,3-Diphenylpropylamine | Methyl | 12.5 | 53.92 |
| Cyclooctylamine | (+)-Isopinocampheylamine | Methyl | 12.5 | |
| Cyclooctylamine | cis-(−)-Myrtanylamine | Methyl | 12.5 | 33.89 |
| 4-Chlorophenylalaninol | Hexetidine (mixture of isomers) | Hydrogen | 12.5 | |
| (−)-Isopinocampheylamine | 3,3-Diphenylpropylamine | Hydrogen | 12.5 | 23.68 |
| (−)-Isopinocampheylamine | (+)-Bornylamine | Hydrogen | 12.5 | 44.85 |
| (−)-Isopinocampheylamine | 2-Amino-1-propanol, d, l | Hydrogen | 12.5 | 46.19 |
| (−)-Isopinocampheylamine | cis-(−)-Myrtanylamine | Hydrogen | 12.5 | 33.87 |
| (−)-Isopinocampheylamine | 2-Adamantanamine, HCl | Hydrogen | 12.5 | 24.29 |
| (−)-Isopinocampheylamine | Aminodiphenylmethane | Hydrogen | 12.5 | 48.35 |
| Allylamine | Hexetidine (mixture of isomers) | Hydrogen | 12.5 | |
| 3-Ethoxypropylamine | Hexetidine (mixture of isomers) | Hydrogen | 12.5 | |
| sec-Butylamine | Dehydroabietylamine | Hydrogen | 12.5 | |
| 2-Aminoheptane | Dehydroabietylamine | Hydrogen | 12.5 | |
| Ethanolamine | Hexetidine (mixture of isomers) | Hydrogen | 12.5 | |
| 3-Methylbenzylamine | 4-Phenylbutylamine | Hydrogen | 12.5 | |
| 3-Methylbenzylamine | 2,4-Dichlorophenethylamine | Hydrogen | 12.5 | |
| 3-Methylbenzylamine | Dehydroabietylamine | Hydrogen | 12.5 | |
| Piperonylamine | Hexetidine (mixture of isomers) | Hydrogen | 12.5 | |
| Piperonylamine | Dehydroabietylamine | Hydrogen | 12.5 | |
| 2-Methoxyethylamine | Dehydroabietylamine | Hydrogen | 12.5 | |
| 4-Fluorophenethylamine | Hexetidine (mixture of isomers) | Hydrogen | 12.5 | |
| 3-o-Methyldopamine, HCl | Hexetidine (mixture of isomers) | Hydrogen | 12.5 | |
| 3-o-Methyldopamine, HCl | Undecylamine | Hydrogen | 12.5 | |
| 3-o-Methyldopamine, HCl | Dehydroabietylamine | Hydrogen | 12.5 | |
| 3-Fluorophenethylamine | Hexetidine (mixture of isomers) | Hydrogen | 12.5 | |
| 3-Fluorophenethylamine | Dehydroabietylamine | Hydrogen | 12.5 | |
| 2-Methoxyphenethylamine | Hexetidine (mixture of isomers) | Hydrogen | 12.5 | |
| 2-Methoxyphenethylamine | Aminodiphenylmethane | Hydrogen | 12.5 | 34.67 |
| 2-Fluoroethylamine, HCl | Hexetidine (mixture of isomers) | Hydrogen | 12.5 | |
| 2-Amino-1-phenylethanol | Hexetidine (mixture of isomers) | Hydrogen | 12.5 | |
| 2-Amino-1-phenylethanol | Dehydroabietylamine | Hydrogen | 12.5 | |
| 2,5-Dimethoxyphenethylamine | 2-Adamantanamine, HCl | Hydrogen | 12.5 | 22.18 |
| 2-(2-Chlorophenyl)ethylamine | N-Allylcyclopentylamine | Hydrogen | 12.5 | 62.31 |
| 2-(2-Chlorophenyl)ethylamine | Hexetidine (mixture of isomers) | Hydrogen | 12.5 | |
| 3-Hydroxytyramine | Hexetidine (mixture of isomers) | Hydrogen | 12.5 | |
| 4-(Trifluoromethoxy)benzylamine | 2-Adamantanamine, HCl | Hydrogen | 12.5 | 28.34 |
| Geranylamine | (+)-Bornylamine | Hydrogen | 12.5 | |
| Geranylamine | 1,3,3-Trimethyl-6-azabicyclo[3.2.1]octane | Hydrogen | 12.5 | 37.42 |
| Geranylamine | 2-Ethylpiperidine | Hydrogen | 12.5 | 29.81 |
| Geranylamine | 1-Adamantanamine | Hydrogen | 12.5 | 16.63 |
| Geranylamine | N-Allylcyclopentylamine | Hydrogen | 12.5 | 74.86 |
| Geranylamine | Aminodiphenylmethane | Hydrogen | 12.5 | 57.93 |
| Geranylamine | Dehydroabietylamine | Hydrogen | 12.5 | |
| 1-Adamantanemethylamine | Decahydroquinoline | Hydrogen | 18.8 | 0 |
| 1-Adamantanemethylamine | 1-Adamantanamine | Hydrogen | 18.8 | 0 |
| 2,2-Diphenylamine | 2,3-Dimethylcyclohexylamine | Hydrogen | 18.8 | 23.60 |
| 2,2-Diphenylamine | tert-Octylamine | Hydrogen | 18.8 | 19.29 |
| 2,2-Diphenylamine | Decahydroquinoline | Hydrogen | 18.8 | 8.96 |
| 4-Methylbenzylamine | Furfurylamine | Hydrogen | 25 | 13.46 |
| 4-Methylbenzylamine | Benzylamine | Hydrogen | 25 | 17.07 |
| 4-Methylbenzylamine | Hexetidine (mixture of isomers) | Hydrogen | 25 | 0 |

TABLE 2-continued

Synthetic Substituted Diethylene Diamines Sorted by Minimum Inhibition Concentration

| N1 | N2 | R4 | MIC (uM) | % Induction |
|---|---|---|---|---|
| 4-Methylbenzylamine | Dehydroabietylamine | Hydrogen | 25 | 0 |
| Cyclopentylamine | Hexetidine (mixture of isomers) | Hydrogen | 25 | 0 |
| Cyclopentylamine | Dehydroabietylamine | Hydrogen | 25 | 0 |
| Furfurylamine | Furfurylamine | Hydrogen | 25 | 0 |
| 1-Methyl-3-phenylpropylamine | Hexetidine (mixture of isomers) | Hydrogen | 25 | 0 |
| 1-Methyl-3-phenylpropylamine | Undecylamine | Hydrogen | 25 | 0 |
| 1,2,3,4-Tetrahydro-1-naphthylamine | Undecylamine | Hydrogen | 25 | 6.24 |
| 1,2,3,4-Tetrahydro-1-naphthylamine | Dehydroabietylamine | Hydrogen | 25 | 0 |
| 2,3-Dimethylcyclohexylamine | Undecylamine | Hydrogen | 25 | 0 |
| 2,3-Dimethylcyclohexylamine | Dehydroabietylamine | Hydrogen | 25 | 0 |
| Tyramine | Hexetidine (mixture of isomers) | Hydrogen | 25 | 0 |
| Tyramine | Undecylamine | Hydrogen | 25 | 0 |
| Tyramine | Dehydroabietylamine | Hydrogen | 25 | 0 |
| Tyramine | cis-(−)-Myrtanylamine | Methyl | 25 | 0 |
| 2-Fluorobenzylamine | Undecylamine | Hydrogen | 25 | 0 |
| (R)-2-Amino-1-butanol | Hexetidine (mixture of isomers) | Hydrogen | 25 | 0 |
| 3,3-Diphenylpropylamine | (S)-(+)-1-Amino-2-propanol | Hydrogen | 25 | 0 |
| 3,3-Diphenylpropylamine | 2-Ethylpiperidine | Hydrogen | 25 | 11.32 |
| 3,3-Diphenylpropylamine | N-Allylcyclopentylamine | Hydrogen | 25 | 11.63 |
| 3,3-Diphenylpropylamine | Aminodiphenylmethane | Hydrogen | 25 | 0 |
| 3,3-Diphenylpropylamine | 3,5-Dimethylpiperidine (cis- and trans-) | Hydrogen | 25 | 30.28 |
| 3,3-Diphenylpropylamine | Allylcyclohexylamine | Hydrogen | 25 | 9.10 |
| Propylamine | Undecylamine | Hydrogen | 25 | 0 |
| Phenethylamine | Undecylamine | Hydrogen | 25 | 0 |
| Tryptamine | (S)-(+)-1-Amino-2-propanol | Hydrogen | 25 | 0 |
| Tryptamine | 2-Amino-2-methyl-1-propanol | Hydrogen | 25 | 0 |
| Cyclohexylamine | Undecylamine | Hydrogen | 25 | 0 |
| Cyclohexylamine | Dehydroabietylamine | Hydrogen | 25 | 0 |
| (+)-Isopinocampheylamine | Dehydroabietylamine | Hydrogen | 25 | 0 |
| Benzylamine | Hexetidine (mixture of isomers) | Hydrogen | 25 | |
| Benzylamine | Undecylamine | Hydrogen | 25 | |
| 3-Amino-1-propanol | Dehydroabietylamine | Hydrogen | 25 | 0 |
| 2-Fluorophenethylamine | 2-Fluorophenethylamine | Hydrogen | 25 | 0 |
| 2-Fluorophenethylamine | Veratryl amine | Hydrogen | 25 | 0 |
| 2-Fluorophenethylamine | 2,4-Dimethoxybenzylamine | Hydrogen | 25 | 0 |
| 2-Fluorophenethylamine | 2-Amino-2-methyl-1-propanol | Hydrogen | 25 | 0 |
| 2-Fluorophenethylamine | 4-Fluorophenethylamine | Hydrogen | 25 | 0 |
| 2-Fluorophenethylamine | Hexetidine (mixture of isomers) | Hydrogen | 25 | 0 |
| 2-Fluorophenethylamine | 1-(1-Naphthyl)ethylamine | Hydrogen | 25 | 0 |
| 2-Fluorophenethylamine | 1-Adamantanemethylamine | Methyl | 25 | 3.21 |
| 2-Fluorophenethylamine | cis-(−)-Myrtanylamine | Methyl | 25 | 4.89 |
| b-Methylphenethylamine | 4-Phenylbutylamine | Hydrogen | 25 | 0 |
| b-Methylphenethylamine | 2,4-Dichlorophenethylamine | Hydrogen | 25 | 0 |
| b-Methylphenethylamine | 1-(1-Naphthyl)ethylamine | Hydrogen | 25 | 0 |
| 4-Methoxyphenethylamine | 1-Adamantanemethylamine | Hydrogen | 25 | 0 |
| 4-Methoxyphenethylamine | 1-(3-Aminopropyl)-2-pyrrolidinone (tech) | Hydrogen | 25 | 0 |
| 4-Methoxyphenethylamine | Veratryl amine | Hydrogen | 25 | 0 |
| 4-Methoxyphenethylamine | Undecylamine | Hydrogen | 25 | 0 |
| 4-Methoxyphenethylamine | Dehydroabietylamine | Hydrogen | 25 | 0 |
| Tetrahydrofurfurylamine | Dehydroabietylamine | Hydrogen | 25 | 0 |
| Amylamine | 2-Fluorophenethylamine | Hydrogen | 25 | 0 |
| Amylamine | 2-(1-Cyclohexenyl)ethylamine | Hydrogen | 25 | 0 |
| Amylamine | 2,4-Dimethoxybenzylamine | Hydrogen | 25 | 0 |
| 3-Phenyl-1-propylamine | 2-Fluorophenethylamine | Hydrogen | 25 | |
| 3-Phenyl-1-propylamine | 1-Adamantanemethylamine | Hydrogen | 25 | |
| 3-Phenyl-1-propylamine | 2,4-Dimethoxybenzylamine | Hydrogen | 25 | |
| 3-Phenyl-1-propylamine | Hexetidine (mixture of isomers) | Hydrogen | 25 | |
| 3-Phenyl-1-propylamine | 4-Phenylbutylamine | Hydrogen | 25 | |
| 3-Phenyl-1-propylamine | 2,4-Dichlorophenethylamine | Hydrogen | 25 | |
| 3-Phenyl-1-propylamine | Undecylamine | Hydrogen | 25 | |
| 3-Phenyl-1-propylamine | Dehydroabietylamine | Hydrogen | 25 | |
| 2,2-Diphenylamine | 4-(2-Aminoethyl)morpholine | Hydrogen | 25 | |
| 2,2-Diphenylamine | 1-(3-Aminopropyl)-2-pyrrolidinone (tech) | Hydrogen | 25 | |
| 2,2-Diphenylamine | 2-(1-Cyclohexenyl)ethylamine | Hydrogen | 25 | |
| 2,2-Diphenylamine | 2,4-Dimethoxybenzylamine | Hydrogen | 25 | |
| 2,2-Diphenylamine | 4-(3-Aminopropyl)morpholine | Hydrogen | 25 | |
| 2,2-Diphenylamine | 4-Fluorophenethylamine | Hydrogen | 25 | |
| 2,2-Diphenylamine | Hexetidine (mixture of isomers) | Hydrogen | 25 | |
| 2,2-Diphenylamine | (S)-(−)-Cyclohexylethylamine | Hydrogen | 25 | |

TABLE 2-continued

Synthetic Substituted Diethylene Diamines Sorted by Minimum Inhibition Concentration

| N1 | N2 | R4 | MIC (uM) | % Induction |
|---|---|---|---|---|
| 2,2-Diphenylamine | 1-Adamantanemethylamine | Methyl | 25 | 5.84 |
| 1-(3-Aminopropyl)-2-pyrrolidinone (tech) | 4-Phenylbutylamine | Hydrogen | 25 | |
| 4-(Trifluoromethyl)benzylamine | 1-Adamantanemethylamine | Hydrogen | 25 | |
| 4-(Trifluoromethyl)benzylamine | tert-Amylamine | Hydrogen | 25 | |
| 4-(Trifluoromethyl)benzylamine | alpha-Methyltryptamine | Hydrogen | 25 | 6.06 |
| 4-(Trifluoromethyl)benzylamine | 4-Phenylbutylamine | Hydrogen | 25 | |
| 4-(Trifluoromethyl)benzylamine | 2-(2-Aminomethyl)phenylthio)benzyl alcohol | Hydrogen | 25 | 5.13 |
| 4-(Trifluoromethyl)benzylamine | Undecylamine | Hydrogen | 25 | |
| 4-(Trifluoromethyl)benzylamine | (−)-3,4-Dihydroxynorephedrine | Hydrogen | 25 | |
| 4-(Trifluoromethyl)benzylamine | Dehydroabietylamine | Hydrogen | 25 | |
| Veratryl amine | tert-Amylamine | Hydrogen | 25 | |
| 5-Amino-1-pentanol | 4-Phenylbutylamine | Hydrogen | 25 | |
| 2-(1-Cyclohexenyl)ethylamine | 2-Fluorophenethylamine | Hydrogen | 25 | |
| 2-(1-Cyclohexenyl)ethylamine | 1-Adamantanemethylamine | Hydrogen | 25 | |
| 1-Aminomethyl-1-cyclohexanol, HCl | 4-Phenylbutylamine | Hydrogen | 25 | |
| 3-Fluorobenzylamine | 4-Phenylbutylamine | Hydrogen | 25 | |
| 3-Fluorobenzylamine | 2-(2-Aminomethyl)phenylthio)benzyl alcohol | Hydrogen | 25 | |
| 2,4-Dimethoxybenzylamine | 1-Adamantanamine | Hydrogen | 25 | |
| 2,4-Dimethoxybenzylamine | Hexetidine (mixture of isomers) | Hydrogen | 25 | |
| 2,4-Dimethoxybenzylamine | Undecylamine | Hydrogen | 25 | |
| 2,4-Dimethoxybenzylamine | Dehydroabietylamine | Hydrogen | 25 | |
| 2-Ethoxybenzylamine | 1-Adamantanamine | Hydrogen | 25 | |
| 2-Ethoxybenzylamine | N-Phenylethyldiamine | Hydrogen | 25 | |
| 2-Ethoxybenzylamine | 2,4-Dichlorophenethylamine | Hydrogen | 25 | |
| 2-Ethoxybenzylamine | 2-(2-Chlorophenyl)ethylamine | Hydrogen | 25 | 3.89 |
| 2-Ethoxybenzylamine | Undecylamine | Hydrogen | 25 | |
| 2-Ethoxybenzylamine | Dehydroabietylamine | Hydrogen | 25 | |
| cis-(−)-Myrtanylamine | 2-(1-Cyclohexenyl)ethylamine | Hydrogen | 25 | |
| cis-(−)-Myrtanylamine | Hexetidine (mixture of isomers) | Hydrogen | 25 | |
| cis-(−)-Myrtanylamine | Aminodiphenylmethane | Hydrogen | 25 | |
| cis-(−)-Myrtanylamine | 2,4-Dichlorophenethylamine | Hydrogen | 25 | |
| cis-(−)-Myrtanylamine | (S)-(−)-Cyclohexylethylamine | Hydrogen | 25 | 28.94 |
| cis-(−)-Myrtanylamine | Undecylamine | Hydrogen | 25 | |
| cis-(−)-Myrtanylamine | (+)-Isopinocampheylamine | Methyl | 25 | |
| cis-(−)-Myrtanylamine | Cyclooctylamine | Methyl | 25 | 24.92 |
| Cyclooctylamine | 2,3-Dimethylcyclohexylamine | Hydrogen | 25 | 50.55 |
| Cyclooctylamine | (S)-2-Amino-1-butanol | Hydrogen | 25 | 100.00 |
| Cyclooctylamine | 2-Adamantanamine, HCl | Hydrogen | 25 | 29.61 |
| Cyclooctylamine | 4-Phenylbutylamine | Hydrogen | 25 | |
| Cyclooctylamine | 2-Chlorobenzylamine | Hydrogen | 25 | |
| Cyclooctylamine | 2-Aminoindan, HCl | Hydrogen | 25 | |
| Cyclooctylamine | Dehydroabietylamine | Hydrogen | 25 | |
| Cyclooctylamine | 1-(1-Naphthyl)ethylamine | Hydrogen | 25 | 4.62 |
| Cyclooctylamine | 1-Adamantanemethylamine | Methyl | 25 | 14.20 |
| 2,3-Dimethoxybenzylamine | Hexetidine (mixture of isomers) | Hydrogen | 25 | |
| 2,3-Dimethoxybenzylamine | Undecylamine | Hydrogen | 25 | |
| 2,3-Dimethoxybenzylamine | Dehydroabietylamine | Hydrogen | 25 | |
| 4-Methylcyclohexylamine | Hexetidine (mixture of isomers) | Hydrogen | 25 | |
| 4-Methylcyclohexylamine | Undecylamine | Hydrogen | 25 | |
| 4-Methylcyclohexylamine | Dehydroabietylamine | Hydrogen | 25 | |
| 4-Fluorobenzylamine | Dibenzylamine | Hydrogen | 25 | 27.98 |
| trans-2-Phenylcyclopropylamine, HCl | Cyclooctylamine | Hydrogen | 25 | 32.80 |
| trans-2-Phenylcyclopropylamine, HCl | 2-Adamantanamine, HCl | Hydrogen | 25 | 18.99 |
| trans-2-Phenylcyclopropylamine, HCl | 1-Adamantanamine | Hydrogen | 25 | 18.84 |
| Thiomicamine | Hexetidine (mixture of isomers) | Hydrogen | 25 | |
| (R)-1-Amino-2-propanol | Hexetidine (mixture of isomers) | Hydrogen | 25 | |
| 4-Chlorophenylalaninol | 2,4-Dichlorophenethylamine | Hydrogen | 25 | |
| 4-Chlorophenylalaninol | Undecylamine | Hydrogen | 25 | |
| 4-Chlorophenylalaninol | Dehydroabietylamine | Hydrogen | 25 | |
| l-Leucinol | Hexetidine (mixture of isomers) | Hydrogen | 25 | |
| l-Leucinol | 2,4-Dichlorophenethylamine | Hydrogen | 25 | |
| l-Leucinol | Dehydroabietylamine | Hydrogen | 25 | |
| (−)-Isopinocampheylamine | 2-Methoxyphenethylamine | Hydrogen | 25 | 29.59 |
| (−)-Isopinocampheylamine | Undecylamine | Hydrogen | 25 | |
| Allylamine | Dehydroabietylamine | Hydrogen | 25 | |
| 3-Amino-1,2-propanediol | Hexetidine (mixture of isomers) | Hydrogen | 25 | |

TABLE 2-continued

Synthetic Substituted Diethylene Diamines Sorted by Minimum Inhibition Concentration

| N1 | N2 | R4 | MIC (uM) | % Induction |
|---|---|---|---|---|
| 3-Ethoxypropylamine | 3,3-Diphenylpropylamine | Hydrogen | 25 | |
| 3-Ethoxypropylamine | Undecylamine | Hydrogen | 25 | |
| 3-Ethoxypropylamine | Dehydroabietylamine | Hydrogen | 25 | |
| sec-Butylamine | 2,4-Dichlorophenethylamine | Hydrogen | 25 | |
| sec-Butylamine | Undecylamine | Hydrogen | 25 | |
| 2-Aminoheptane | Hexetidine (mixture of isomers) | Hydrogen | 25 | |
| 2-Aminoheptane | 4-Phenylbutylamine | Hydrogen | 25 | |
| 2-Aminoheptane | 2,4-Dichlorophenethylamine | Hydrogen | 25 | |
| 1-Naphthalenemethylamine | Hexetidine (mixture of isomers) | Hydrogen | 25 | |
| 1-Naphthalenemethylamine | 4-Phenylbutylamine | Hydrogen | 25 | |
| 1-Naphthalenemethylamine | 2,4-Dichlorophenethylamine | Hydrogen | 25 | |
| 1-Naphthalenemethylamine | Undecylamine | Hydrogen | 25 | |
| Ethanolamine | Dehydroabietylamine | Hydrogen | 25 | |
| Piperonylamine | 4-Phenylbutylamine | Hydrogen | 25 | |
| 1-Ethylpropylamine | Hexetidine (mixture of isomers) | Hydrogen | 25 | |
| 1-Ethylpropylamine | Dehydroabietylamine | Hydrogen | 25 | |
| Isopropylamine | Hexetidine (mixture of isomers) | Hydrogen | 25 | |
| 4-Fluorophenethylamine | 4-Phenylbutylamine | Hydrogen | 25 | |
| 4-Fluorophenethylamine | 2,4-Dichlorophenethylamine | Hydrogen | 25 | |
| 4-Fluorophenethylamine | Dehydroabietylamine | Hydrogen | 25 | |
| 3-Fluorophenethylamine | Undecylamine | Hydrogen | 25 | |
| 2-Thiopheneethylamine | 2-Adamantanamine, HCl | Hydrogen | 25 | 19.09 |
| 2-Methylcyclohexylamine (mix of cis and trans) | Hexetidine (mixture of isomers) | Hydrogen | 25 | |
| 2-Methylcyclohexylamine (mix of cis and trans) | Dehydroabietylamine | Hydrogen | 25 | |
| 2-Methoxyphenethylamine | 2-Adamantanamine, HCl | Hydrogen | 25 | 26.77 |
| 2-Methoxyphenethylamine | (−)-Isopinocampheylamine | Hydrogen | 25 | 31.95 |
| 2-Methoxyphenethylamine | 1-Adamantanamine | Hydrogen | 25 | 24.38 |
| 2-Methoxyphenethylamine | N-Allylcyclopentylamine | Hydrogen | 25 | 14.56 |
| 2-Methoxyphenethylamine | 4-Phenylbutylamine | Hydrogen | 25 | |
| 2-Methoxyphenethylamine | Undecylamine | Hydrogen | 25 | |
| 2-Methoxyphenethylamine | Dehydroabietylamine | Hydrogen | 25 | |
| 2-Fluoroethylamine, HCl | Undecylamine | Hydrogen | 25 | |
| 2-Fluoroethylamine, HCl | Dehydroabietylamine | Hydrogen | 25 | |
| 2-Aminoindan, HCl | 2-Adamantanamine, HCl | Hydrogen | 25 | 17.72 |
| 2-Amino-1-phenylethanol | Undecylamine | Hydrogen | 25 | |
| 2,5-Dimethoxyphenethylamine | (+)-Bornylamine | Hydrogen | 25 | 25.78 |
| 2,5-Dimethoxyphenethylamine | Noradamantamine, HCl | Hydrogen | 25 | 11.73 |
| 2,5-Dimethoxyphenethylamine | 1-Adamantanamine | Hydrogen | 25 | 12.57 |
| 2-(2-Chlorophenyl)ethylamine | 4-Phenylbutylamine | Hydrogen | 25 | |
| 2-(2-Chlorophenyl)ethylamine | Undecylamine | Hydrogen | 25 | |
| 2-(2-Chlorophenyl)ethylamine | 1-(1-Naphthyl)ethylamine | Hydrogen | 25 | |
| 2-(2-Aminomethyl)phenylthio)benzyl alcohol | Hexetidine (mixture of isomers) | Hydrogen | 25 | |
| 2-(2-Aminomethyl)phenylthio)benzyl alcohol | 4-Phenylbutylamine | Hydrogen | 25 | |
| 2-(2-Aminomethyl)phenylthio)benzyl alcohol | Undecylamine | Hydrogen | 25 | |
| 1-Aminoindan | Hexetidine (mixture of isomers) | Hydrogen | 25 | |
| 1-Aminoindan | Undecylamine | Hydrogen | 25 | |
| 1-Aminoindan | Dehydroabietylamine | Hydrogen | 25 | |
| 1,3-Dimethylbutylamine | Hexetidine (mixture of isomers) | Hydrogen | 25 | |
| 1,3-Dimethylbutylamine | Undecylamine | Hydrogen | 25 | 5.92 |
| 1,3-Dimethylbutylamine | Dehydroabietylamine | Hydrogen | 25 | |
| (S)-(−)-Cyclohexylethylamine | (−)-Isopinocampheylamine | Hydrogen | 25 | 19.31 |
| (S)-(−)-Cyclohexylethylamine | Hexetidine (mixture of isomers) | Hydrogen | 25 | |
| (S)-(−)-Cyclohexylethylamine | Undecylamine | Hydrogen | 25 | 10.88 |
| (S)-(−)-Cyclohexylethylamine | Dehydroabietylamine | Hydrogen | 25 | |
| (S)-(−)-2-Amino-3-phenyl-1-propanol | Hexetidine (mixture of isomers) | Hydrogen | 25 | |
| (S)-(−)-2-Amino-3-phenyl-1-propanol | Undecylamine | Hydrogen | 25 | |
| (S)-(−)-2-Amino-3-phenyl-1-propanol | Dehydroabietylamine | Hydrogen | 25 | |
| (1S,2S)-(+)-2-Amino-3-methoxy-1-phenyl-1-propanol | Hexetidine (mixture of isomers) | Hydrogen | 25 | |
| Octadecylamine | (+)-Bornylamine | Hydrogen | 25 | |
| Octadecylamine | 1-Adamantanamine | Hydrogen | 25 | |
| Geranylamine | 2,3-Dimethylcyclohexylamine | Hydrogen | 25 | 14.53 |
| Geranylamine | tert-Octylamine | Hydrogen | 25 | 15.22 |

TABLE 2-continued

Synthetic Substituted Diethylene Diamines Sorted by Minimum Inhibition Concentration

| N1 | N2 | R4 | MIC (uM) | % Induction |
|---|---|---|---|---|
| Geranylamine | 1-Adamantanemethylamine | Hydrogen | 25 | 4.37 |
| Geranylamine | Decahydroquinoline | Hydrogen | 25 | 31.79 |
| Geranylamine | Dibenzylamine | Hydrogen | 25 | 6.48 |
| Geranylamine | N-Butylbenzylamine | Hydrogen | 25 | 16.44 |
| Geranylamine | Cyclooctylamine | Hydrogen | 25 | 12.37 |
| Geranylamine | (−)-Isopinocampheylamine | Hydrogen | 25 | 8.95 |
| Geranylamine | 1-(1-Adamantyl)ethylamine, HCl | Hydrogen | 25 | 32.95 |
| Geranylamine | Undecylamine | Hydrogen | 25 | |
| Geranylamine | 1-(1-Naphthyl)ethylamine | Hydrogen | 25 | |
| Amylamine | 1-Adamantanamine | Hydrogen | 37.5 | 0 |
| 3-Phenyl-1-propylamine | 3,3-Diphenylpropylamine | Hydrogen | 37.5 | |
| 3-Phenyl-1-propylamine | 2,2-Diphenylamine | Hydrogen | 37.5 | |
| 3-Phenyl-1-propylamine | 1-Adamantanamine | Hydrogen | 37.5 | 18.65 |
| 2,2-Diphenylamine | 3,3-Diphenylpropylamine | Hydrogen | 37.5 | |
| 2,2-Diphenylamine | 2,2-Diphenylamine | Hydrogen | 37.5 | 5.56 |
| 2,2-Diphenylamine | 1,3,3-Trimethyl-6-azabicyclo[3.2.1]octane | Hydrogen | 37.5 | 8.67 |
| 2,2-Diphenylamine | 1-Adamantanamine | Hydrogen | 37.5 | 58.10 |
| 4-(Trifluoromethyl)benzylamine | tert-Octylamine | Hydrogen | 37.5 | 7.47 |
| 4-(Trifluoromethyl)benzylamine | 138 | Hydrogen | 37.5 | |
| 4-Methylbenzylamine | 2-Fluorobenzylamine | Hydrogen | 50 | 22.10 |
| 4-Methylbenzylamine | 4-Fluorobenzylamine | Hydrogen | 50 | 14.62 |
| 4-Methylbenzylamine | alpha-Methyltryptamine | Hydrogen | 50 | 0 |
| 4-Methylbenzylamine | Undecylamine | Hydrogen | 50 | 0 |
| Cyclopentylamine | Undecylamine | Hydrogen | 50 | 0 |
| Furfurylamine | 2-Fluorobenzylamine | Hydrogen | 50 | 0 |
| Furfurylamine | Benzylamine | Hydrogen | 50 | 0 |
| Furfurylamine | 4-Fluorobenzylamine | Hydrogen | 50 | 0 |
| Furfurylamine | alpha-Methyltryptamine | Hydrogen | 50 | 0 |
| Furfurylamine | Undecylamine | Hydrogen | 50 | 0 |
| Furfurylamine | Dehydroabietylamine | Hydrogen | 50 | 0 |
| Furfurylamine | Furfurylamine | Hydrogen | 50 | 0 |
| 3,4,5-Trimethoxybenzylamine | 2-Fluorobenzylamine | Hydrogen | 50 | 0 |
| 3,4,5-Trimethoxybenzylamine | Benzylamine | Hydrogen | 50 | 0 |
| 3,4,5-Trimethoxybenzylamine | alpha-Methyltryptamine | Hydrogen | 50 | 0 |
| 3,4,5-Trimethoxybenzylamine | Undecylamine | Hydrogen | 50 | 0 |
| 3,4,5-Trimethoxybenzylamine | Dehydroabietylamine | Hydrogen | 50 | 0 |
| 1-Methyl-3-phenylpropylamine | alpha-Methyltryptamine | Hydrogen | 50 | 0 |
| 1-Methyl-3-phenylpropylamine | Octadecylamine | Hydrogen | 50 | 0 |
| Cyclobutylamine | Octadecylamine | Hydrogen | 50 | 0 |
| Cyclobutylamine | Undecylamine | Hydrogen | 50 | 0 |
| Cyclobutylamine | Dehydroabietylamine | Hydrogen | 50 | 0 |
| 1,2,3,4-Tetrahydro-1-naphthylamine | Hexetidine (mixture of isomers) | Hydrogen | 50 | 0 |
| 1,2,3,4-Tetrahydro-1-naphthylamine | Aminodiphenylmethane | Hydrogen | 50 | 4.31 |
| 1,2,3,4-Tetrahydro-1-naphthylamine | alpha-Methyltryptamine | Hydrogen | 50 | 0 |
| 1,2,3,4-Tetrahydro-1-naphthylamine | 2-Methoxyphenethylamine | Hydrogen | 50 | 0 |
| 2,3-Dimethylcyclohexylamine | Hexetidine (mixture of isomers) | Hydrogen | 50 | 0 |
| 2,3-Dimethylcyclohexylamine | Aminodiphenylmethane | Hydrogen | 50 | 3.64 |
| 2,3-Dimethylcyclohexylamine | alpha-Methyltryptamine | Hydrogen | 50 | 0 |
| Tyramine | Furfurylamine | Hydrogen | 50 | 0 |
| Tyramine | 2-Fluorobenzylamine | Hydrogen | 50 | 4.07 |
| Tyramine | Benzylamine | Hydrogen | 50 | 0 |
| Tyramine | 2,4-Dichlorophenethylamine | Hydrogen | 50 | 0 |
| 2-Fluorobenzylamine | Aminodiphenylmethane | Hydrogen | 50 | 0 |
| 2-Fluorobenzylamine | 4-Phenylbutylamine | Hydrogen | 50 | 0 |
| 2-Fluorobenzylamine | 2-Methoxyphenethylamine | Hydrogen | 50 | 0 |
| 2-Fluorobenzylamine | 2,4-Dichlorophenethylamine | Hydrogen | 50 | 0 |
| 2-Fluorobenzylamine | 1,3-Dimethylbutylamine | Hydrogen | 50 | 0 |
| 2-Fluorobenzylamine | 1-(1-Adamantyl)ethylamine, HCl | Hydrogen | 50 | 0 |
| (R)-2-Amino-1-butanol | Dehydroabietylamine | Hydrogen | 50 | 0 |
| 3,4-Dimethoxyphenethylamine | Aminodiphenylmethane | Hydrogen | 50 | 0 |
| 3,4-Dimethoxyphenethylamine | 4-Phenylbutylamine | Hydrogen | 50 | 0 |
| 3,4-Dimethoxyphenethylamine | 2-Methoxyphenethylamine | Hydrogen | 50 | 0 |
| 3,4-Dimethoxyphenethylamine | 2,4-Dichlorophenethylamine | Hydrogen | 50 | 0 |
| 3,4-Dimethoxyphenethylamine | 1,3-Dimethylbutylamine | Hydrogen | 50 | 0 |
| 3,3-Diphenylpropylamine | Piperidine | Hydrogen | 50 | 0 |
| 3,3-Diphenylpropylamine | 2,3-Dimethylcyclohexylamine | Methyl | 50 | 7.81 |
| 3,3-Diphenylpropylamine | (−)-Isopinocamphenylamine | Methyl | 50 | 13.06 |

TABLE 2-continued

Synthetic Substituted Diethylene Diamines Sorted by Minimum Inhibition Concentration

| N1 | N2 | R4 | MIC (uM) | % Induction |
|---|---|---|---|---|
| Propylamine | (S)-(+)-1-Amino-2-propanol | Hydrogen | 50 | 0 |
| Phenethylamine | (S)-(+)-1-Amino-2-propanol | Hydrogen | 50 | 0 |
| Phenethylamine | 4-Phenylbutylamine | Hydrogen | 50 | 0 |
| Phenethylamine | 2,4-Dichlorophenethylamine | Hydrogen | 50 | 0 |
| Phenethylamine | 1,3-Dimethylbutylamine | Hydrogen | 50 | 0 |
| Phenethylamine | 1-(1-Adamantyl)ethylamine, HCl | Hydrogen | 50 | 0 |
| Phenethylamine | 1-(1-Naphthyl)ethylamine | Hydrogen | 50 | 0 |
| 4-(2-Aminoethyl)morpholine | 2-Amino-2-methyl-1-propanol | Hydrogen | 50 | 0 |
| Cyclohexylamine | 2,4-Dichlorophenethylamine | Hydrogen | 50 | 0 |
| exo-Aminonorbornane | Benzylamine | Hydrogen | 50 | 0 |
| (+)-Isopinocampheylamine | Hexetidine (mixture of isomers) | Hydrogen | 50 | 0 |
| (+)-Isopinocampheylamine | Aminodiphenylmethane | Hydrogen | 50 | 5.07 |
| (+)-Isopinocampheylamine | 4-Phenylbutylamine | Hydrogen | 50 | 0 |
| (+)-Isopinocampheylamine | 2,4-Dichlorophenethylamine | Hydrogen | 50 | 0 |
| (+)-Isopinocampheylamine | Undecylamine | Hydrogen | 50 | 0 |
| Benzylamine | 3,3-Diphenylpropylamine | Hydrogen | 50 | |
| Benzylamine | 2-Amino-2-methyl-1-propanol | Hydrogen | 50 | |
| Benzylamine | 1-(1-Naphthyl)ethylamine | Hydrogen | 50 | |
| Benzylamine | 2,4-Dichlorophenethylamine | Hydrogen | 50 | |
| 3-Amino-1-propanol | Undecylamine | Hydrogen | 50 | 0 |
| 2-Fluorophenethylamine | 3,3-Diphenylpropylamine | Hydrogen | 50 | 0 |
| 2-Fluorophenethylamine | 1-Adamantanemethylamine | Hydrogen | 50 | 0 |
| 2-Fluorophenethylamine | 1-(3-Aminopropyl)-2-pyrrolidinone (tech) | Hydrogen | 50 | 0 |
| 2-Fluorophenethylamine | Decahydroquinoline | Hydrogen | 50 | 0 |
| 2-Fluorophenethylamine | 1-Adamantanamine | Hydrogen | 50 | 24.34 |
| 2-Fluorophenethylamine | 2,4-Dichlorophenethylamine | Hydrogen | 50 | 0 |
| 2-Fluorophenethylamine | Undecylamine | Hydrogen | 50 | 0 |
| 2-Fluorophenethylamine | Dehydroabietylamine | Hydrogen | 50 | 0 |
| 2-Fluorophenethylamine | 2-(1-Cyclohexenyl)ethylamine | Methyl | 50 | 0 |
| 2-Fluorophenethylamine | Clyclooctylamine | Methyl | 50 | 5.81 |
| b-Methylphenethylamine | 3,3-Diphenylpropylamine | Hydrogen | 50 | 0 |
| b-Methylphenethylamine | tert-Octylamine | Hydrogen | 50 | 0 |
| b-Methylphenethylamine | 2-(1-Cyclohexenyl)ethylamine | Hydrogen | 50 | 0 |
| b-Methylphenethylamine | 2-Amino-2-methyl-1-propanol | Hydrogen | 50 | 0 |
| b-Methylphenethylamine | 4-Fluorophenethylamine | Hydrogen | 50 | 0 |
| b-Methylphenethylamine | Geranylamine | Hydrogen | 50 | 0 |
| b-Methylphenethylamine | 5-Methoxytryptamine | Hydrogen | 50 | 0 |
| 4-Methoxyphenethylamine | 3,3-Diphenylpropylamine | Hydrogen | 50 | 0 |
| 4-Methoxyphenethylamine | 2-Amino-2-methyl-1-propanol | Hydrogen | 50 | 0 |
| 4-Methoxyphenethylamine | 2,4-Dichlorophenethylamine | Hydrogen | 50 | 0 |
| 4-Methoxyphenethylamine | 1-(1-Naphthyl)ethylamine | Hydrogen | 50 | 0 |
| L-Methioninol | Hexetidine (mixture of isomers) | Hydrogen | 50 | 0 |
| Tetrahydrofurfurylamine | 1-Adamantanemethylamine | Hydrogen | 50 | 0 |
| Tetrahydrofurfurylamine | 2-(1-Cyclohexenyl)ethylamine | Hydrogen | 50 | 0 |
| Tetrahydrofurfurylamine | 4-Fluorophenethylamine | Hydrogen | 50 | 0 |
| Tetrahydrofurfurylamine | Undecylamine | Hydrogen | 50 | 0 |
| Amylamine | 1-Adamantanemethylamine | Hydrogen | 50 | 0 |
| Amylamine | Hexetidine (mixture of isomers) | Hydrogen | 50 | 0 |
| Amylamine | Undecylamine | Hydrogen | 50 | 0 |
| Amylamine | Dehydroabietylamine | Hydrogen | 50 | 0 |
| 1-Adamantanemethylamine | cis-(−)-Myrtanylamine | Methyl | 50 | 0 |
| 3-Phenyl-1-propylamine | 4-(2-Aminoethyl)morpholine | Hydrogen | 50 | |
| 3-Phenyl-1-propylamine | 1-(3-Aminopropyl)-2-pyrrolidinone (tech) | Hydrogen | 50 | |
| 3-Phenyl-1-propylamine | Veratryl amine | Hydrogen | 50 | |
| 3-Phenyl-1-propylamine | Aminodiphenylmethane | Hydrogen | 50 | |
| 3-Phenyl-1-propylamine | 2-(2-Aminomethyl)phenylthio)benzyl alcohol | Hydrogen | 50 | |
| 2,2-Diphenylamine | 2-Fluorophenethylamine | Hydrogen | 50 | |
| 2,2-Diphenylamine | 3,3-Diphenylpropylamine | Methyl | 50 | |
| 2,2-Diphenylamine | (+)-Isopinocampheylamine | Methyl | 50 | |
| 2,2-Diphenylamine | (+)-Bornylamine | Methyl | 50 | |
| 2,2-Diphenylamine | Cyclooctylamine | Methyl | 50 | |
| 2,2-Diphenylamine | (−)-Isopinocampheylamine | Methyl | 50 | 3.81 |
| 4-(Trifluoromethyl)benzylamine | 4-(2-Aminoethyl)morpholine | Hydrogen | 50 | |
| 4-(Trifluoromethyl)benzylamine | 2-(1-Cyclohexenyl)ethylamine | Hydrogen | 50 | |
| 4-(Trifluoromethyl)benzylamine | Hexetidine (mixture of isomers) | Hydrogen | 50 | |
| 4-(Trifluoromethyl)benzylamine | 2,4-Dichlorophenethylamine | Hydrogen | 50 | |
| 4-(Trifluoromethyl)benzylamine | (S)-(−)-Cyclohexylethylamine | Hydrogen | 50 | |
| Veratryl amine | 1-Adamantanemethylamine | Hydrogen | 50 | |
| Veratryl amine | 2-(1-Cyclohexenyl)ethylamine | Hydrogen | 50 | |

TABLE 2-continued

Synthetic Substituted Diethylene Diamines Sorted by Minimum Inhibition Concentration

| N1 | N2 | R4 | MIC (uM) | % Induction |
|---|---|---|---|---|
| Veratryl amine | 4-Fluorophenethylamine | Hydrogen | 50 | |
| Veratryl amine | Hexetidine (mixture of isomers) | Hydrogen | 50 | |
| Veratryl amine | 2,4-Dichlorophenethylamine | Hydrogen | 50 | |
| Veratryl amine | (S)-(−)-Cyclohexylethylamine | Hydrogen | 50 | |
| Veratryl amine | Undecylamine | Hydrogen | 50 | |
| Veratryl amine | Dehydroabietylamine | Hydrogen | 50 | |
| Veratryl amine | 1-(1-Naphthyl)ethylamine | Hydrogen | 50 | |
| 5-Amino-1-pentanol | 1-Adamantanemethylamine | Hydrogen | 50 | |
| 5-Amino-1-pentanol | Dibenzylamine | Hydrogen | 50 | |
| 5-Amino-1-pentanol | cis-(−)-Myrtanylamine | Hydrogen | 50 | 12.97 |
| 2-(1-Cyclohexenyl)ethylamine | 2,4-Dimethoxybenzylamine | Hydrogen | 50 | |
| 1-Aminomethyl-1-cyclohexanol, HCl | tert-Amylamine | Hydrogen | 50 | |
| 1-Aminomethyl-1-cyclohexanol, HCl | 2-(2-Aminomethyl)phenylthio)benzyl alcohol | Hydrogen | 50 | |
| 1-Aminomethyl-1-cyclohexanol, HCl | Undecylamine | Hydrogen | 50 | |
| 1-Aminomethyl-1-cyclohexanol, HCl | 1-(1-Naphthyl)ethylamine | Hydrogen | 50 | |
| 3-Fluorobenzylamine | tert-Amylamine | Hydrogen | 50 | |
| 3-Fluorobenzylamine | Hexetidine (mixture of isomers) | Hydrogen | 50 | |
| 3-Fluorobenzylamine | Undecylamine | Hydrogen | 50 | |
| 4-Amino-1-butanol | Undecylamine | Hydrogen | 50 | |
| 4-Amino-1-butanol | Dehydroabietylamine | Hydrogen | 50 | |
| 2,4-Dimethoxybenzylamine | N-Phenylethyldiamine | Hydrogen | 50 | |
| 2,4-Dimethoxybenzylamine | Aminodiphenylmethane | Hydrogen | 50 | |
| 2,4-Dimethoxybenzylamine | 4-Phenylbutylamine | Hydrogen | 50 | |
| 2,4-Dimethoxybenzylamine | 2-Chlorobenzylamine | Hydrogen | 50 | |
| 2,4-Dimethoxybenzylamine | 2,4-Dichlorophenethylamine | Hydrogen | 50 | |
| 2,4-Dimethoxybenzylamine | 2-(2-Chlorophenyl)ethylamine | Hydrogen | 50 | |
| 2,4-Dimethoxybenzylamine | 4-(Trifluoromethoxy)benzylamine | Hydrogen | 50 | |
| 2-Ethoxybenzylamine | Aminodiphenylmethane | Hydrogen | 50 | |
| 2-Ethoxybenzylamine | 4-Phenylbutylamine | Hydrogen | 50 | |
| 2-Ethoxybenzylamine | 2-Chlorobenzylamine | Hydrogen | 50 | |
| 2-Ethoxybenzylamine | 2-Aminoindan, HCl | Hydrogen | 50 | |
| 2-Ethoxybenzylamine | 2,5-Dimethoxyphenethylamine | Hydrogen | 50 | |
| 2-Ethoxybenzylamine | 4-(Trifluoromethoxy)benzylamine | Hydrogen | 50 | |
| 2-Ethoxybenzylamine | 1-(1-Naphthyl)ethylamine | Hydrogen | 50 | |
| cis-(−)-Myrtanylamine | 4-(2-Aminoethyl)morpholine | Hydrogen | 50 | |
| cis-(−)-Myrtanylamine | 2-Fluorophenethylamine | Hydrogen | 50 | |
| cis-(−)-Myrtanylamine | 1-(3-Aminopropyl)-2-pyrrolidinone (tech) | Hydrogen | 50 | |
| cis-(−)-Myrtanylamine | Veratryl amine | Hydrogen | 50 | |
| cis-(−)-Myrtanylamine | N-Butylbenzylamine | Hydrogen | 50 | |
| cis-(−)-Myrtanylamine | 2,4-Dimethoxybenzylamine | Hydrogen | 50 | |
| cis-(−)-Myrtanylamine | 1,2,3,4-Tetrahydropyridoindole | Hydrogen | 50 | |
| cis-(−)-Myrtanylamine | 4-Phenylbutylamine | Hydrogen | 50 | |
| cis-(−)-Myrtanylamine | 2-(2-Chlorophenyl)ethylamine | Hydrogen | 50 | 3.91 |
| cis-(−)-Myrtanylamine | 1-(1-Adamantyl)ethylamine, HCl | Hydrogen | 50 | 10.85 |
| cis-(−)-Myrtanylamine | (R)-(−)-Cyclohexylethylamine | Hydrogen | 50 | 5.89 |
| cis-(−)-Myrtanylamine | Dehydroabietylamine | Hydrogen | 50 | |
| cis-(−)-Myrtanylamine | 1-(1-Naphthyl)ethylamine | Hydrogen | 50 | |
| cis-(−)-Myrtanylamine | (+)-Bornylamine | Methyl | 50 | 4.04 |
| Cyclooctylamine | 4-Methylcyclohexylamine | Hydrogen | 50 | 4.55 |
| Cyclooctylamine | N-Phenylethyldiamine | Hydrogen | 50 | |
| Cyclooctylamine | 4-(Hexacylamino)benzylamine | Hydrogen | 50 | |
| Cyclooctylamine | 2,5-Dimethoxyphenethylamine | Hydrogen | 50 | |
| Cyclooctylamine | 2,4-Dichlorophenethylamine | Hydrogen | 50 | 3.36 |
| Cyclooctylamine | 2-(2-Chlorophenyl)ethylamine | Hydrogen | 50 | 9.15 |
| Cyclooctylamine | 1-(1-Adamantyl)ethylamine, HCl | Hydrogen | 50 | 10.62 |
| Cyclooctylamine | (S)-(−)-Cyclohexylethylamine | Hydrogen | 50 | 5.85 |
| Cyclooctylamine | (R)-(−)-Cyclohexylethylamine | Hydrogen | 50 | |
| Cyclooctylamine | 4-(Trifluoromethoxy)benzylamine | Hydrogen | 50 | 4.54 |
| 2-Adamantanamine, HCl | cis-(−)-Myrtanylamine | Hydrogen | 50 | 49.73 |
| 4-Methylcyclohexylamine | N-Phenylethyldiamine | Hydrogen | 50 | |
| 4-Methylcyclohexylamine | 4-Phenylbutylamine | Hydrogen | 50 | |
| 4-Fluorobenzylamine | N-Benzyl-2-phenethylamine | Hydrogen | 50 | |
| 4-Fluorobenzylamine | Hexetidine (mixture of isomers) | Hydrogen | 50 | |

TABLE 2-continued

Synthetic Substituted Diethylene Diamines Sorted by Minimum Inhibition Concentration

| N1 | N2 | R4 | MIC (uM) | % Induction |
|---|---|---|---|---|
| 4-Fluorobenzylamine | Undecylamine | Hydrogen | 50 | |
| 4-Fluorobenzylamine | Dehydroabietylamine | Hydrogen | 50 | |
| trans-2-Phenylcyclopropylamine, HCl | Hexetidine (mixture of isomers) | Hydrogen | 50 | |
| trans-2-Phenylcyclopropylamine, HCl | Undecylamine | Hydrogen | 50 | |
| trans-2-Phenylcyclopropylamine, HCl | Dehydroabietylamine | Hydrogen | 50 | |
| (R)-1-Amino-2-propanol | 4-(Hexacylamino)benzylamine | Hydrogen | 50 | |
| (R)-1-Amino-2-propanol | Undecylamine | Hydrogen | 50 | |
| (R)-1-Amino-2-propanol | Dehydroabietylamine | Hydrogen | 50 | |
| I-Leucinol | Undecylamine | Hydrogen | 50 | |
| (−)-Isopinocampheylamine | 2-Ethoxybenzylamine | Hydrogen | 50 | 27.27 |
| (−)-Isopinocampheylamine | Hexetidine (mixture of isomers) | Hydrogen | 50 | |
| (−)-Isopinocampheylamine | 4-Phenylbutylamine | Hydrogen | 50 | |
| (−)-Isopinocampheylamine | Dehydroabietylamine | Hydrogen | 50 | |
| (−)-Isopinocampheylamine | 1-(1-Naphthyl)ethylamine | Hydrogen | 50 | |
| Allylamine | 3,3-Diphenylpropylamine | Hydrogen | 50 | |
| Allylamine | 2-Amino-1-propanol, d, l | Hydrogen | 50 | |
| Allylamine | Undecylamine | Hydrogen | 50 | |
| 3-Amino-1,2-propanediol | Dehydroabietylamine | Hydrogen | 50 | |
| 3-Ethoxypropylamine | 2,2-Diphenylamine | Hydrogen | 50 | 95.81 |
| 3-Ethoxypropylamine | cis-(−)-Myrtanylamine | Hydrogen | 50 | |
| 2-Aminoheptane | 2-(2-Aminomethyl)phenylthio)benzyl alcohol | Hydrogen | 50 | |
| 1-Naphthalenemethylamine | Geranylamine | Hydrogen | 50 | |
| 1-Naphthalenemethylamine | Dehydroabietylamine | Hydrogen | 50 | |
| 1-Aminopyrrolidine, HCl | Hexetidine (mixture of isomers) | Hydrogen | 50 | |
| 1-Aminopyrrolidine, HCl | Undecylamine | Hydrogen | 50 | |
| 1-Aminopyrrolidine, HCl | Dehydroabietylamine | Hydrogen | 50 | |
| Ethanolamine | 3,3-Diphenylpropylamine | Hydrogen | 50 | |
| 3-Methylbenzylamine | Geranylamine | Hydrogen | 50 | |
| 3-Methylbenzylamine | 5-Methoxytryptamine | Hydrogen | 50 | |
| Piperonylamine | Aminodiphenylmethane | Hydrogen | 50 | |
| Piperonylamine | 2,4-Dichlorophenethylamine | Hydrogen | 50 | |
| Piperonylamine | 2-(2-Aminomethyl)phenylthio)benzyl alcohol | Hydrogen | 50 | |
| Isopropylamine | Dehydroabietylamine | Hydrogen | 50 | |
| 4-Fluorophenethylamine | 2,4-Dimethoxybenzylamine | Hydrogen | 50 | |
| 4-Fluorophenethylamine | Aminodiphenylmethane | Hydrogen | 50 | |
| 4-Fluorophenethylamine | 2-(2-Aminomethyl)phenylthio)benzyl alcohol | Hydrogen | 50 | |
| 4-Chloroamphetamine, HCl | N-Allylcyclopentylamine | Hydrogen | 50 | 10.25 |
| 4-Chloroamphetamine, HCl | Hexetidine (mixture of isomers) | Hydrogen | 50 | |
| 4-Chloroamphetamine, HCl | 4-Phenylbutylamine | Hydrogen | 50 | |
| 4-Chloroamphetamine, HCl | 2-Methoxyphenethylamine | Hydrogen | 50 | |
| 4-Chloroamphetamine, HCl | Undecylamine | Hydrogen | 50 | |
| 4-Chloroamphetamine, HCl | Dehydroabietylamine | Hydrogen | 50 | |
| 3-Fluorophenethylamine | (−)-Isopinocampheylamine | Hydrogen | 50 | |
| 3-Fluorophenethylamine | 1-Adamantamine | Hydrogen | 50 | 8.59 |
| 3-Fluorophenethylamine | 4-Phenylbutylamine | Hydrogen | 50 | |
| 2-Methylcyclohexylamine (mix of cis and trans) | Undecylamine | Hydrogen | 50 | |
| 2-Methoxyphenethylamine | 3,3-Diphenylpropylamine | Hydrogen | 50 | |
| 2-Methoxyphenethylamine | (+)-Bornylamine | Hydrogen | 50 | |
| 2-Methoxyphenethylamine | tert-Octylamine | Hydrogen | 50 | 20.46 |
| 2-Methoxyphenethylamine | 1-Adamantanemethylamine | Hydrogen | 50 | |
| 2-Methoxyphenethylamine | Dibenzylamine | Hydrogen | 50 | |
| 2-Methoxyphenethylamine | N-Butylbenzylamine | Hydrogen | 50 | 5.20 |
| 2-Methoxyphenethylamine | 1,3,3-Trimethyl-6-azabicyclo[3.2.1]octane | Hydrogen | 50 | 8.59 |
| 2-Methoxyphenethylamine | N-Phenylethyldiamine | Hydrogen | 50 | |
| 2-Methoxyphenethylamine | 2,4-Dichlorophenethylamine | Hydrogen | 50 | |
| 2-Methoxyphenethylamine | 2-(2-Chlorophenyl)ethylamine | Hydrogen | 50 | |
| 2-Methoxyphenethylamine | 1-(1-Adamantyl)ethylamine, HCl | Hydrogen | 50 | 3.61 |
| 2-Aminoindan, HCl | (+)-Bornylamine | Hydrogen | 50 | |
| 2-Aminoindan, HCl | Noradamantamine, HCl | Hydrogen | 50 | 7.43 |
| 2-(2-Chlorophenyl)ethylamine | N-Phenylethyldiamine | Hydrogen | 50 | |
| 2-(2-Chlorophenyl)ethylamine | Aminodiphenylmethane | Hydrogen | 50 | |
| 2-(2-Chlorophenyl)ethylamine | 2,4-Dichlorophenethylamine | Hydrogen | 50 | |

TABLE 2-continued

Synthetic Substituted Diethylene Diamines Sorted by Minimum Inhibition Concentration

| N1 | N2 | R4 | MIC (uM) | % Induction |
|---|---|---|---|---|
| 2-(2-Chlorophenyl)ethylamine | 1-(1-Adamantyl)ethylamine, HCl | Hydrogen | 50 | |
| 2-(2-Chlorophenyl)ethylamine | Dehydroabietylamine | Hydrogen | 50 | |
| 2-(2-Aminomethyl)phenylthio)benzyl alcohol | 2-Methoxyphenethylamine | Hydrogen | 50 | |
| 2-(2-Aminomethyl)phenylthio)benzyl alcohol | 2,5-Dimethoxyphenethylamine | Hydrogen | 50 | |
| 2-(2-Aminomethyl)phenylthio)benzyl alcohol | 2-(2-Chlorophenyl)ethylamine | Hydrogen | 50 | |
| 2-(2-Aminomethyl)phenylthio)benzyl alcohol | 1-(1-Adamantyl)ethylamine, HCl | Hydrogen | 50 | |
| 2-(2-Aminomethyl)phenylthio)benzyl alcohol | Dehydroabietylamine | Hydrogen | 50 | |
| 1-Aminoindan | 4-Phenylbutylamine | Hydrogen | 50 | |
| 1-Aminoindan | 2,4-Dichlorophenethylamine | Hydrogen | 50 | |
| 1,3-Dimethylbutylamine | 4-Phenylbutylamine | Hydrogen | 50 | |
| (S)-(−)-Cyclohexylethylamine | Aminodiphenylmethane | Hydrogen | 50 | |
| (S)-(−)-Cyclohexylethylamine | 4-Phenylbutylamine | Hydrogen | 50 | |
| (S)-(−)-Cyclohexylethylamine | 2,4-Dichlorophenethylamine | Hydrogen | 50 | |
| (S)-(−)-Cyclohexylethylamine | 1-(1-Adamantyl)ethylamine, HCl | Hydrogen | 50 | |
| (1S,2S)-(+)-2-Amino-3-methoxy-1-phenyl-1-propanol | Dehydroabietylamine | Hydrogen | 50 | |
| Octadecylamine | 2-Adamantanamine, HCl | Hydrogen | 50 | |
| 3-Hydroxytyramine | (1R,2S)-(−)-2-Amino-1,2-diphenylethanol | Hydrogen | 50 | |
| 3-Hydroxytyramine | Dehydroabietylamine | Hydrogen | 50 | |
| Geranylamine | 3,3-Diphenylpropylamine | Hydrogen | 50 | |
| Geranylamine | N-Phenylethyldiamine | Hydrogen | 50 | |
| Geranylamine | Hexetidine (mixture of isomers) | Hydrogen | 50 | |
| Geranylamine | 2-Thiopheneethylamine | Hydrogen | 50 | |
| Geranylamine | 2-Methoxyphenethylamine | Hydrogen | 50 | |
| Geranylamine | 2,5-Dimethoxyphenethylamine | Hydrogen | 50 | |
| Geranylamine | 2,4-Dichlorophenethylamine | Hydrogen | 50 | |
| Geranylamine | 2-(2-Chlorophenyl)ethylamine | Hydrogen | 50 | |
| 2-Fluorophenethylamine | 2,3-Dimethylcyclohexylamine | Methyl | >50 | 2.07 |
| 4-(Trifluoromethyl)benzylamine | 2,3-Dimethylcyclohexylamine | Hydrogen | >50 | 8.20 |
| 4-(Trifluoromethyl)benzylamine | 1-Adamantanamine | Hydrogen | >50 | 32.02 |
| 5-Aminoquinoline | exo-Aminonorbornane | Hydrogen | >50 | 17.87 |

TABLE 3

Compounds Synthesized in Larger Quantities for Further in vitro Evaluations

| Cmpd # | Name | Structure | Amount, mg | Yields, % |
|---|---|---|---|---|
| 1 | N-(4-Methylphenyl)-N'-(furfuryl)ethane-1,2-diamine | [structure] | 23 | 25 |
| 2 | N-(4-Methylphenyl)-N'-(benzyl)ethane-1,2-diamine | [structure] | 27 | 29 |

TABLE 3-continued

Compounds Synthesized in Larger Quantities for Further in vitro Evaluations

| Cmpd # | Name | Structure | Amount, mg | Yields, % |
|---|---|---|---|---|
| 3 | N-[1-(1,2,3,4-Tetrahydro-naphthalene)-N'-(undecenyl)-ethane-1,2-diamine | 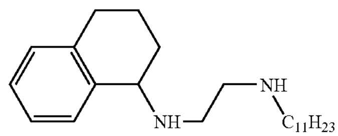 | 11 | 10 |
| 4 | N-[2-(3,4-Dimethoxy-phenyl)-ethyl-N'-(1-methyladamantyl)-ethane-1,2-diamine | 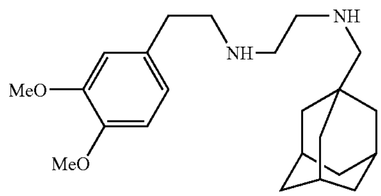 | 13 | 11 |
| 5 | N-[2-(3,4-Dimethoxy-phenyl)ethyl-N'-(norbornyl)-ethane-1,2-diamine | 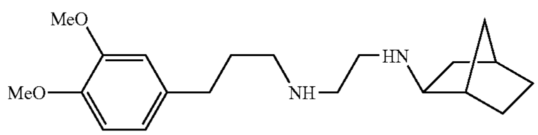 | 9 | 8 |
| 6 | N-(1-Adamantylmethyl)-N'-(3,3-diphenylpropyl)propane-1,2-diamine | 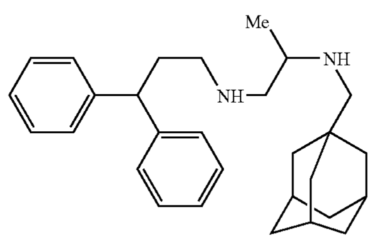 | 55 | 36 |
| 7 | N-(1-Adamantylmethyl)-N'-(3,3-diphenylpropyl)ethane-1,2-diamine | 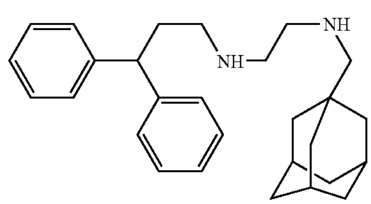 | 28 | 22 |
| 8 | N-[2-(Cyclohexen-1-yl)ethyl]-N'-(3,3-diphenylpropyl)-propane-1,2-diamine | 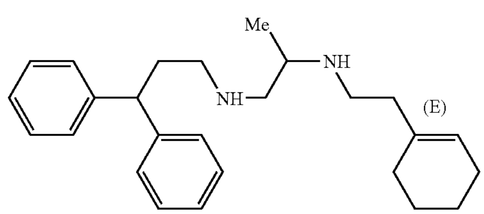 | 46 | 37 |
| 10 | N-(−)-cis-Myrtanyl-N'-(3,3-diphenylpropyl)ethane-1,2-diamine | 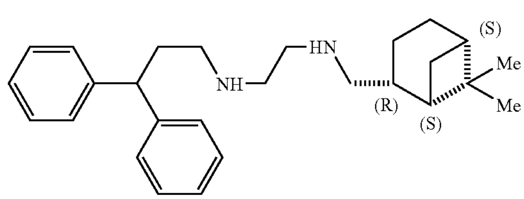 | 14 | 11 |

TABLE 3-continued

Compounds Synthesized in Larger Quantities for Further in vitro Evaluations

| Cmpd # | Name | Structure | Amount, mg | Yields, % |
|---|---|---|---|---|
| 11 | N-Cyclooctyl-N'-(3,3-diphenylpropyl)ethane-1,2-diamine | 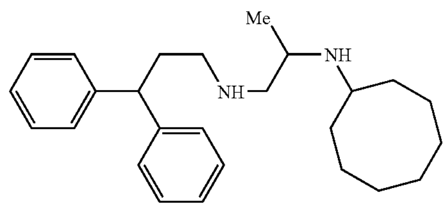 | 22 | 18 |
| 13 | N-Allyl-N-cyclopentyl-N'-(3,3-diphenylpropyl)ethane-1,2-diamine | 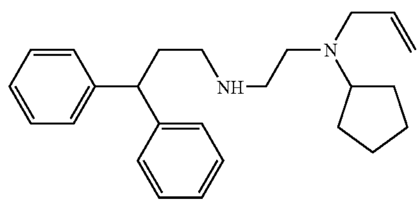 | 33 | 27 |
| 14 | N-(3,3-Diphenylpropyl)-N'-exo-(2-norborny)ethane-1,2-diamine | 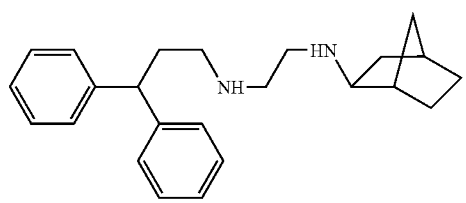 | 17 | 16 |
| 15 | 1-{2-[N-(3,3-Diphenylpropyl)]-aminoethyl}-3,5-dimethyl-piperidine | 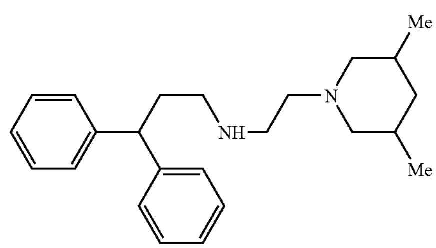 | 6.2 | 5 |
| 17 | N-2-(2-Methoxyphenyl)ethyl-N'-(3,3-diphenylethyl)ethane-1,2-diamine | 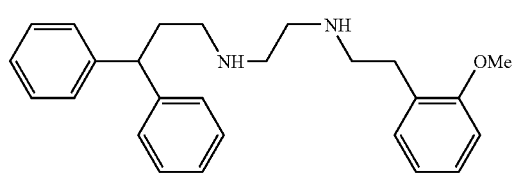 | 50 | 40 |
| 21 | N-(3,3-Diphenylpropyl)-N'-(1S)-(1-ethylcyclohexane)-ethane-1,2-diamine | 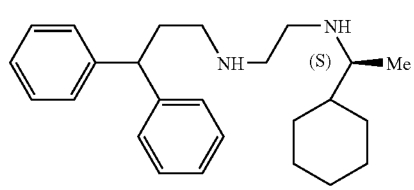 | 5 | 4 |
| 22 | N-(3,3-Diphenylpropyl)-N'-(1R)-(1-ethylcyclohexane)-ethane-1,2-diamine | 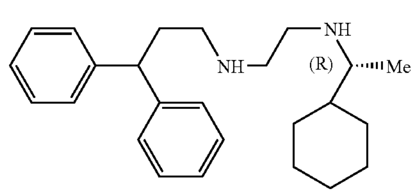 | 21 | 17 |

TABLE 3-continued

Compounds Synthesized in Larger Quantities for Further in vitro Evaluations

| Cmpd # | Name | Structure | Amount, mg | Yields, % |
|---|---|---|---|---|
| 23 | N-Allyl-N-cyclohexyl-N'-(3,3-diphenylpropyl)ethane-1,2-diamine | 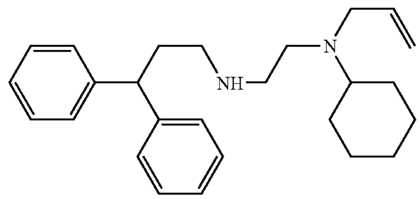 | 6 | 5 |
| 24 | N-2-(2-Methoxyphenyl)ethyl-N'-(4-fluorophenylethyl)-ethane-1,2-diamine | 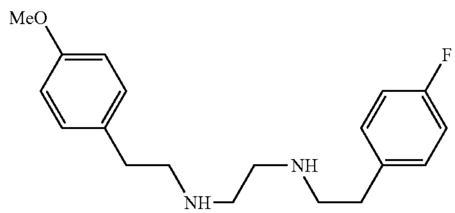 | 10 | 9 |
| 27 | N-(3-Phenylpropyl)-N'-(1-adamantyl)ethane-1,2-diamine | 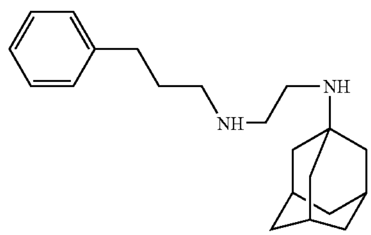 | 11 | 10 |
| 28 | N-(3-Phenylpropyl)-N'-(4-fluorophenyl)ethane-1,2-diamine | 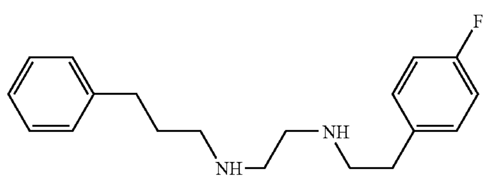 | 11 | 10 |
| 29 | N-(2,2-Diphenylethyl)-N'-(2,3-dimethylcylcohexyl)ethane-1,2-diamine | 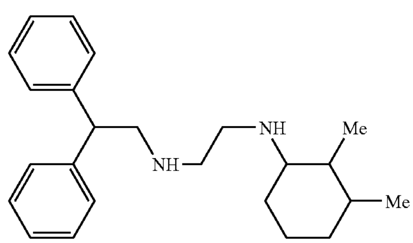 | 4.5 | 4 |
| 31 | N-(2,2-Diphenylethyl)-N'-(1S)-(1-ethylcyclohexane)-ethane-1,2-diamine | 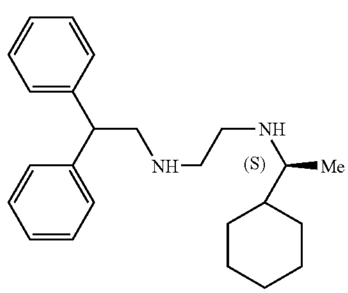 | 24 | 20 |

TABLE 3-continued

Compounds Synthesized in Larger Quantities for Further in vitro Evaluations

| Cmpd # | Name | Structure | Amount, mg | Yields, % |
|---|---|---|---|---|
| 32 | N-(2,2-Diphenylethyl)-N'-(R)-(+)- | 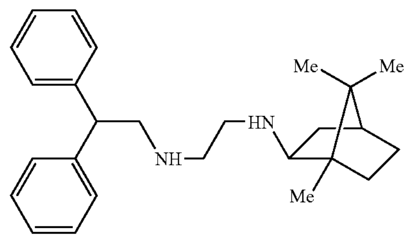 | 58 | 48 |
| 33 | N-(2,2-Diphenylethyl)-N'-(1,1,3,3-tetramethylbutyl)-ethane-1,2-diamine | 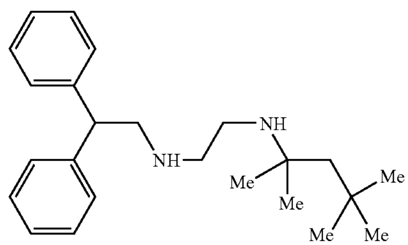 | 11 | 9 |
| 34 | N-(2,2-Diphenylethyl)-N'-(1-methyladamantyl)ethane-1,2-diamine | 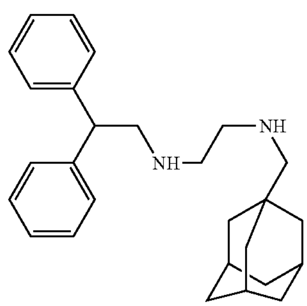 | 6.8 | 6 |
| 35 | N-(2-2-Diphenylethyl)-N'-{1,1,3-trimethyl-6-azabicyclo-[3.2.1]octyl}ethane-1,2-diamine | 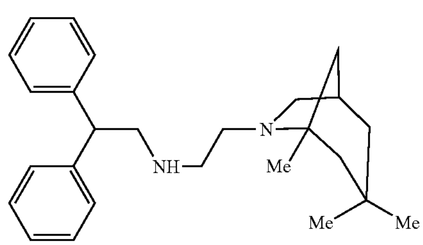 | 38 | 30 |
| 36 | N-{2-[N'-(2,2-Diphenylethyl)]-aminoethyl}-decahydroquinoline | 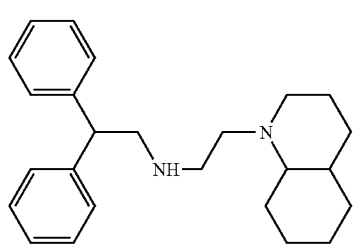 | 28 | 24 |

TABLE 3-continued

Compounds Synthesized in Larger Quantities for Further in vitro Evaluations

| Cmpd # | Name | Structure | Amount, mg | Yields, % |
|---|---|---|---|---|
| 37 | N-(2,2-Diphenylethyl)-N'-(−)-cis-(myrtanyl)ethane-1,2-diamine | 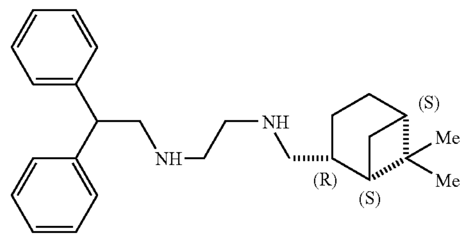 | 54 | 38 |
| 38 | N-(−)-cis-(Myrtanyl)-N'-(2,2-diphenylethyl)propyl-1,2-diamine | 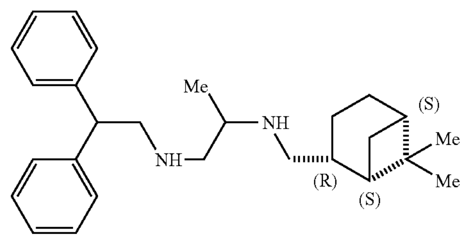 | 39 | 30 |
| 40 | N-(2,2-Diphenylethyl)-N'-(1R, 2R, 3R, 5S)-(−)-isopinocampheylethane-1,2-diamine | 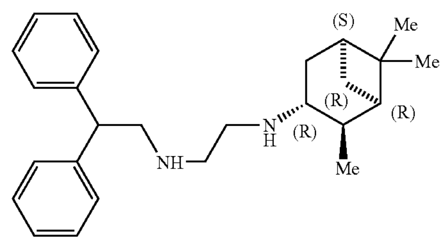 | 33 | 23 |
| 41 | N-(−)-cis-(Myrtanyl)-N'-(2,3-dimethylcyclohexyl)ethane-1,2-diamine | 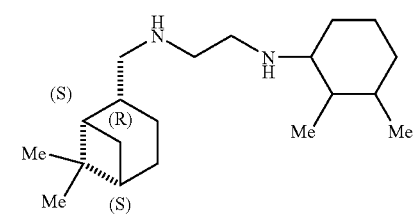 | 66 | 62 |
| 42 | N-(3,3-Diphenylpropyl)-N'-(−)-cis-myrtanylethane-1,2-diamine | 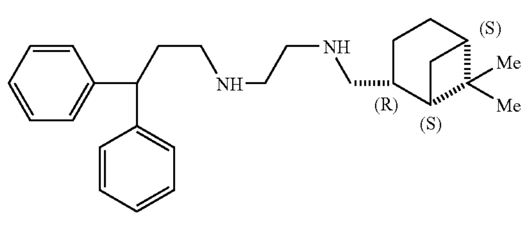 | 11 | 9 |
| 43 | N-(−)-cis-Myrtanyl-N'-(1S, 2S, 3S, 5R)-(+)-isopinocampheylethane-1,2-diamine | 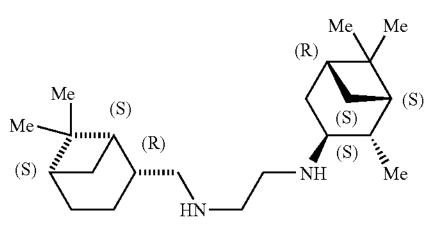 | 31 | 27 |

TABLE 3-continued

Compounds Synthesized in Larger Quantities for Further in vitro Evaluations

| Cmpd # | Name | Structure | Amount, mg | Yields, % |
|---|---|---|---|---|
| 47 | N-(−)-cis-Myrtanyl-N'-(1R, 2R, 3R, 5S)-(−)-isopinocampheylethane-1,2-diamine | 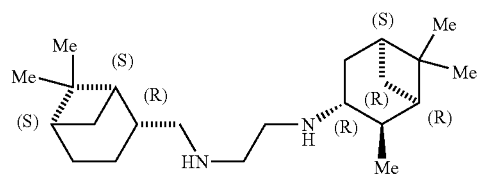 | 42 | 33 |
| 51 | N-(Cyclooctyl)-N'-(2,3-dimethylcyclohexyl)ethane-1,2-diamine | 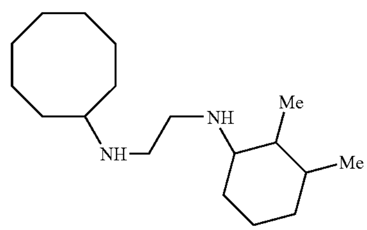 | 5.1 | 2 |
| 52 | N-(Cyclooctyl)-N'-(3,3-diphenylpropyl)ethane-1,2-diamine | 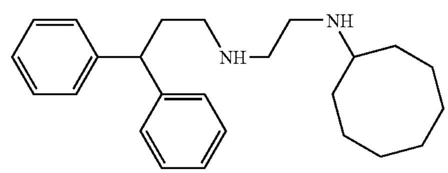 | 20 | 18 |
| 53 | N-Cyclooctyl-N'-(1S, 2S, 3S, 5R)-(+)-isopinocampheyl-ethane-1,2-diamine | 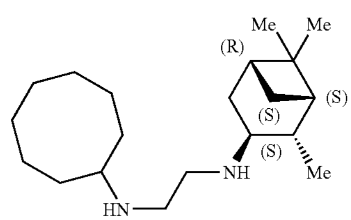 | 7.4 | 7 |
| 54 | N-Cyclooctyl-N'-(R)-(+)-bornylethane-1,2-diamine | 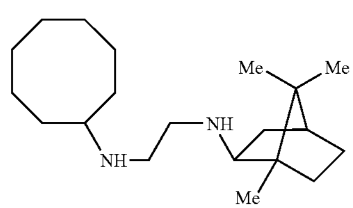 | 17 | 16 |
| 55 | N-(Cyclooctyl)-N'-(1-methyladamantyl)ethane-1,2-diamine | 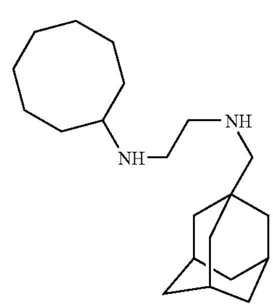 | 7 | 6 |

TABLE 3-continued

Compounds Synthesized in Larger Quantities for Further in vitro Evaluations

| Cmpd # | Name | Structure | Amount, mg | Yields, % |
|---|---|---|---|---|
| 56 | N-(Cyclooctyl)-N'-(2S)-[2-(1-hydroxybutyl)]ethane-1,2-diamine | 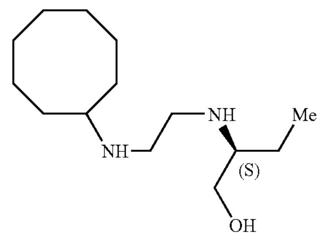 | 1.1 | 1 |
| 57 | N-(−)-cis-Myrtanyl-N'-(cyclooctyl)ethane-1,2-diamine | 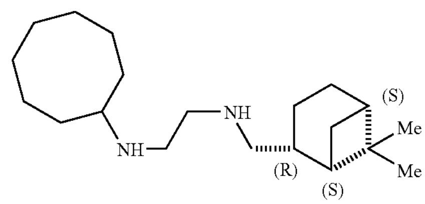 | 18 | 18 |
| 58 | N-(Cyclooctyl)-N'-(2-adamantyl)ethane-1,2-diamine | 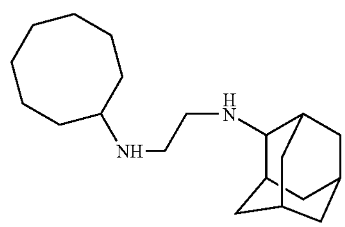 | 25 | 23 |
| 59 | N-(Cyclooctyl)-N'-(1R, 2R, 3R, 5S)-(−)-isopinocampheylethane-1,2-diamine | 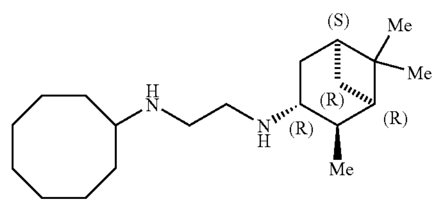 | 15 | 14 |
| 61 | N-(Cyclooctyl)-N'-[1-ethyl-(1-naphthyl)]ethane-1,2-diamine | 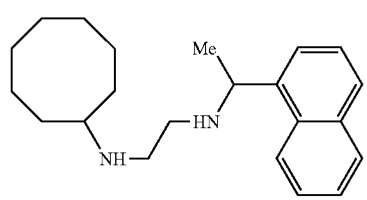 | 16 | 14 |
| 62 | N-(−)-cis-Myrtanyl-N'-(1S)-(1-ethylcyclohexane)ethane-1,2-diamine | 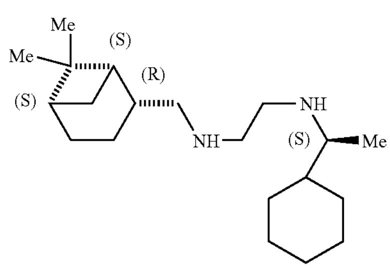 | 48 | 46 |

TABLE 3-continued

Compounds Synthesized in Larger Quantities for Further in vitro Evaluations

| Cmpd # | Name | Structure | Amount, mg | Yields, % |
|---|---|---|---|---|
| 63 | N-(Cyclooctyl)-N'-trans-(2-phenylcyclopropyl)ethane-1,2-diamine | 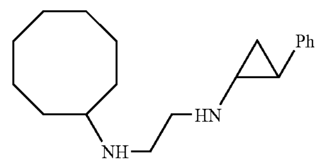 | 47 | 46 |
| 64 | N-(2-Adamantyl)-N'-trans-(2-phenylcyclopropyl)ethane-1,2-diamine | 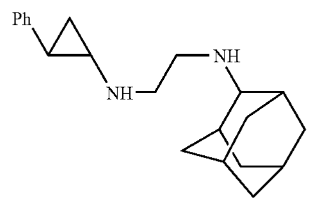 | 49 | 46 |
| 65 | N-(1-Adamantyl)-N'-trans-(2-phenylcyclopropyl)ethane-1,2-diamine | 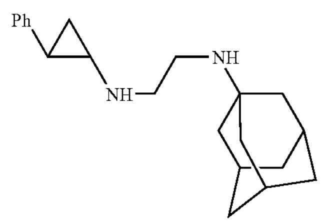 | 18 | 16 |
| 66 | N-(3,3-Diphenylpropyl)-N'-(1R, 2R, 3R, 5S)-(−)-isopinocampheylethane-1,2-diamine | 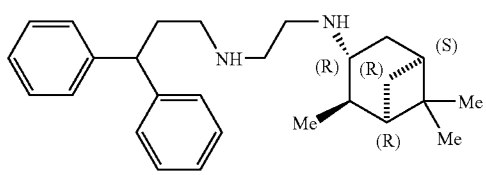 | 2.3 | 2 |
| 68 | N-(+/−)-[2-(1-Hydroxybutyl)]-N'-(1R, 2R, 3R, 5S)-(−)-isopinocampheylethane-1,2-diamine | 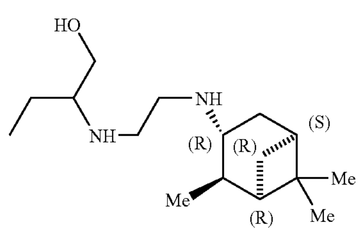 | 0.8 | 1 |
| 71 | N-(1,1-Diphenylmethyl)-N'-(1R, 2R, 3R, 5S)-(−)-isopinocampheylethane-1,2-diamine | 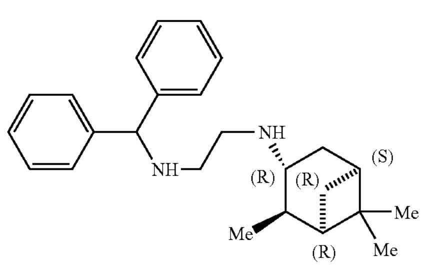 | 2.9 | 2 |

TABLE 3-continued

Compounds Synthesized in Larger Quantities for Further in vitro Evaluations

| Cmpd # | Name | Structure | Amount, mg | Yields, % |
|---|---|---|---|---|
| 73 | N-(2-Adamantyl)-N'-[2-(2-methoxyphenyl)ethyl]ethane-1,2-diamine | 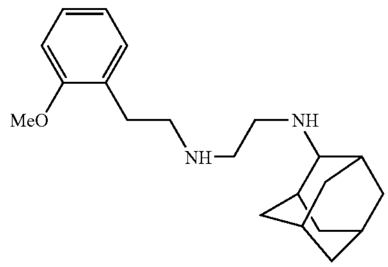 | 21 | 19 |
| 76 | N-Allyl-N-cyclopentyl-N'-[2-(2-methoxyphenyl)ethyl]ethane-1,2-diamine | 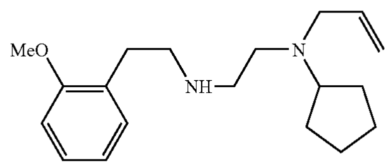 | 8 | 7 |
| 77 | N-(1,1-Diphenylmethyl)-N'-[2-(2-methoxyphenyl)-ethyl]ethane-1,2-diamine | 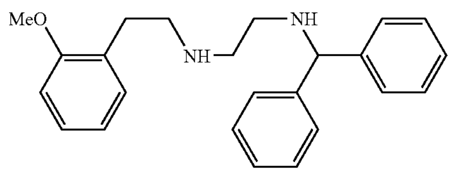 | 32 | 27 |
| 78 | N-2-Adamantyl-N'-2,3-dihydro-1H-inden-2-yl-ethane-1,2-diamine | 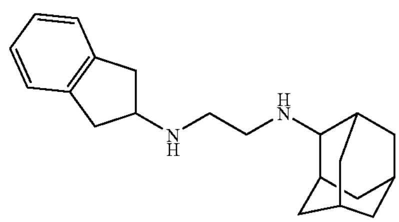 | 4.3 | 3 |
| 79 | N-[2-(2,5-Dimethoxyphenyl)-ethyl]-N'-(R)-(+)-bornylethane-1,2-diamine | 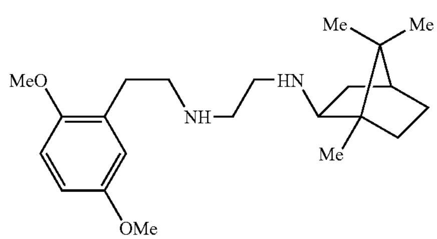 | 59 | 49 |
| 103 | N,N'-Bis(cyclooctyl)ethane-1,2-diamine | 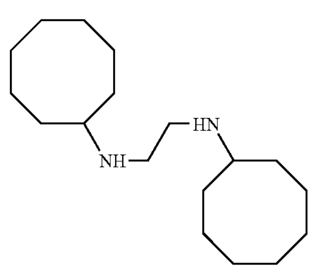 | 6.3 | 4 |

TABLE 3-continued

Compounds Synthesized in Larger Quantities for Further in vitro Evaluations

| Cmpd # | Name | Structure | Amount, mg | Yields, % |
|---|---|---|---|---|
| 107 | N-(2,2-Diphenylethyl)-N-(3-ethoxypropyl)ethane-1,2-diamine | 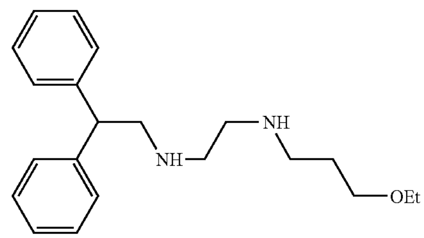 | 58 | 52 |
| 109 | N-Geranyl-N'-(2-adamanthyl)ethane-1,2-diamine | 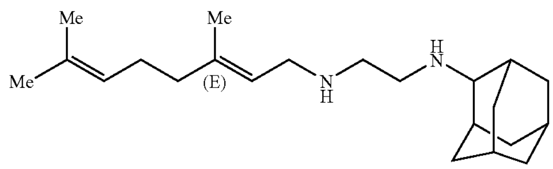 | 27 | 24 |
| 111 | N-[2-(N'-Geranyl)aminoethyl]-2-ethylpiperidine | 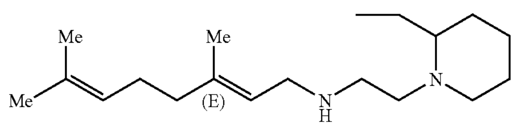 | 24 | 24 |
| 116 | N-Geranyl-N'-allyl-N'-(cyclopentyl)ethane-1,2-diamine | 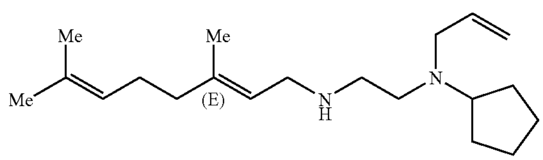 | 45 | 42 |
| 117 | N-Geranyl-N'-(1,1-diphenyl-methyl)ethane-1,2-diamine | 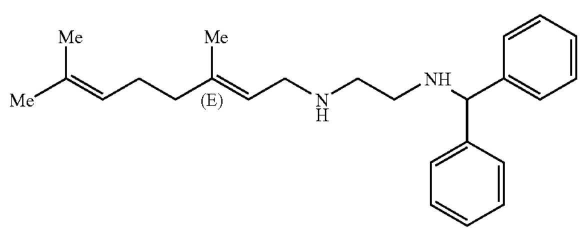 | 24 | 20 |
| 118 | N-2-(2-Chlorophenyl)ethyl-N'-allyl-N'-(cyclopentyl)ethane-1,2-diamine | 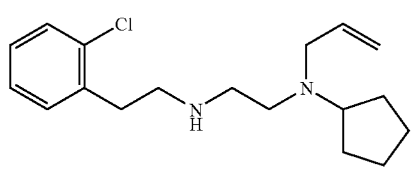 | 6.4 | 6 |
| 119 | N-2-(2-Chlorophenyl)ethyl-N'-[2-(3-fluorophenyl)-ethyl]ethane-1,2-diamine | 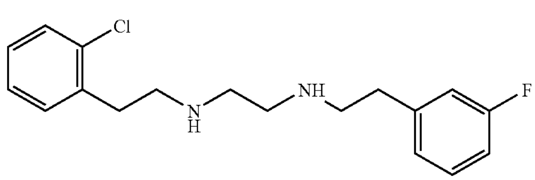 | 30 | 27 |

TABLE 3-continued

Compounds Synthesized in Larger Quantities for Further in vitro Evaluations

| Cmpd # | Name | Structure | Amount, mg | Yields, % |
|---|---|---|---|---|
| 125 | N,N'-bis-(−)-cis-Myrtanylpropane-1,2-diamine | 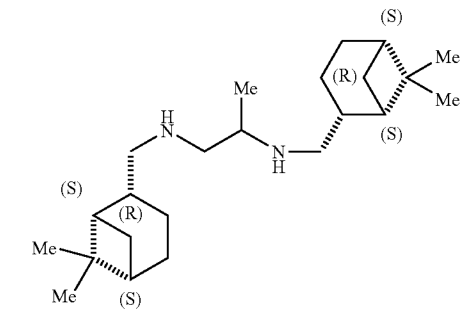 | 41 | 35 |
| 134 | N-[2-(N'-2,2-Diphenylethyl)-aminoethyl]-(−)-3,4-dihydroxynorephedrine | 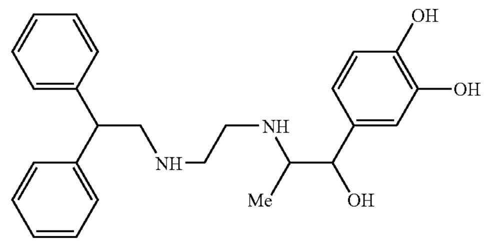 | 20 | 15 |
| 151 | N-[2-(2-Methoxy)phenylethyl]-N'-(1R, 2R, 3R, 5S)-(−)-isopinocampheyl-ethane-1,2-diamine | 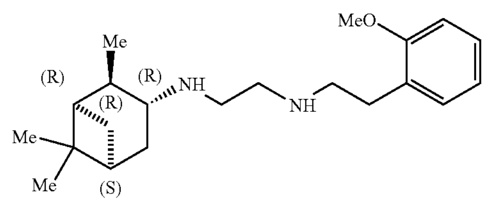 | 67 | 60 |
| 164 | $N^1$-[2-(4-fluorophenyl)ethyl]-$N^2$-[2-(4-Methoxy)phenylethyl]-1-phenylethane-1,2-diamine | 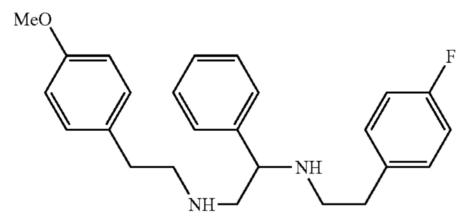 | 94 | 73 |
| 165 | N1-[2-(4-fluorophenyl)ethyl]-N2-(3-Phenylpropyl)-1-phenylethane-1,2-diamine | 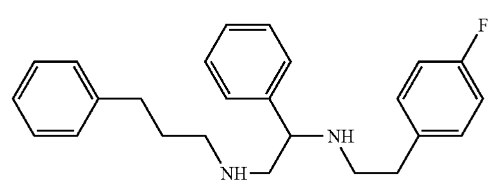 | 23 | 19 |

Figure 42:
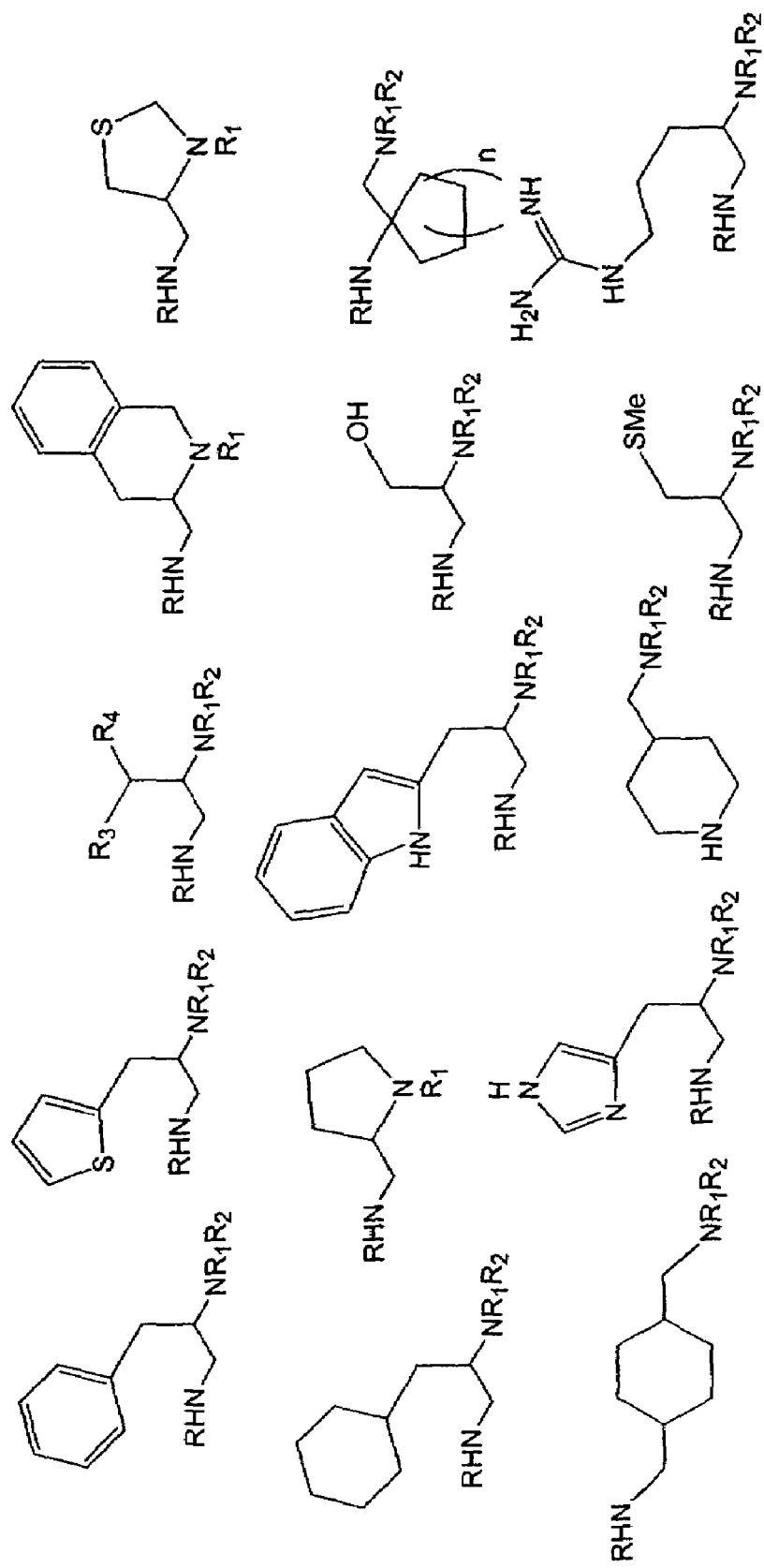
FIG. 42 provides structures of representative targeted diamines prepared via acylation by amino acids.

The present invention is also directed to a new library of diamine compounds useful against infectious disease. To further enhance the structural diversity of prior diamine compounds, a synthetic scheme to incorporate amino acids into a bridging linker between the two amine components has been developed. The use of amino acids allowed for diverse linker elements, as well as chirality see FIG. 42 for representative examples. The diamine compounds were prepared on mmol scale in 96-well format in pools of 10 compounds per well (for the vast majority of the plates). Table 25 (FIG. 43) summarizes data for the synthesized plates.

Figure 44:
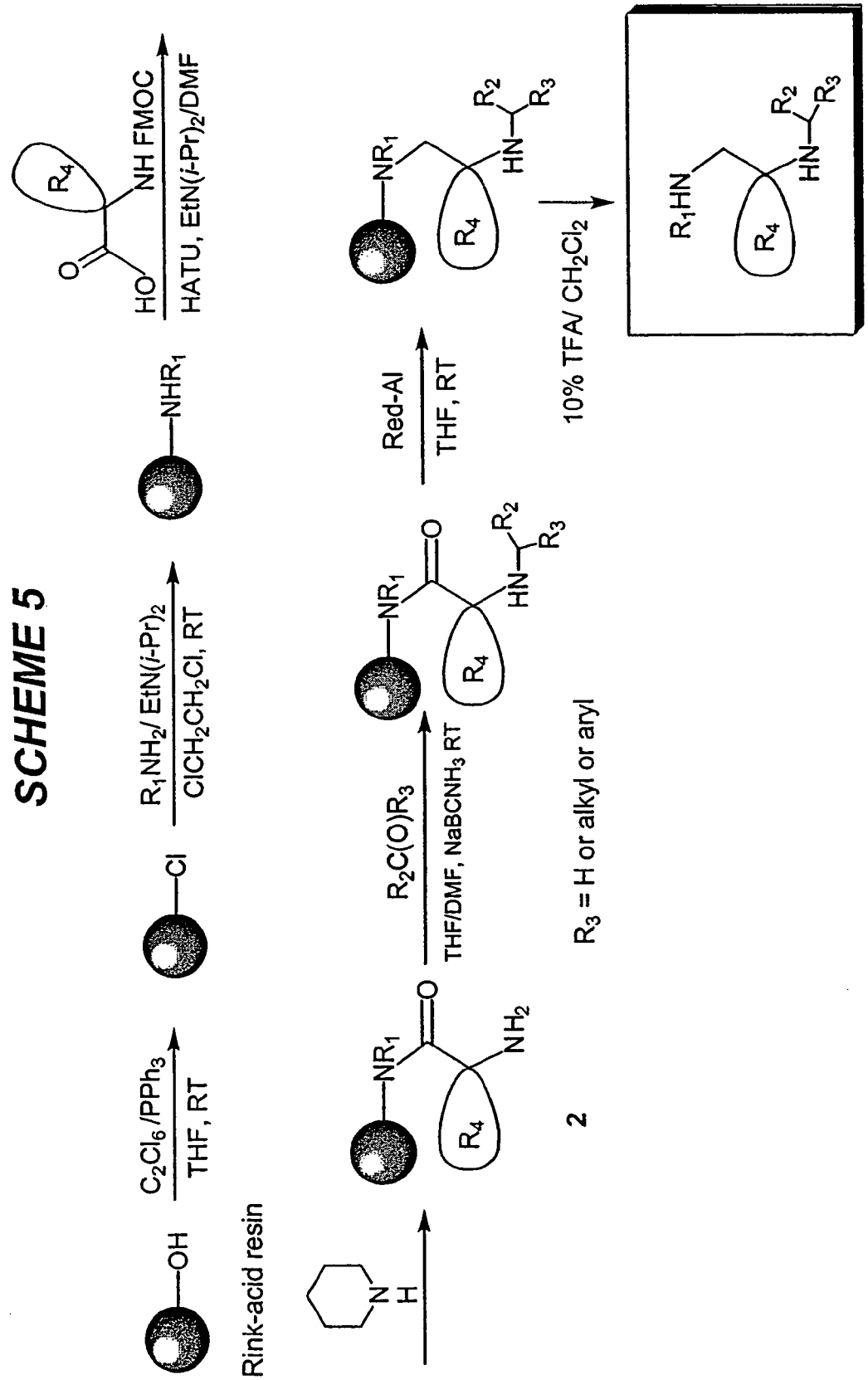
FIG. 44 provides Scheme 5 showing the synthesis of the diamine library using amino acids as linkers.

The reaction scheme followed is shown in FIG. 44.

Solid phase syntheses using Rink resin. Twenty one 96-well plates have been prepared. Six-step synthetic route starting from the Rink resin similar to what that had been used to create our first 100,000 compound library (Scheme 1, FIG. 41), was applied to make targeted diamines (Scheme 5, FIG. 44). Overall, all steps of these schemes are similar, except one (step 4) when formation of the second amino functionality occurs. In Scheme 1, the second amine is introduced into the molecule as a whole synthon via nucleophilic displacement of Cl-function of the linker, while in the Scheme 5, it proceeds through modification of the existing amino moiety by carbonyl compounds.

Figure 45:
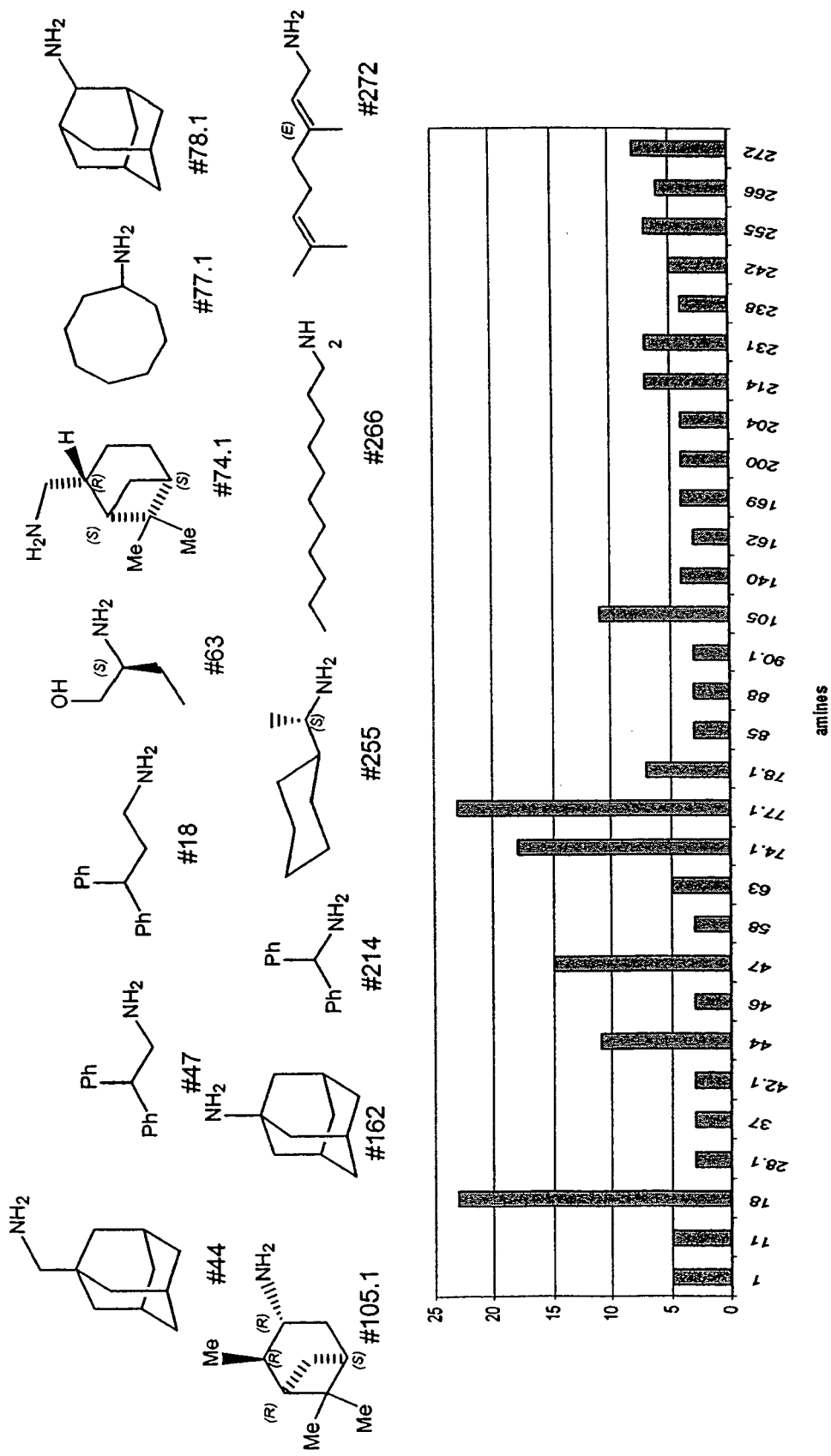
FIG. 45 provides a schematic showing the occurrence of amine monomers in the hits that were generated in the original 100,000 compound library of EMB analogs.
Figure 46:
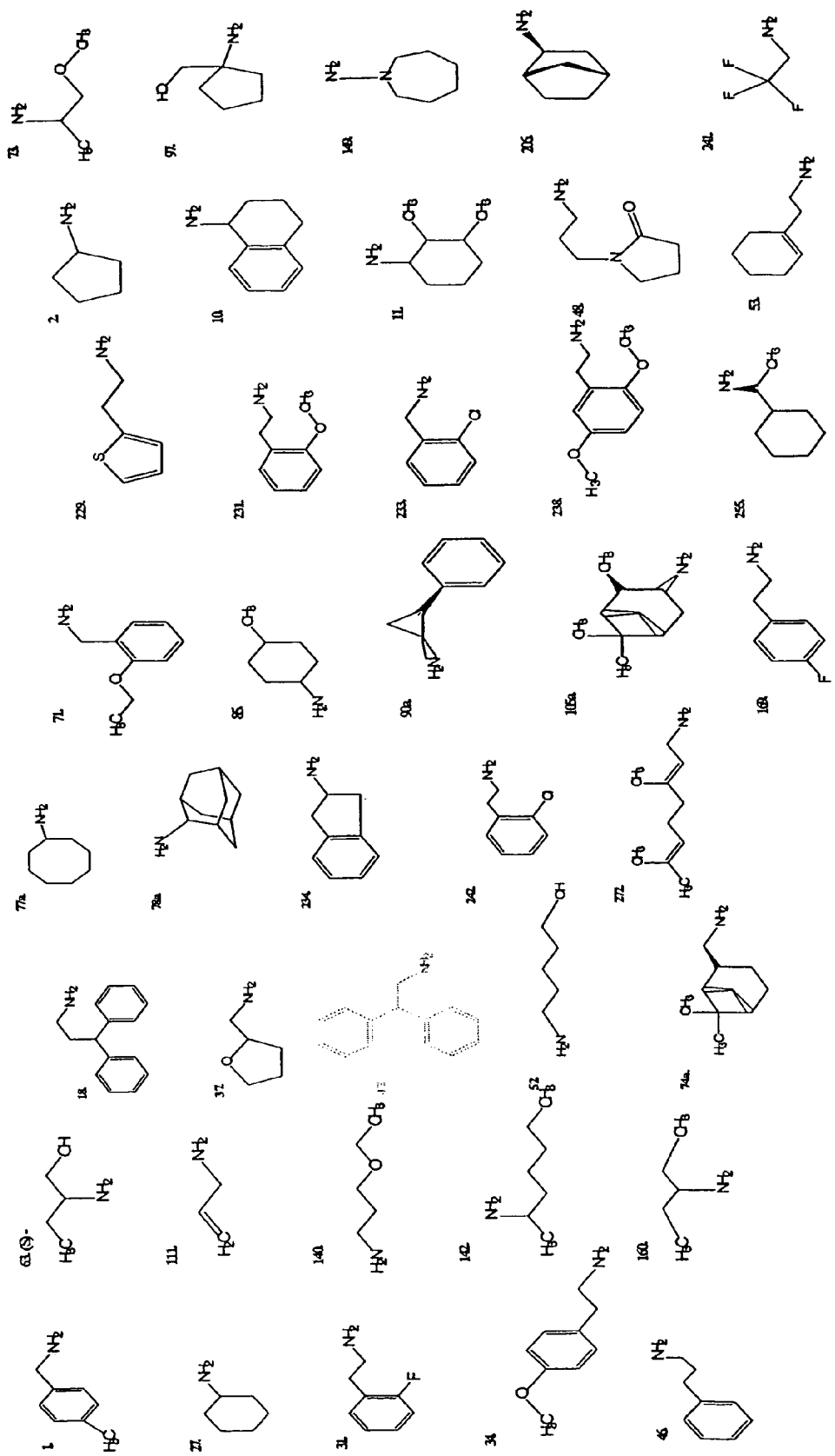
FIG. 46 provides a schematic showing structural diversity among primary amines.

Attachment of the first amine to the support was done according to the Garigipati protocol. Rink acid resin (Novabiochem) was converted into the Rink-chloride upon treatment with triphenylphosphine and dichloroethane in THF. This activated resin was then loaded by addition of an amine N1 in presence of Hunig's base in dichloroethane. The amine N1 includes, but is not limited to, alkyl and aryl primary amines. Out of 177 primary amines that had been previously used as N1 for 100,000 library preparation, only 30 were selected in this Scheme, based upon in vitro activity data of their ethylenediamine derivatives (from the previous ~100K library) as well as structural diversity (FIGS. 45 and 46).

On the next step, the acylation reaction was accomplished via peptide coupling with FMOC protected amino acids in presence of HATU (O-(7-Azabenzotriazol-1-yl)-N,N,N,N-tetramethyluronium hexafluorophosphate) and EtN(iso-Pr)$_2$ in DCM/DMF mixture at room temperature. The reaction was done twice to improve product yields. The list of the amino acids used to create this library is shown in the Table 26 (FIG. 47).

Figure 48:
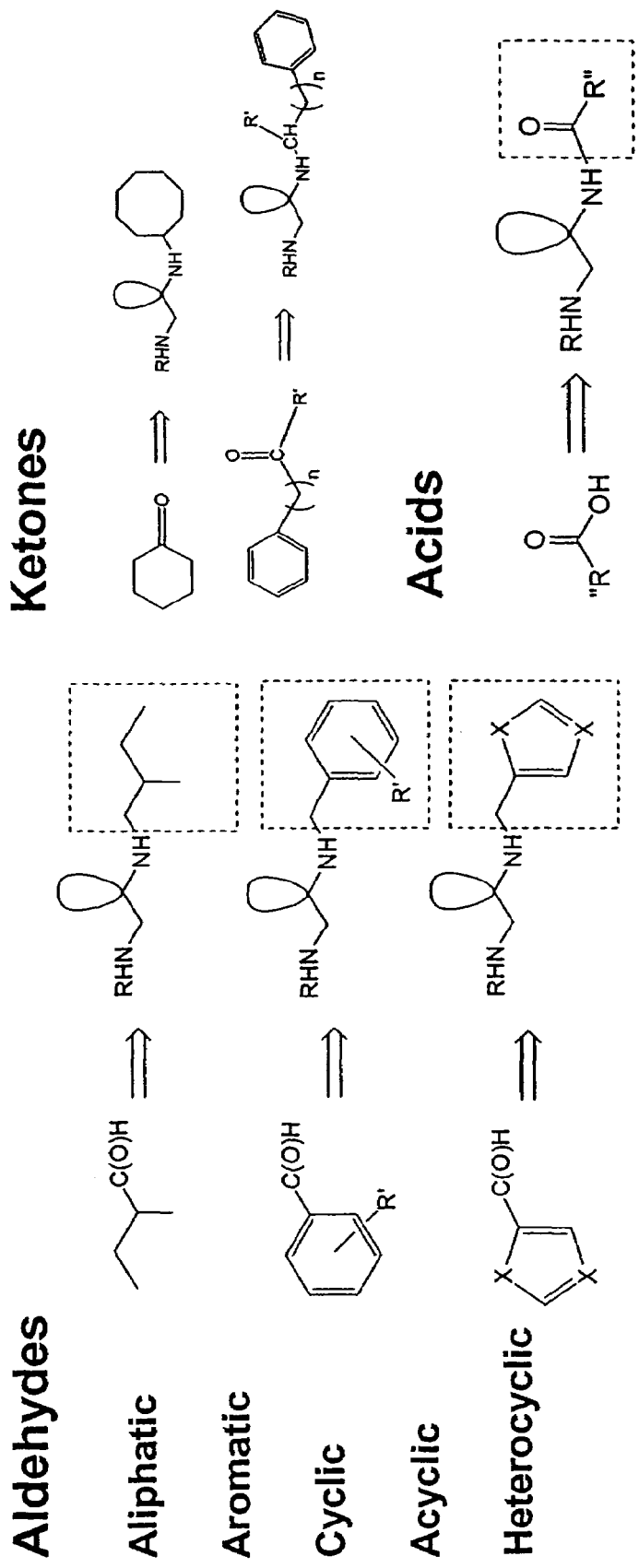
FIG. 48 provides carbonyl compounds used as reagents in the synthesis of the diamine library.
Figure 50:
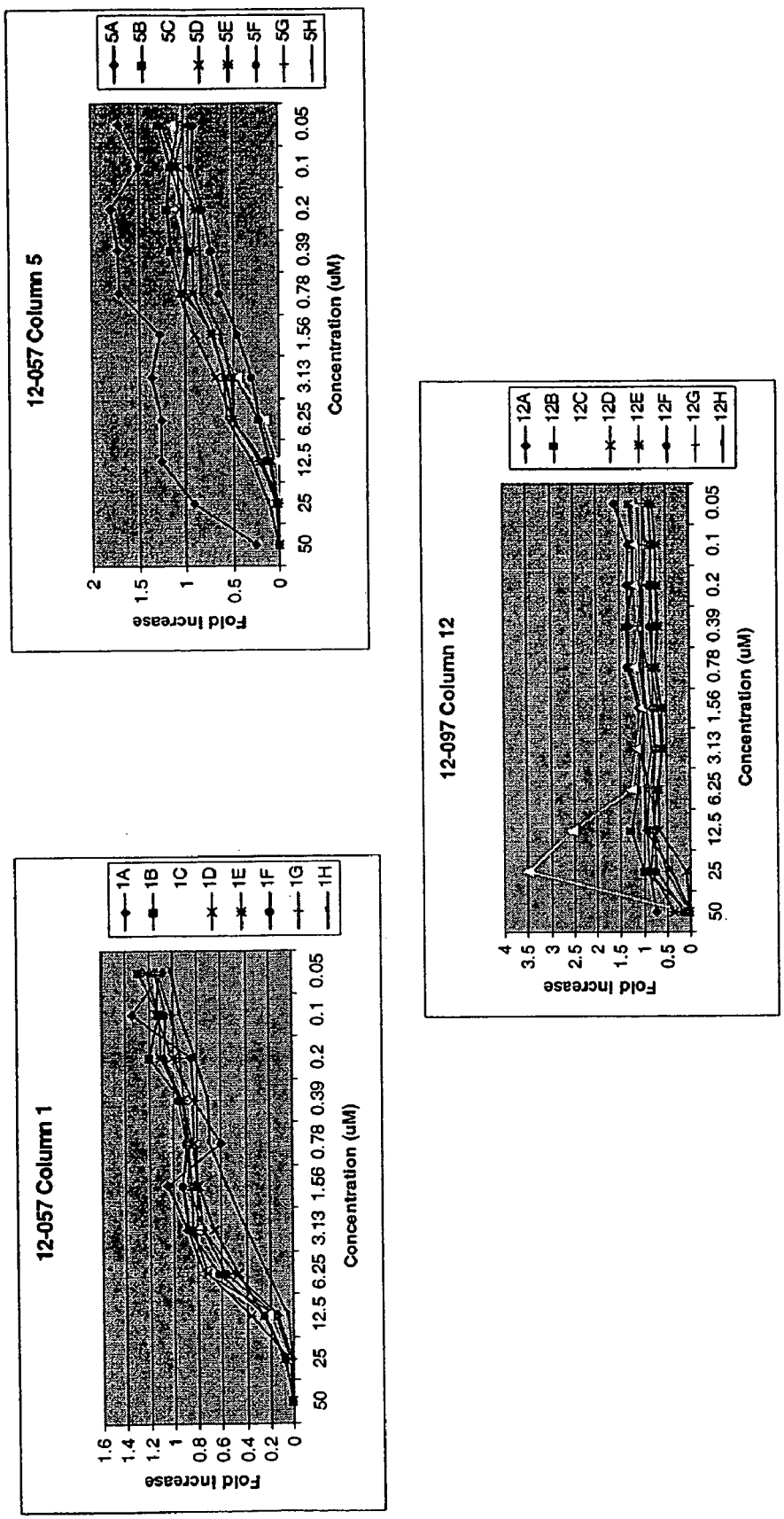
FIG. 50 provides representative examples of MIC and Lux data for the diamine library.
Figure 51:
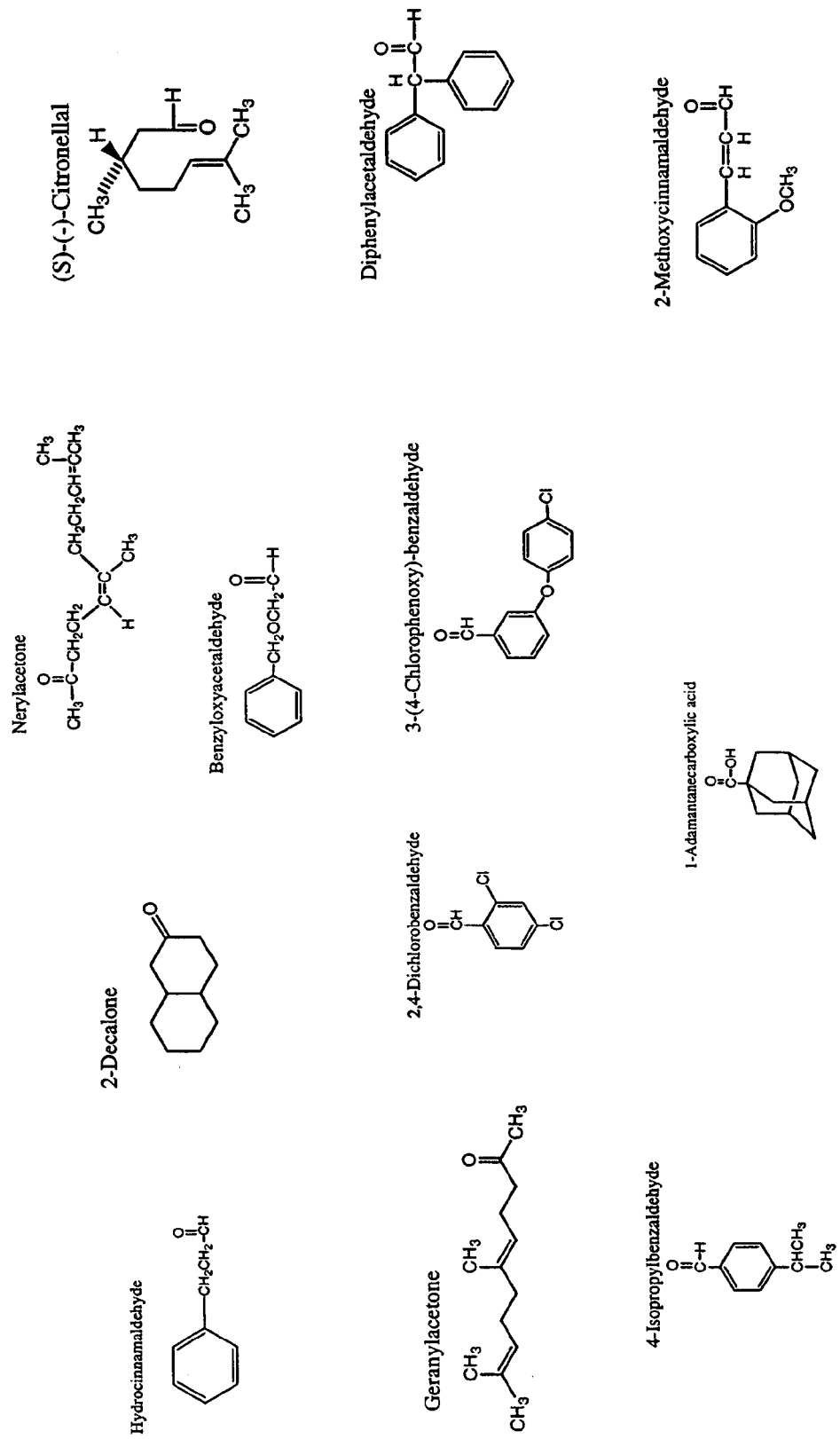
FIG. 51 provides a schematic showing the occurrence of alkylating monomers in final diamine products with anti-TB activity.

Deprotection (removal of the FMOC group) was carried out by reaction with piperidine at room temperature. Derivatization of the amino group was achieved by reductive alkylation with various carbonyl compounds, such as aldehydes, ketones, and carboxylic acids, in the presence of NaBCNH$_3$ at room temperature for 72-96 h. The selection of the carbonyl compounds was made so that the final diamine products would carry the same or similar types of substituents that had been observed in the hit compounds generated from the previous library of ethambutol analogs, as well as structural diversity (FIG. 48). A complete list of the carbonyl compounds used is shown in Table 27 (FIG. 49).

Reduction of the aminoethyleneamides into corresponding diamines was carried out using the soluble reducing reagent 65+w % Red-Al at room temperature. Cleavage of the products from the resin was achieved with a 10% solution of trifluoroacetic acid in dichloromethane resulting in the formation of TFA salts of the diamines.

For library production the first three steps of the synthetic scheme (resin activation, amine loading, and acylation) were carried out using a Quest 210 Synthesizer on scale of 0.1-0.15 g of resin per tube. Following the acylation, formed resins were thoroughly washed, dried, and then groups of ten resins were pooled together. A small amount of each resin (~0.05 g) was archived prior to pooling to facilitate re-synthesis and deconvolution of actives.

Deprotection of the FMOC group, addition of the carbonyl component, reduction, and cleavage were carried out in 96-well reaction blocks using the Combiclamps system by Whatman Polyfiltronics or the FlexChem system by Robbins Scientific. A suspension of the pooled resins in 2:1 mixture of DCM/THF was evenly distributed into one reaction plate resulting in approximately 10 mg of the resin per well. The 96 diverse carbonyl compounds were arrayed in one 96-well plate template and added, one carbonyl compound per well, to each individual pool of ten resins, resulting in an anticipated 960 diamines produced per plate. Reduction was carried out in the same format and cleavage and filtering into storage plates was followed by evaporation of the TFA prior to biological assay.

Quality assessment of the prepared compounds was done by Electrospray Ionization mass spectrometry using two randomly selected rows (16 samples) per plate, 17% of the total number. Successful production of a compound was based on an appearance of a molecular ion of the calculated mass. Depending on the amino acid that had been used for the synthesis, the percentage of the predicted ions were observed, and therefore the predicted compounds were formed, varied from 5-60% (Table 25, FIG. 43). Based on MS analysis, out of targeted 20,000 compounds, 4,500 diamines were actually formed.

As discussed herein, there is a need in the art for novel compounds and methods that are effective against infectious disease. More particularly, there is a need for novel compounds and methods for the effective treatment of Mycobacterial disease. The instant invention satisfies the long felt need of the prior art by providing novel compositions and methods that are effective in the treatment of infectious disease, including but not limited to, tuberculosis.

In one embodiment the instant invention comprises at least two novel compounds from Table 3 (compounds 1-165) for the treatment of infectious disease.

In another embodiment, the instant invention comprises one or more novel compounds of Table 3 (compounds 1-165) in combination with one or more drugs for the treatment of infectious disease.

In another embodiment, a composition comprising at least one of compound 1-165 is combined with one or more drugs for the treatment of *M. tuberculosis*.

In a further embodiment, a composition comprising one or more novel compounds selected from the group consisting of compounds 1-165 is combined with one or more drug to provide a synergistic effect that is active as a method of treating Mycobacterial disease.

In one embodiment the instant invention comprises a composition comprising one or more compounds of Table 3 in combination with at least one known standard tuberculosis drug.

In yet another embodiment a method of treating infectious disease comprises one or more compounds of Table 3 in combination with at least one known standard tuberculosis drug. While not wishing to be bound by the following theory it is believed that the combination of a standard tuberculosis drug with at least one or more of compounds comprising compounds 1-165 produces a synergistic effect resulting in the treatment or prevention of infectious disease, including but not limited to, tuberculosis.

In another embodiment, the present invention comprises a composition effective against *Mycobacterium-fortuitum*, *Mycobacterium marinum*, *Helicobacter pylori*, *Streptococcus pneumoniae* and *Candida albicans* comprising at least one compound selected from the group consisting of compounds 1-165.

Formulations

Therapeutics, including compositions containing the substituted ethylene diamine compounds of the present invention, can be prepared in physiologically acceptable formulations, such as in pharmaceutically acceptable carriers, using known techniques. For example, a substituted ethylene diamine compound is combined with a pharmaceutically acceptable excipient to form a therapeutic composition.

The compositions of the present invention may be administered in the form of a solid, liquid or aerosol. Examples of solid compositions include pills, creams, soaps and implantable dosage units. Pills may be administered orally. Therapeutic creams and anti-mycobacteria soaps may be administered topically. Implantable dosage units may be administered locally, for example, in the lungs, or may be implanted for systematic release of the therapeutic composition, for example, subcutaneously. Examples of liquid compositions include formulations adapted for injection intramuscularly, subcutaneously, intravenously, intraarterially, and formulations for topical and intraocular administration. Examples of aerosol formulations include inhaler formulations for administration to the lungs.

A sustained release matrix, as used herein, is a matrix made of materials, usually polymers, which are degradable by enzymatic or acid/base hydrolysis, or by dissolution. Once inserted into the body, the matrix is acted upon by enzymes and body fluids. The sustained release matrix is chosen desirably from biocompatible materials, including, but not limited to, liposomes, polylactides, polyglycolide (polymer of glycolic acid), polylactide co-glycolide (coplymers of lactic acid and glycolic acid), polyanhydrides, poly(ortho)esters, polypeptides, hyaluronic acid, collagen, chondroitin sulfate, carboxylic acids, fatty acids, phospholipds, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide.

The dosage of the composition will depend on the condition being treated, the particular composition used, and other clinical factors, such as weight and condition of the patient, and the route of administration. A suitable dosage may range from 100 to 0.1 mg/kg. A more preferred dosage may range from 50 to 0.2 mg/kg. A more preferred dosage may range from 25 to 0.5 mg/kg. Tablets or other forms of media may contain from 1 to 1000 mg of the substituted ethylene diamine. Dosage ranges and schedules of administration similar to ethambutol or other anti-tuberculosis drugs may be used.

The composition may be administered in combination with other compositions and procedures for the treatment of other disorders occurring in combination with mycobacterial disease. For example, tuberculosis frequently occurs as a secondary complication associated with acquired immunodeficiency syndrome (AIDS). Patients undergoing AIDS treatment, which includes procedures such as surgery, radiation or chemotherapy, may benefit from the therapeutic methods and compositions described herein.

The following specific examples will illustrate the invention as it applies to the particular synthesis of the substituted ethylene diamine compounds, and the in vitro and in vivo suppression of the growth of colonies of *M. tuberculosis*. In additiona, the teachings of R. Lee et al. J. Comb. Chem 2003, 5, 172-187 are hereby incorporated by reference in their entirety. It will be appreciated that other examples, including minor variations in chemical procedures, will be apparent to those skilled in the art, and that the invention is not limited to these specific illustrated examples.

EXAMPLE I

Generating the Ethylene Diamine Library

The Rink-acid resin was obtained from NOVABIOCHEM® Inc., San Diego, Calif. Solvents: acetonitrile, dichloromethane, dimethylformamide, ethylenedichloride, methanol and tetrahydrofuran were purchased from ALDRICH®, Milwaukee, Wis., and used as received. All other reagents were purchased from SIGMA-ALDRICH®, West Monroe Highland, Ill. Solid phase syntheses were performed on a QUEST® 210 Synthesizer, from ARGONAUT TECHNOLOGIES®, Foster City, Calif., with the aid of combinatorial chemistry equipment, from WHATMAN® POLYFILTRONICS® (Kent, England; Rockland, Mass.) and ROBBINS SCIENTIFIC®, Sunnyvale, Calif. Evaporation of solvents was done using SPEEDVAC® AES, from SAVANT®, Holbrook, N.Y. All necessary chromatographic separations were performed on a WATERS' ALLIANCE HT SYSTEM®, Milford, Mass. Analytical thin-layer chromatography was performed on MERCK® silica gel $60F_{254}$ plates, purchased from SIGMA-ALDRICH®, West Monroe Highland, Ill.

The activation of the Rink-acid resin, the addition of the first amine, and the acylation step were carried out in 10 ml tubes using the QUEST® 210 Synthesizer. The addition of the second amine, the reduction with Red-AL, and the cleavage from the solid support were carried out in 96-deep (2 ml) well, chemically resistant plates.

A. Activation of the Rink-Acid Resin

The Rink-acid resin had a coverage of 0.43-0.63 mmol of linker per gram resin. Four to five grams of this resin were suspended in 80 ml of a 2:1 mixture of dichloromethane and tetrahydrofuran (THF), and distributed into ten, 10 ml tubes, with 8 ml of resin suspension per tube. Each suspension was filtered and washed twice with THF. A solution of triphenylphosphine (3.80 g, 14.5 mmol) in 30 ml of THF was prepared, and 3 ml of this solution was added to each tube, followed by the addition of 3 ml of a solution of hexachloroethane in THF (3.39 g/14.3 mmol hexachloroethane in 30 ml THF). After agitation for six hours at room temperature, each activated resin was washed twice with THF and twice with dichloromethane.

B. Addition of the First Amine

Each tube, containing the activated rink resin, was charged with 3 ml of dichloroethane, 0.3 ml (1.74 mmol) $N_1$N-diisopropylethylamine ($EtN(iPr)_2$) and the corresponding amine (around 1 mmol). If the selected amine was a solid at room temperature, it was added as a solution, or a suspension in DMF. Enough dichloroethane was added to each tube for a final volume of 8 ml. The reaction mixture was heated at 45° C. for 6-8 hours. The resins were filtered, washed with a 2:1 mixture of dichloromethane and methanol (1×8 ml), then with methanol (2×8 ml), and then dried under argon for 10 minutes.

C. Acylation with the Halo-Acylchloride a. Acylation with Chloroacetyl Chloride. Each resin was prewashed with THF (2×8 ml), and then charged with THF (8 ml), pyridine (0.3 ml, 3.67 mmole) and chloroacetyl chloride (0.25 ml, 2.5 mmole). The reaction mixture was stirred for 8 hours at 45° C., and then for 6-8 hours at room temperature. Each resin was filtered, washed with a 2:1 mixture of dichloromethane/methanol (1×8 ml), methanol (2×8 ml) and THF (2×8 ml). The acylation was repeated using the same loading of reagents, but a shorter reaction time of 4 hours at 45° C., and 2 hours at room temperature. Each resin was then filtered, washed with a 2:1 mixture of dichloromethane and methanol (1×8 ml), and then with methanol (3×8 ml). Each resin was dried under argon for 10 minutes. Each resin was then transferred into a vial and dried in a desiccator under vacuum for 1 hour.

b. Acylation with α-Phenyl-α-Chloroacetyl Chloride. The same procedure set out for the acylation with chloroacetyl chloride was used. A 2.5 mmol excess of α-phenyl-α-chloroacetyl chloride, relative to mmol amount of linker in the rink-acid resin, was used.

c. Acylation with α-Halo-α-Methyl; α-Halo-α-Ethyl and α-Halo-α-Butylacetyl Bromide. A 1:1:1 mixture (by volume) of the α-bromoproponyl bromide ($R_4$=Me), α-bromobutyryl bromide ($R_4$=Et), and α-bromohexanoyl bromide ($R_4$=Bu) was used to give a molar ratio of 0.52:0.56:0.42 (in mmols).

This resulted in a molar excess of 1.65, 1.75 and 1.31, respectively, if the original coverage of the resin was 0.63 mmol/g (0.5 g resin per tube), and 2.4, 2.6 and 1.9 if the original coverage of the resins was 0.43 mmol/g (0.5 g resin per tube).

d. Acylation with α-Chloro-α-Methyl Acetic acid. Each resin was prewashed with dichloromethane. Each tube was charged with 3 ml of a solution of PyBrop (0.29 g, 0.62 mmole) in dichloromethane, a solution of the α-chloro-α-methylacetic acid (0.095 g, 0.62 mmole) in 3 ml of DMF, and EtN(iPr)$_2$ (0.2 ml, 1.2 mmole). Each reaction mixture was allowed to react for 16-18 hours at room temperature. Each resin was then filtered, washed with dichcloromethane (2×8 ml) and methanol (2×8 ml), and the acylation was repeated. Each resin was then filtered, washed with dichloromethane (2×8 ml), methanol (3×8 ml), and dried under argon for about 10 minutes. Each resin was transferred into a vial, and dried in a desiccator under vacuum for one hour.

D. Addition of the Second Amine

Ten, or thirty prepared α-haloacetyl amide resins from the first three steps were pooled together, leaving 0.05-0.10 gram of each individual resin for necessary deconvolutions. A suspension of the pooled resin mixture in 100 ml of a 2:1 mixture of dichloromethane and THF was distributed into one, two or three, 96-well reaction plates. For one reaction plate, 1.7 to 2.0 grams of resin were used. For two reaction plates, 3.0 to 3.3 grams of resin were used, and for three reaction plates, 4.7 to 5.0 grams of resin were used. The distributed suspension was then filtered using a filtration manifold, a small light-weight manifold that is generally used for drawing solvents and reagents from the chambers of the 96-well reaction plates. The reaction plates were transferred into COMBICLAMPS® (Huntington, W. Va.), and 10% EtN(iPr)$_2$ in DMF was added at 0.2 ml per well (0.21 mmole of EtN(iPr)$_2$ per well), followed by the addition of a 1.0M solution of the appropriate amine from the corresponding master plate, 0.1 ml per well (0.1 mmole amine per well). The COMBICLAMPS® are used to accommodate 96-well reaction plates during synthesis, allowing for the addition of reagents into the plates, and a proper sealing that maintains reagents and solvents for hours at elevated temperatures. These clamps consist of a top and bottom cover provided with changeable, chemically resistant sealing gaskets. They are designed to accommodate 96-well reaction plates between the top and bottom covers. The reaction plates were sealed and kept in an oven at 70-75° C. for 16 hours. After cooling to room temperature, the resins were filtered, washed with a 1:1 mixture of DCM/methanol (1×1 ml), methanol (2×1 ml), and then dried in a desiccator under vacuum for 2 hours.

E. Reduction with Red-Al

The reaction plates were placed into COMBICLAMPS®. A 1:6 mixture of Red-Al (65+w % in toluene) and THF was added, at 0.6 ml per well (0.28 mmole of Red-Al per well), and allowed to react for 4 hours. Each resin was then filtered, washed with THF (2×1 ml), and methanol (3×1 ml). The addition of methanol should proceed with caution. Each resin was then dried under vacuum.

F. Cleavage of Final Ethylene Diamine Compound

This step was carried out using a cleavage manifold, a Teflon coated aluminum, filter/collection vacuum manifold, designed for recovering cleavage products from the reaction plates into collection plates. The manifold is designed to ensure that the filtrate from each well is directed to a corresponding well in a receiving 96-well collection plate. The reaction plates (placed on the top of the collection plates in this manifold) were charged with a 10:85:5 mixture of TFA, dichloromethane, and methanol (0.5 ml of mixture per well). After fifteen minutes, the solutions were filtered and collected into proper wells on the collection plates. The procedure was repeated. Solvents were evaporated on a SPEED VAC®, Holbrook, N.Y., and the residual samples (TFA salts) were tested without further purification.

EXAMPLE II

Deconvolution Example

Deconvolution of the active wells was performed by re-synthesis of discrete compounds, from the archived α-haloacetyl amide resins (10 resins, 0.05-0.10 g each), which were set aside at the end of the acylation step before the pooling. Each resin was assigned a discrete column (1, or 2, or 3, etc., see the template) in a 96 well filterplate, and was divided between X rows (A, B, C, etc), where X is the number of hits discovered in the original screening plate. To each well, in a row, a selected N2 (R$_3$R$_2$NH) hit amine (0.1 mmol), DMF (180 ml) and EtNiPr$_2$ (20 ml) were added: the first selected amine was added to the resins in the row "A", the second amine—to the resins in the row "B", the third amine—to the resins in the row "C", etc. A lay-out of a representative 96-well filter plate is shown in Table 4.

Deconvolution of the active wells was performed by re-synthesis of discrete compounds, from the archived α-haloacetyl amide resins (10 resins, 0.05-0.10 g each), which were set aside at the end of the acylation step before the pooling. Each resin was assigned a discrete column (1, or 2, or 3, etc., see the template) in a 96 well filterplate, and was divided between X rows (A, B, C, etc), where X is the number of hits discovered in the original screening plate. To each well, in a row, a selected N2 (R$_3$R$_2$NH) hit amine (0.1 mmol), DMF (180 ml) and EtNiPr$_2$ (20 ml) were added: the first selected amine was added to the resins in the row "A", the second amine—to the resins in the row "B", the third amine—to the resins in the row "C", etc. A lay-out of a representative 96-well filter plate is shown in Table 4.

The reaction plates were sealed and kept in an oven at 70-75° C. for 16 hours. After cooling to room temperature, the resins were filtered, washed with a 1:1 mixture of DCM and methanol (1×1 ml), methanol (2×1 ml), and dried in desiccator under vacuum for 2 h. Reduction and cleavage were performed according to steps 5 and 6 in the original synthetic protocol. The product wells from the cleavage were analyzed by ESI-MS (Electro Spray Ionization Mass Spectroscopy) to ensure the identity of the actives, and were tested in the same Luc and MIC assays.

TABLE 4

| | | | | | | | | | | |
|---|---|---|---|---|---|---|---|---|---|---|
| Lay-Out of Representative 96-Well Filter Plate | | | | | | | | | | |
| A1 | A2 | A3 | A4 | A5 | A6 | A7 | A8 | A9 | A10 | Selected amine N2, Added to A1-A10 |
| B1 | B2 | B3 | B4 | B5 | B6 | B7 | B8 | B9 | B10 | Selected amine N2, Added to B1-B10 |

TABLE 4-continued

Lay-Out of Representative 96-Well Filter Plate

| C1 | C2 | C3 | C4 | C5 | C6 | C7 | C8 | C9 | C10 | Selected amine N2, Added to C1-C10 |
|---|---|---|---|---|---|---|---|---|---|---|
| D1 | D2 | D3 | D4 | D5 | D6 | D7 | D8 | D9 | D10 | Selected amine N2, Added to D1-D10 |
| E1 | E2 | E3 | E4 | E5 | E6 | E7 | E8 | E9 | E10 | Selected amine N2, Added to E1-E10 |
| F1 | F2 | F3 | F4 | F5 | F6 | F7 | F8 | F9 | F10 | Selected amine N2, Added to F1-F10 |
| G1 | G2 | G3 | G4 | G5 | G6 | G7 | G8 | G9 | G10 | Selected amine N2, Added to G1-G10 |
| H1 | H2 | H3 | H4 | H5 | H6 | H7 | H8 | H9 | H10 | Selected amine N2, Added to H1-H10 |
| Resin #1 | Resin #2 | Resin #3 | Resin #4 | Resin #5 | Resin #6 | Resin #7 | Resin #8 | Resin #9 | Resin #10 | *X* selected Amines N2 to be added on the step 4 Individual resins ##1-10, preloaded with proper amine N1. |

EXAMPLE III

Solid-Phase Synthesis of Selected Substituted Ethylenediamine Compounds Using the QUEST® 210 Synthesizer The solid-phase protocol described above in Example I was applied to the scaled-up synthesis of the selected substituted ethylene diamine compounds. Here, all reaction steps, from the activation of the Rink-acid resin to the cleavage of the final product, were carried out using the QUEST® instrument only, which allowed for the simultaneous syntheses of twenty parallel reactions. Purification of all crude samples was done by HPLC to yield desirable products in purity greater than 90%. Table 3 lists the scale-ups of substituted ethylene diamines. Here, the synthesis of one of the active compounds, N-Geranyl-N'-(2-adamanthyl)ethane-1,2-diamine is described below as an example.

Figure 12:
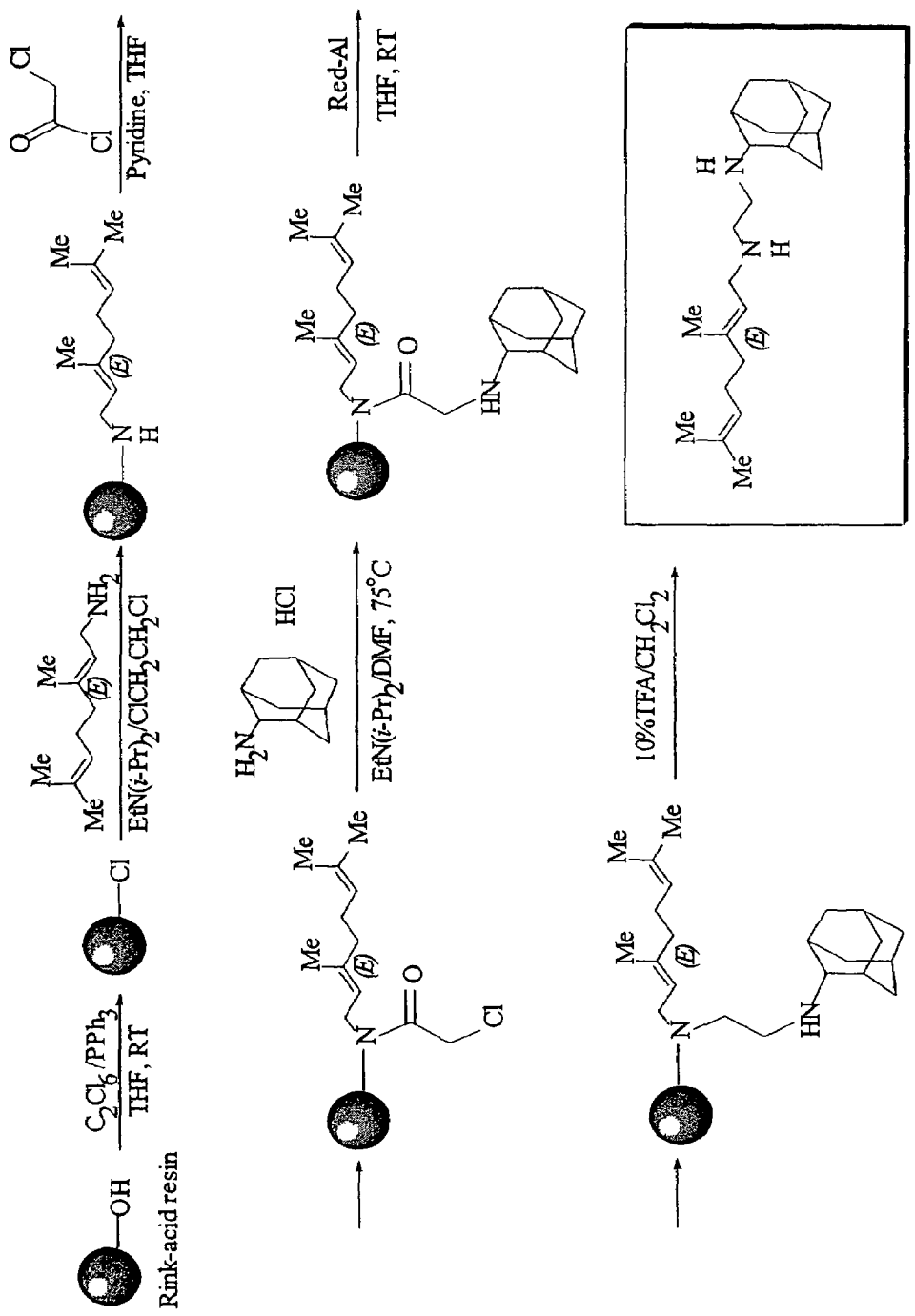
FIG. 12 represents a flow schematic showing a synthesis of N-Geranyl-N'-(2-adamanthyl)ethane-1,2-diamine (compound 109).

The Preparation of N-Geranyl-N'-(2-adamanthyl)ethane-1,2-diamine (compound 109) is set forth in FIG. 12.

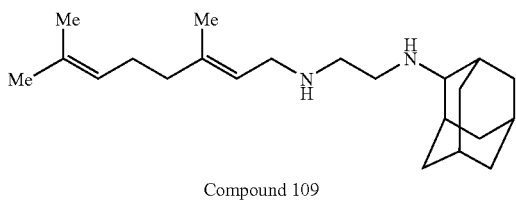

Compound 109

1. Activation of the Rink-acid resin. Synthesis of Rink-C1 resin. Rink-acid resin, coverage (linker) of 0.43 to 0.63 mmol/g (0.8 g, 0.5 mmol), was placed into one of the 10 ml tubes of QUEST® 210 Synthesizer, and washed twice with THF. A solution of triphenylphosphine (0.380 g, 1.45 mmol) in THF (3 ml) was added, followed by the addition of a solution of hexachloroethane (0.4 g, 1.43 mmol) in THF (3 ml). THF was added up to the volume of the tube (approximately 2 ml). After 6 hours, the resin was filtered, washed with THF (2×8 ml) and dichloromethane (2×8 ml).

2. Addition of the first amine. Synthesis of resin attached geranylamine. The tube with activated resin was charged with 3 ml of dichloroethane, EtN(iPr)$_2$, (0.3 ml, 1.74 mmol), and geranylamine (0.230 g, 1.5 mmol). Dichloroethane was added to a volume of 8 ml. The reaction was carried for 8 hours at 45° C., and for 6-8 hours at room temperature. Geranylamine loaded resin was filtered, washed with a 2:1 mixture of dichloromethane and methanol (1×8 ml), then with methanol (2×8 ml), and suck dried for 10 minutes under argon.

3. Acylation with chloroacetyl chloride. Synthesis of resin attached N-Geranyl-α-chloroacetamide. The resin was prewashed with THF (2×8 ml). The tube was charged with 8 ml of THF, pyridine (0.3 ml, 3.67 mmol), and chloroacetyl chloride (0.2 ml, 2.5 mmol), and allowed to stir for 8 h at 45° C., and 6-8 h at room temperature (RT). After the reaction was complete, the resin was filtered, washed with a 2:1 mixture of dichloromethane and methanol (1×8 ml), methanol (2×8 ml), and THF, and the acylation was repeated using the same loads of the reagents, but shorter reaction time: 4 hours at 45° C. and 2 hours at room temperature. At the end, the α-chloroacetamide loaded resin was filtered, washed with a 2:1 mixture of dichloromethane and methanol (1×8 ml), methanol (3×8 ml), and suck dried for 15 min under argon.

4. Addition of the second amine. Synthesis of resin attached N-Geranyl-N'-(2-adamantyl)acetamide. The tube with the resin was charged with DMF (3 ml) and EtN(iPr)$_2$ (0.6 ml, 4.4 mmol), followed by the addition of a suspension of 2-adamantamine hydrochloride (2.0 g, 1.1 mmol) in DMF (4 ml), and was allowed to stir at 70-75° C. for 16 hours. After cooling down to the room temperature, the resin was filtered, washed with a 1:1 mixture of DCM and methanol (1×8 ml), methanol (2×8 ml), and suck dried for 15 minutes under argon.

5. Reduction with Red-Al. Synthesis of resin attached N-Geranyl-N'-(2-adamantyl)ethane-1,2-diamine. The resultant resin was suspended in anhydrous THF (3 ml) in a tube, and stirred for 15 min. Commercially available Red-Al, 65+w % in toluene, was added (2.0 ml, 6.4 mmol), followed by addition of 2-3 ml of anhydrous THF (to fill up the volume of the tube). The mixture was allowed to react for 4 hours. After the reaction, the resin was filtered, washed with THF (1×8 ml), a 1:1 mixture of THF and methanol (1×8 ml) (addition of MeOH should proceed with caution), methanol (3×8 ml), and then dried.

6. Cleavage from the resin and purification. Synthesis of N-Geranyl-N'-(2-adamanthyl)ethane-1,2-diamine acetate. For this last step of the synthesis, the tube with the resin was charged with a 10:90 mixture of TFA and dichloromethane, and the formed bright red suspension was allowed to stir for 30 min. After addition of MeOH (0.5 ml), the colorless suspension was filtered, and the filtrate was collected into a proper tube. The procedure was repeated, and solvents were evaporated on a SPEEDVAC®. Half of the amount of crude N-Geranyl-N'-(2-adamanthyl)ethane-1,2-diamine (in a form of trifluoroacetate salt) was purified by HPLC using following conditions: column C18, flow 4 ml/min, 30 min run, gradient starting with 5% AcOH/MeOH (100%) finishing up with acetonitrile (100%). Obtained: 27 mg of N-Geranyl-N'-(2-adamanthyl)ethane-1,2-diamine diacetate, 24% yield, 98% purity by NMR.

EXAMPLE IV

Representative Solution Phase Synthesis of the Active Compounds

Figure 13:
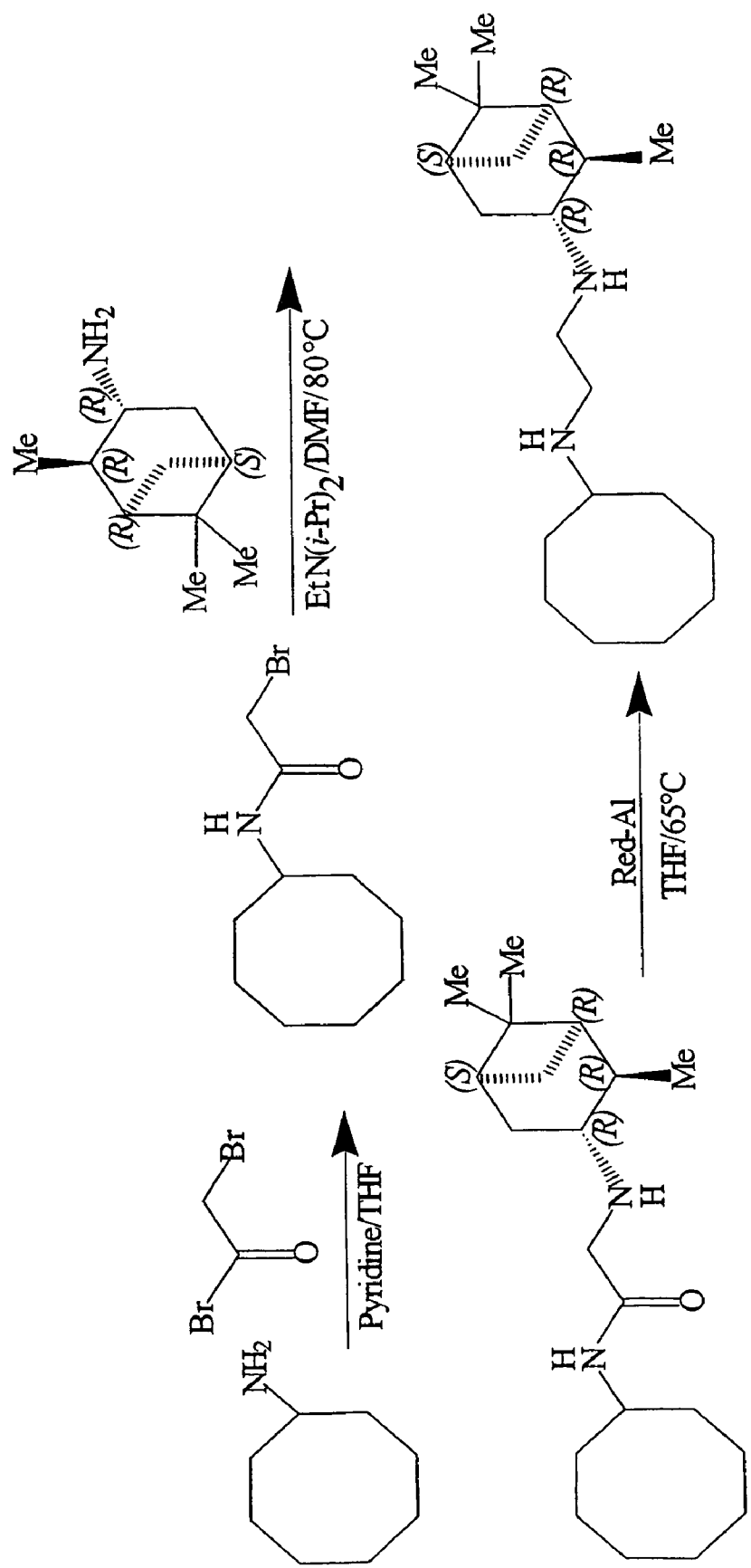
FIG. 13 is a flow schematic showing a synthesis of N-(Cyclooctyl)-N'-(1R,2R,3R,5S)-(−)-isopinocampheylethane-1, 2-diamine as hydrochloride (compound 59).

Preparation of N-(Cyclooctyl)-N'-(1R,2R,3R, 5S)-(−)-isopinocampheylethane-1,2-diamine as hydrochloride (compound 59) is set forth in FIG. 13.

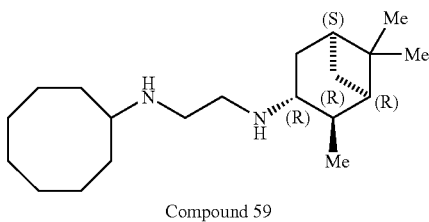

Compound 59

Bromocyclooctylacetylamide. To a mixture of cyclooctylamine (3.3 g, 0.026 mol) and pyridine (2.42 g, 0.031 mmol) in anhydrous THF (80 ml) at 0° C. was added dropwise, via syringe, bromoacetylbromide (5.78 g, 0.029 mol). The reaction temperature was maintained by an ice bath. The reaction mixture was allowed gradually to warm up to room temperature, and was stirred at room temperature for 1 hour. The precipitate was removed by filtration, washed with ethyl ether (1×30 ml), and the filtrate was concentrated to dryness on a rotory evaporator. Bromocyclooctylacetylamide was forwarded to the second step without additional purification.

N-(Cyclooctyl)-N'-(1R,2R,3R,5S)-(−)-isopinocampheyl-1-carbonylethane-1,2-diamine. To a solution of the bromocyclooctylacetylamide in DMF (60 ml) were added Hunig's base (4.64 g, 0.036 mol) and (1R,2R, 3R, 5S)-(−)-isopinocampheylamine (4.5 g, 0.029 mol), and the reaction mixture was stirred at 80° C. for 16 hours. After cooling off to the room temperature, the reaction mixture was diluted with 150 ml of ethyl ether, and washed with 1M NaOH solution (2×50 ml). The organic layer was washed with brine (1×50 ml), dried over MgSO$_4$, and concentrated to dryness on the rotory evaporator. The residue (11.04 g) as brown oil was purified on COMBIFLASK® (Isco, Lincoln, Nebr., USA), using Silicagel catridges commercially available from BIOTAGE® (Biotage, Inc. of Dyax Corp, Va, USA), and the following mobile phase gradient: 30 min run, starting with DCM, 100%, and finishing up with a mixture DCM:MeOH:NH$_4$OH (600:400:10). The final product (7.29 g) was obtained as a brown oil; 76% yield, purity 90%.

N-(Cyclooctyl)-N'-(1R,2R,3R,5S)-(−)-isopinocampheylethane-1,2-diamine. To a solution of the amide, from previous step, in anhydrous THF (160 ml), was added dropwise via syringe commercially available (SIGMA-ALDRICH®) Red-Al, as 65 wt % solution in THF (28 ml, 0.09 mol). The reaction mixture was stirred at reflux for 20 hours. After cooling down to the room temperature, the reaction mixture was poured into 1.5M NaOH (200 ml), and extracted with ethyl ether (2×100 ml). The organic layer was washed with brine (1×100 ml), dried over MgSO$_4$, and evaporated to dryness on the rotory evaporator to yield 7.2 g of a crude product, as a brown oil. Chromatographic purification of the crude using the same equipment and conditions as for the previous step, gave 3.5 g of the diamine. The diamine was treated with 2.0M solution of HCl in ethyl ether (25 ml), and kept in a refrigerator overnight. A dark yellow solid (4.2 g) formed, and was filtered off, and recrystallized from MeOH and ethyl ether to yield 1.5 g of the diamine as an HCl salt (of purity greater than 98%, NMR and MS are available), 19% overall yield.

EXAMPLE V

Mass Spectroscopy Analysis

Mass spectra data were obtained by Elecrospray Ionization technique on a PERKIN ELMER®/SCIEX®, API-300, TQMS with an autosampler, manufactured by SCIEX®, Toronto, Canada.

A. Library of Substituted Ethylenediamines

Mass spectroscopy served as a means for monitoring the reaction results of the library of ethylenediamines. Mass spectroscopy was done on two randomly selected rows (24 samples) per reaction plate, for roughly 28,000 compounds in pool of 10 or 30 compounds per well. Thus, if ten compounds per well were synthesized, the mass spectra for each well should contain ten signals, correlating with the proper molecular ions for each compound. The presence or absence of a particular signal indicated the feasibility of the particular synthesis. Based on the mass spectral data, and on a general analysis of the reactivity of the various amines, it is estimated that 67,000 compounds were formed out of 112,000 compounds.

Figure 14:
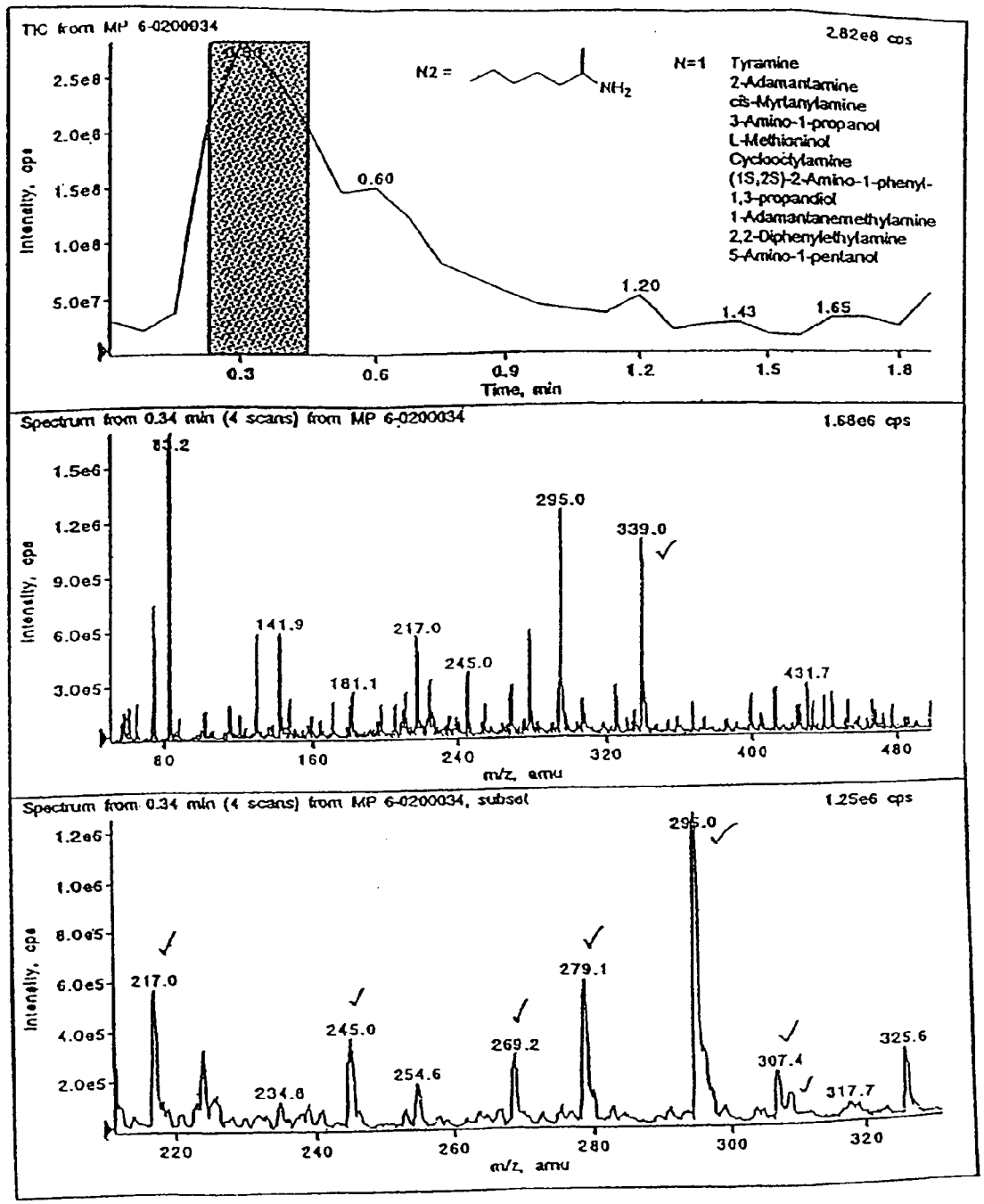
FIG. 14 is a mass spec profile for one representative sample well containing pooled substituted ethylene diamine compounds.
Figure 15:
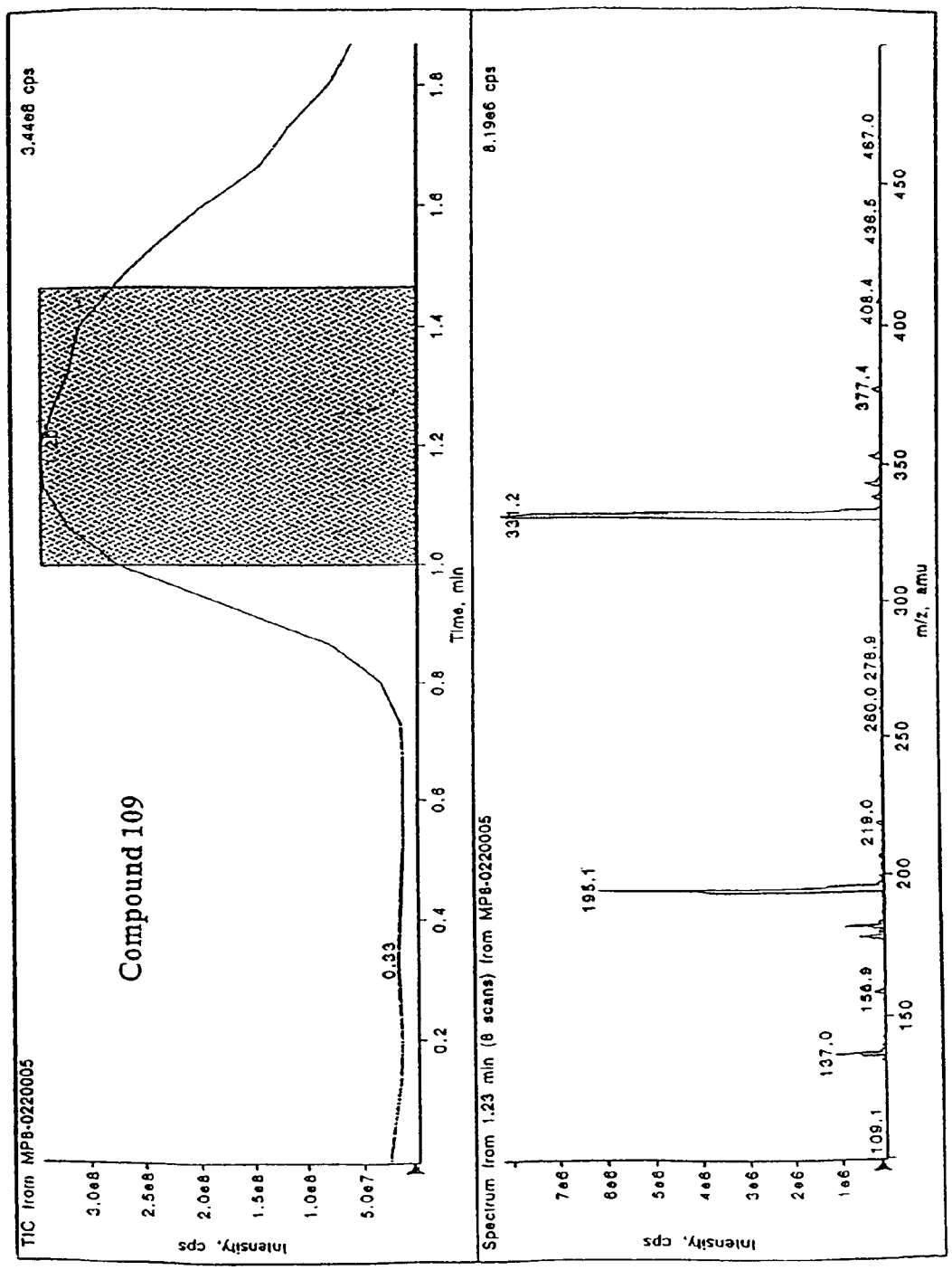
FIG. 15 is a mass spec profile for compound 109, N-Geranyl-N$^1$-(2-adamanthyl) ethane-1,2-diamine.

FIG. 14 is a representative mass spec profile for one sample well. Mass spectra for a representative ethylene diamine compound is shown in FIG. 15. Tables 5 to 8, below, list illustrative examples of mass spec data for representative reaction wells, with each well containing ten substituted ethylene diamines.

TABLE 5

ILLUSTRATIVE EXAMPLES OF MASS SPEC DATA FOR REPRESENTATIVE ETHYLENEDIAMINES (TEN COMPOUNDS PER WELL).

| $R_1NH_2$ in the 1st position (pool of 10 resins) | $R_2R_3NH$ in the 2nd position (from the master plate of the amines) | $[M + 1]^+$ of the product $R_1NHCH_2CH_2NR_2R_3$ |
|---|---|---|
| Plate # 4-034-2, well D10 | | |
| 1-(2-Aminoethyl)piperidine | 2-Aminoheptane | 270 absent |
| Phenethylamine | | 263 |
| 4-(2-Aminoethyl)morpholine | | 272 absent |
| Tryptamine | | 302 |
| Cyclohexylamine | | 241 |
| Exo-2-Aminonorbornane | | 253 |
| Benzylamine | | 249 |
| 2-Fluorophenethylamine | | 281 |
| ?-Methylphenethylamine | | 277 |
| 4-Methoxyphenethylamine | | 293 |
| Plate # 4-56-1, well C4 | | |
| 4-Methylbenzylamine | exo-2-Aminonorbornane | 259 |
| Cyclopentylamine | | 223 |
| 2-(Aminomethyl)piperidine | | 246 low intensity |
| Furfurylamine | | 235 |
| 3,4,5-Trimethoxybenzylamine | | 335 |
| 1-Methyl-3-phenylpropylamine | | 287 |
| Cylcobutylamine | | 209 |
| 1,2,3,4-Tetrahydro-1-naphthylamine | | 258 |
| 2,3-Dimethylcyclohexylamine | | 265 |
| 2-Amino-1-butanol | | 227 low intensity |
| Plate # 4-44-2, well G1 | | |
| Veratrylamine | 4-Fluorophenethylamine | 333 |
| 2-(1-Cyclohexenyl)ethylamine | | 291 |
| 5-Aminoquinolone | | 310 absent |
| 1-(1-Naphthyl)ethylamine | | 337 absent |
| 1-Aminopiperidine | | 266 |
| 3-Fluorobenzylamine | | 291 |
| 2,4-Dimethoxybenzylamine | | 333 |
| 3-Amino-1,2,4-triazine | | 262 absent |
| 2-Ethoxybenzylamine | | 317 |
| 4-(3-Aminopropyl)morpholine | | 310 absent |

TABLE 6

Mass Spec Data for Synthesized Ethylenediamines

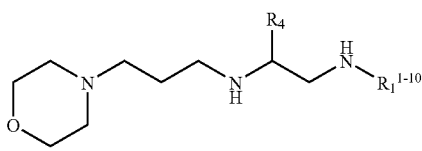

| $R_1NH_2$ in the 1st position | $[M + 1]^+$ of the products, $R_4 = H$ | $[M + 1]^+$ of the products, $R_4 = Ph$ | |
|---|---|---|---|
| | | Diamines, 1 | Amino alcohols, 13 |
| Tyramine | 308 | 384 | 258 formed |
| 2-Adamantamine | 321 absent | 398 absent | 272 formed |
| cis-Myrtanylamine | 324 | 400 | 274 formed |
| 3-Amino-1-propanol | 246 | 322 | 196 absent |
| L-Methioninol | 305 absent | 382 absent | 256 absent |
| Cyclooctylamine | 298 | 374 | 248 formed |
| (1S,2S)-2-Amino-1-phenyl-1,3-propandiol | 337 absent | 414 absent | 288 absent |

TABLE 6-continued

Mass Spec Data for Synthesized Ethylenediamines

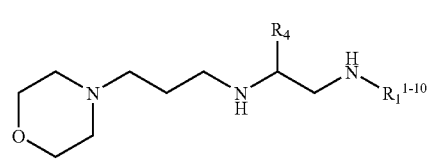

| $R_1NH_2$ in the 1st position | $[M + 1]^+$ of the products, $R_4 = H$ | $[M + 1]^+$ of the products, $R_4 = Ph$ | |
|---|---|---|---|
| | | Diamines, 1 | Amino alcohols, 13 |
| 1-Adamantane-methylamine | 336 | 412 absent | 286 formed |
| 2,2-Diphenyl-ethylamine | 368 | 444 | 318 formed |
| 5-Amino-1-pentanol | 274 | 350 | 224 formed |

TABLE 7

Mass Spec Data for Synthesized Ethylenediamines, $R_4$ = H and Me

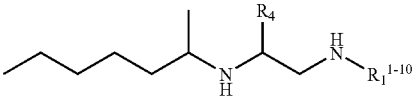

| $R_1NH_2$ in the 1st position | [M + 1]+ of the products, $R_4$ = H | [M + 1]+ of the products, $R_4$ = Me Diamines, 1 | Amino alcohols, 13 |
|---|---|---|---|
| Tyramine | 278 | 293 | 196 absent |
| 2-Adamantamine | 293 absent | 307 absent | 210 low intensity |
| cis-Myrtanylamine | 293 | 309 | 212 formed |
| 3-Amino-1-propanol | 217 | 231 | 134 absent |
| L-Methioninol | 277 absent | 291 absent | 194 formed |
| Cyclooctylamine | 269 | 269 absent | 186 absent |
| (1S,2S)-2-Amino-1-phenyl-1,3-propandiol | 309 low intensity | 323 absent | 226 formed |
| 1-Adamantane-methylamine | 307 | 321 | 224 formed |
| 2,2-Diphenyl-ethylamine | 339 | 353 | 256 formed |
| 5-Amino-1-pentanol | 245 | 259 | 162 absent |

TABLE 8

Mass Spec Data for Synthesized Ethylenediamines, $R_4$ = H and Me

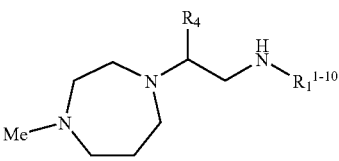

| $R_1NH_2$ in the 1st position | [M + 1]+ of the products, $R_4$ = H | [M + 1]+ of the products, $R_4$ = Ph Diamines, 1 | Amino alcohols, 13 |
|---|---|---|---|
| Tyramine | 278 | 292 absent | 196 absent |
| 2-Adamantamine | 292 absent | 306 absent | 210 formed |
| cis-Myrtanylamine | 294 | 308 absent | 212 formed |
| 3-Amino-1-propanol | 216 | 230 absent | 134 absent |
| L-Methioninol | 276 absent | 290 absent | 194 absent |
| Cyclooctylamine | 268 | 282 absent | 186 absent |
| (1S,2S)-2-Amino-1-phenyl-1,3-propandiol | 308 | 322 absent | 226 formed |
| 1-Adamantane-methylamine | 306 absent | 320 absent | 224 formed |
| 2,2-Diphenyl-ethylamine | 338 | 352 absent | 256 formed |
| 5-Amino-1-pentanol | 244 | 258 absent | 162 absent |

EXAMPLE VI

$^1$H NMR Spectroscopy

Proton NMR data was recorded on a VARIAN® Nuclear Magnetic Resonance Spectrometer (Palto Alto, Calif.) at 500 MHz.

Figure 16:
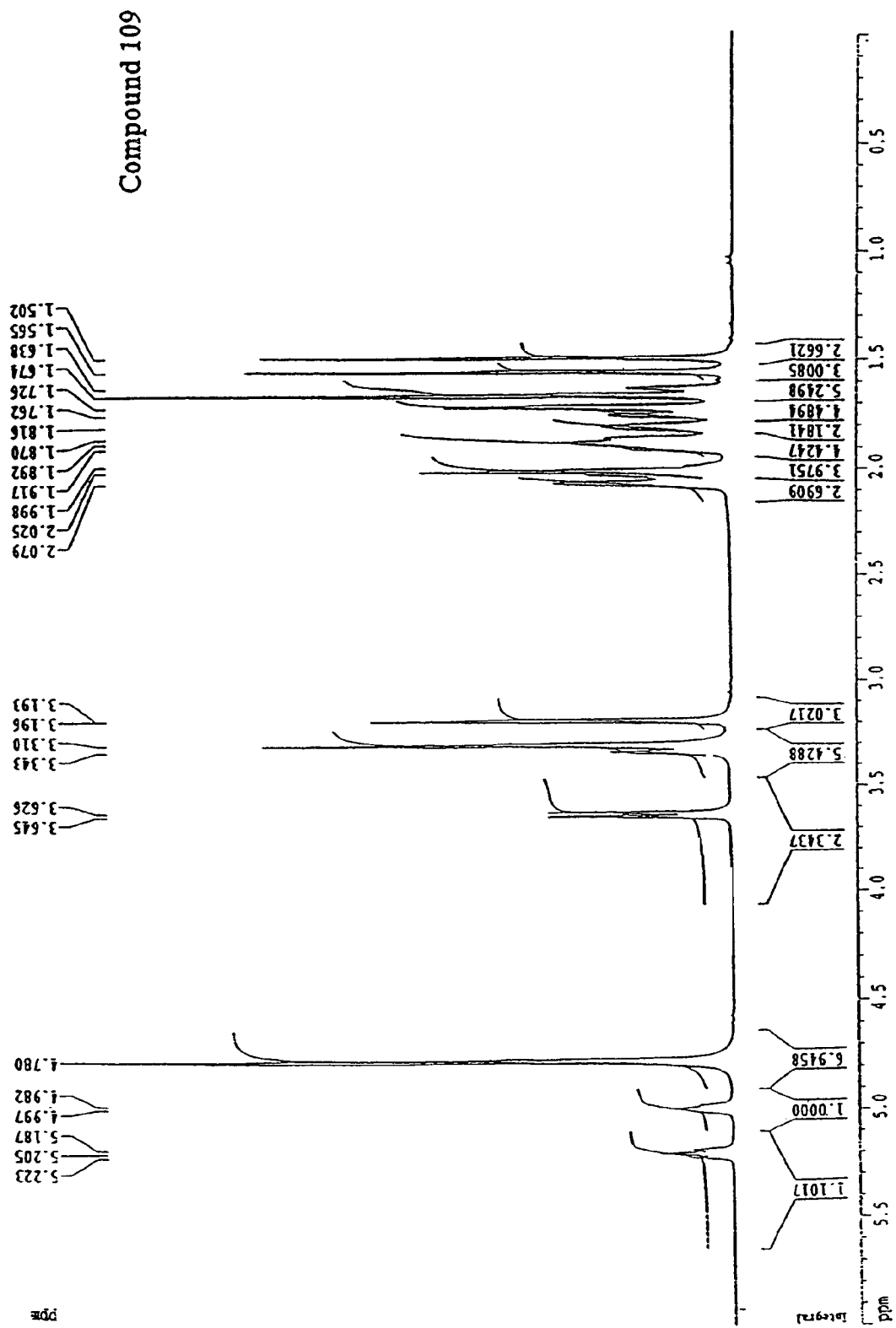
FIG. 16 is a proton NMR profile for compound 109, N-Geranyl-N$^1$-(2-adamanthyl) ethane-1,2-diamine.

Representative substituted ethylene diamines were purified by HPLC, and analyzed by proton NMR. A representative proton NMR profiles is shown in FIG. 16. NMR and MS data for some representative hit compounds are shown below.

Compound 6.

$N^2$-(1-Adamantylmethyl)-$N^1$-(3,3-diphenylpropyl)propane-1,2-diamine. 55 mg, 36% yield. $^1$H NMR: δ 7.28-7.15 (m, 5H), 3.95 (t, J=7.9 Hz, 1H), 2.94 (br s 4H), 2.71 (dd, J=7.6, 9.8 Hz, 2H), 2.41 (s, 2H), 2.32 (dd, J=7.6, 7.9 Hz, 2H), 2.16 (s), 2.08-1.98 (m, 4H), 1.72 (m, 6H), 1.62 (m, 6H), 1.51 (d, J=2.4 Hz, 3H). Mass spectrum (ESI) m/z (MH)+ 417.

Compound 7.

N-(3,3-Diphenylpropyl)-N'-(1-adamanthylmethyl)ethane-1,2-diamine. 28 mg, 22% yield. 1H NMR (500 MHz) δ 7.30-7.12 (m, 10H); 3.95 (t, J=7.6 Hz, 1H); 2.91 (d, J=1.2 Hz, 4H); 2.70 (dd, J=7.6 and 1.2 Hz, 2H); 2.40 (d, J=1.3 Hz, 2H); 2.32 (q, J=8.0 Hz, 2H); 1.98 (br d, J=1.7 Hz, 4H); 1.72 (d, J=12.2 Hz, 4H); 1.62 (d, m? J=12.2 Hz, 4H); 1.51 (br s, 6H). Mass spectrum (ESI) m/z (MH)+ 403.6.

Compound 10.

N-(−)-cis-Myrtanyl-N'-(3,3-diphenylpropyl)ethane-1,2-diamine. 14 mg, 11% yield. 1H NMR (500 MHz) δ 7.30-7.10 (m, 10H); 3.95 (m, 1H); 2.92-2.83 (m, 4H); AB: 2.80 (d, J=7 Hz, 1H); 2.76 (d, J=8 Hz, 1H); 2.65 (dd, J=9.6 and 7.6 Hz, 2H); 2.42-2.20 (m, 4H); 2.29 (d, J=8 Hz, 2H); 1.90 (m, 8H); 1.42 (m, 1H); 1.19 (m, 2H); 1.17 (s, 3H); 0.95 (s, 3H); 1.00-0.8 (m, 2H). Mass spectrum (ESI) m/z (MH)+391.3.

Compound 14.

N-(3,3-Diphenylpropyl)-N'-exo-(2-norborny)ethane-1,2-diamine. 17 mg, 16% yield. 1H NMR (500 MHz) δ 7.30-7.15 (m, 10H); 3.95 (t, J=7.9 Hz, 1H); 2.86 (dd, J=11.5 and 1.5 Hz, 4H); 2.73 (dd, J=8.0 and 3.3 Hz, 1H); 2.64 (t, J=7.6 Hz, 2H); 2.29 (t, J=7.5 Hz, 2H), 2.31-2.26 (m, 2H) 2.30 1.96 (s, 3H); 1.63 (ddd, J=13.1, 7.9 and 2.5 Hz, 1H); 1.60-1.50 (m, 1H); 1.50-1.43 (m, 2H); 1.30 (dq, J=4.0 and 13.5 Hz, 1H), (1H, m); 1.20 (dd, J=10.4 and 1.1 Hz, 1H), 1.11 (dd, J=2.0, and 8.5 Hz, 1H), 1.08 (dd, J=2.5, and 8.5 Hz, 1H), 1.10 (dq, J=8.3 and 2.1, 2H). Mass spectrum (ESI) m/z (MH)+ 349.1.

Compound 21.

N-(3,3-Diphenylpropyl)-N'-(1S)-(1-ethylcyclohexane)ethane-1,2-diamine. 5 mg, 4% yield. Mass spectrum (ESI) m/z (MH)+ 365.5.

Compound 32.

N-(2,2-Diphenylethyl)-N'-®-(+)-bornylethane-1,2-diamine. 58 mg, 48% yield. 1H NMR (500 MHz): δ 7.30-7.10 (m, 10H); 4.18 (t, J=6.8 Hz, 1H); 3.34 (d, J=7.6 Hz, 2H); 3.02 (m, 4H); 2.95-2.90 (m, 1H); 2.15-2.08 (m, 1H); 1.94 (m, 1H); 1.72-1.65 (m, 2H); 1.48-1.30 (m, 2H); 1.27-1.10 (m, 2H); 1.06 (dd, J=13.6 and 4.1 Hz, 1H); 0.82 (s, 3H); 0.81 (s, 3H); 0.78 (s, 3H). Mass spectrum (ESI) m/z (MH)+ 377.2

Compound 34.

N-(2,2-Diphenylethyl)-N'-(1-adamanthylmethyl)ethane-1,2-diamine. 6.8 mg, 6% yield. 1H NMR (500 MHz) δ 7.30-7.15 (m, 10H); 4.15 (t, J=7.6 Hz, 1H); 3.24 (dd, J=7.9 and 1.2 Hz, 2H); 2.79 (t, J=6.5 Hz, 2H); 2.74 (t, J=6.0 Hz, m, 2H); 1.95 (m, 8H); 1.69 (d, J=12.5 Hz, 4H); 1.59 (d, J=11.9 Hz, 4H); 1.40 and 1.39 (br s, 3H); Mass spectrum (ESI) m/z (MH)+389.0.

Compound 37.

N-(2,2-Diphenylethyl)-N'-(−)-cis-myrtanylethane-1,2-diamine. 54 mg, 38% yield. $^1$H NMR: δ 7.31-7.18 (m, 10H), 4.13 (t, J=7.6 Hz, 1H), 3.26 (d, J=7.6 Hz, 2H), 2.86 (dd, J=4.3, 8.0 Hz, 4H), 2.76 (dd, J=7.6, 12.2 Hz, 2H), 2.37 (ddd, J=1.8, 9.0, 12.5 Hz, 1H), 2.12 (dq, J=1.8, 7.6 Hz, 1H), 1.98 (br s, 2H), 1.98-1.84 (m, 4H), 1.39 (ddd, J=2.4, 4.0, 6.1 Hz, 1H), 1.18 (s, 3H), 0.95 (s, 3H), 0.91 (d, J=10.0 Hz, 1H) Mass spectrum (ESI) m/z (MH)$^+$ 377.2.

Compound 38.

N-(−)-cis-Myrtanyl-N'-(2,2-diphenylethyl)propane-1,2-diamine. 39 mg, 30% yield. 1H NMR (500 MHz) δ 7.30-7.15 (m, 10H); 4.13 (t, J=8.0 Hz, 1H); AB: 3.28 (d, J=7.5 Hz, 1H); 3.24 (d, J=7.5 Hz, 1H), 3.26 (d, J=6.1 Hz, 2H); 2.96 (m, 1H); 2.88-2.75 (m, 2H); 2.71 (ddd, J=4.5, 9.0, 13.0 Hz, 1H); 2.58 (ddd, J=7.0, 10.0, 14.0 Hz, 1H); 2.35 (m, 1H); 2.21 (m, 1H); 2.00-1.80 (m, 6H); 1.40-1.20 (m, 1H); 1.17 (s, 3H); 0.93 (s, 3H); 0.89 (dd, J=9.7 and 4.2 Hz, 1H). Mass spectrum (ESI) m/z (MH)$^+$ 391.0.

Compound 40.

N-(2,2-Diphenylethyl)-N'-(1R,2R, 3R, 5S)-(−)-isopinocampheylethane-1,2-diamine. 33 mg, 23% yield. $^1$H NMR: δ 7.31-7.18 (m, 10H), 4.13 (t, J=7.5 Hz, 1H), 3.27 (d, J=8.0 Hz, 2H), 3.14 (dt, J=6.0, 10 Hz, 1H), (4H), 2.36 (qd, J=2.0, 6.0 Hz, 1H), 2.34 (dt, J=2.0, 10 Hz, 1H), 2.07-1.96 (m, 3H), 1.82 (dt, J=2.0, 6.0 Hz, 1H), 1.71 (ddd, J=2.5, 5.5, 13.5 Hz, 1H), 1.22 (s, 3H), 1.09 (d, J=7.0 Hz, 3H), 0.96 (d, J=10.5 Hz, 1H), 0.91 (s, 3H). Mass spectrum (ESI) m/z(MH)$^+$ 377.3.

Compound 47.

N-(−)-cis-Myrtanyl-N'-(1R,2R, 3R, 5S)-(−)-isopinocampheylethane-1,2-diamine. 42 mg, 33% yield. $^1$H NMR: δ 3.35-3.20 (m, 6H), 2.93 (dd, J=4.6, 2.0 Hz, 2H), 2.45-2.33 (m, 4H), 2.17 (s, 3H), 2.06 (quint, J=7.0 Hz, 1H), 2.0-1.9 (m, 6H), 1.90 (dd, J=2.1, 5.2 Hz, 1H), 1.87 (dt, J=1.8, 4.6 Hz, 1H), 1.51 (ddd, J=4.6, 10.0, 13.0 Hz, 1H), 1.23 (s, 3H), 1.19 (s, 3H), 1.12 (d, J=8 Hz, 3H), 1.03 (d, J=10.3 Hz, 1H), 0.98 (s, 3H), 0.94 (d, J=9.8 Hz, 1H), 0.94 (s, 3H). Mass spectrum (ESI) m/z (MH)$^+$ 333.6.

Compound 52.

N-(3,3-Diphenylpropyl)-N'-cyclooctylethane-1,2-diamine. 20 mg, 18% yield. 1H NMR (500 MHz): δ 7.30-7.10 (m, 10H); 3.96 (t, J=7.9 Hz, 1H); 3.00 (m, 1H); 2.90 (dd, $J_1$=$J_2$=5.5 Hz, 2H); 2.84 (dd, $J_1$=$J_2$=5.0 Hz, 2H); 2.61 (t, J=7.3 Hz, 2H), 2.27 (q, J=7.6 Hz, 2H); 1.83 (m, 2H); 1.74 (m, 2H); 1.65-1.40 (m, 10H).

Compound 55.

N-(1-Adamantylmethyl)-N'-cyclooctylethane-1,2-diamine. 6.7 mg, 6% yield. 1H NMR (500 MHz): δ 3.08-3.02 (m, 1H); 3.02-2.98 (m, 2H); 2.97-2.92 (m, 2H); 2.36 (s, 2H); 1.98 (m, 2H); 1.93-1.86 (m, 2H); 1.80-1.50 (m, 19H).

Compound 57.

N-(−)-cis-Myrtanyl-N'-(cyclooctyl)ethane-1,2-diamine. 18 mg, 18% yield. 1H NMR (500 MHz) δ 3.05-2.95 (m, 4H); AB: 2.76 (d, J=7.5 Hz, 1H), 2.23 (d, J=8.0 Hz, 1H); 2.76 (dd, J=11.6 and 7.3 Hz, 1H); 2.73 (dd, J=11.9 and 8.2 Hz, 1H); 2.40-2.34 (m, 1H); 2.28 (quintet, J=8.0 Hz, 1H); 1.97 (s, 3H); 2.00-1.84 (m, 6H); 1.80-1.70 (m, 2H); 1.68-1.38 (m, 11H); 1.18 (s, 3H); 0.97 (s, 3H); 0.92 (d, J=9.8 Hz, 1H). Mass spectrum (ESI) m/z (MH)+307.5.

Compound 58.

N-(2-Adamantyl)-N'-cyclooctylethane-1,2-diamine. 25 mg, 23% yield. $^1$H NMR: δ 3.06 (m, 1H), 3.00 (m, 2H), 2.93 (t, J=5,5 Hz, 2H), 2.83 (br s, 1H), 1.96 (s, 3H), 1.92-1.80 (m, 10H), 1.80-1.50 (m, 20H). Mass spectrum (ESI) m/z (MH)$^+$ 305.1.

Compound 59.

N-(Cyclooctyl)-N'-(1R,2R, 3R, 5S)-(−)-isopinocampheylethane-1,2-diamine. 15 mg, 14% yield. 1H NMR (400 MHz): δ 3.47 (dt, J=6.0, 10.0 Hz, 1H), 3.40-3.28 (m, 7H), 2.44 (tq, J=2.0, 10.0 Hz, 1H), 2.36 (dtd, J=2.0, 6.0, 10.0 Hz, 1H), 2.09 (dq, J=2.0, 7.2 Hz, 1H), 2.00-1.90 (m, 3H), 1.88-1.78 (m, 2H), 1.78-1.63 (m, 4H), 1.65-1.30 (m, 8H), 1.18 (d, J=6.0 Hz, 3H), 1.16 (s, 3H), 1.17 (d, J=7.2 Hz, 1H), 0.90 (s, 3H). Mass spectrum (ESI) m/z (MH)$^+$ 307.4.

Compound 62.

N-(−)-cis-Myrtanyl-N'-(1S)-(1-ethylcyclohexane)ethane-1,2-diamine. 48 mg, 46% yield. 1H NMR (500 MHz): δ 3.06-3.00 (m, 1H); 2.98-2.95 (m, 2H); 2.92-2.84 (m, 1H); 2.79 (dd, J=11.9 and 7.0 Hz, 1H); 2.75 (dd, J=11.9 and 7.9 Hz, 1H); 2.73 (m, 1H); 2.39 (m, 1H); 2.28 (quintet, J=8.5 Hz, 1H); 2.00-1.86 (m, 6H); 1.82-1.76 (m, 2H); 1.68 (m, 2H); 1.54-1.42 (m, 2H); 1.32-1.10 (m, 6H); 1.19 (s, 3H); 1.13 (d, J=6.7 Hz, 3H); 1.07 (dd, J=12 and 3 Hz, 1H); 1.02 (dd, J=12 and 3 Hz, 2H); 0.98 (s, 3H); 0.93 (d, J=9.7 Hz, 1H). Mass spectrum (ESI) m/z (MH)$^+$ 306.9.

Compound 65.

N-trans-(2-phenylcyclopropyl)-N'-(1-adamanthyl)ethane-1, 2-diamine. 18 mg, 16% yield. Mass spectrum (ESI) m/z (MH)$^+$ 311.3.

Compound 66.

N-(3,3-Diphenylpropyl)-N'-(1R,2R, 3R, 5S)-(−)-isopinocampheylethane-1,2-diamine. 2 mg, 2% yield. 1H NMR (500 MHz) δ 7.26 (m, 10H); 3.96 (t, J=7.6 Hz, 1H); 3.09 (m, 1H); 2.92 (m, 1H); 2.84 (m, 2H); 2.62 (m, 2H); 2.35 (m, 4H); 1.97 (s, 3H); 1.82 (m, 1H); 1.68 (m, 1H); 1.21 (s, 3H); 1.12 (d, J=7.3 Hz; 3H); 1.01 (m, 1H); 0.92 (s, 3H). Mass spectrum (ESI) m/z (MH)$^+$ 391.4.

Compound 73.

N-(2-Adamantyl)-N'-[2-(2-methoxyphenyl)ethyl]ethane-1, 2-diamine. 21 mg, 19% yield. $^1$H NMR: δ 7.22 (dd, J=8.2, 7.3 Hz, 1H), 7.14 (d, J=7.3 Hz, 1H), 6.89 (d, J=7.1, Hz, 1H), 6.87 (d, J=8.2, Hz, 1H), 3.81 (s, 3H), 3.06 (t, J=7.1 Hz, 2H), 3.06 (m, 2H), 3.01 (m, 2H), 2.93 (t, J=7.1, 2H), 1.95 (br s, 2H), 1.90-1.80 (m, 7H), 1.78-1.66 (m, 6H), 1.59 (d, J=2.5 Hz, 2H). Mass spectrum (ESI) m/z (MH)$^+$ 329.4.

Compound 78.

N-2-Adamantyl-N'-2,3-dihydro-1H-inden-2-yl-ethane-1,2-diamine. 4.3 mg, 3% yield. $^1$H NMR: δ 7.20 (dd, J=4.9, 8.5 Hz, 2H), 7.14 (dd, J=5.5, 2.1 Hz, 2H), 3.71 (quint, J=6.1 Hz, 2H), 3.19 (dd, J=5.8, 15.9 Hz, 2H), 3.13 (br.s, 1H), 3.05 (m, 4H), 2.86 (dd, J=4.8, 15.8 Hz, 2H), 2.08 (m, 2H), 2.00 (m, 6H), 1.96-1.88 (m, 4H), 1.88-1.80 (m, 3H), 1.74 (m, 4H), 1.68-1.60 (m, 2H). Mass spectrum (ESI) m/z (MH)$^+$ 303.4.

Compound 109.

N-Geranyl-N'-(2-adamanthyl)ethane-1,2-diamine. 27 mg, 24% yield. 1H NMR (400 MHz): δ 5.40 (t, J=7.2 Hz, 1H), 4.78 (br s, 1H), 3.64 (d, J=7.6 Hz, 2H), 3.34 (m, 2H), 2.07 (m, 2H), 2.08-1.95 (m, 4H), 1.95-1.85 (m, 4H), 1.82 (m, 2H), 1.88-1.70 (m, 4H), 1.70-1.62 (m, 3H), 1.67 (s, 3H), 1.56 (s, 3H), 1.50 (s, 3H). Mass spectrum (ESI) m/z (MH)$^+$ 307.4.

Compound 111.

N-Geranyl-N'-(2-ethylpiperidine)ethane-1,2-diamine. 44 mg, 42% yield. 1H NMR (500 MHz): δ 5.22 (t, J=6.1 Hz, 1H); 5.04 (m, 1H), 3.52 (d, J=7.3 Hz, 2H); 3.05-2.85 (m, 4H); 2.66 (m, 1H); 2.44 (m, 2H); 2.08 (m, 4H); 1.80-1.50 (m, 2H); 1.70(s, 3H); 1.65 (s, 3H); 1.58 (s, 3H); 1.50-1.35 (m, 2H), 0.89 (t, J=7.3, 3H). Mass spectrum (ESI) m/z (MH)$^+$ 293.4.

Compound 116.

N-Geranyl-N'-allyl-N'-(cyclopentyl)ethane-1,2-diamine. 45 mg, 42% yield. $^1$H NMR: δ 5.86 (ddd, J=10.0, 16.1, 6.7 Hz, 1H), 5.28 (d, J=15.9 Hz, 1H), 5.25 (d, J=8.7 Hz, 1H), 5.23 (t, J=7.3 Hz, 1H), 5.30 (m, 1H), 3.59 (d, J=7.3 Hz, 2H), 3.28 (br d, J=6.4 Hz, 2H), 3.16 (quintet, J=8.2 Hz, 1H), 3.02 (m, 2H), 2.95-2.86 (m, 2H), 1.88-1.80 (m, 4H), 1.70 (s, 3H), 1.74-1.66 (m, 3H), 1.65 (s, 3H), 1.58 (s, 3H), 1.56-1.50 (2H), 1.50-1.40 (m, 2H). Mass spectrum (ESI) m/z (MH)$^+$ 305.3.

Compound 117.

N-Geranyl-N'-diphenylmethylethane-1,2-diamine. 24 mg, 20% yield. 1H NMR (500 MHz): δ 7.40 (d, J=7.2 Hz, 4H); 7.29 (t, J=7.3 Hz, 4H); 7.21 (t, J=7.0 Hz, 2H); 5.15 (t, J=7.5, 1H); 5.01 (m, 1H); 4.89 (br s, 1H); 3.42 (d, J=7.0 Hz, 2H); 3.00-2.78 2.93 (m, 4H); 2.20-2.00 2.17 (m, 4H); 1.63 (s, 3H); 1.59 (s, 3H); 1.56 (s, 3H). Mass spectrum (ESI) m/z (MH)$^+$ 363.3.

Compound 125.

N,N'-bis-(−)-cis-Myrtanylpropane-1,2-diamine. 82 mg, 70% yield. 1H NMR (500 MHz): δ 3.62 (m, 1H); 3.18 (dd, J=13.7 and 3.7 Hz, 1H); 3.05 (dt, J=11.5 and 7.5 Hz, 1H); 3.06-2.92 (m, 2H); 2.86 (dt, J=12.2 and 7.3 Hz, 1H); 2.40 (m, 4H); 2.06-1.84 (m, 10H); 1.56-1.46 (m, 2H); 1.37 and 1.36 (two d, J=6.7 and J=7.0 Hz, 3H); 1.20 (s, 3H); 1.19 (m, 3H), 0.99 and 0.98 (two s, 3H) Hz, H); 0.97 (s, 3H); 0.94 (two d, J=10.1 Hz, 2H). Mass spectrum (ESI) m/z (MH)$^+$ 346.9.

Compound 151.

N-[2-(2-Methoxy)phenylethyl]-N'-(1R,2R, 3R, 5S)-(−)-isopinocampheyl-ethane-1,2-diamine. 67 mg, 60% yield. 1H NMR (500 MHz): δ 7.23 (t, J=5.8 Hz, 1H); 7.13 (dd, J=5.8 and 1.8 Hz, 1H); 6.88 (m, 2H); 3.81 (s, 3H); 3.13 (m, 1H); 3.1-3.0 (m, 3H); 3.01 (t, J=7.0 Hz, 2H); 2.89 (t, J=7.0 Hz, 2H); 2.42-2.35 (m, 2H); 2.00 (m, 3H); 1.82 (dt, J=6.0 and 2.0 Hz, 1H); 1.72 (ddd, J=2.5, 5.5, 13.5 Hz, 1H); 1.22 (s, 3H) 1.13 (d, J=7.3 Hz, 3H). 0.99 (d, J=10.1 Hz, 1H); 0.93 (s, 3H). Mass spectrum (ESI) m/z (MH)$^+$ 331.5.

N-2-(2-Methoxyphenyl)ethyl-N'-allyl-N'-cyclopentyl-ethane-1,2-diamine. 8 mg, 7% yield. $^1$H NMR: δ 7.26 (dd, J=7.3, 8.5, 1H), 7.18 (d, J=7.2 Hz, 1H), 6.91 (m, 2H), 5.61 ddd, (J=6.7, 17.0, 9.4 Hz, 1H), 5.13 (d, J=15.3 Hz, 1H), 5.10 (d, J=9.2 Hz, 1H), 3.83 (s, 3H), 3.13 (dd, J=7.0, 6.7 Hz, 2H), 3.10 (d, J=6.7 Hz, 1H), 3.00 (d, J=7.3 Hz, 1H), 3.05-2.90 (m, 2H), 2.97 (dd, J=8.2, 6.1 Hz, 2H), 2.75 (t, J=6.1 Hz, 2H), 1.73 (m, 2H), 1.62 (m, 2H), 1.50 (m, 2H), 1.22 (m, 2H). Mass spectrum (ESI) m/z (MH)$^+$ 311.4.

N$^2$-(3-Phenylpropyl)-N$^1$-[2-(4-fluorophenyl)ethyl]-1-phenylethane-1,2-diamine. 23 mg, 19% yield. $^1$H NMR: δ 7.35 (d, J=7.6 Hz, 2H), 7.34 (quart, J=7. Hz, 1H), 7.26 (d, J=6.4 Hz, 3H), 7.23 (d, J=7.6 Hz, 2H), 7.17 (dd, J=7.3, 6.4 Hz, 1H), 7.12 (d, J=7.0 Hz, 2H), 3.21 (m, 1H), 3.03 (ddd, J=4.2, 8.0, 12.8 Hz, 4H), 2.86 (t, J=8.0 Hz, 2H), 2.85-2.79 (m, J=12. Hz, 2H), 2.74-2.64 (m, 4H), 2.61 (t, J=7.7 Hz, 2H), 1.96 (quint, J=7.6 Hz, 2H). Mass spectrum (ESI) m/z (MH)$^+$ 377.3.

EXAMPLE VII

*M. Tuberculosis* Rv0341p Lucs Drug Response

Substituted ethylene diamines, as described herein, were tested on *Mycobacterium tuberculosis* using high-throughout screening assay with recombinant mycobacterial containing promoter fusion of luciferase to Rv0341 EMB-inducible promoter. This assay quickly and reliably identifies antimycobacterial activity in compound mixtures and/or in individual compounds. In this assay, bioluminescence increases when the mycobacteria is tested against an active compound, or an active compound mixture. During this assay, a theoretical yield of 100% was assumed for every unpurified substituted ethylene diamine, and the activity of each sample was compared to commercially available ethambutol (99.0% purity). Results were reported in LCPS, and % Max. LCPS based on the activity of EMB at 3.1 μM.

The substituted ethylene diamines were analyzed according to the following procedure. The diamines were dried in a speed vacuum to an approximate concentration of 6.3 mmoles per well. Each diamine, or diamine mixture, was then resuspended or dissolved in 200 μl of methanol for a concentration of 31.5 mM diamine(s). The diamine(s) solution was diluted to a concentration of 200 μM in 7H9 broth medium (a 1:15.75 dilution of the 31.5 mM stock, followed by a 1:10 dilution; each dilution in 7H9 broth medium). Next, 50 μl of the diluted diamine(s) solution was added to the first well of a row of twelve in an opaque, 96-well plate. The 7H9 broth medium, 25 μl, was added to each of the remaining wells (#2-12) in the row. The diamine(s) solution in "well one" was serially diluted by transferring 25 μl from "well one" to "well two", and repeating a 25 μl transfer from "well two" to "well three", and so on, on through "well eleven". In "well eleven", the extra 25 μl of solution was discarded. "Well twelve" was used as a growth control to assess background activity of the reporter strain. The plate was then covered and incubated at 37° C. for 24 hours. Immediately prior to analysis, the following substrates were prepared: a buffer solution containing 50 mM HEPES at pH 7.0 and 0.4% Triton X-100. Then, 0.25 ml of 1M DTT, and 14 μl of 10 mg/ml luciferin in DMSO were added to 5 ml of the buffer solution. This final solution (50 μl) was added to each of the twelve wells, immediately after the incubation period had run. The luminescence from each well was measured 20 minutes after the luciferin substrate was added, using a TOPCOUNT® (Downers, Grove, Ill.) NXT luminometer (55/well).

Figure 6:
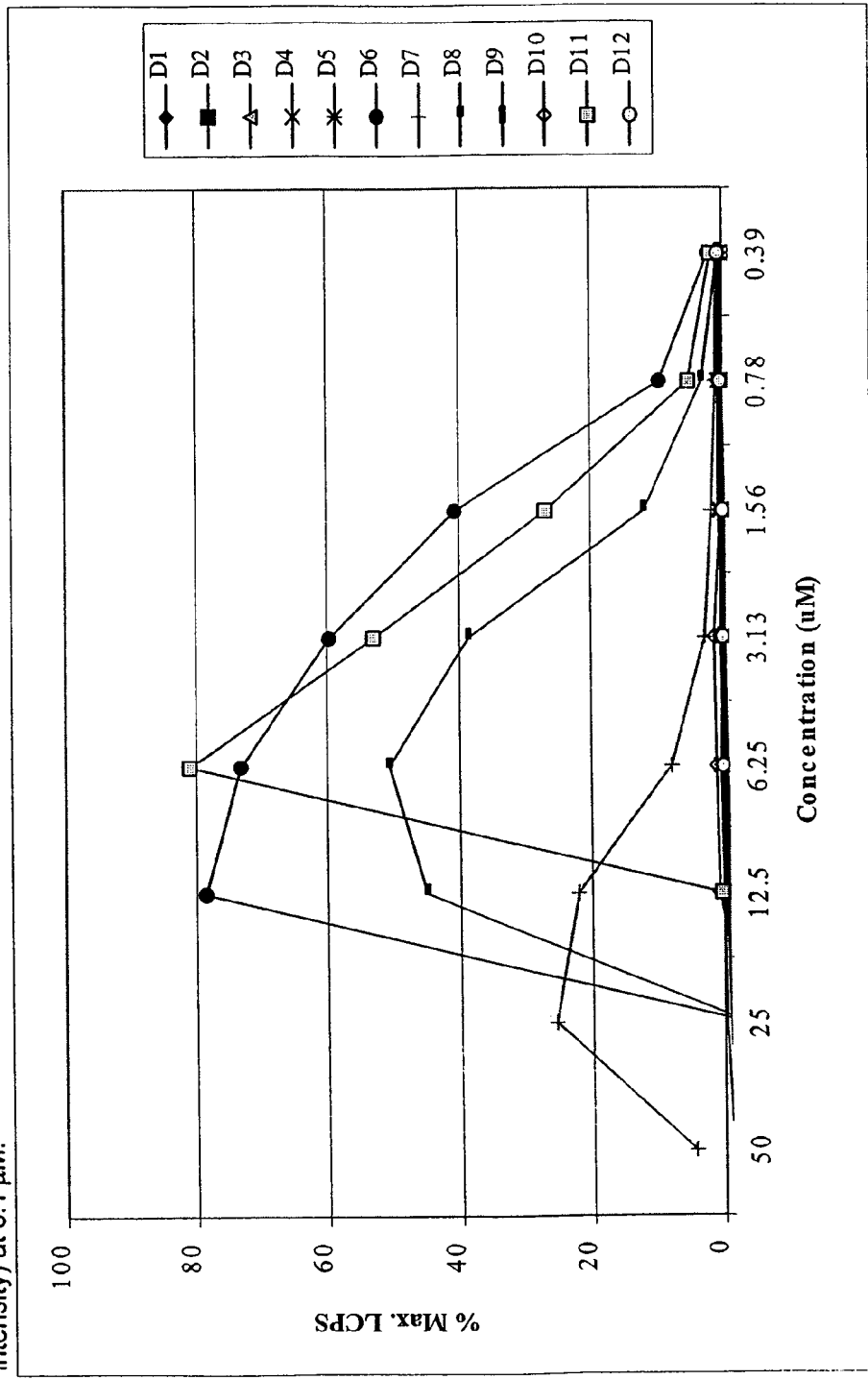
FIG. 6 is a graph of Luminescence Count per Second (LCPS) versus concentration showing HTS Luc assay results for pooled substituted ethylene diamine compounds.
Figure 7:
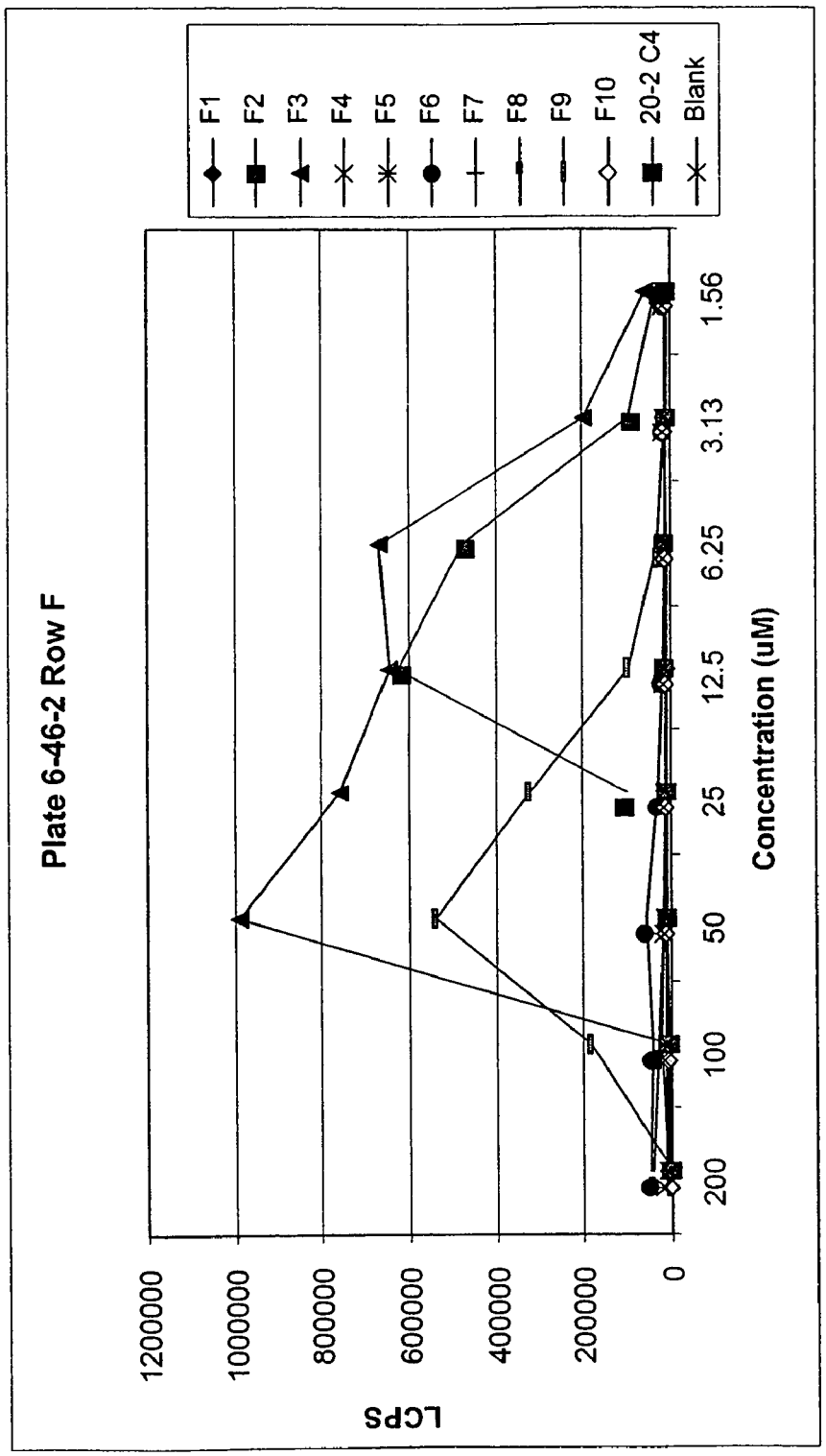
FIG. 7 is a graph of LCPS versus concentration showing HTS Luc assay results for individual substituted ethylene diamine compounds.
Figure 8:
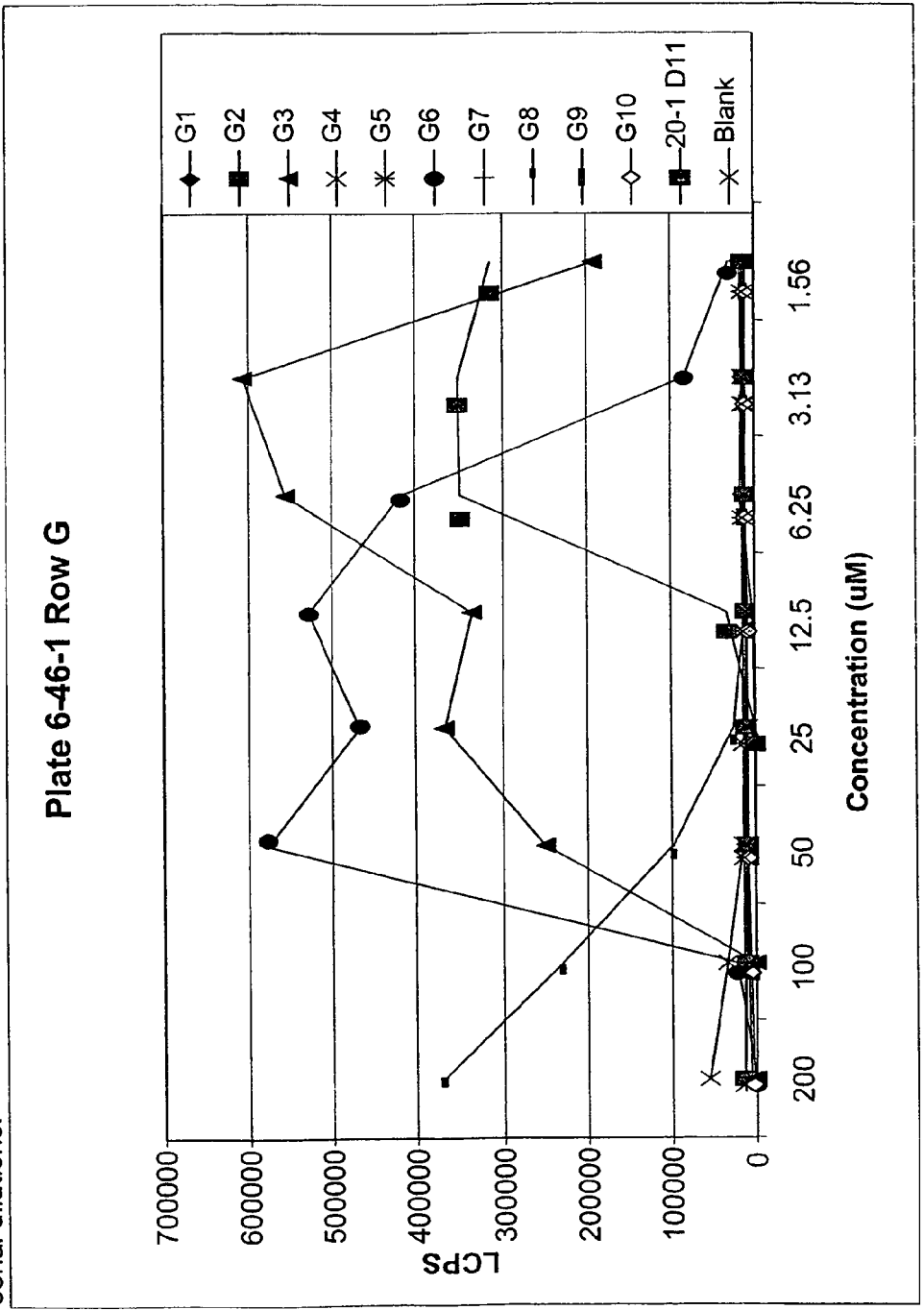
FIG. 8 is a graph of LCPS versus concentration showing HTS Luc assay results for individual substituted ethylene diamine compounds.
Figure 9:
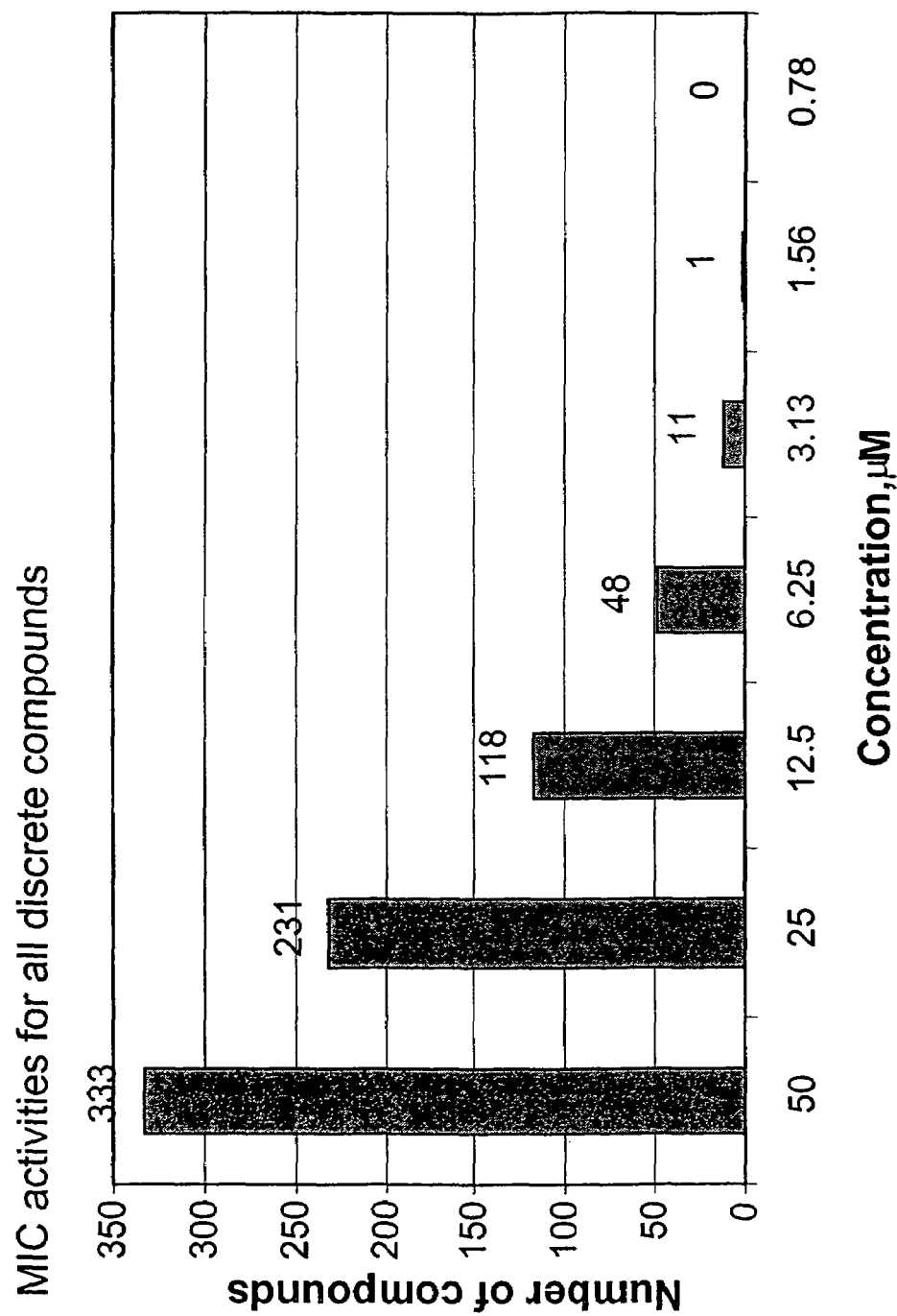
FIG. 9 is a bar graph providing a summary of MIC activities for discrete substituted ethylene diamines.
Figure 10:
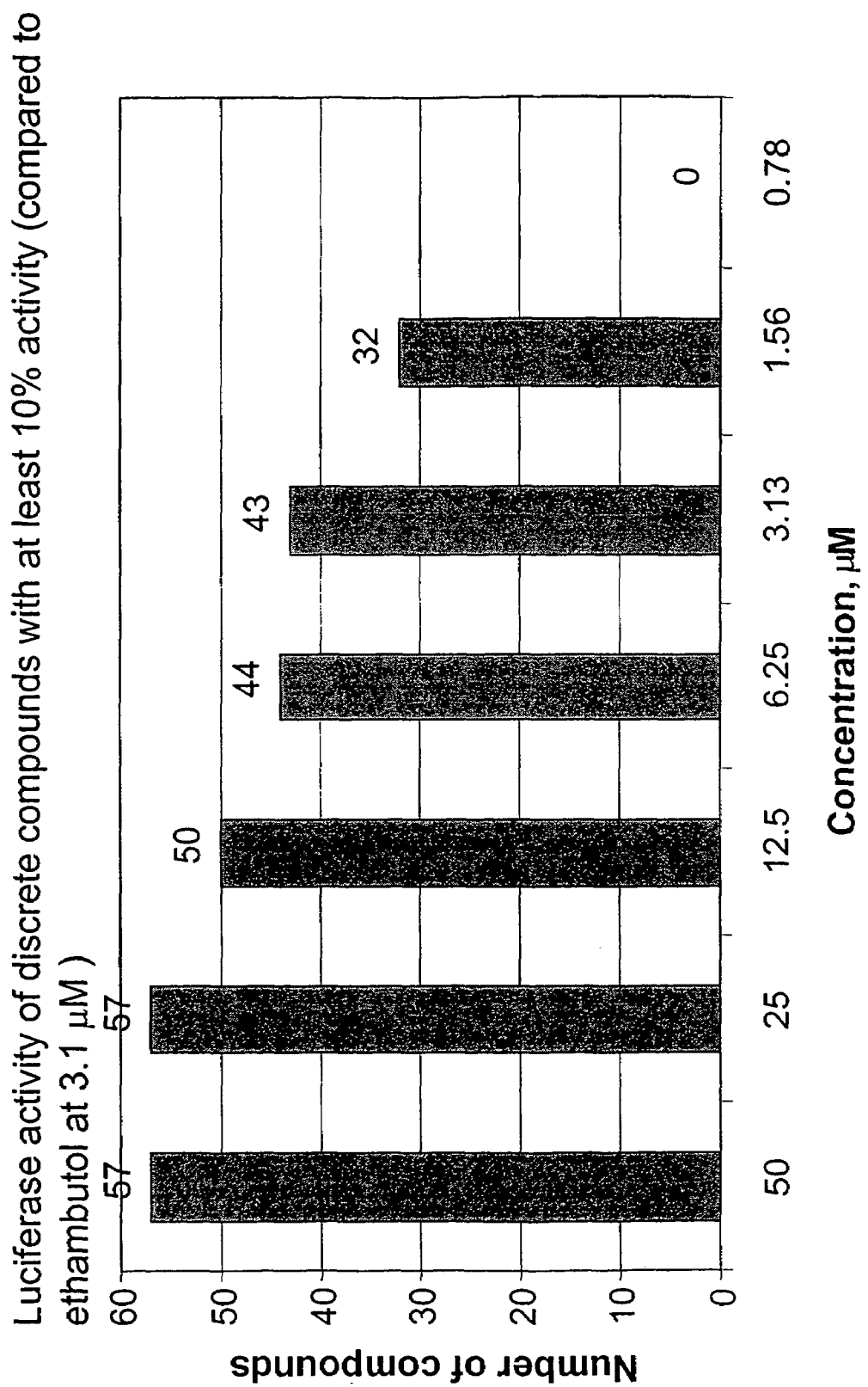
FIG. 10 is a bar graph providing a summary of Luciferase activity of discrete substituted ethylene diamines with at least 10% activity in reference to ethambutol at 3.1 µM.
Figure 11:
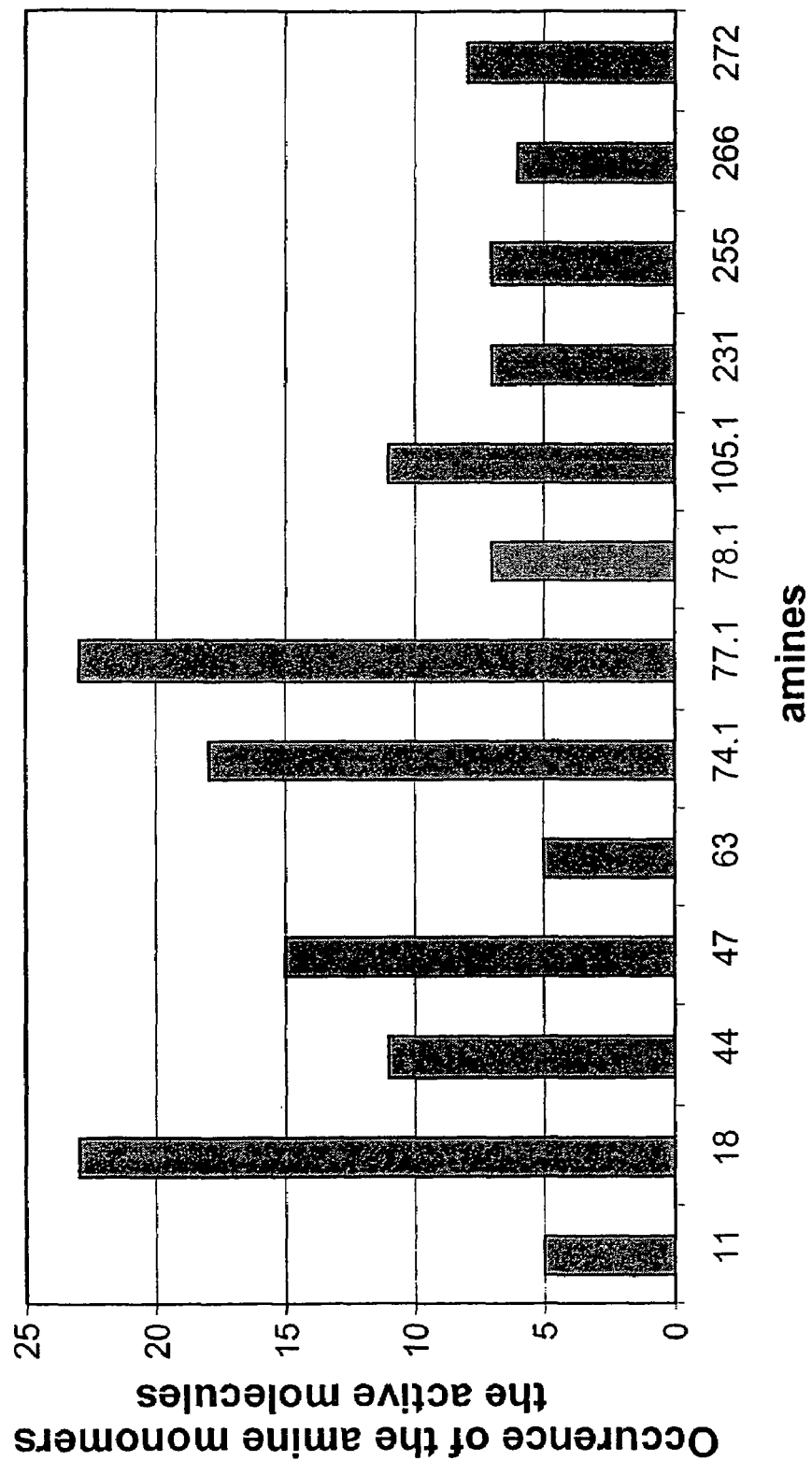
FIG. 11 is a bar graph showing the frequency of occurrences of the selected amine monomers in the substituted ethylene diamine compounds that were active against TB. Amine monomers are represented by their numerical designations.

FIGS. 6-8 show typical assay data for the luciferase reporter strain containing an Rv0341 EMB-inducible promoter with serial dilution of 12 wells (1 row) of a 96-well library plate. FIG. 10 shows the number of substituted ethylene diamines with at least 10% luciferase activity, based on the activity of ethambutol at 3.1 μM.

FIG. 6 represents typical assay data in the luciferase reporter strain containing an Rv0341 EMB-inducible promoter. The data represents values obtained from the HTS Luc assay for compound mixtures of one row (row D) in the 96-well library. Row D was subject to several serial dilutions. The effectiveness of the compound mixture in the assay was measured by the intensity of luminescence, and compared to ethambutol (100% intensity, 99% purity) at 3.1 μM. Each curve in FIG. 6 represents one well, or ten compounds. Results are reported in percent maximum Luminescence Count per Second (% Max. LCPS). During the screening, a theoretical 100% chemical yield was assumed for every unpurified compound. Concentrations are given for a single compound. Based on this initial screening, 300+compound mixtures showed anti-TB activity

EXAMPLE VIII

Representative MIC Experiment

The Minimum Inhibition Concentration (MIC) is the concentration of the growth inhibitor, here a substituted ethylene diamine, at which there is no multiplication of seeded cells. A microdilution method was used to determine the MIC of the substituted ethylene diamines, capable of inhibiting the growth of *Mycobacterium tuberculosis* in vitro. In a representative MIC experiment, bacteria, the H37Rv strain of *Mycobacterium tuberculosis* (M.tb), was cultivated in 7H9 medium to a density of 0.2 OD (optical density) at 600 nm. The bacterial culture was then diluted 1:100 in 7H9 broth medium. Stock solutions of isoniazid and ethambutol were each prepared at 32 μg/ml in 7H9 medium. A 3.2 mg/ml solution of isonizid and ethambutol were each prepared in water. The solutions were then filtered, and diluted 1:100 in 7H9 medium. Each drug, purchased from Sigma, was "laboratory use only" grade. A 10 mM solution of each substituted ethylene diamine was prepared in methanol. Next, 100 μl of the 7H9 medium was added to each well in a 96-well plate (rows (A through H) x columns (1 through 12)). To the first wells in rows C through H was added an additional 80 μl of the 7H9 medium. The isoniazid solution, 100 μl, was added to well A1, and the ethambutol solution, 100 μl, was added to well B1. Six substituted ethylene diamines, 20 μl each, were added to wells C1 through H1 (column 1), respectively. A serial dilution of each substituted ethylene diamine and the isoniazid and ethambutol controls, was performed across each row. For example, a serial dilution across row C1-C12 was done by mixing and transferring 100 μl of the previous well to the next consecutive well. In each well in "column 12," 100 μl of the final dilution was discarded. Next, 100 μl of the diluted H37Rv strain of M.tb was added to each well. The 96-well plate was then covered and incubated at 37° C. for 10 days. The plate was read for bacterial growth, or non-growth, using an inverted plate reader. The MIC was determined to be the lowest concentration of substituted ethylene diamine that inhibited visible growth of the *M. tuberculosis*.

A representative plate layout, listing concentration in each well, is shown in Table 9. Table 10 lists MIC and LD50 data for selected compounds. The LD50 is the concentration of the substituted ethylene diamine at which 50% of the cells (H37Rv strain of M.tb) are killed. Table 11 lists MIC data for purified substituted ethylene diamines in comparison to ethambutol (EMB). FIG. 9 shows the number of substituted ethylene diamine compounds with MIC activity at various concentration levels.

TABLE 9

| DRUG | Concentration in Each Well (μM) Based on Columns 1-12 | | | | | | | | | | | |
|---|---|---|---|---|---|---|---|---|---|---|---|---|
| Isoniazid | 58.25 | 29.13 | 14.56 | 7.28 | 3.64 | 1.82 | 0.91 | 0.45 | 0.23 | 0.11 | 0.06 | 0.03 |
| Ethambutol | 28.75 | 14.38 | 7.19 | 3.60 | 1.80 | 0.90 | 0.45 | 0.22 | 0.11 | 0.06 | 0.03 | 0.01 |
| Subst. Ethylene Diamine | 500 | 250 | 125 | 62.5 | 31.25 | 15.63 | 7.81 | 3.91 | 1.96 | 0.98 | 0.49 | 0.24 |

TABLE 10

Selectivity Index for Selected Compounds

| Cmpd | MIC (uM) | LD50 (uM) | MW | MIC (ug/ml) | LD50 (ug/ml) | SI |
|---|---|---|---|---|---|---|
| 6 | 7.813 | 20 | 536 | 4.187768 | 10.72 | 2.559836 |
| 34 | 7.813 | 32 | 508 | 3.969004 | 16.256 | 4.095738 |
| 37 | 15.625 | 32 | 496 | 7.75 | 15.872 | 2.048 |
| 47 | 15.625 | 25 | 452 | 7.0625 | 11.3 | 1.6 |
| 57 | 15.625 | 18 | 426 | 6.65625 | 7.668 | 1.152 |
| 59 | 15.625 | 32 | 426 | 6.65625 | 13.632 | 2.048 |
| 65 | 15.625 | 60 | 430 | 6.71875 | 25.8 | 3.84 |
| 109 | 1.953 | 32 | 450 | 0.87885 | 14.4 | 16.38505 |
| 111 | 7.813 | 44 | 412 | 3.218956 | 18.128 | 5.63164 |
| 151 | 7.813 | 41 | 450 | 3.51585 | 18.45 | 5.247664 |

The above procedure was also used to examine batched compounds (10 compounds per well). Synthesized batches of substituted ethylene diamines were dried in speed vacuum and then resuspended in DMSO or sterile water to a concentration of 2.5 mg/ml.

TABLE 11

MIC Data for Purified Samples

Plate set-up

| | | | | | | | | |
|---|---|---|---|---|---|---|---|---|
| INH | | | | | | | | |
| 58.25 | 29.125 | 14.56 | 7.28 | 3.64 | 1.82 | 0.91 | 0.45 | 0.23 |
| EMB | | | | | | | | |
| 28.75 | 14.375 | 7.1875 | 3.594 | 1.797 | 0.898 | 0.449 | 0.2245 | 0.1125 |
| CMPD | | | | | | | | |
| 500 | 250 | 125 | 62.5 | 31.25 | 15.625 | 7.813 | 3.9063 | 1.953 |

| | | | |
|---|---|---|---|
| Avg INH MIC (uM) 0.91 | Avg INH MIC (uM) 0.91 | | |
| Avg EMB MIC (uM) 7.1875 | Avg EMB MIC (uM) 8.37 | Avg EMB 7.25 | Avg EMB 7.25 |

| Cmpd | MIC (uM) | | | | BACTEC (EMB: 2.5 UG/ML) |
|---|---|---|---|---|---|
| 1 | 250 | 250 | 125 | 125 | |
| 2 | 250 | 250 | 250 | 250 | |
| 3 | 31.25 | 62.5 | 15.6 | 15.6 | |
| 4 | 125 | 62.5 | 62.5 | 62.5 | |
| 5 | >500 | 500 | 500 | 500 | |
| 6 | 7.813* | 7.813 | 3.9 | 3.9 | |
| 7 | 15.625* | 7.813 | 3.9 | 3.9 | |
| 8 | 125 | 125 | 31.25 | 31.25 | |
| 10 | 7.813* | 15.625 | 7.8 | 7.8 | |
| 11 | 31.25 | contaminated | 3.9 | 3.9 | |
| 13 | 31.25 | 31.25 | 15.6 | 15.6 | 15 |
| 14 | 15.625" | 15.625 | 7.8 | 7.8 | |
| 15 | >500 | >500 | 250 | 500 | |

TABLE 11-continued

MIC Data for Purified Samples

| | | | | | |
|---|---|---|---|---|---|
| 17 | 62.5 | 62.5 | 15.6 | 15.6 | |
| 21 | 15.625* | 31.25 | 7.8 | 7.8 | |
| 22 | 31.25 | 31.25 | 7.8 | 15.6 | |
| 23 | 31.25 | 31.25 | 15.6 | 15.6 | |
| 24 | 125 | 125 | 31.25 | 31.25 | |
| 27 | 125 | 62.5 | 15.6 | 31.25 | |
| 28 | 125 | 62.5 | 31.25 | 31.25 | |
| 29 | 62.5 | 62.5 | 31.25 | 62.5 | |
| 31 | 31.25 | 61.25 | 15.6 | 15.6 | |
| 32 | 15.625* | 15.625 | 7.8 | 7.8 | |
| 33 | 62.5 | 62.5 | 31.25 | 31.25 | |
| 34 | 7.813* | 7.813 | 3.9 | 3.9 | |
| 35 | 62.5 | 62.5 | 15.6 | 31.25 | |
| 36 | 31.25 | 62.5 | 15.6 | 15.6 | |
| 37 | 15.625* | 15.625 | 3.9 | 7.8 | 1.25 |
| 38 | 7.813 | 7.813 | 3:9 | 7.8 | |
| 40 | 15.625* | 15.625 | 7.8 | 7.8 | |
| 41 | 31.25 | 15.625 | 15.6 | 15.6 | |
| 42 | 31.25 | 31.25 | 1.95 | 3.9 | |
| 43 | 31.25 | 31.25 | 3.9 | 7.8 | 12.5 |
| 47 | 15.625* | 15.625 | 1.95 | 7.8 | 5 |
| 51 | 31.25 | 250 | 31.25 | 31.25 | |
| 52 | 15.625* | 15.625 | 3:9 | 3.9 | |
| 53 | 31.25 | 31.25 | 31.25 | 31.25 | |
| 54 | 31.25 | 31.25 | 15.6 | 31.25 | |
| 55 | 15.625* | 15.625 | 15.6 | 15.6 | 25 |
| 56 | 500 | >500 | 500 | 500 | |
| 57 | 15.625* | 7.813 | 7.8 | 7.8 | |
| 58 | 15.625* | 15.625 | 7.8 | 7.8 | 5 |
| 59 | 15.625* | 31.25 | 15.6 | 15.6 | 12.5 |
| 61 | 62.5 | 62.5 | 31.25 | 31.25 | |
| 62 | 15.625* | 31.25 | 15.6 | 31.25 | |
| 63 | 62.5 | 62.5 | 31.25 | 62.5 | |
| 64 | 31.25 | 31.25 | 31.25 | 31.25 | |
| 65 | 15.625* | 31.25 | 31.25 | 31.25 | |
| 66 | 15.625* | 15.625 | 7.8 | 7.8 | |
| 68 | 500 | 500 | 500 | 500 | |
| 71 | 62.5 | 62.5 | 31.25 | 31.25 | |
| 73 | 62.5 | | 15.6 | 15.6 | |
| 76 | 62.5 | 62.5 | 31.25 | 31.25 | |
| 77 | 31.25 | 31.25 | 15.6 | 15.6 | |
| 78 | 15.625* | 31.25 | 15.6 | 15.6 | |
| 79 | 31.25 | 31.25 | 15.6 | 15.6 | |
| 103 | 31.25 | 31.25 | 62.5 | 62.5 | |
| 107 | 500 | 500 | 250 | 250 | |
| 109 | 1.953* | 1.953 | 1.95 | 1.95 | 0.63 |
| 111 | 7.813* | 7.813 | 7.8 | 7.8 | 5 |
| 116 | 15.625* | 15.625 | 7.8 | 15.6 | 12.5 |
| 117 | 7.813* | 15.625 | 7.8 | 7.8 | |
| 118 | 31.25 | 62.5 | 31.25 | no data | |
| 119 | 125 contam | 62.5 | cont | no data | |
| 125 | 15.625* | 15.625 | cont | no data | 6.25 |
| 134 | >500 | >500 | 500 | no data | |
| 151 | 15.625* | 7.813 | cont | no data | 6.25 |
| 164 | 62.5 | 125 | cont | no data | |
| 165 | 62.5 | 62.5 | 15.6 | 15.6 | |

EXAMPLE IX

Secondary Screening and Evaluation of Substituted Ethylene Diamines Against Drug Resistant Patient Isolates Secondary screening was performed on some of the substituted ethylene diamine compounds to examine their activity against three clinically resistant MDR patient isolates. MDR Strain TN576 is classified as a W1 strain ($STP^R$, $INH^R$, $RIF^R$, $EMB^R$, $ETH^R$, $KAN^R$, $CAP^R$) strain TN587 is classified as a W strain ($STP^R$, $INH^R$, $RIF^R$, $EMB^R$, $KAN^R$), and the third strain TN3086 is classified as a W1 strain ($STP^R$, $INH^R$, $RIF^R$, $EMB^R$, $KAN^R$). Each MDR strain is highly resistant to ethambutol with MIC values exceeding 12.5-25 µM. The MICs for the following substituted ethylene diamines, MP 116, MP 117, RL 241, compounds #59 and #109, were determined for all three patient isolates.

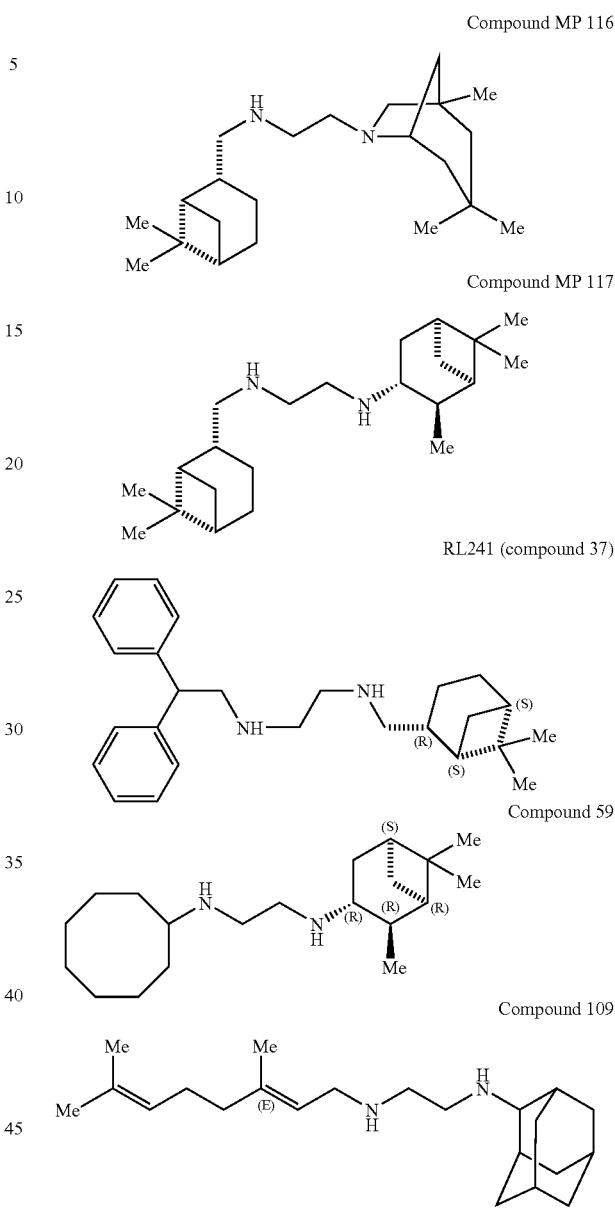

Compound MP 116

Compound MP 117

RL241 (compound 37)

Compound 59

Compound 109

The results from this study are shown in Tables 12-13. Table 14 characterizes each MDR strain according to its resistance.

TABLE 12

Screening of Substituted Ethylene Diamines Against Drug Resistant Patient Isolates - (MIC values in ug/ml)

| | WT | 576 | 587 | 3806 |
|---|---|---|---|---|
| EMB | 3.12 (or 11.1 uM) | 12.5-25 | 12.5-25 | 12.5-25 |
| MP 116 | 6.25 | 3.15 | 6.25 | 3.15 |
| MP 117 | 6.25 | 3.15 | 3.15 | 3.15 |
| RL 241 | 1.5 (or 3.34 uM) | 1.5 | 1.5 | 1.5 |

WT = wild type of M.tb
EMB as 2HCl salt
RL241 as 2HCl salt

TABLE 13

Screening of Substituted Ethylene Diamines Against
Drug Resistant Patient Isolates - (MIC values in ug/ml)

|  | WT | 576 | 587 | 3806 |
| --- | --- | --- | --- | --- |
| EMB | 1.6-1.8 | 50 | 50 | 50 |
| Cmpd#59 | 0.05 (or 0.13 uM) | 0.1 | 0.05 | 0.05 |
| Cmpd#109 | 0.10 (or 0.18 uM) | 0.2 | 0.2 | 0.1 |

Cmpd#59 as a 2HCl salt
Cmpd#109 as a $2CF_3COOH$ salt

TABLE 14

Drug Resistance of Each MDR Strain

| Strain | STP | STP 2 | INH 1 | INH 2 | Rif | Emb | Eth | Kan | Cip | Cap | Cyc |
| --- | --- | --- | --- | --- | --- | --- | --- | --- | --- | --- | --- |
| 576 W1 | R | R | R | R | R | R | R | R | S | R | S |
| 587 W | R | R | R | R | R | R | S | R | S | S | S |
| 3806 W1 |  | R |  | R | R | R | S | R |  |  |  |

R = resistant
S = susceptible
STP = Streptomycin
INH = Isoniazid
Rif = Rifampicin
Emb = Ethambutol
Eth = Ethionamide
Kan = Kanamycin
Cip = Ciprofloxacin
Cap = Capreomycin
Cyc = Cycloserine

EXAMPLE X

In Vivo Animal Studies

Animal models were used in the final stages of the drug discovery cycle to assess the anti-microbial efficacy of some substituted ethylanediamine compounds in a representative system of human disease state. The in vivo testing approach involves the inoculation of four-six week old C57BL/6 mice via aerosol, containing approximately 200 colony forming units of M. tuberculosis $H37R_v$.

A. CFU Lung Study

Figure 17:
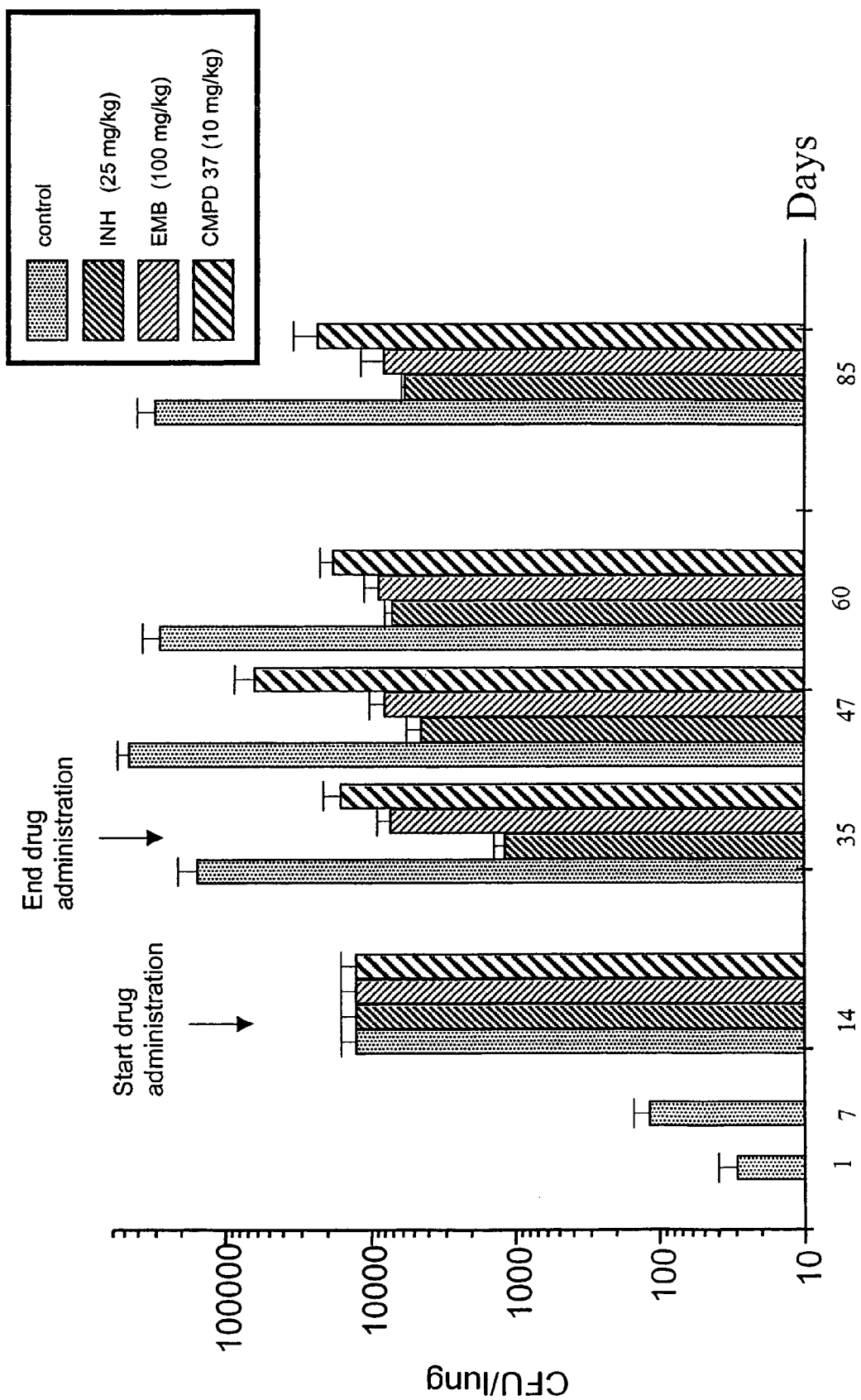
FIG. 17 is a bar graph of data from a Colony Forming Units/Lung (CFU/Lung) study showing CFU/Lung growth over time in days for various compounds.
Figure 18:
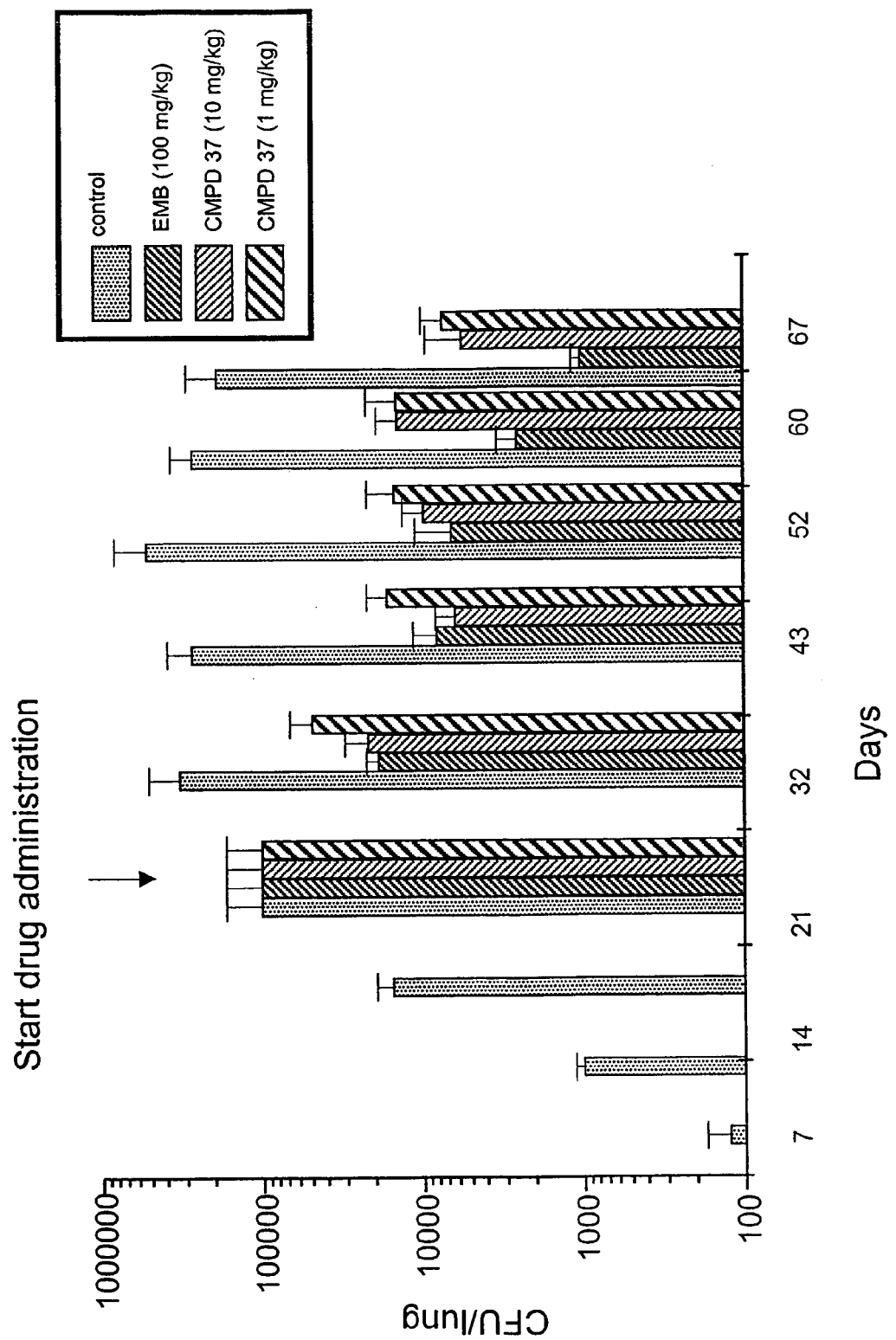
FIG. 18 is a bar graph of data from a CFU/Lung study showing CFU/Lung growth over time in days for various compounds.
Figure 19:
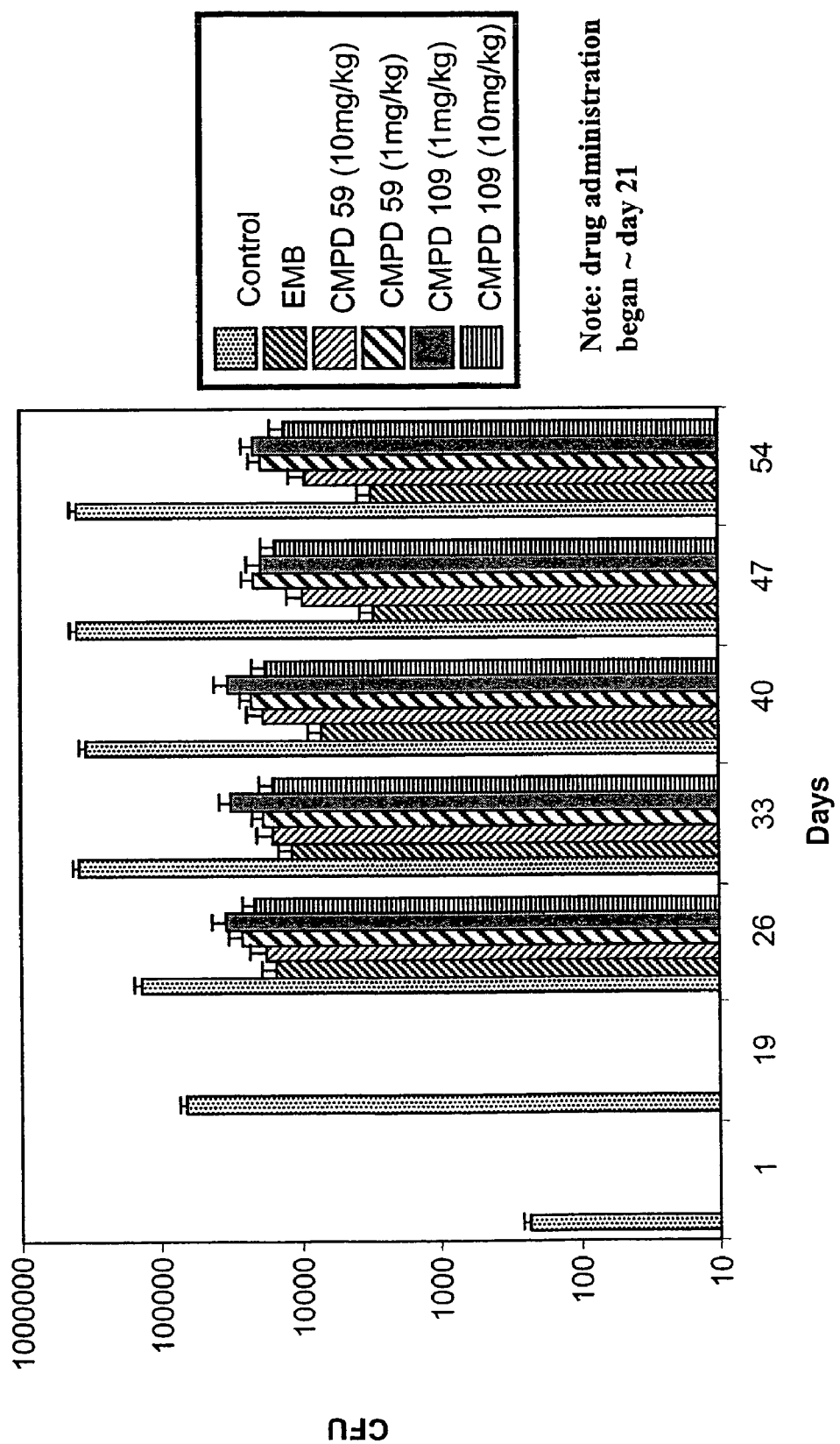
FIG. 19 is a bar graph of data from a CFU/Lung study showing CFU/Lung growth over time in days for various compounds.

Mice aerosolized with M. tuberculosis $H37R_v$ were examined for 10 to 12 weeks following inoculation. Drugs (substituted ethylene diamines) were administered via the esophageal cannula (gavage) 7 days/week, starting at either 14 or 21 days post infection. Bacterial load in the lungs of five mice per group were determined at approximately one-week intervals by viable colony counts. The drugs tested were directly compared to the front line anti-tuberculosis drug isoniazid, and to the second line drug, ethambutol. Isoniazid and ethambutol were tested at 25 mg/kg and 100 mg/kg, respectively. The substituted ethylene diamines, compound 37, compound 59 and compound 109, were each tested at 1 mg/kg and 10 mg/kg. FIGS. 17 to 19 represent data from three, independent CFU Lung studies. In each study, the number of colony forming units (CFU) that were recoverable and cultivatable, were determined during various time intervals (days).

B. Lesion Study

Figure 20:
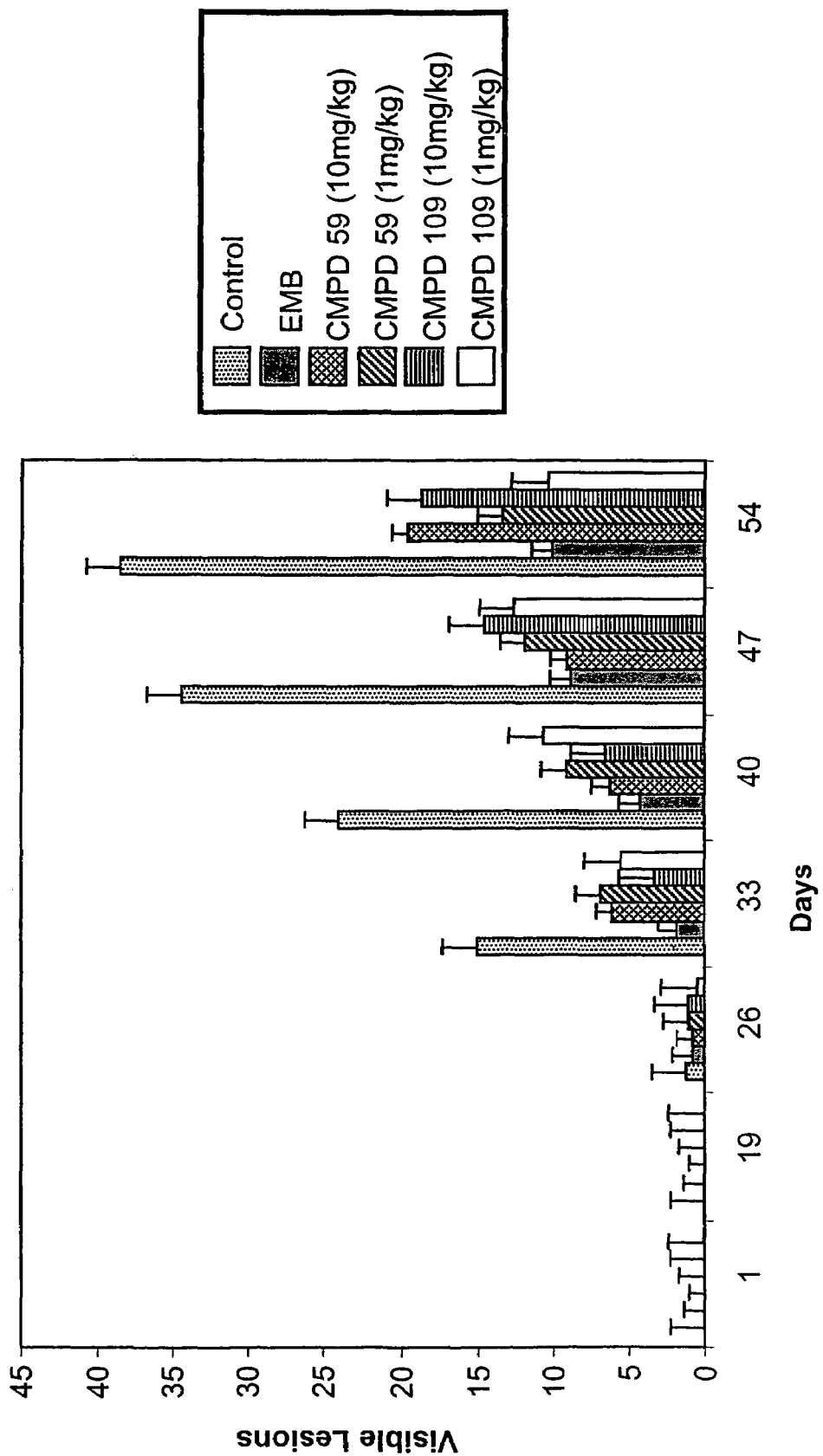
FIG. 20 is a bar graph of data from a lesion study showing visible lesions over time after treatment with various compounds.

The ability of compound 59 and compound 109 to prevent the development of gross pathology due to bacterial burden was determined in conjunction with the CFU/Lung Study. The gross pathology was determined by visible quantitation of lesions on the surface of the lungs. Quantitation by inspection is a good surrogate for CFU determination, and directly correlates to the bacterial burden, as determined by the actual colony forming units. The lesions are first visibly examined, and then the lungs are processed and plated for CFU quantification. The lesion study demonstrates the ability of the drug to prevent the development of the disease pathology. FIG. 20 represents data from a lesion study. The corresponding CFU results are shown in FIG. 19.

C. Toxicity Study

Toxicity was assessed using a dose escalation study. This study was performed with ten C57BL/6 mice per candidate. Every two days, the mice were administered an increased concentration of the drug, and monitored for detrimental effects. The administration scheme was 50, 100, 200, 400, 600, 800 and 1000 mg/kg. The maximum limit of 1000 kg/mg was based on the goal of dose escalation, and the solubility of the drugs in the delivery vehicle. Compound 37 was toxic in mice at 100 kg/mg. Compound 59 and compound 109 were tolerated in mice at 1000 mg/kg and 800 mg/kg, respectively.

It should be understood that the foregoing relates only to preferred embodiments of the present invention, and that numerous modifications, or alterations, may be made therein without departing from the spirit and scope of the invention. The entire text of each reference mentioned herein is hereby incorporated, in its entirety, by reference.

EXAMPLE XI

In vitro Toxicity and Selectivity Indexes for Hit Compounds

Twenty six compounds (including 37, 59 and 109) were tested in an in vitro model of toxicity using monkey kidney cells (Vero) and human cervical cancer cells (HeLa) using methods well known to those skilled in the art. The data from this toxicity testing and the MIC data were used to calculate a selectivity index (SI), the ratio of IC50:MIC (Table 15). Selectivity Indexes were ranging from 1.76 to 16.67. Compound 109 has the best selectivity index.

TABLE 15

In vitro data for representative compounds

| Compound | MIC (μM) | Vero IC50 (μM) | SI (IC50:MIC) |
|---|---|---|---|
| 66 | 15.6 | 28 | 1.76 |
| 40 | 15.6 | 25 | 1.88 |
| 41 | 3.13 | 19 | 2.05 |
| 59 | 15.6 | 36 | 2.30 |
| 55 | 15.6 | 34 | 2.32 |
| 57 | 11.7 | 22 | 2.40 |
| 37 | 7.8 | 32 | 4.10 |
| 38 | 6.25 | 33 | 5.28 |
| 111 | 7.81 | 45 | 5.76 |
| 73 | 12.5 | 81 | 6.48 |
| 58 | 12.5 | 82 | 6.56 |
| 78 | 15.6 | 130 | 8.33 |
| 109 | 1.56 | 26 | 16.67 |

EXAMPLE XII

In vivo Efficacy of Ethambutol Analogues

Compounds 58, 59, 73, 109, and 111 were selected for in vivo efficacy studies in a mouse model of TB. Compounds 58 and 59 share the same cyclooctyl fragment in their molecules; compounds 58, 73, and 109 share adamantly moiety, and 109 and 111—the geranyl fragment (FIG. 22).

Figure 23:
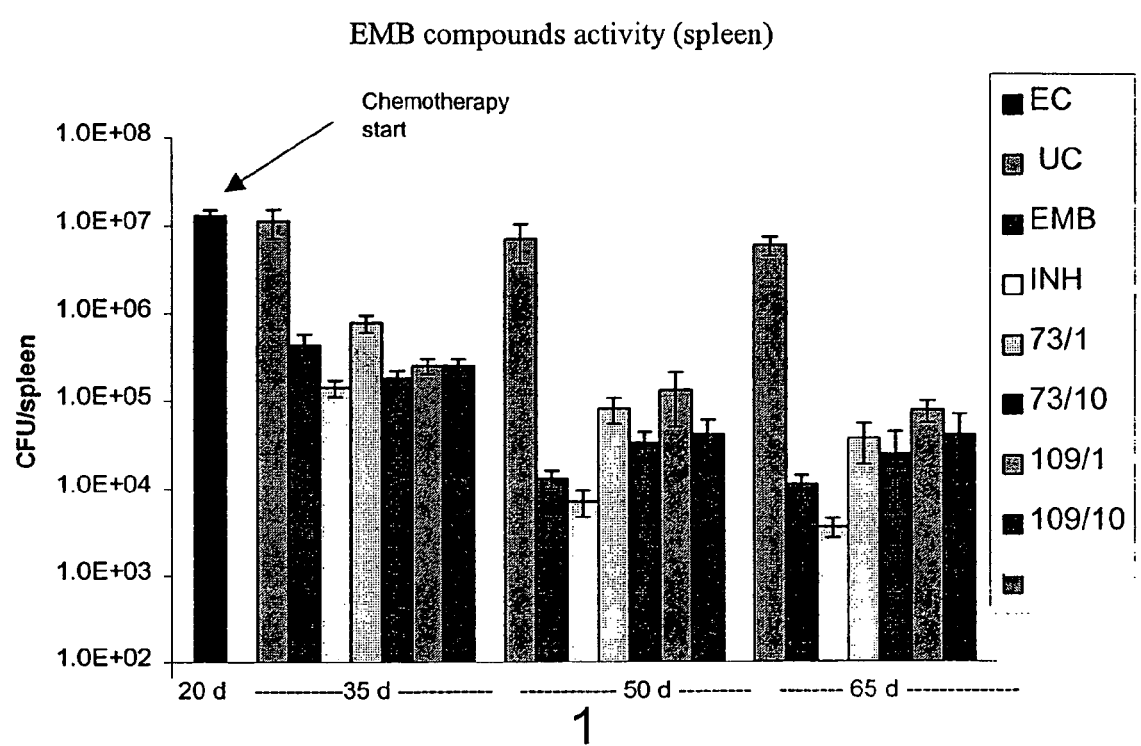
FIG. 23 is a graph showing the results of in vivo studies of compounds 73 and 109 at 1 and 10 mg/kg doses (spleen).
Figure 24:
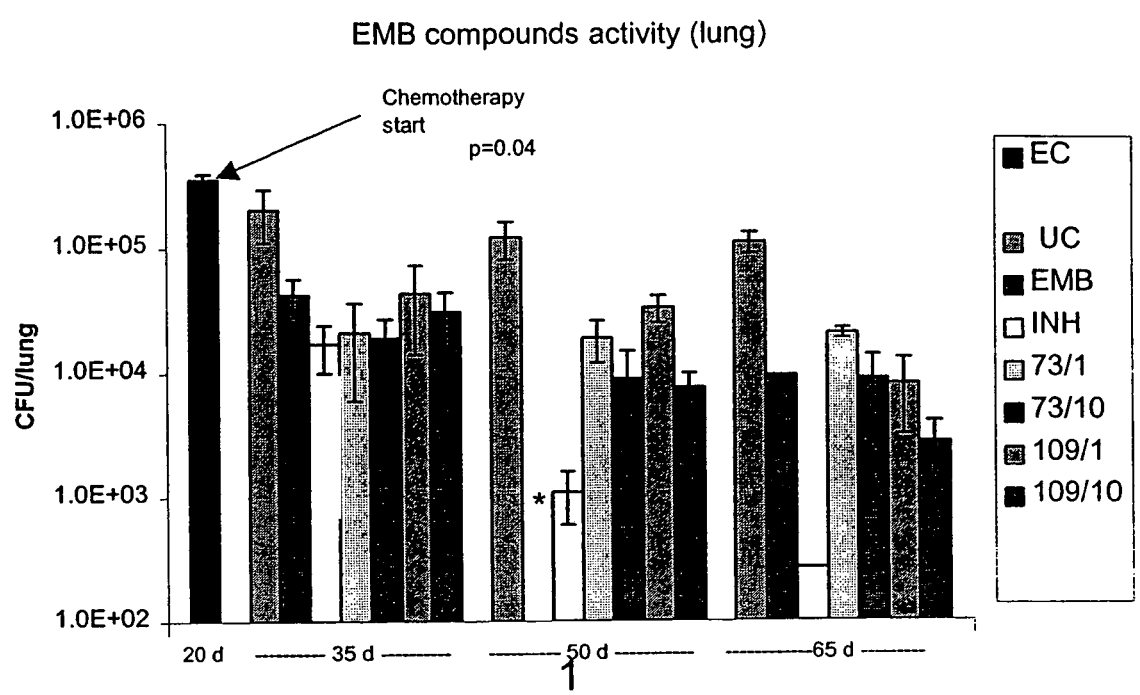
FIG. 24 is a graph showing the results of in vivo studies of compounds 73 and 109 at 1 and 10 mg/kg doses (lungs).

In these studies, 8-week old inbred female mice C57BL/6 were intravenously infected with *M. tuberculosis*. 3 weeks following infection drug treatment was initiated (detailed protocol is provided). The drugs were administered orally by gavage. Mice were sacrificed at three timepoints (15, 30, and 45 days post infection), and CFUs in spleen and lungs were determined (FIGS. 23 and 24). These studies demonstrated that compound 109 had activity at doses 1 and 10 mg/kg equal to that of ethambutol at 100 mg/kg Materials and Methods Mice. Female C57BL/6 mice of 8 weeks old were purchased from Charles River (Raleigh, N.C.), housed in BSL-2 facility of BIOCAL, Inc. (Rockville, Md.), and were allowed to acclimate at least 4 days prior infection.

Mycobacteria. An example of frozen and thawed of *M. tuberculosis* H37Rv Pasteur was added to 5 ml 7H10 broth medium, with 0.5% BSA and 0.05% Tween 80, incubated 1 week at 37° C., and then 1 ml was added into 25 ml medium (2-d passage during 2 weeks). Culture was washed twice and resuspended in PBS with 0.5% BSA and 0.05% Tween 80, aliquoted and frozen at −80° C. To determined CFU of the culture aliquot was thawed, and 10-fold dilutions will be plated on agar 7H9 and CFU count will be calculated 20 days later.

Infection: Frozen sample of culture was thawed, and diluted for concentration about $10^6$ CFU/ml. Mice were infected with *M. tuberculosis* H37Rv intravenously through lateral tail vein in corresponded dose in 0.2 ml of PBS.

Antimicrobial agents. INH, EMB, Ethambutol analogues.

Protocol of drug treatment: Treatment of mice with compounds was initiated 20 days following infection. Compounds were dissolved in 10% ethanol in water and administered by gavage (0.2 ml per mouse). Therapy was given 5 days per week and continued for four or six weeks. Two, four and six weeks following chemotherapy start mice (6 mice per group) were sacrificed, lungs and spleens were removed and homogenized in sterile in 2 ml PBS with 0.05% Tween-80. Homogenates were plated in serial dilutions on 7H10 agar dishes, and incubated at 37° C. CFU counts were calculated three weeks later.

Statistic analysis. To analyze results of CFUs in organs ANOVA test was performed; the significance of the differences was estimated by Student's test, $p<0.05$ was considered statistically significant.

Results

Figure 21:
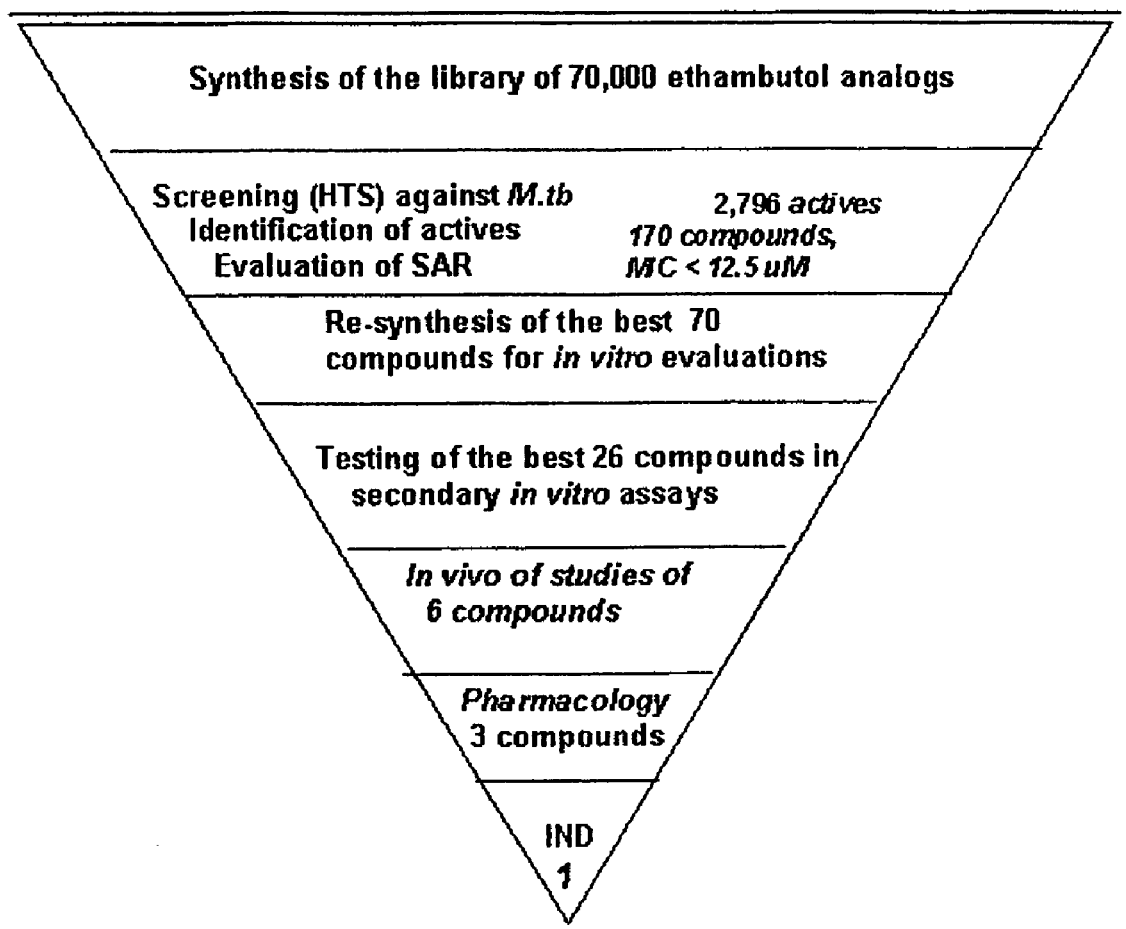
FIG. 21 provides a schematic demonstrating the identification of a drug candidate.

In vivo activities of new compounds. The activities of these compounds are presented in FIGS. 21-24. In the experiment presented in FIGS. 21 (spleen) and 22 (lung) mice were infected with $5 \times 10^5$ CFU *M. tuberculosis* H37Rv and chemotherapy was started 20 days following infection. Mice were treated with INH (25 mg/kg), EMB (100 mg/kg), compounds 73 and 109 (both 1 mg/kg and 10 mg/kg). The results indicate that in the spleen, compounds 73 and 109 have activities equal to that of EMB at 100 mg/kg (FIG. 21). In spleen there are no statistical differences between activities of these compounds at 1 mg/kg or 10 mg/kg. In the lung, compound 109 at concentration 10 mg/kg after 4 and 6 weeks was more effective than EMB at 100 mg/kg. In the lung, statistically sufficient difference was shown for compound 109 at concentrations 1 mg/kg and 10 mg/kg (FIG. 22). INH was the most active drug in both spleen and lung.

Compounds 73 and 109 were also tested in shorter model with using higher dose of infection (FIGS. 23 and 24). Mice were infected with $5 \times 10^6$ CFU *M. tuberculosis* H37Rv and chemotherapy was started 15 days following infection. Mice were treated with INH (25 mg/kg), EMB (100 mg/kg), compounds 109 (0.1 mg/kg, 10 mg/kg, and 25 mg/kg), 58, 73 and 111 (all 25 mg/kg). Mice were treated for 4 weeks. In both the spleen and lung, compound 109 at concentrations 10 mg/kg and 25 mg/kg had activity equal to that of EMB at 100 mg/kg, and at concentration 0.1 mg/kg minimal but sufficient difference with untreated control appeared after 4 weeks of therapy (FIGS. 23 and 24). Statistically sufficient difference between compounds 73 (25 mg/kg) and 109 (25 mg/kg) was detected. In the lung significant difference between activities of these compounds was not detected. Compounds 58 and 111 are active in vivo in both spleen and lung; however, compounds 73 and 109 are preferable. The results of these experiments indicate that compounds 73 and 109 in low concentration show activity equal that of EMB at 100 mg/kg, and in some cases compound 109 shows higher activity.

Figure 25:
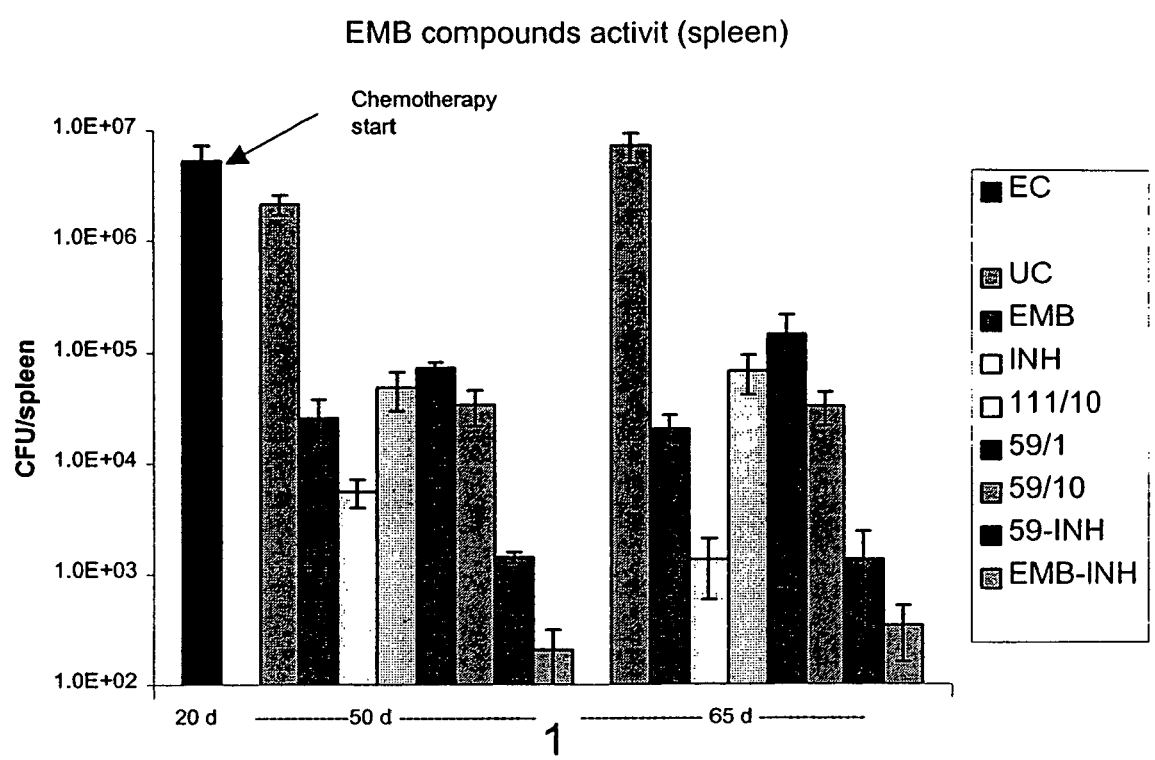
FIG. 25 is a graph showing in vivo studies of compounds 59 and 111 at 1 and 10 mg/kg doses (spleen).
Figure 26:
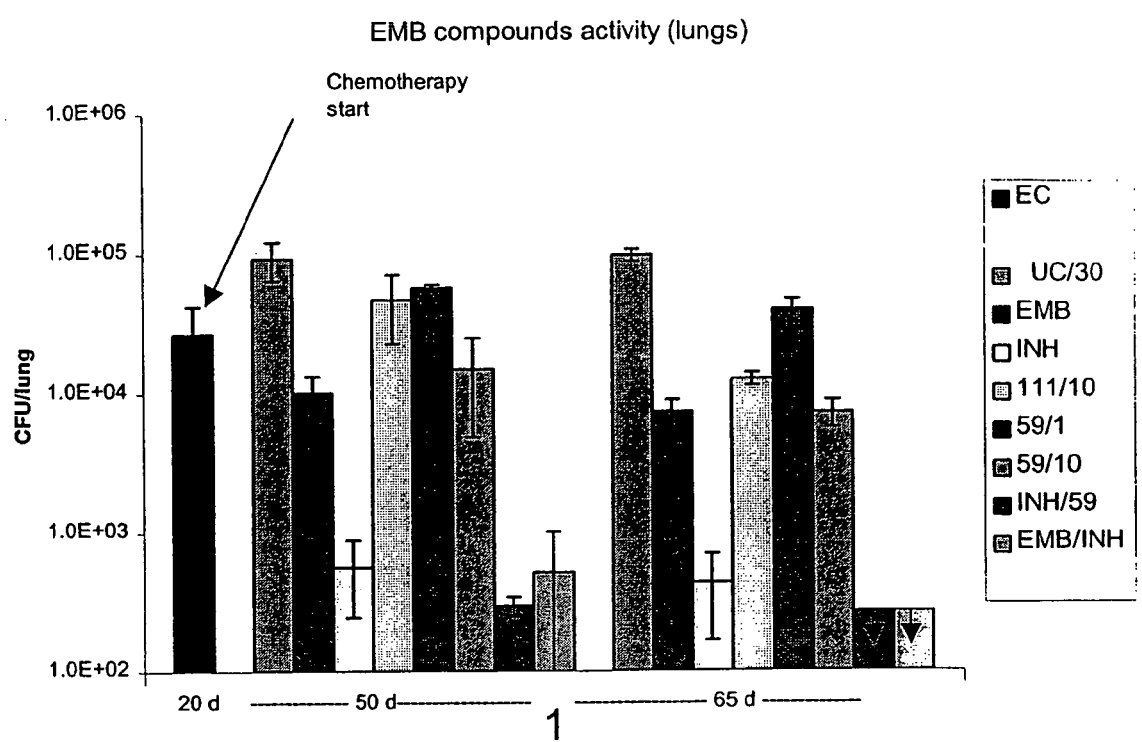
FIG. 26 is a graph showing in vivo studies of compounds 59 and 111 at 1 and 10 mg/kg doses (lungs).
Figure 27:
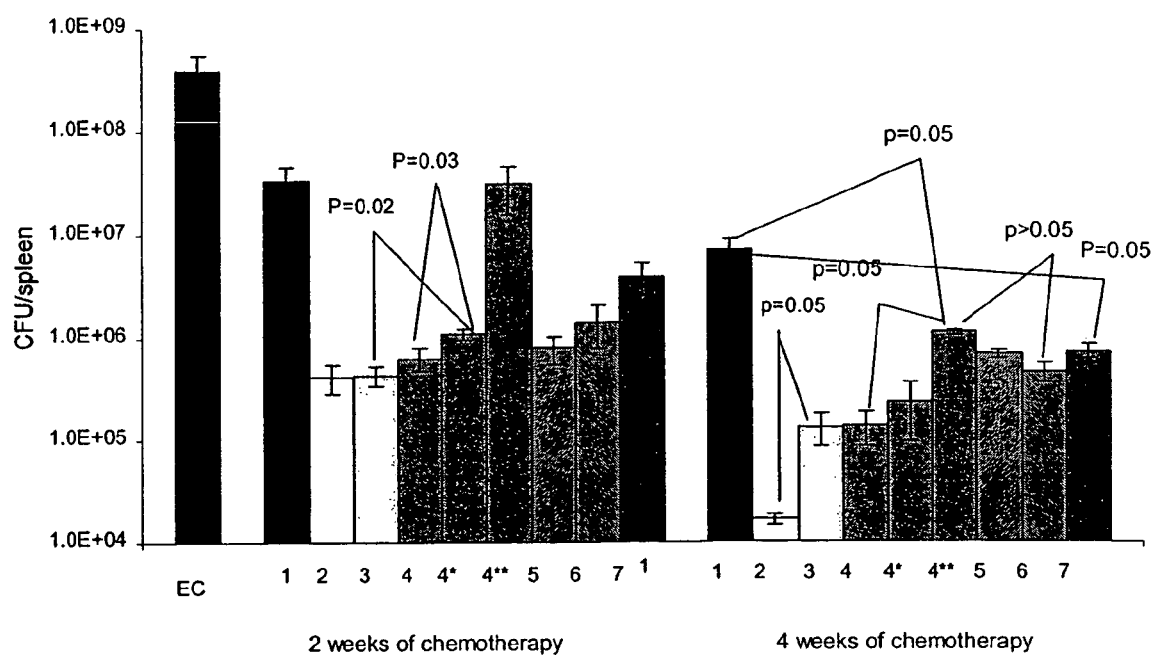
FIG. 27 is a graph showing the results of efficacy testing of the compounds 58, 73, 109, and 111 in C57BL.6 mice infected with *M. tuberculosis* H37Rv (spleen). Mice were infected i.v. with $5 \times 10^6$ CFU *M. tuberculosis* H37Rv; treatment with drugs started 18 days following infection. EC-EC—early control, CFU in lungs of mice at the day of chemotherapy start. Mice received: 1—untreated mice, 2—INH (25 mg/kg), 3—EMB (100 mg/kg), 4—comp. 109 (25 mg/kg), 4*—comp.109 (10 mg/kg), 4**—comp. 109 (0.1 mg/kg), 5—comp. 58 (25 mg/kg), 6—comp.73 (25 mg/kg), 7—comp. 111 (25 mg/kg).
Figure 28:
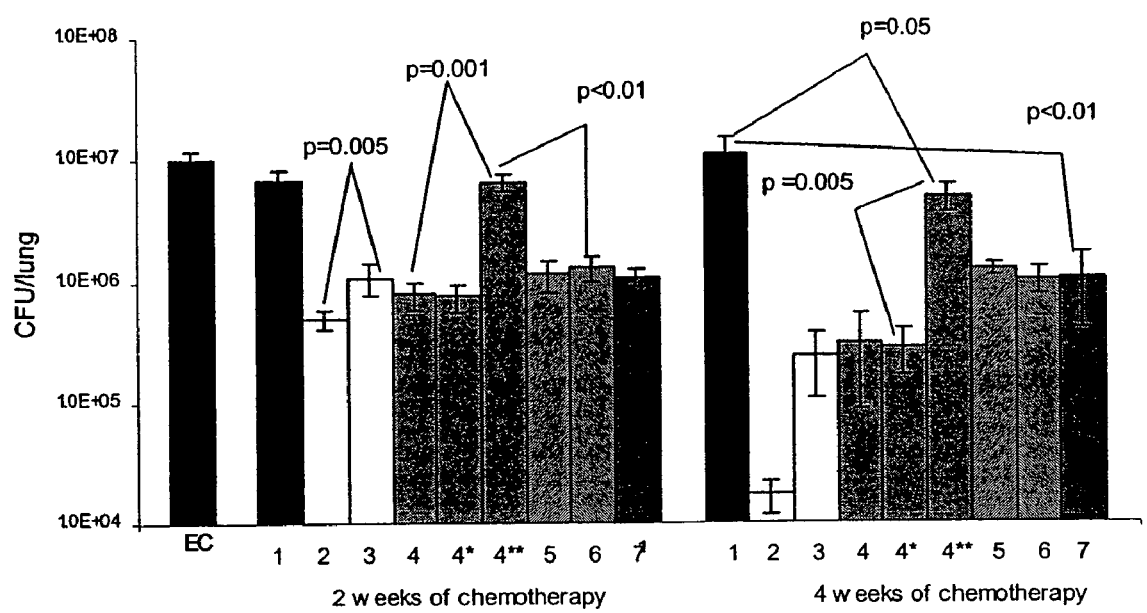
FIG. 28 is a graph showing the results of efficacy testing of the compounds 58, 73, 109, and 111 in C57BL.6 mice infected with *M. tuberculosis* H37Rv (lungs). Mice were infected i.v. with $5 \times 10^6$ CFU *M. tuberculosis* H37Rv; treatment with drugs started 18 days following infection. EC-EC—early control, CFU in lungs of mice at the day of chemotherapy start. Mice received: 1—untreated mice, 2—INH (25 mg/kg), 3—EMB (100 mg/kg), 4—comp. 109 (25 mg/kg), 4*—comp.109 (10 mg/kg), 4**—comp. 109 (0.1 mg/kg), 5—comp. 58 (25 mg/kg), 6—comp.73 (25 mg/kg), 7—comp. 111 (25 mg/kg).

Testing of compounds 111 and 59 was performed in B6 mice infected with $5 \times 10^5$ CFU *M. tuberculosis* H37Rv and beginning chemotherapy 20 days following infection (FIGS. 25 and 26). Both compounds showed anti-tuberculosis activity at concentration 10 mg/kg comparable to that of EMB at 100 mg/kg.

In all experiments, INH showed higher activity than EMB and other compounds decreasing load of bacteria in organs on 2-3 logs during 4-6 weeks of chemotherapy; new compounds similar to EMB (100 mg/kg) decreased load of bacteria on 1.0-2.0 logs. Among studied compounds 73 and 109 are the most preferable, because the highest capacity to decrease mycobacteria in organs and its parameters of toxicity and pharmacology kinetics.

EXAMPLE XIII

In vivo Toxicity

Preliminary dose acceleration studies in mice have indicated that compound 109 can be well tolerated at doses up to 800 mg/kg and compound 59 up to 1000 mg/kg. Compound 37 was fatal at doses 100 mg/kg (Clif Barry, NIAID, unpublished results).

Compound 109 was mostly used in the form of dihydrochloride at five different doses, and 37—solely as hydrochloride salt at two doses.

Mice were given a one-time dose of the compounds at concentrations 100, 300 or 1000 mg/kg using the gavage method. Each dose of each compound consisted of one group of 3 mice. Monitoring of the mice was done twice a day for the duration of the experiment. Mice surviving one week post-drug administration were sacrificed; critical organs were aseptically removed and observed for abnormalities and evidence of drug toxicity. The MTD (mg/kg) is the highest dose that results in no lethality/tissue abnormality.

Methods:

1. Treatment of mice: C57BL/6 female mice (6-8 weeks in age) are given a one-time dose of the compound at concentrations 100, 300 or 1000 mg/kg using the gavage method. The compounds are dissolved in the appropriate concentration of ethanol in distilled water and administered in a volume of 0.2 ml per mouse.

2. Observation of mice: Mice will be observed 4 and 6 hours post administration, then twice daily for one week. Survival and body weight of mice will be closely monitored throughout the study.

3. Assessment of drug toxicity: Mice exhibiting signs of any abnormal appearance or behavior or those remaining in a group in which other mice did not survive to day 7 will be sacrificed for assessment of drug toxicity. Critical organs will be aseptically removed and observed; tissues from the liver, heart, and kidneys are extracted and placed into 10% formalin solution. These fixed tissues are sectioned and examined for abnormalities resulting from drug toxicity.

These studies indicate that the maximum tolerated dose for the compound 109 is 600 mg/kg (Table 16). No visible changes in organs were observed. Dose 800 mg/kg was fatal: out of a group of 3 mice, two animals died within 3 days (Table 17). Compound 37 was well tolerated at doses 100 and 300 mg/kg. No visible changes in organs were observed. Additional experiments to evaluate maximum tolerated dose and in vivo efficacy for the compound 37 are being conducted.

TABLE 16

Determination of a maximum tolerated dose for the compounds 109 and 37 in mice.

|  |  | 109 at 100 mg/kg | | 109 at 300 mg/kg | | 109 at 600 mg/kg | | 109 at 1000 mg/kg | | 37 at 100 mg/kg | |
| --- | --- | --- | --- | --- | --- | --- | --- | --- | --- | --- | --- |
| Date | Day | Mice | Day of death | Mice | Day of death | Mice | Day of death | Mice | Day of death | Mice | Day of death |
| Apr. 8, 2003 | 1 | 3 |  | 3 |  | 3 |  | 3 |  | 2-4 h | 1 |
| Apr. 9, 2003 | 2 | 3 |  | 3 |  | 3 |  | 2 | 2 | 2 |  |
| Apr. 10, 2003 | 3 | 3 |  | 3 |  | 3 |  | 2 |  | 2 |  |
| Apr. 11, 2003 | 4 | 3 |  | 3 |  | 3 |  | 1 | 4 | 2 |  |
| Apr. 13, 2003 | 6 | 3 |  | 3 |  | 3 |  | 0 | 6 | 2 |  |
| Apr. 14, 2003 | 7 | 3 |  | 3 |  | 3 |  | — |  | 2 |  |

TABLE 17

Determination of a maximum tolerated dose for the compounds 109 And 37 in mice

|  |  | 37 at 100 mg/kg | | 37 at 300 mg/kg | | 109 as HCl salt at 800 mg/kg | | 109 as TFA salt at 800 mg/kg | |
| --- | --- | --- | --- | --- | --- | --- | --- | --- | --- |
| Date | Day | Mice | Day of death | Mice | Day of death | Mice | Day of death | Mice | Day of death |
| Apr. 29, 2003 | 1 | 3 |  | 3 |  | 3 |  | 1 |  |
| Apr. 30, 2003 | 2 | 3 |  | 3 |  | 2/1 | 2 | 1 |  |
| May 1, 2003 | 3 | 3 |  | 3 |  | 1/1 | 3 | 1 |  |
| May 2, 2003 | 4 | 3 |  | 3 |  | 1 |  | 1 |  |
| 05.03. | 5 | 3 |  | 3 |  | 1 |  | 1 |  |
| 05.04 | 6 | 3 |  | 3 |  | 1 |  | 1 |  |
| May 5, 2003 | 7 | 3 |  | 3 |  | 1 |  | 1 |  |

EXAMPLE XIV

Pharmacokinetic Studies of the Compounds 37, 59, and 109

Figure 29:
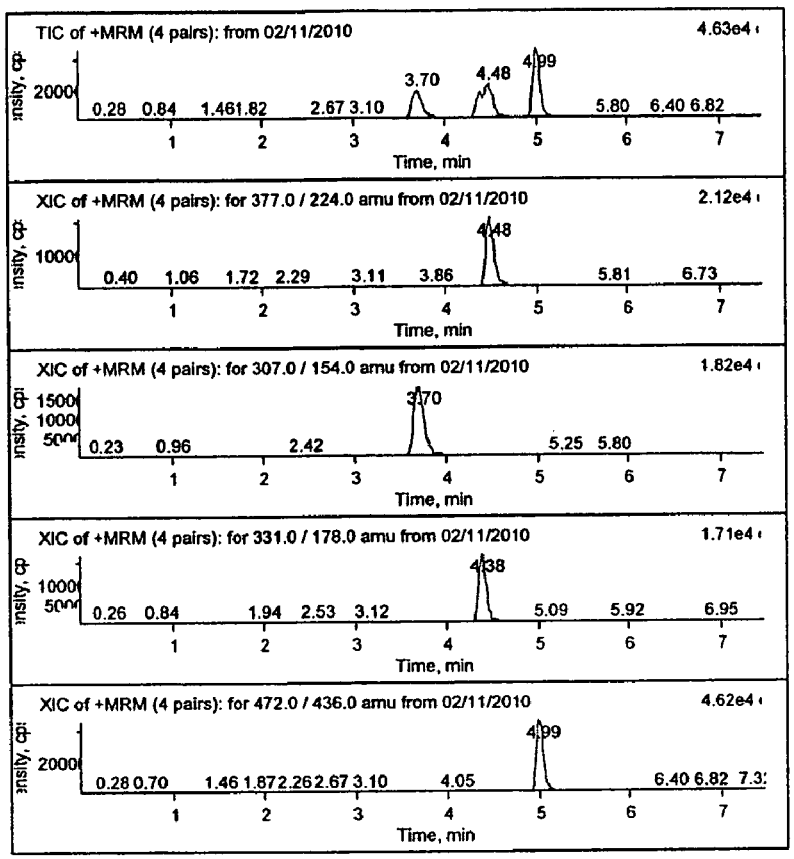
FIG. 29 provides LC/MS data of tested compounds.

Initially, analytical methods for determination of the compounds had been developed that allowed to carry out all the PK experiments, see FIG. 29. Here is a brief description of the experiment: (1) plasma spiked with tested compounds and 10 uL of Terfenadine or plasma samples (200 uL) added; (2) ACN (2 mL) added to precipitate protein and spin at 2,500 rpm; (3) evaporate supernatant to dryness; (4) add 200 uL of the diluting solvent: methanol (with 0.1% of trifluoroacetic acid): ammonium acetate (80/20); (5) vortex, spin, and use supernatant; (6) run LC/MS/MS on Sciex API 3000.

Biostability studies of the compounds in plasma were carried out using concentrations 1 and 15 mg/ml. The compounds were incubated for 1, 2, 3 & 6 hr at 37° C. (Table 18). In addition, it was found that all tested compounds were stable in plasma at 24° C., pH 2 and 7.4 up to 24 hr.

TABLE 18

Biostability of tested compounds in plasma.

| Comp. | Human | Dog | Rat | Mouse |
|---|---|---|---|---|
| 37 | 20% ↓ | stable | 35% ↓ | stable |
| 59 | stable | stable | stable | stable |
| 109 | 30% ↓ | 40% ↓ | stable | stable |

Figure 30:
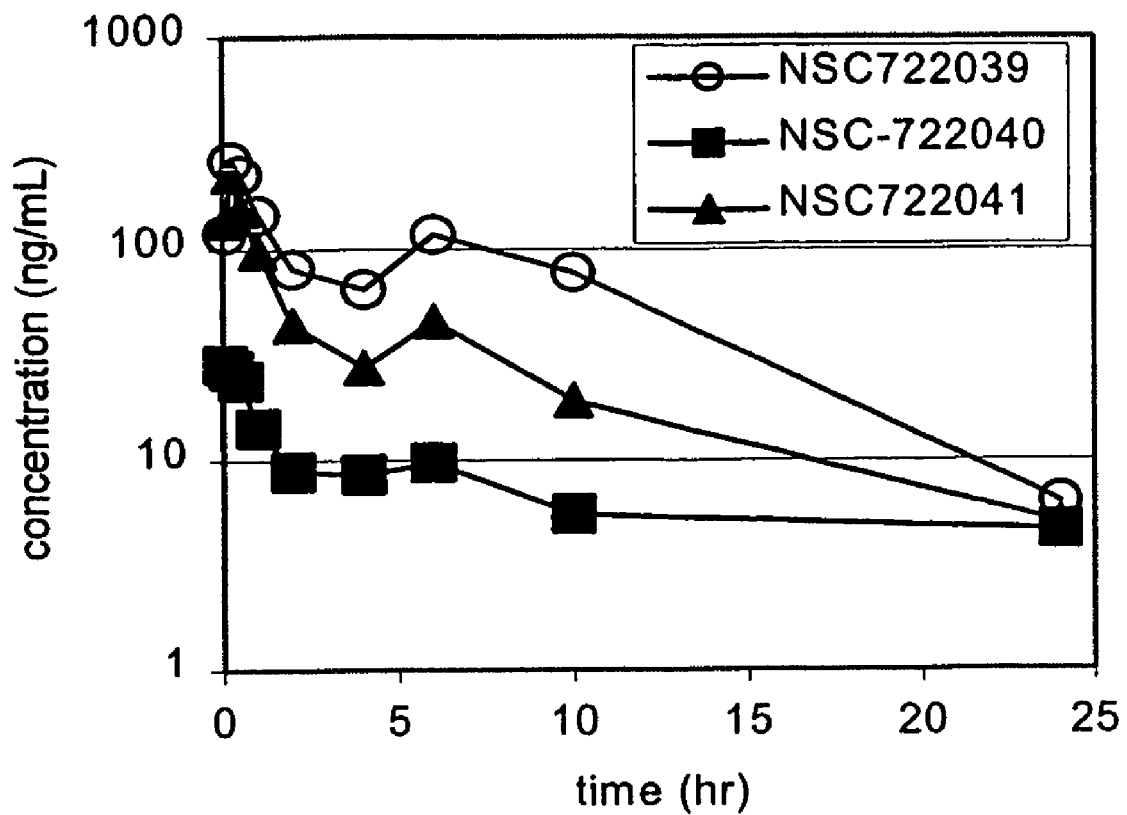
FIG. 30 provides a graph showing results of PK studies with a cassette dosing of tested compounds to mice. Oral delivery. Compound NSC 722039 in the study reads as the compound 37, NSC 722040—compound 59, NSC 722041—compound 109.
Figure 31:
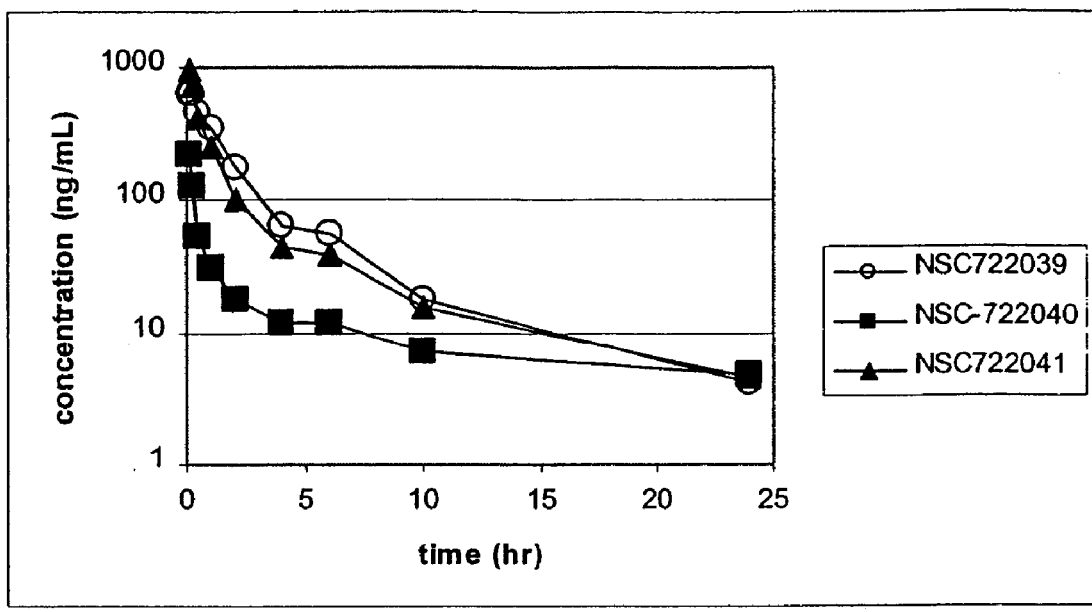
FIG. 31 provides a graph showing results of PK studies with a cassette dosing of tested compounds to mice. Peritoneal delivery. Compound NSC 722039 in the study reads as the compound 37, NSC 722040—compound 59, NSC 722041—compound 109.
Figure 32:
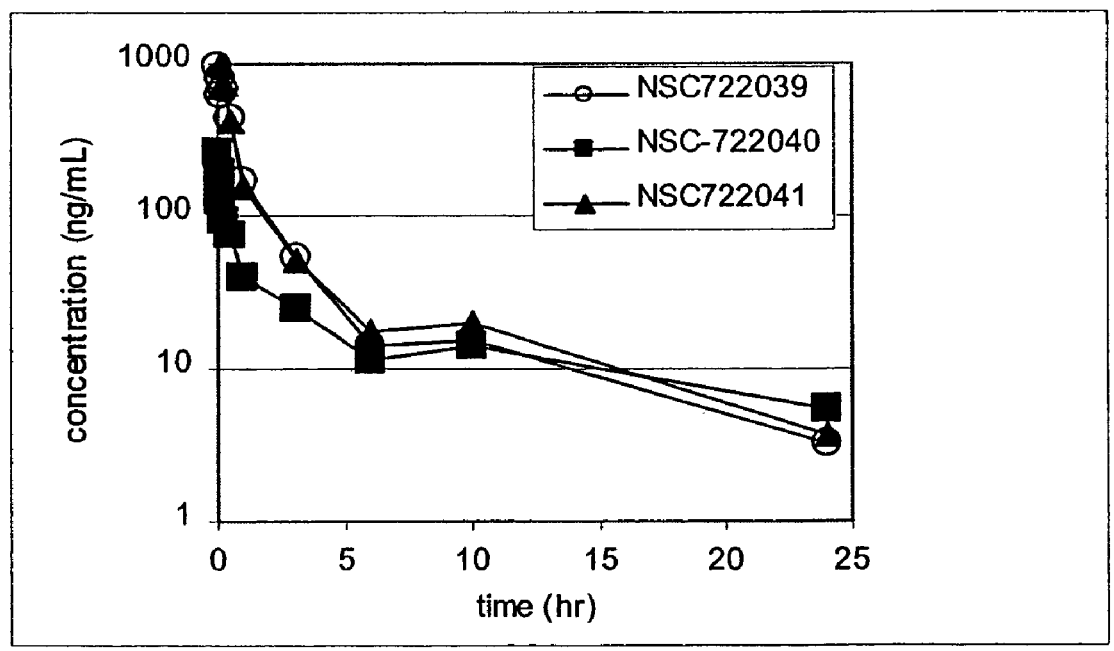
FIG. 32 provides a graph showing results of PK studies with a cassette dosing of tested compounds to mice. Intravenous delivery. Compound NSC 722039 in the study reads as the compound 37, NSC 722040—compound 59, NSC 722041—compound 109.

Pilot PK study of the compounds 37, 59, and 109 in mice was conducted using a cassette dosing: all the three analogs were formulated together in saline at 1.5 mg/mL, and administered to mice simultaneously orally at 25 mg/kg, peritoneally at 6 mg/kg, and intravenously. It was found that doses 15 and 7.5 mg/kg caused death of mice, 3.75 mg/kg appeared lethargic immediately after dosing but then appeared normal appearance a few minutes later; 3 mg/kg displayed no adverse reactions and hence was used as intravenous dose. Obtained data are presented on FIGS. 30, 31, and 32 (tested compounds were studied under the NCI' indexation NSC) and summarized in Table 19.

TABLE 19

PK Parameters of tested compounds 37, 59, and 109 after a cassette dosing to mice.

| Route | i.v. | i.v. | i.v. | i.p. | i.p. | i.p. | p.o. | p.o. | p.o. |
|---|---|---|---|---|---|---|---|---|---|
| Compounds | 37 | 59 | 109 | 37 | 59 | 109 | 37 | 59 | 109 |
| Dose (mg/kg) | 3 | 3 | 3 | 6 | 6 | 6 | 25 | 25 | 25 |
| AUC (ng · h/mL) | 954 | 384 | 1006 | 1372 | 272 | 1099 | 1602 | 169 | 655 |
| Cmax (ng/mL) | 970 | 296 | 1192 | 630 | 217 | 935 | 263 | 28.7 | 227 |
| T½ (h) | 4.8 | 6.4 | 5.5 | 4.9 | 9.7 | 4.4 | N/A | N/A | N/A |
| CL (mL/kg/h) | 3530 | 8043 | 3240 | | | | | | |
| Bioavailability (%) | | | | 72 | 35 | 55 | 3.3 | 0.9 | 2.7 |
| Urine excretion (%) | .71 | 1.9 | .92 | <0.01 | <0.01 | <0.01 | N/A | N/A | N/A |

N/A—not detectable.

Conducted pharmacokinetic studies indicated that compound 59 (NSC 722040 by the NCI index) has relatively poor PK profiling (AUC, Cmax) and further testing of this compound was abandoned. Based on preliminary toxicity data compound 37 was also ruled out as possible candidate. Therefore, compound 109 (NSC 722041 by the NCI) was selected for further PK analyses.

Figure 33:
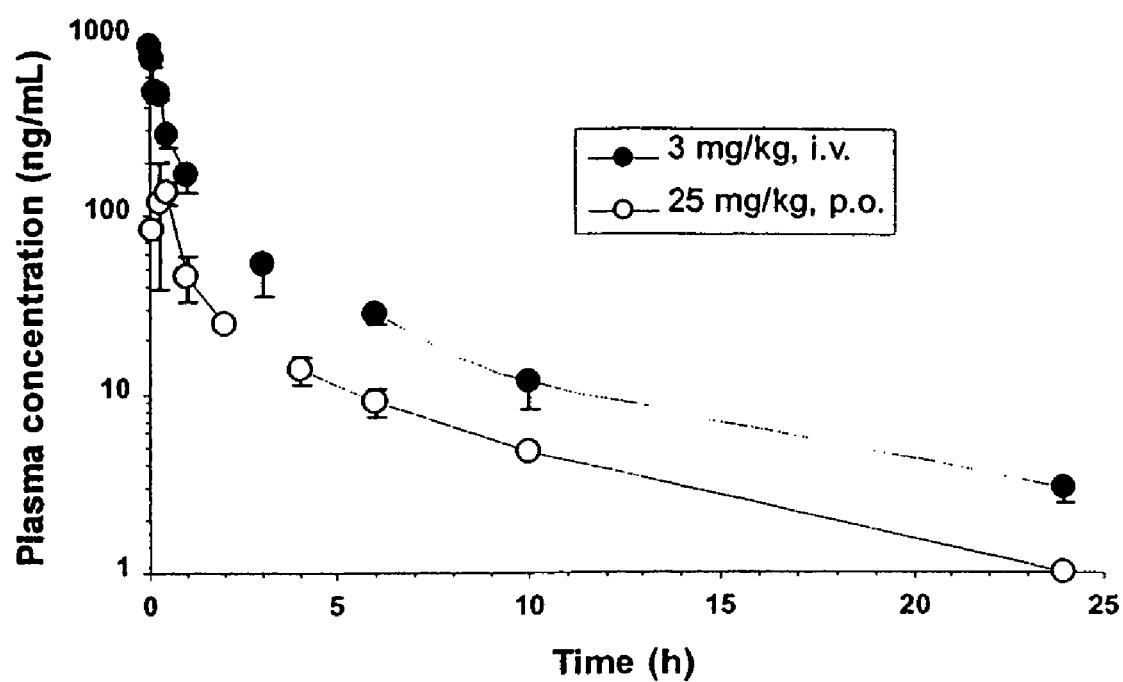
FIG. 33 provides a graph showing the results of PK Studies of the compound 109 in mice.

It has been shown that compound SQ109 reaches and exceeds its Minimum Bactericidal Concentration MBC (313 ng/ml) in plasma when administered either iv or inatraveneously orally (p.o.), has a half-life of 5.2 h, and has total clearance less than hepatic blood flow (FIG. 33, Table 20).

TABLE 20

Pharmacokinetic parameters of the compound 109

| Parameters | i.v. | p.o. |
|---|---|---|
| Dose (mg/kg) | 3 | 25 |
| AUC (ng · h/mL) | 792 | 254 |
| $T_{1/2\,el}$ (h) | 3.5 | 5.2 |
| $C_{max}$(ng/mL) | 1038 | 135 |
| $T_{max}$(h) | 0 | 0.31 |
| CL (mL/kg/h) | 3788 | |

TABLE 20-continued

Pharmacokinetic parameters of the compound 109

| Parameters | i.v. | p.o. |
|---|---|---|
| $Vd_{ss}$ (mL/kg) | 11826 | |
| Bioavailability | | 3.8 |

Figure 34:
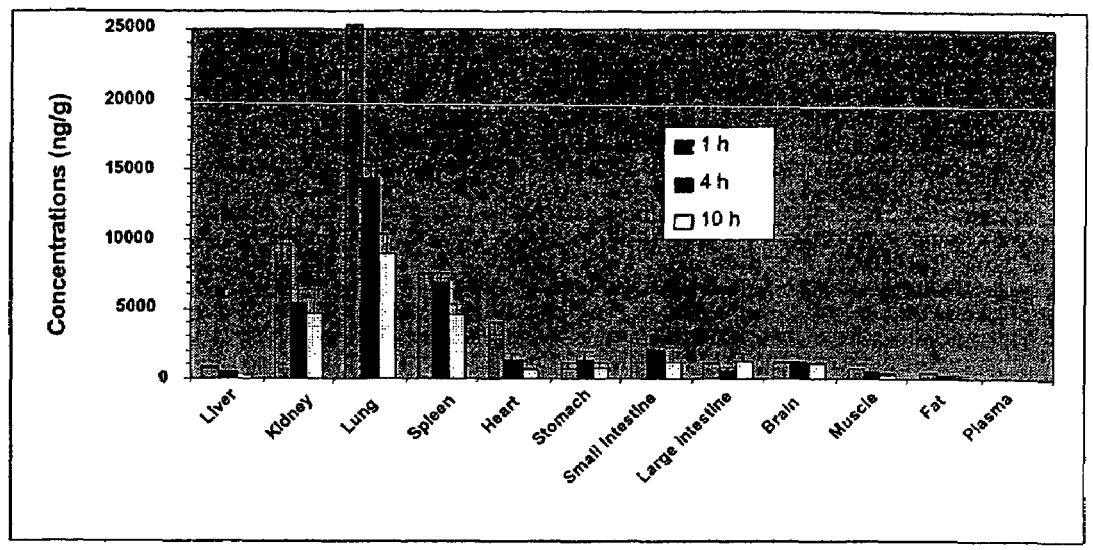
FIG. 34. Tissue distribution of 109 in mice (i.v., 3 mg/kg).
Figure 35:
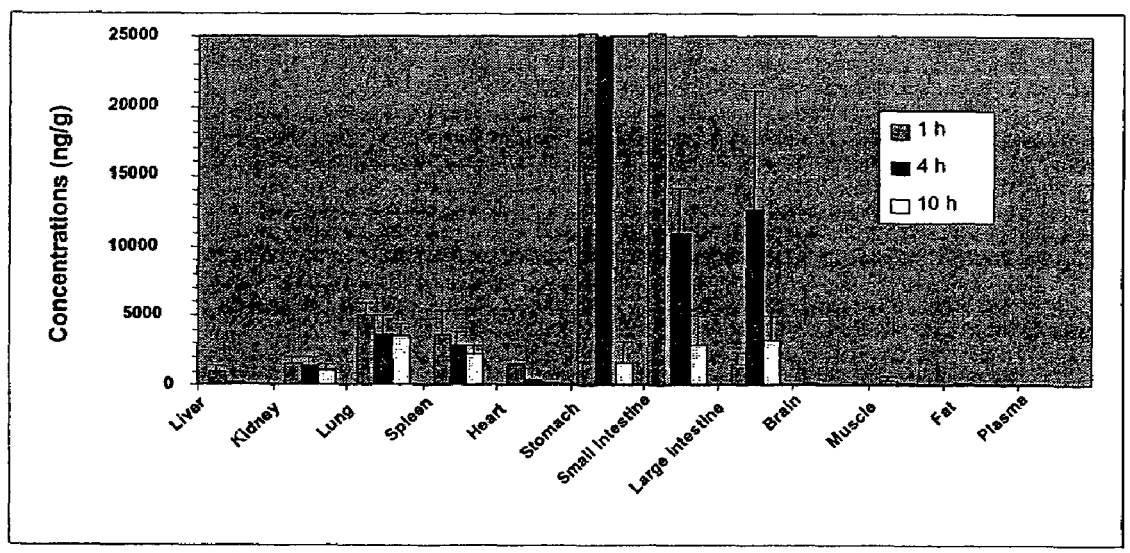
FIG. 35. Tissue distribution of 109 in mice (p.o., 25 mg/kg).

Its oral bioavailability is only 3.8% when administered p.o but this is explained by its unique tissue distribution pattern. Tissue distribution studies have demonstrated that SQ109 primarily distributes into the lungs and spleen (FIGS. 34 and 35), which is highly advantageous for a infection that characteristically manifests as a lung disease.

By using an ultracentrifugation method, it was found that plasma protein binding of the compound 109 is concentration dependent and varies from 15% (20 ng/ml) to 74% (200 ng/ml) to 48% (2000 ng/ml). After i.v. dosing (3 mg/kg) the compound distributes between plasma and red blood cells in a ratio 70.6:29.4.

Little is known of the fate of the compound in the body, since the total amount of the compound after excretion (urine and feces) does not exceed 3% of the delivered dose (Table 2).

TABLE 21

Amounts of the compound 109 cumulatively excreted in mouse urine and feces following single administration

| Dose/ Route | Samples | Total 0-4 | Period after dosing (h) | | | |
|---|---|---|---|---|---|---|
| | | | 4-8 | 8-24 | 24-32 | 0-32 |
| 3 mg/kg i.v. | Urine | <0.01 | <0.01 | 0.03 | 0.01 | 0.04 |
| | Feces | <0.01 | 0.01 | 0.04 | <0.01 | 0.06 |
| 25 mg/kg p.o. | Urine | — | — | — | — | — |
| | Feces | 0.48 | 0.31 | 1.12 | 0.08 | 2.0 |

Figure 36:
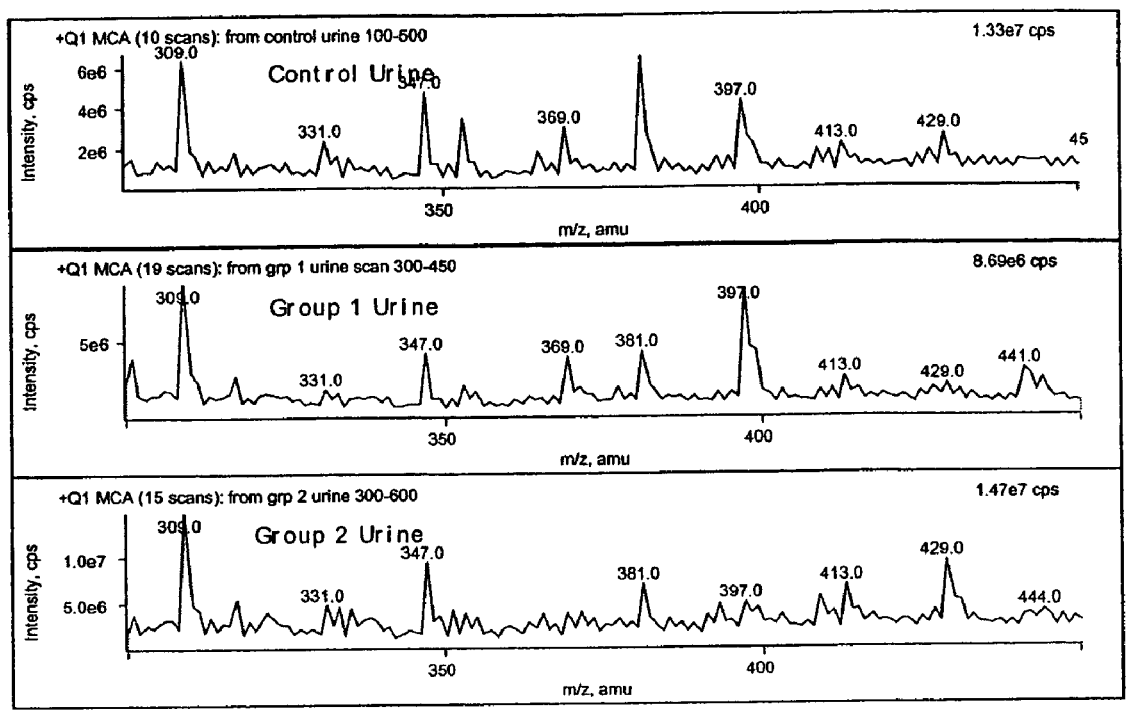
FIG. 36 Metabolism of the compound 109 in mouse urine.
Figure 37:
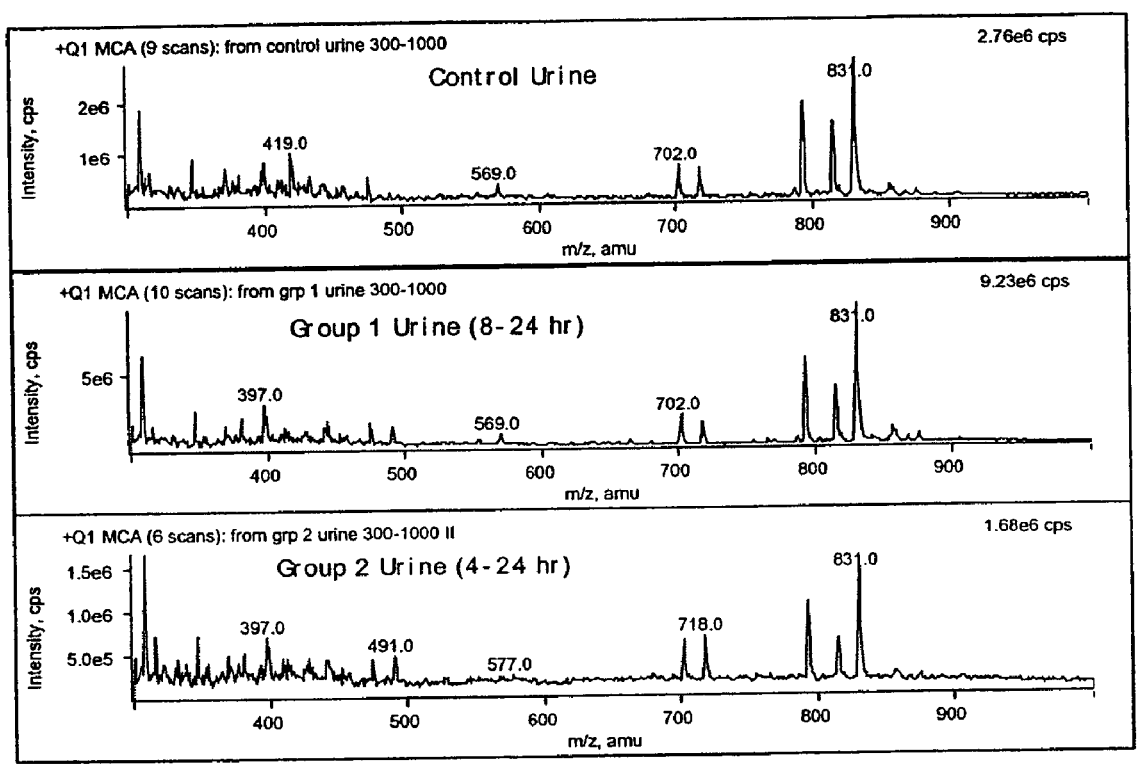
FIG. 37. No glucoronidation metabolites of 109 were found in mouse urine.

Initial attempts to identify metabolites of the compound 109 in urine, did not provide evidence of breakdown products, FIG. 36. For example, there was no evidence for the formation of conjugated metabolites ($M^+$ 521) in the mouse urine during first 24 hr following compound's administration, FIG. 37. Conjugated metabolites are products of the typical metabolic pathway N-glucoronidation formed by reaction with glucuronic acid (D. A. Williams and T. L. Lemke in *Foye's Principals of Medicinal Chemistry*, 5th Ed., p. 202).

EXAMPLE XV

In vitro Pharmacokinetic Studies of Compound 109

In vitro Pharmacology and early ADMET (Absorption, Distribution, Metabolism, Excretion, Toxicity) studies of the compound 109 were contracted out to CEREP (15318 NE 95th Street, Redmond, Wash. 98052, USA, www.cerep.com, tel 425 895 8666) under a Service Agreement and included testing against 30 standard receptors (see CEREP Tables 22 and 23, provided in FIGS. 38 and 39, five CYP450 enzymes, HERG (K+ channel), aqueous solubility, predicted intestinal permeability, and metabolic stability (data presented in FIG. 40 Tables 24(a-m)).

EXAMPLE XVI

Bis(2-Adamantyl)ethylenediamine, SQBisAd

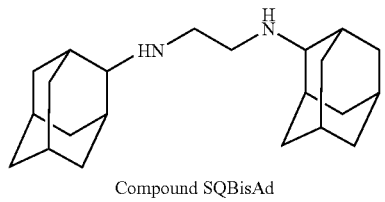

Compound SQBisAd

Compounds with the best Selectivity Indexes, such as 109, 58, 73, 78, (Table 15) and good in vivo data share the same adamantane fragment (FIG. 20). A compound that would have solely this fragment (on both sides of the ethylene linker) was contemplated. During preparation of targeted 100,000 compound library of ethambutol analogues, 70,000 compounds were proven to be formed, but 30,000 were failures. This particular compound was not initially detected perhaps because it was synthesized in very low yield or because it was never made due to steric factors.

In the synthetic scheme used for preparation of the library Scheme 1 (FIG. 41), sterically hindered amines on the second step rarely gave products. Analyzing MS data for a number of original plates it can be stated that 2-adamantanamine when used as $R_1NH_2$ seldom yield desirable products and this can be explained because of existence of sterically hindered reaction site on the step 2 or step 3 of the synthesis Scheme 2 (FIG. 41).

Compound SQBisAd can be prepared by "wet chemistry" using the same route, Scheme 3 (FIG. 41), it is documented that 2-adamantamine (used as commercially available hydrochloride) does provide products when used on the 1 and 2 steps. Due to the symmetrical nature, this compound can be synthesized by alternative routes. We have prepared SQBisAd by reductive alkylation of ethylnediamine by 2-adamantanone using sodium cyanoborohydride. Final product (without additional purification) demonstrated MIC (Minimal Inhibitory Concentration) equal or better than compound 109.

EXAMPLE VIII

Generating the Diamine Library with a Modified Linker

General Methods: All reagents were purchased from Sigma-Aldrich. Rink acid resin was purchased from Nova-Biochem, Inc. Solvents acetonitrile, dichloromethane, dimethylformamide, ethylene dichloride, methanol, and tetrahydrofuran were purchased from Aldrich and used as received. Solid phase syntheses were performed on Quest 210 Synthesizer (Argonaut Technologies) and combinatorial chemistry equipment (Whatman Polyfiltronics and Robbins Scientific). Evaporation of the solvents was done using SpeedVac AES (Savant). Mass spectra data were obtained by Electrospray Ionization technique on Perkin Elmer/Sciex, API-300, TQMS with an autosampler.

The activation of the Rink-resin, the addition of the amine, and the acylation step were carried out in 10 ml tubes using the Quest 210 Synthesizer. Removal of the FMOC group, reductive alkylation reaction with carbonyl compounds, the reduction with Red-Al, and the cleavage from the solid support were carried out in 96-deep (2 ml) well, chemically resistant plates.

Step 1. Activation of the Rink-Acid Resin.

A suspension of the Rink-acid resin (coverage of 0.43-0.63 mmol/g), 6 g (up to 3.78 mmol), in 80 ml of 2:1 mixture of dichloromethane and THF was disitrubuted into 20 tubes, 4 ml per tube, filtered and washed twice with THF. A solution of triphenylphosphine (5.7 g, 21.75 mmol) in 40 ml of THF was added, 2 ml/tube, followed by the addition of a solution of hexachloroethane (5.09 g, 21.45 mmol) in 20 ml of THF, 1 ml/tube. After 6 h the resins were washed with THF (2×4 ml) and dichloromethane (2×4 ml).

Step 2. Addition of the First Amine.

Each tube was charged with 3 ml of dichloroethane, $EtNiPr_2$, (0.2 ml, 1.15 mmol), and the corresponding amine (1 mmol). (When a selected amine was a solid, it was added as a solution or a suspension in DMF). Dichloroethane was added to each tube to fill up the volume 4 ml. The reaction was carried for 8 h at 45° C. and 6-8 h at room temperature. The resins were filtered, washed with a 2:1 mixture of dichloromethane and methanol (1×4 ml), then with methanol (2×4 ml), and suck dry.

Step 3. Acylation with Fmoc Protected Amino Acid.

The resins were pre-washed with dichloromethane (2×4 ml). Each tube was charged with 2 ml of dichloromethane, HATU (2 mol excess to loaded resin, 0.14 g, 0.39 mmol, dissolved in 1 ml of DMF), and 0.47 mmol (2.5 mol excess to loaded resin) of amino acid dissolved in 1 ml of DMF, and allowed to stir for 8 h at 45° C. and 6-8 h at room temperature. After 16 h the resins were filtered, washed with 1:1 mixture of DMF and dichloromethane (1×3 ml), dichloromethane (1×3 ml) and acylation was repeated with the same amount of reagents. At the end, the resins were filtered, washed with 1:1 mixture of DMF and dichloromethane (1×3 ml), and methanol (3×3 ml), sucked dry (on Quest) for 30 min and transferred into vials (one resin per vial), and dried in a desiccator under vacuum for 1 h. After this step all resins were subjected for quality control using MS spectra.

Step 4. Alkylation of the Amino Group.

Deprotection. Ten prepared resins from the first three steps were pooled together, leaving approximately 0.05 g of each in the individual vials for all necessary deconvolutions. A suspension of the resin mixture (2.0-2.5 g) in 100 ml of a 2:1 mixture of dichloromethane and THF was distributed into two 96-well filterplates and filtered using a filtration manifold. The reaction plates were transferred into combiclamps, and 0.2 ml of 20% solution of piperidine in DMF was added to remove Fmoc protecting group and allowed to stay for 10 min. After 10 min plate was filtered, washed with 0.2 ml of DMF, and deprotection was repeated with 0.2 ml of 20% solution of piperidine in DMF and allowed to stay for 20 min.

After that plate was filtered, washed with DMF (0.2 ml per well) and dichloromethane (2×0.5 ml per well).

Reaction with the carbonyl compounds. Each well in row A on the reaction plate was charged with 0.1 ml of dichloromethane, 0.08 ml of ~1.0M solution of appropriate acid in DMF from master plate, 0.05 ml DMF solution of PyBrop, (0.015 g, 0.03 mmol, 2.5 mol excess to loaded resin) and 0.05 ml of EtNiPr$_2$ in dichloromethane (0.022 ml, 0.13 mmol, 10 mol excess to loaded resin). Each well in rows B through H was charged with 0.1 ml of THF, 0.160 ml of ~1.0 M solution of appropriate aldehyde or ketone in DMF from master plate and allowed to react for 30 min. After 30 min 0.075 ml (0.075 mmol) of 1.0 M solution of NaBCNH$_3$ were added. The reaction plates were sealed and kept at RT for 72 h. At the end, the resins were filtered, washed with THF, DCM (1×1 ml), methanol (2×1 ml) and dried in desiccator under vacuum for 2 h.

Step 5. Reduction with Red-Al.

The reaction plates were placed into combiclamps. A 1:6 mixture of Red-Al (65+w % in toluene) and THF was added, 0.6 ml per well (0.28 mmol of Red-Al per well), and allowed to react for 4 h. After the reaction completion the resins were filtered, washed with THF (2×1 ml), methanol (3×1 ml) and dried in the filtration manifold.

Step 6. Cleavage.

This step was carried out using a cleavage manifold. The reaction plates (placed on the top of the collection plates in this manifold) were charged with a 10:85:5 mixture of TFA, dichloromethane, and methanol, 0.5 ml per well. After 15 min, the solutions were filtered and collected into proper wells of the collection plates. The procedure was repeated. Solvents were evaporated on a speedvac, and the residual samples were ready for testing.

Deconvolution Example.

Deconvolution of the active wells was performed by re-synthesis of discrete compounds, from the archived FMOC-protected a-aminoacetamide resins (10 resins, 0.05-0.10 g each), which were set aside at the end of the acylation step before the pooling. Each resin was assigned a discrete column (1, or 2, or 3, etc.) in a 96-well filterplate, and was divided between X rows (A, B, C, etc), where X is the number of hits discovered in the original screening plate. To each well, in a row, a selected carbonyl compound (present in the hit) was added along with other required reagents: the first selected carbonyl compound was added to the resins in the row "A", the second carbonyl compound—to the resins in the row "B", the third carbonyl compound—to the resins in the row "C", etc. A lay-out of a representative 96-well deconvolution plate is shown in Table 28, FIG. 52.

The reaction plates were sealed and kept at RT for 72 h. At the end, the resins were filtered, washed with THF, DCM (1×1 ml), methanol (2×1 ml) and dried in desiccator under vacuum for 2 h. Reduction and cleavage were performed according to steps 5 and 6 of the synthetic protocol. The product wells from the cleavage were analyzed by ESI-MS (Electrospray Ionization Mass Spectroscopy) to ensure the identity of the actives, and were tested in the MIC assay. A summary of the ESI-MS data is provided below. A list of compound hits and structures is provided in Table 30, FIG. 53.

Compound 673

N$^2$-[(2-methoxy-1-naphthyl)methyl]-3-phenyl-N$^1$-(3-phenylpropyl)propane-1,2-diamine. Mass spectrum (ESI) m/z (MH)$^+$ 439.2

Compound 674

N$^2$-[2-(benzyloxy)ethyl]-N$^1$-(3,3-diphenylpropyl)-4-(methylthio)butane-1,2-diamine. Mass spectrum (ESI) m/z (MH)$^+$ 463.4.

Compound 675

N$^1$-(3,3-diphenylpropyl)-4-(methylthio)-N$^2$-(3-phenylpropyl)butane-1,2-diamine. Mass spectrum (ESI) m/z (MH)$^+$ 447.2

Compound 676

N$^2$-(cyclohexylmethyl)-N$^1$-(3,3-diphenylpropyl)-4-(methylthio)butane-1,2-diamine. Mass spectrum (ESI) m/z (MH)$^+$ 425.1

Compound 677

N$^1$-(3,3-diphenylpropyl)-N$^2$-(2-ethoxybenzyl)-4-(methylthio)butane-1,2-diamine. Mass spectrum (ESI) m/z (MH)$^+$ 463.1

Compound 678

N$^2$-[2-(benzyloxy)ethyl]-N$^1$-[(6,6-dimethylbicyclo[3.1.1]hept-2-yl)methyl]-4-(methylthio)butane-1,2-diamine. Mass spectrum (ESI) m/z (MH)$^+$ 405.3

Compound 679

N$^1$-[(6,6-dimethylbicyclo[3.1.1]hept-2-yl)methyl]-4-(methylthio)-N$^2$-(3-phenylpropyl)butane-1,2-diamine. Mass spectrum (ESI) m/z (MH)$^+$ 389.5

Compound 680

N$^2$-(2-chloro-4-fluorobenzyl)-4-methyl-N$^1$-(4-methylbenzyl)pentane-1,2-diamine. Mass spectrum (ESI) m/z (MH)$^+$ 363.3, 365.5; (MCH$_3$CN) 403.3, 405.3.

Compound 681.

N$^2$-[2-(benzyloxy)ethyl]-N$^1$-[2-(4-methoxyphenyl)ethyl]-4-methylpentane-1,2-diamine. Mass spectrum (ESI) m/z (MH)$^+$ 385.1.

Compound 682.

N$^2$-[3-(4-chlorophenoxy)benzyl]-N$^1$-[2-(4-methoxyphenyl)ethyl]-4-methylpentane-1,2-diamine. Mass spectrum (ESI) m/z (MH)$^+$ 467.1, 469.2.

Compound 683.

N$^2$-(4-isopropylbenzyl)-N$^1$-[2-(4-methoxyphenyl)ethyl]-4-methylpentane-1,2-diamine. Mass spectrum (ESI) m/z (MH)$^+$ 383.3

Compound 684.

N$^1$-[2-(4-methoxyphenyl)ethyl]-4-methyl-N$^2$-[(2E)-3-phenylprop-2-enyl]pentane-1,2-diamine. Mass spectrum (ESI) m/z (MH)$^+$ 367.3; [M-(CH$_2$CH=CHPh)2H]+251.

Compound 685

N$^2$-[2-(benzyloxy)ethyl]-4-methyl-N$^1$-(3-phenylpropyl)pentane-1,2-diamine. Mass spectrum (ESI) m/z (MH)$^+$ 369.1.

Compound 686.

N$^2$-(2-chloro-4-fluorobenzyl)-4-methyl-N$^1$-(3-phenylpropyl)pentane-1,2-diamine. Mass spectrum (ESI) m/z (MH)$^+$ 377.2, 378.9.

Compound 687.

N²-[3-(4-chlorophenoxy)benzyl]-4-methyl-N¹-(3-phenyl-propyl)pentane-1,2-diamine. Mass spectrum (ESI) m/z (MH)⁺ 451.1, 453.3.

Compound 688.

N²-(4-isopropylbenzyl)-4-methyl-N¹-(3-phenylpropyl)pentane-1,2-diamine. Mass spectrum (ESI) m/z (MH)⁺ 367.3.

Compound 689

4-methyl-N²-[(2E)-3-phenylprop-2-enyl]-N¹-(3-phenylpropyl)pentane-1,2-diamine. Mass spectrum (ESI) m/z (MH)⁺ 351.2.

Compound 690

N²-(2-ethoxybenzyl)-4-methyl-N¹-(3-phenylpropyl)pentane-1,2-diamine. Mass spectrum (ESI) m/z (MH)⁺ 369.1.

Compound 691.

N²-decahydronaphthalen-2-yl-N¹-[2-(4-fluorophenyl)ethyl]-3-thien-3-yipropane-1,2-diamine. Mass spectrum (ESI) m/z (MH)⁺ 415.3.

EXAMPLE XIX

In vitro Activity of Rifampicin with Compound 109 or Isoniazid

Figure 54:
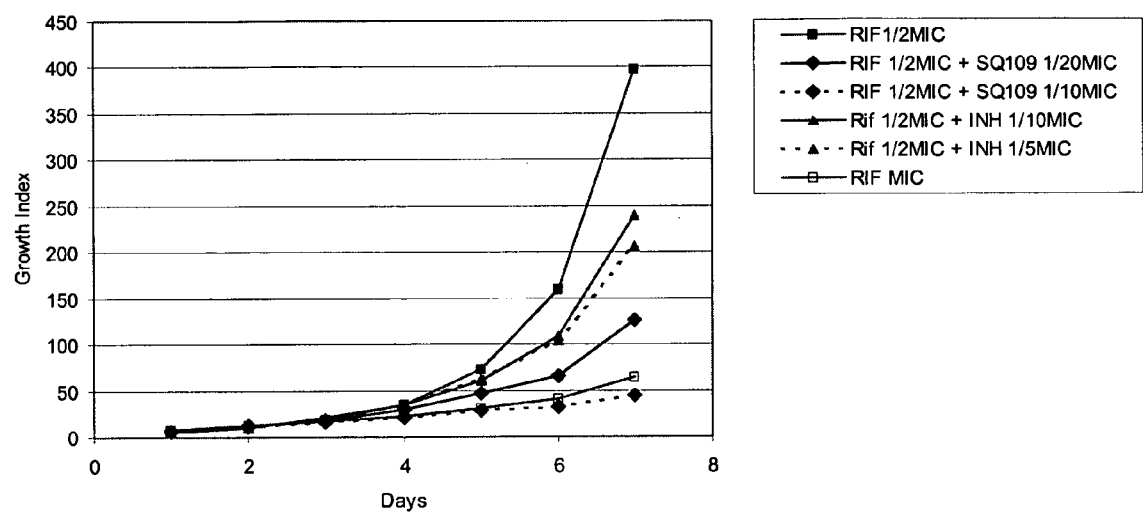
FIG. 54 provides a graph showing the results of in vivo activity of Rifampin, compound 109 (SQ109) or Isoniazid (INH). The study was carried out using BACTEC system. MIC for RIF was 0.2 ug/ml, SQ109 (compound 109) 0.32 ug/ml, and INH 0.025 ug/ml.

Compound 109 demonstrated potent in vitro and in vivo killing of *M. tuberculosis* as an individual compound. Herein, are examples providing a multi-drug regime to evaluate the effects of the compounds of table 3 on inhibition of bacterial growth in vitro and in mouse models of tuberculosis when used in combination with standard tuberculosis drugs. Rifampicin, compound 109 and isoniazid were selected for in vitro activity (FIG. 54). The study was carried out using BACTEC growth kinetics. MIC for RIF was 0.2 ug/ml, SQ109 (compound 109) 0.32 ug/ml, and INH 0.025 ug/ml. These studies demonstrated that compound 109 in combination with Rifampicin suppresses the growth index over the length of study. The growth suppression of Rif and compound 109 is achieved even when the MIC concentration of compound 109 is $1/10^{th}$ and $1/20^{th}$ MIC. Clearly, the combination of Rif and compound 109 is superior to Rif alone, or Rif and INH. Compound 109 at 0.5 MIC inhibited greater than 99% growth of *M. tuberculosis* (H37Rv) inoculum when used in combination with as low as 0.1 MIC RIF. The x/y quotient value was 0.29, indicating synergistic drug action. This synergy was also seen when 0.5 MIC RIF was used in combination with 0.05, 0.1, and 0.2 MIC SQ109, with corresponding x/y quotient values of 0.32, 0.16, 0.4, respectively. The results indicate synergistic activity for growth inhibition of *M. tuberculosis* by the combination of RIF and SQ109.

EXAMPLE XX

In vivo Activity of Compound 109 with Standard Tuberculosis Drugs

Figure 55:
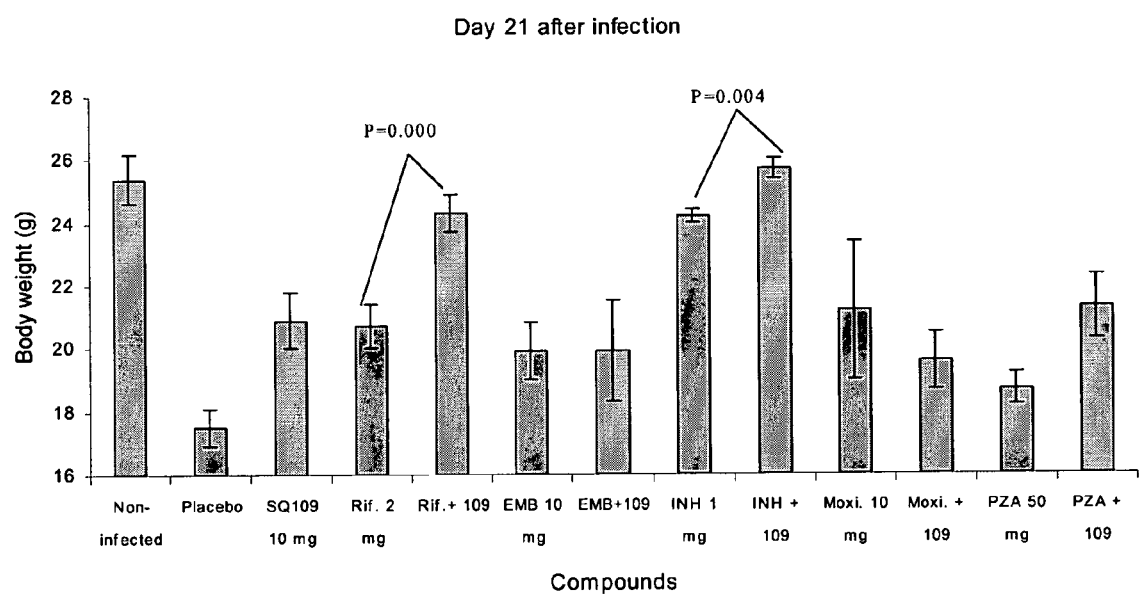
FIG. 55 is a graph showing the results of in vivo studies in mice using a rapid model, wherein body weight of mice is used as a marker to estimate drug efficacy. The results are of a 21 day combination therapy study in the rapid model. C3H female mice were infected i.v. with $10^6$ CFU *M. tuberculosis* H37Rv (Pasteur). 7 days following inoculation chemotherapy was initiated and continued for 2 weeks (5 days/week). Mice treated with a single drug, uninfected, and infected untreated placebo were used as controls. Rif at 2 mg/kg, INH at 1 mg/kg, EMB at 10 mg/kg, Moxi at 10 mg/kg, PZA at 50 mg/kg. Body weight of mice monitored from day 0 through day 21.

A rapid in vivo model of TB where infected animal weight loss is the indicator for tuberculosis disease progression was used to elevated novel compounds and combinational therapies. Rifampicin, INH, EMB, PZA, Moxi (standard tuberculosis drugs) and compound 109 were selected for in vivo studies in mice (FIG. 55). These studies demonstrated that compound 109 in combination with one or more standard tuberculosis drugs modulates mice body weight and is an indicator of drug efficacy. In this study, Rifampicin and compound 109, or INH and compound 109, achieved body weights that were comparable to non-infected controls. Conversely, Moxi and compound 109, or EMB and compound 109, resulted in body weights that were closer to placebo treated controls. Clearly, the combination of Rifampicin and compound 109 is superior to Rifampicin or INH alone.

EXAMPLE XXI

Figures 56A, 56B:
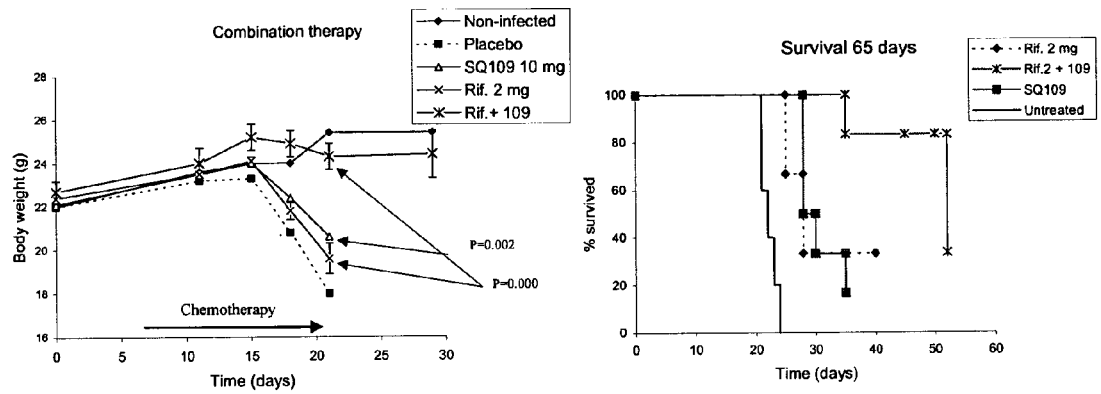
FIGS. 56A and 56B are graphs disclosing dynamics in body weight (FIG. 56A) and the mortality data (FIG. 56B) of H37Rv infected animals treated with SQ109 (10 mg/kg), Rifampin (2 mg/kg), and SQ109 (compound 109) (10 mg/kg)-Rif(2 mg/kg) combination, and of the placebo (infected non-treated) in the rapid model. C3H female mice were infected i.v. with $10^6$ CFU *M. tuberculosis* H37Rv (Pasteur). 7 days following inoculation chemotherapy was initiated and continued for 2 weeks (5 days/week). Body weight of mice monitored from day 0 through the end of chemotherapy (day 21).

Rapid Model, In vivo Activity of Compound 109 Against Standard Tuberculosis Drugs In this example Rifampicin and compound 109 were selected for in vivo studies in mice (FIG. 56A and FIG. 56B). In this study, Rifampicin and compound 109 achieved body weights that were comparable to non-infected controls. Conversely, compound 109, or rifampicin alone resulted in body weights that were closer to placebo treated controls over the course of chemotherapy. Clearly, the combination of Rifampicin and compound 109 is superior to Rifampicin or compound 109 alone.

EXAMPLE XXII

In vivo Activity of Combination Therapy

Figure 57:
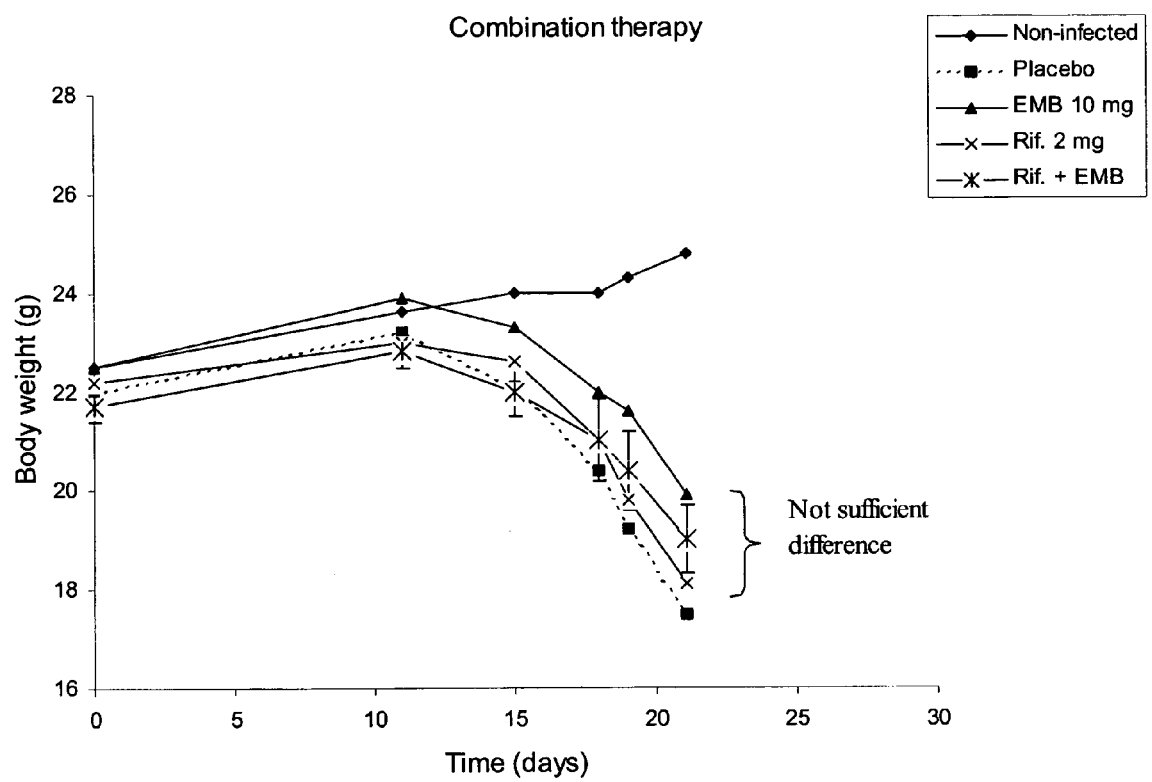
FIG. 57 is a graph showing the dynamics of body weight of mice treated with combination, Rif-EMB. Dynamics in body weight of H37Rv infected animals treated with Ethambutol (10 mg/kg), Rifampin (2 mg/kg), and Ethambutol (10 mg/kg)-Rif (2 mg/kg) combination, and of the placebo. C3H female mice were infected i.v. with $10^6$ CFU *M. tuberculosis* H37Rv (Pasteur). 7 days following inoculation chemotherapy was initiated and continued for 2 weeks (5 days/week). Body weight of mice were monitored from day 0 through the end of chemotherapy (day 21).

A combination therapy of SQ109 (compound 109) at 10 mg/kg and RIF at 2 mg/kg given orally was more efficacious in preventing body weight loss in infected mice than either single drug therapy given at the same dose (FIG. 57). By the 3 wk of chemotherapy, average body weight of 6 mice that received combination RIF+SQ109 therapy was 24.3 grams and indistinguishable from the 24.5 g of the uninfected control group. In comparison, mice receiving SQ 109 or RIF alone at the corresponding doses had average weights of 21.3 g and 19.7 g, respectively: the average weight for infected mice not treated with drugs was 17 g.

EXAMPLE XXIII

In vivo Activity of Combination Therapy (Standard Chronic Model)

Figure 58:
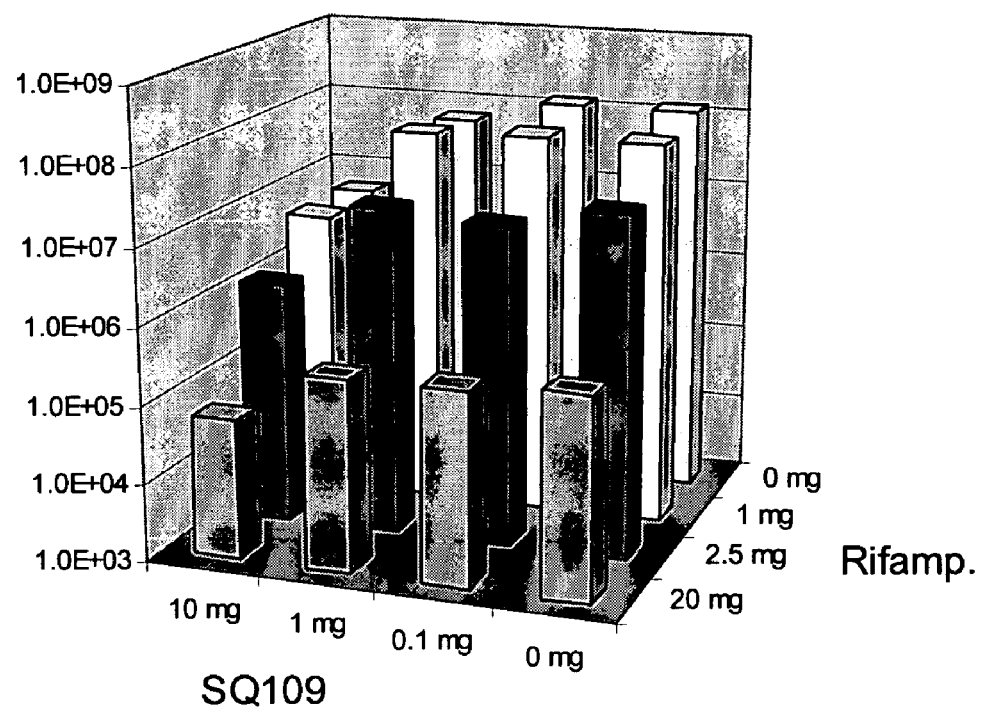
FIG. 58 provides a graph showing the in vivo efficacy studies of compound 109 in combination with Rifampin in a mouse model of chronic tuberculosis infection. C57BL/6 female mice were inoculated i.v. with $10^5$ CFU *M. tuberculosis* H37Rv. Chemotherapy was initiated three weeks following the infection and continued for 4 weeks. At the end of therapy, mice were sacrificed; lungs homogenates in sterile 2 ml PBS with 0.05% Tween-80 were plated in 10-fold serial dilutions on 7H10 agar dishes, and were incubated at 37° C. CFU were calculated after 3 wk of growth. 16 groups of mice were used (6 mice per group). Compound 109 (SQ109) was used at 0, 0.1, 1, and 10 mg/kg; RIF at 0, 1, 2, and 20 mg/kg.
Figure 59:
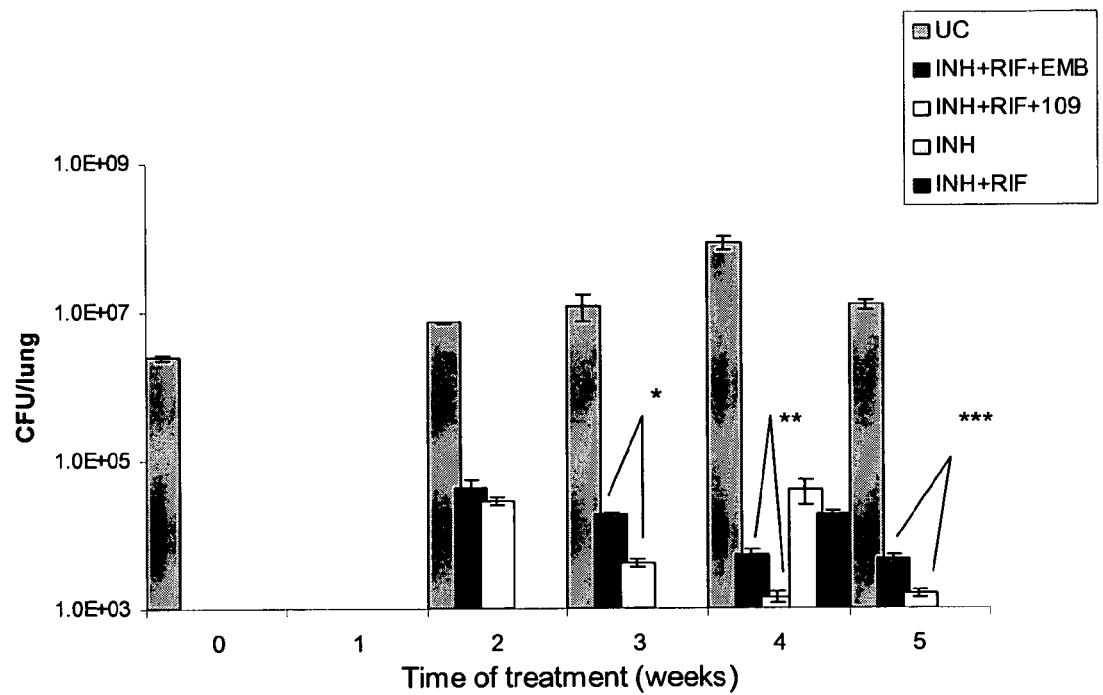
FIG. 59 shows the results of compound 109 in a multi-drug intensive phase regime in combaintion wih Rif and INH using the chronic mouse model. C57BL/6 female mice were inoculated i.v. with $10^5$ CFU *M. tuberculosis* H37Rv. Chemotherapy was initiated three weeks following the infection and continued for 5 weeks with time points at 2, 3, 4, and 5 weeks. At each timepoint, one group of mice for tested drug combinations (6 mice per group) was sacrificed; lungs homogenates in sterile 2 ml PBS with 0.05% Tween-80 were plated in 10-fold serial dilutions on 7H10 agar dishes, and were incubated at 37° C. CFU were calculated after 3 wk of growth. INH was used at 25 mg/kg, RIF at 20 mg/kg, SQ109 (compound 109) at 10 mg/kg, EMB at 100 mg/kg. Statistic analysis was done using the ANOVA test: significance of any differences was estimated by Student's T-test and $p<0.05$ was considered statistically significant. 3 weeks*–$p=0.001$, 4 weeks  $p=0.008$, and for 5 weeks * $p=0.005$.

The in vivo enhanced activity of combination treatment was confirmed through the use of a standard chronic mouse model of tuberculosis (FIG. 58). During 4 week therapy in the chronic TB model, SQ109 by itself reduced CFU in lung from 8.1 $\log_{10}$CFU (control untreated animals) to 6.6 $\log_{10}$CFU; RIF (20 mg/kg) by itself reduced CFU to 5.8 $\log_{10}$; but the combination of SQ109+RIF (given at their most efficacious doses 10 and 20 mg/kg respectively) reduced CFU to 4.8 $\log_{10}$, an additional $\log_{10}$CFU lower than either drug alone. Combination of INH+RIF+SQ109 (at 25, 20 and 10 mg/kg) achieved the same CFU at wk 3 as INH+RIF+EMB (at 25, 20 and 100 mg/kg) at wk 4, 1 wk earlier than standard drug combination (FIG. 59). By wk 4 the SQ109 combination was more effective by a half $\log_{10}$ (3.2 $\log_{10}$CFU) than EMB combination therapy (3.7 $\log_{10}$ CFU). The difference in CFU reduction was statistically significant. Compound 109 also enhanced in vivo killing of *M. tuberculosis* in TB mouse models when used in combination with RIF alone or RIF+INH. On the basis of these results, it is proposed that the synergistic activity of compound 109 with RIF suggests that it could replace ethambutol in the intensive phase of TB therapy with the 3- or 4-drug combination. Further, compound SQ 109 may provide additional benefit when combined with RIF in the continuation phase, because it has potent activity by itself. Moreover, given that the mode of action is distinct from RIF, this aspect will assist RIF from the emergence of resistant organisms, while simultaneously providing a synergistically enhanced activity.

EXAMPLE XXIV

In vitro Pharmacokinetic Studies of Compound 109

In vitro testing for safety pharmacology and early ADMET (Absorption, Distribution, Metabolism, Excretion, Toxicity) studies of compound 109 were contracted out to CEREP (15318 NE 95$^{th}$ Street, Redmond, Wash., 98052, USA www.cerep.com) under a service agreement and included evaluation of inhibitory binding to a panel of 27 standard receptors and three transporters (See FIG. 60 (Table 31) and FIG. 61 (Table 32)) which included: adenosine receptors (A1 and A2A), adrenergic receptors (alpha 1, alpha 2, beta 1), angiotensin II receptor (AT1), benzodiazapene receptor (BZD), bradykinin receptor (B2), cholecystokinin receptor (CCK1), dopamine receptors (D1, D2S), endothelin receptor (ETA), GABA receptor (GABA), glutamate receptor (NMDA), histamine receptor (H1 central), melanocortin receptor (MC4), muscarinic receptor (M, non-selective), neurokinin receptor (NK1), neuropeptide Y receptor (Y), nicotinic receptor (neuronal, alpha-BGTX-insensitive), opiate receptor (non-selective opiate), orphanin receptor (ORL1), phencyclidine receptor (PCP), serotonin receptor (5-HT), sigma receptor (sigma non-selective), steroid receptor (glucocorticoid receptor, GR), and NE, DA, and 5-HT transporters.

The specific ligand binding to the receptors is defined as the difference between the total binding and the nonspecific binding determined in the presence of an excess of unlabelled ligand. Compound 109 (SQ109) was tested at 10 µM, and the results were expressed as a percent of control specific binding (Table 31) or as a percent of inhibition of control specific binding (Table 32) obtained in the presence of SQ109.

In summary it can be seen that greater than 50% inhibition was observed for D1 and D2S dopamine receptors (51% and 73%). Similarly, very significant inhibition was observed for melanocortin MC4 receptor (90%) which is known to exert a large influence on food intake. Furthermore, a very significant inhibition was observed for muscarinic M receptors (96%).

Opiate receptors which control pain, immune responses, and functions and are linked to effects of morphine and heroin were observed to display a 58% inhibition of control specific binding. Sigma receptors that have been shown to play an important role in antidepressive effects also demonstrated a high degree of inhibition (106%). Norepinephrine NE transporter plays an important role in the pathophysiology of depression and in the mechanism of action of antidepressant drugs was observed to have 87% inhibition of control specific binding. Another transporter, Dopamine DA transporter linked to substance abuse and attention deficit hyperactivity disorder (ADHD) was observed to display 63% inhibition. Serotonin 5-HT transporter implicated in the etiology of several disease states including, but not limited to, mental illnesses, for example, depression, anxiety, schizophrenia, eating disorders, migraines, obsessive compulsive disorder, and panic disorder were also observed to display a 95% inhibition of control specific binding. While not wishing to be bound by the following theory, it is believed that compounds comprising a Ph-ethyleneamine component, including but not limited to, compound 73 also share CNS activity.

EXAMPLE XXV

Spectrum of Activity Testing—Aerobic and Anaerobic Bacteria

Compound 109 was tested against a representative panel of commonly encountered clinical microorganisms comprising opportunistic pathogens, target pathogens and normal human flora. The spectrum of activity of compound 109 was evaluated by performing antimicrobial susceptibility testing against a collection of aerobic and anaerobic bacteria, fungi, and mycobacteria. MICs for all organisms were established using the appropriate NCCLS (National Committee for Clinical Laboratory Standards) recommended standard methods and quality control strains.

Compound 109 displayed activity against gram-positive aerobes. In particular, compound 109 (SQ-109) demonstrated the best activity against *Streptococcus pneumoniae* with MICs ranging from 4-8 ug/ml. MICs for all species of enterococci tested ranged from 16-64 ug/ml while MICs for all Staphylococci tested ranged from 16-32 ug/ml (FIG. 62, Table 33).

Compound 109 displayed activity against gram-negative aerobes. SQ-109 demonstrated limited activity against all enterobacteriaceae tested with MICs ranging from 32->64 ug/ml with slightly lower MICs seen among the non-enterobacteriaceae (16->64 ug/ml). MICs for three *Haemophilus influenzae* isolates tested ranged from 1-32 ug/ml. SQ-109 demonstrated the best activity when tested against *Helicobacter pylori* with an MIC of 4 ug/ml for all three strains tested (FIG. 63A and FIG. 63B (Table 34)).

Compound 109 displayed activity against anaerobes. SQ-109 MICs ranged from 16-64 ug/ml for anaerobes *Propionibacterium acnes, Bacteroides fragilis*, and *Clostridium difficile* (see FIG. 64, Table 35).

EXAMPLE XXVI

Spectrum of Activity Testing—Fungi

Compound 109 was tested against a representative panel of commonly encountered clinical microorganisms comprising opportunistic pathogens, target pathogens and normal human flora. The spectrum of activity of compound 109 was evaluated by performing recommended broth microdilution methods. NCCLS M27-A2, 2003 for yeast and NCCLS M38-A, 2003 for mold.

SQ-109 demonstrated good activity against *Candida albicans* with MICs ranging from 4-8 ug/ml. Additionally, Mold MICs for three isolates of *Aspergillus fumigatus* tested were 16 ug/ml (FIG. 65, Table 36).

EXAMPLE XXVII

Spectrum of Activity Testing—Mycobacteria

Compound 109 was tested against a representative panel of commonly encountered clinical microorganisms comprising opportunistic pathogens, target pathogens and normal human flora. The spectrum of activity of compound 109 was performed by using the BACTEC 460 TB system (Becton Dickinson, Cockeysville, Md., USA) according to the manufacturers instructions. MICs for MOTT were determined suing the agar proportion method recommended for testing slow-growing mycobacterium species, while MICs for the rapid-grower mycobacteria were performed suing the recommended broth microdilution method (NCCLS M24-A, 2003).

SQ-109 demonstrated very good activity when tested against *M. tuberculosis* [MTB] (0.25-0.5 ug/ml), *M. bovis* (0.25 ug/ml), and *M. bovis* BCG (0.5 ug/ml). Among resistant MTB strains tested; SQ-109 had an MIC of 0.25 ug/ml for an INH-resistant MTB strain, and an MIC of 0.5 ug/ml against an EMB-resistant strain (Table 37).

SQ-109 showed less activity against Mycobacteria-other-than-TB (MOTT) with an MIC of 8 ug/ml for three *M. mari-*

*num* strains tested, an MIC of 16 ug/ml for three *M. kansasii* tested, and MICs ranging from 8-32 ug/ml for three *M. avium* complex (MAC) isolates examined (Table 38).

SQ-109 showed good activity against rapid-grower *M. fortuitum* with an MIC of 1 ug/ml for all strains tested and less activity against the more resistant members of the *M. chelonae* group (*M. chelonae* and *M. abscessus*) with an MIC of 16 ug/ml for three strains tested (FIG. 66, Table 39).

The results of examples XXV-XXVII demonstrate the best inhibitory activity against several species of mycobacterium in the MTB complex (*M. tuberculosis*, *M. bovis*, and *M. bovis* BCG), *Mycobacterium-fortuitum, Mycobacterium marinum, Helicobacter pylori, Streptococcus pneumoniae* and *Candida albicans*. SQ-109 was also found to be equally active against susceptible and resistant strains of *M. tuberculosis*.

REFERENCES

1. Dye, C.; Scheele, S.; Dolin, P.; Pathania, V.; Raviglione, M. C., "Consensus statement. Global Burden of Tuberculosis: Estimate Incidence, Prevalence, and Mortality By Country. WHO Global Survailance and Monitoring Project." *J. Am Med Association* 1999, 282, 677-686.
2. Bass, J. B.; Farer, L. S.; Hopewell, P. C.; O'Brein, R.; Jacobs, R. F.; Ruben, F.; Snider, D. E. Jr.; Thornton, G., "Treatment of Tuberculosis and Tuberculosis Infection in Adults and Children. The American Thoracic Society and the Canters for Disease Control and Prevention," *Am. J. Respir. Crit. Care Med.* 1994, 149, 1359-1374.
3. Farmer, P.; Bayona, J.; Becerra, M.; Furin, J.; Henry, C.; Hiatt, H.; Kim, J.Y.; Mitnick, C.; Nardell, E.; Shin, S., "The Dilemma of MDR-TB in the Global Era," *Int. J. Tuberc. Lung Dis.* 1998, 2, 869-876.
4. Pablos-Mendez, A.; Raviglione, M. C.; Laszlo, A.; Binkin, N.; Rieder, H. L.; Bustreo, F.; Cohn, D. L.; Lambregts van Weesenbeek, C. S.; Kim, S. J.; Chaulet, P.; Nunn, P., "Global Surveillance for Antituberculosis-drug Resistance," 1994-1997. *N. Engl. J. Med* 1998, 338, 1641-1649. [Erratum, *N. Engl. J. Med.* 1998, 339, 139].
5. Chan-Tack, K. M., "Antituberculosis-drug Resistance," *N. Engl. J. Med.* 1998, 339, 1079.
6. Cole, S. T.; Brosch, R.; Parkhill, J.; Garnier, T.; Churcher, C.; Harris, D.; Gordon, S. V.; Eiglmeier, K.; Gas, S.; Barry, C. E. $3^{RD}$; Tekaia, Badcock, K.; Basham, D.; Brown, D.; Chillingworth, T.; Connor, R.; Davies, R.; Devlin, K.; Feltwell, T.; Gentles, S.; Hamlin, N.; Holroyd, S.; Hornsby, T.; Jagels, K.; Barrell, B. G., "Deciphering the Biology of *Mycobacterium tuberculosis* From The Complete Genome Sequence," [published erratum appears in *Nature* 1998 Nov. 12; 396, 190]; *Nature* 1998, 393, 537-544.
7. O'Brien, R. J., "Scientific Blueprint for Tuberculosis Drug Development," The Global Alliance for TB Drug Development, Inc. 2001.
8. Barry, C. E., III; Slayden, R. A.; Sampson, A. E.; Lee, R. E., "Use of Genomics and Combinatorial Chemistry in the Development of New Antimycobacterial Drugs," *Biochem. Pharmacol* 2000, 59, 221.
9. Cynamon, M. H.; Klemens, S. P.; Sharpe, C. A.; Chase, S., "Activities of Several Novel Oxazolidinones Against *Mycobacterium Tuberculosis* In A Murine Model," *Antimicrob Agents Chemother.* 1999, 43, 1189-91.
10. Shepard, R. G.; Baughn, C.; Cantrall, M. L.; Goodstein, B.; Thomas, J. P.; Wilkinson, R. G., "Structure-activity Studies Leading To Ethambutol, A New Type of Antituberculosis Compound," *Ann, N.Y. Acad. Sci* 1966, 135, 686.
11. Deng, L.; Mikusova, K.; Robuck, K. G.; Scherman, M.; Brennan, P. J., McNeil, M. R., "Recognition of Multiple Effects of Ethambutol on Metabolism of Mycobacterial Cell Envelope," *Antimicrob. Agents Chemother.* 1995, 39, 694-701.
12. Lee, R. E.;. Mikusova, K.; Brennan, P. J.; and Besra, G. S.; "Synthesis of the Mycobacterial Arabinose Donor β-D-Arabinofuranosyl-1-monophosphoryl-decaprenol, Development of a Basic Arabinosyl-transferase Assay, and Identification of Ethambutol As An Arabinosyl Transferase Inhibitor," *J. Am. Chem. Soc.* 1995, 117, 11829-11832.
13. Belanger, A. E.; Bestra, G. S.; Ford, M. E.; Mikusova, K.; Belisle, J. T.; Brennan, P. J.; Inamine, J. M, "The EmbAB Genes of *Mycobacterium avium* Encode An Arabinosyl Transferase Involved in Cell Wall Arabinan Biosynthesis That is The Target for The Antimycobacterial Drug Ethambutol," *Proc. Natl. Acad. Sci USA* 1996, 93, 11919.
14. Telenti, A.; Phillip, W. J.; Sreevatsan, S.; Bernasconi, C.; Stockbauer, K. E.; Wieles, B.; Musser, J. M.; Jacobs, W. R. Jr., "The Emb Operon, A Gene Cluster of *Mycobacterium Tuberculosis* Involved in Resistance to Ethambutol," *Nat. Med.* 1997, 3, 567.
15. Cuervo, J. H.; Weitl, F.; Ostretch, J. M.; Hamashin, V. T; Hannah, A. L.; Houghten, R. A. in *Peptides* 1994: *Proceedings of the European Peptide Symposium*; Maia HSL Ed., Esom: Leiden, 1995, 465-466.
16. Silen, J. L; Lu, A. T.; Solas, D. W.; Gore, M. A.; Maclean, D.; Shah, N. H.; Coffin, J. M.; Bhinderwala, N. S.; Wang, Y.; Tsutsui, K. T.; Look, G. C.; Campbell, D. A.; Hale, R. L.; Navre, M.; Deluca-Flaherty, C. R., "Screening For Novel Antimicrobials from Encoded Combinatorial Libraries by Using a Two-Dimensional Agar Format," *Antimicrob. Agents Chemother.* 1998, 42, 1147.
17. Gustafson, G. R.; Baldino, C. M.; O'Donnel, M.-M. E.; Sheldon, A.; Tarsa, R. J.; verni, C. J.; Coffen, D. L., "Incorporation of Carbohydrates and Peptides Into Large Triazine-based Screening Libraries Using Automated Parallel Synthesis," *Tetrahedron* 1998, 54, 4067.
18. H. Rink *Tetrahedron Lett.* 1987, 28, 3787.
19. Garigipati, R. V., "Reagents for Combinatorial Organic Synthesis: Preparation and Uses of Rink-chloride," *Tetrahedron Lett.* 1997, 38, 6807.
20. Brown, D. S.; Revill, J. M.; Shute, R. E. Merrifield, "Alpha-Methoxyphenyl (MAMP) Resin; A New Versatile Solid Support for The Synthesis of Secondary Amines," *Tetrahedron Lett.* 1998, 39, 8533.
21. Zuckermann, R. N.; Kerr, S. B. H.; Moos, W. H., "Efficient Method for The Preparation of Peptoids [oligo(N-substituted glycines)] by Submonomer Solid-phase Synthesis," *J. Am. Chem. Soc.* 1992, 114, 10646-10647.
22. Gordon, D. W.; Steele, J., "Reductive Alkylation on a Solid Phase: Synthesis of a piperazidione Combinatorial Library, *Bioorg. Med. Chem. Lett.* 1995, 5, 47.
23. Liu, G.; Ellman J. A., "A General Solid-phase Synthesis Strategy for The Preparation of 2-Pyrrolidinemethanol Ligands," *J. Org. Chem.* 1995, 60, 7712.
24. March, J., "Advanced Organic Chemistry," $3^{rd}$ Ed., Wiley, New York, p. 916.
25. Luknitskii, Vovsi., *Russ. Chem. Rev.,* 1969, 38, 487-494.
26. Lee, M. H.; Pascopella, L.; Jacobs, W. R.; Hatfull, G. F., "Site Specific Integration of Mycobacteriophage L5: Integration-Proficient Vectors for *Mycobacterium smegmatis, Mycobacterium tuberculosis*, and *bacilli* Calmette-Guerin," *Proc. Matl Acad. Sci USA* 1991, 88, 3111.
27. Shawar, R. M.; Humble, D. J.; Van Dalfsen, J. M.; Stover, C. K.; Hickey, M. J.; Steele, S.; Mitscher, L. A.; Baker, W., "Rapid Screening of Natural Products for Antimycobacterial Activity By Using Luciferase-Expressing Strains of *Mycobacterium bovis* BCG and *Mycobacterium intracellulare,"Antimicrob. Agents Chemother.* 1997, 41, 570-574.
28. Arain, T. M.; Resconi, A. E.; Hickey, M. J.; Stover, C. K., "Bioluminesence Screening In Vitro (Bio-Siv) Assays for High-Volume Antimycobacterial Drug Discovery," *Antimicrob. Agents Chemother.* 1996, 40, 1536-1541.

We claim:

1. A method of treating disease caused by an a mycobacterial agent comprising administering an effective amount of a substituted ethylene diamine compound of the formula

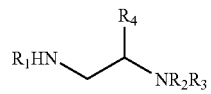

wherein $R_4$ is selected from H, alkyl, aryl, heteroatom substituted alkyl and aryl, alkenyl, alkynyl, aralkyl, aralkynyl, cycloalkyl, cycloalkenyl;

and wherein $R_1$, $R_2$ and $R_3$ are independently selected from H, alkenyl, alkynyl, aralkyl, aralkenyl, aralkynyl, cycloalkyl, cycloalkenyl, or heteroaryl; or wherein $R_1$ is selected from H, alkenyl, alkynyl, aralkyl, aralkenyl, aralkynyl, cycloalkyl, cycloalkenyl, silyl, and $NR_2R_3$ is derived from a cyclic secondary amine;

including straight or branched chain derivative thereof, cyclic derivative thereof, substituted derivative thereof, functionalized derivative thereof, salts thereof, isomers thereof, or a combination thereof;

optionally in a pharmaceutical carrier.

2. The method of claim 1, wherein $NHR_1$ or $NR_2R_3$ of the substituted ethylene diamine has the chemical structure

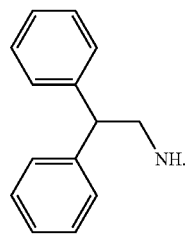

3. The method of claim 2 wherein the substituted ethylene diamine compound is selected from

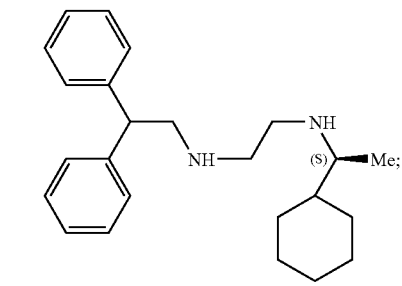

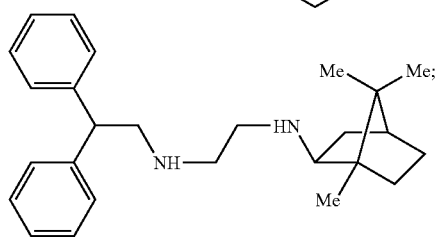

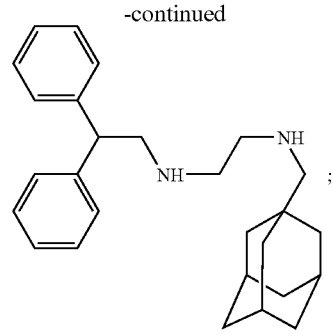

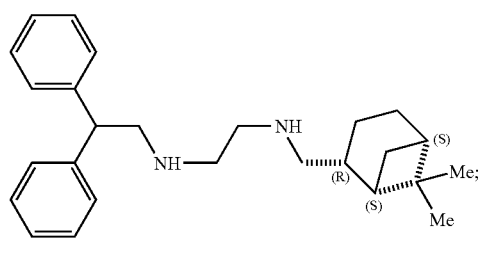

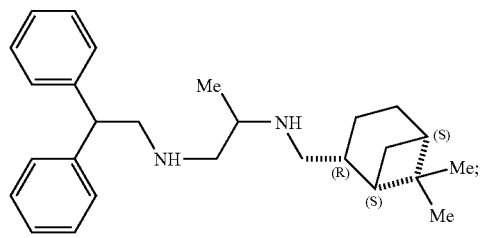

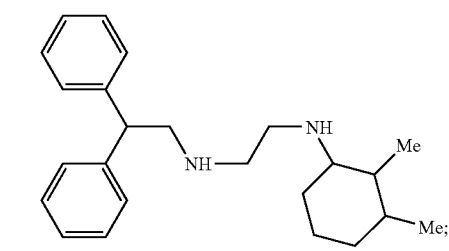

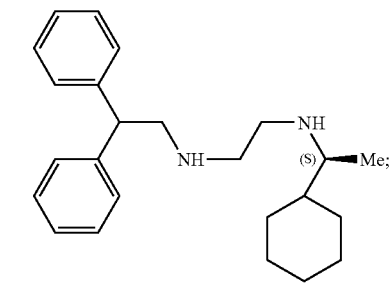

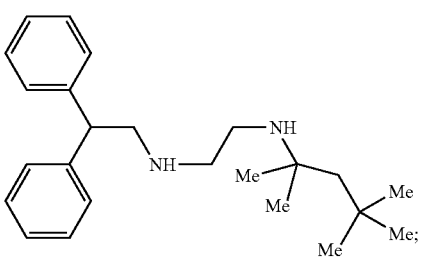

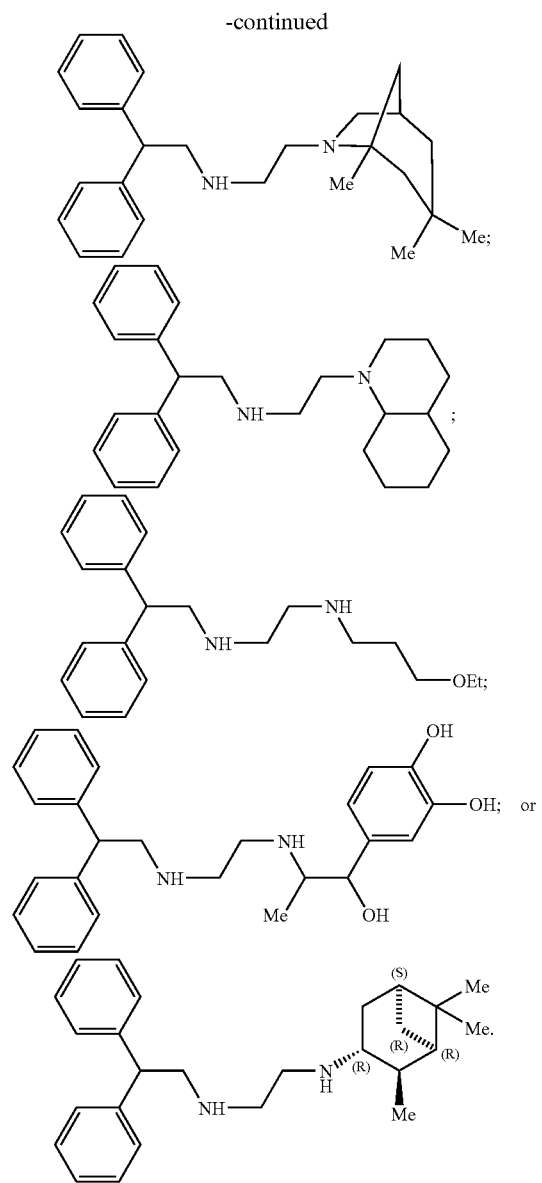
4. The method of claim 1, wherein $NHR_1$ or $NR_2R_3$ of the substituted ethylene diamine has the chemical structure
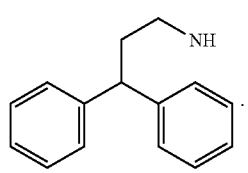
5. The method of claim 4, wherein the substituted ethylene diamine compound is selected from
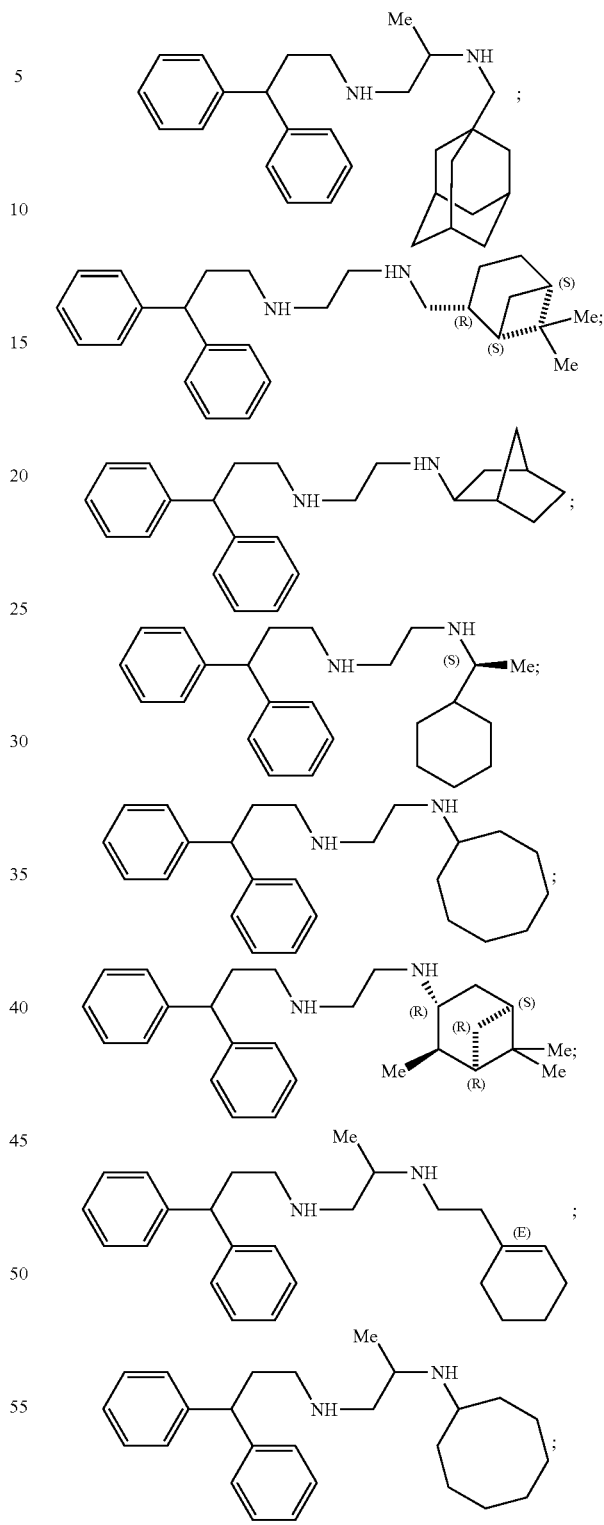

-continued
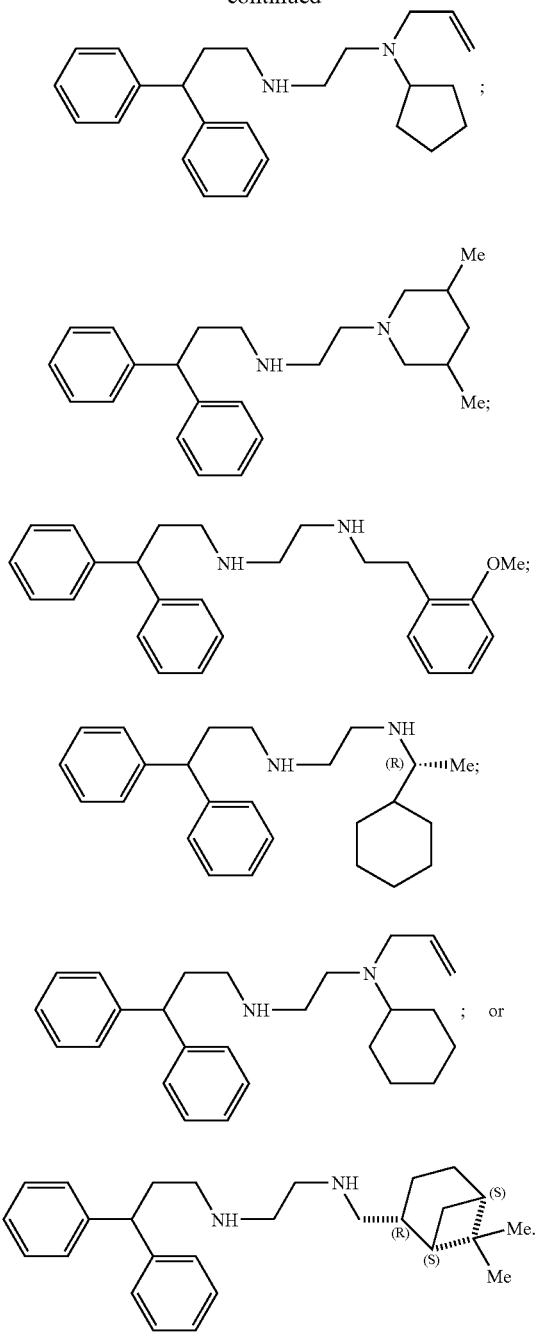
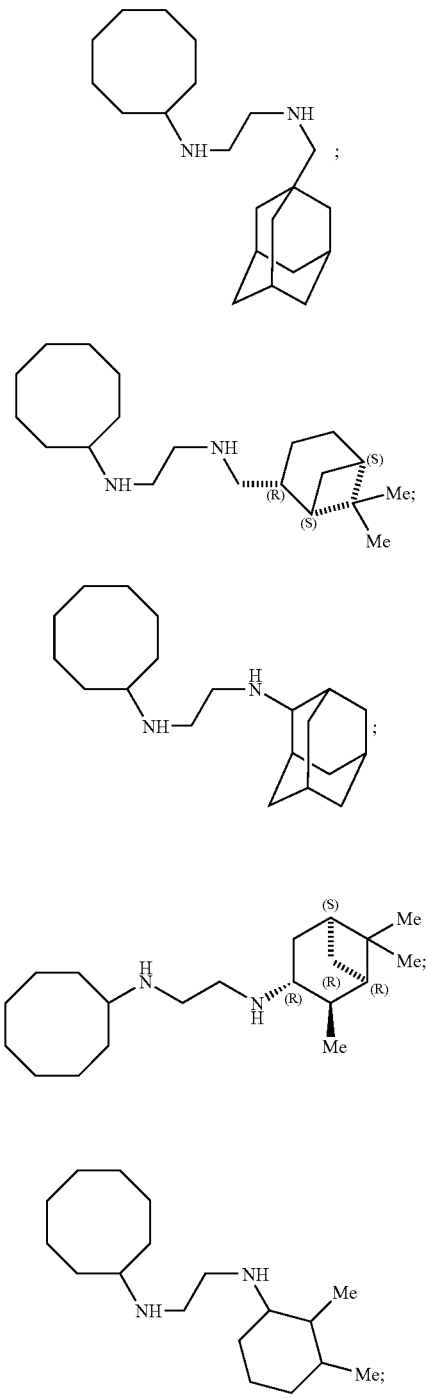
6. The method of claim 1, wherein NHR$_1$ or NR$_2$R$_3$ of the substituted ethylene diamine has the chemical structure
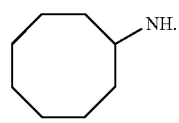
7. The method of claim 6, wherein the substituted ethylene diamine compound is selected from
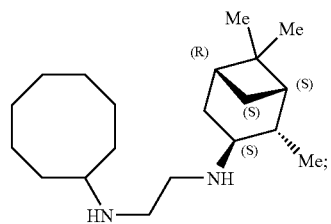

-continued
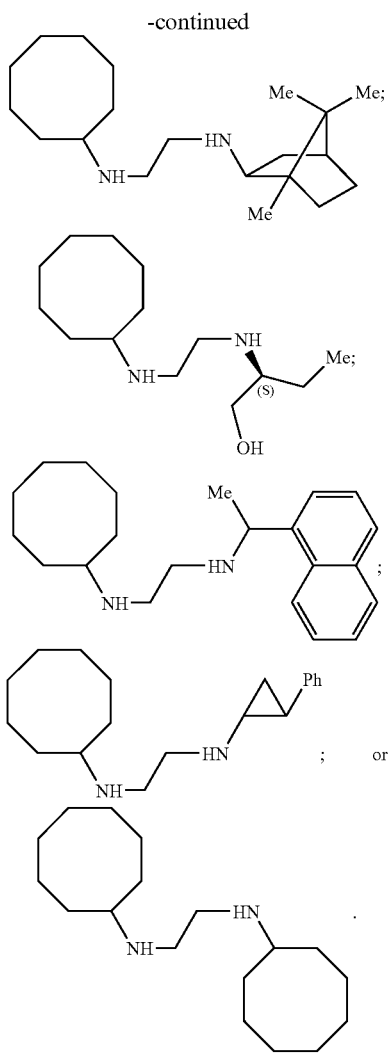
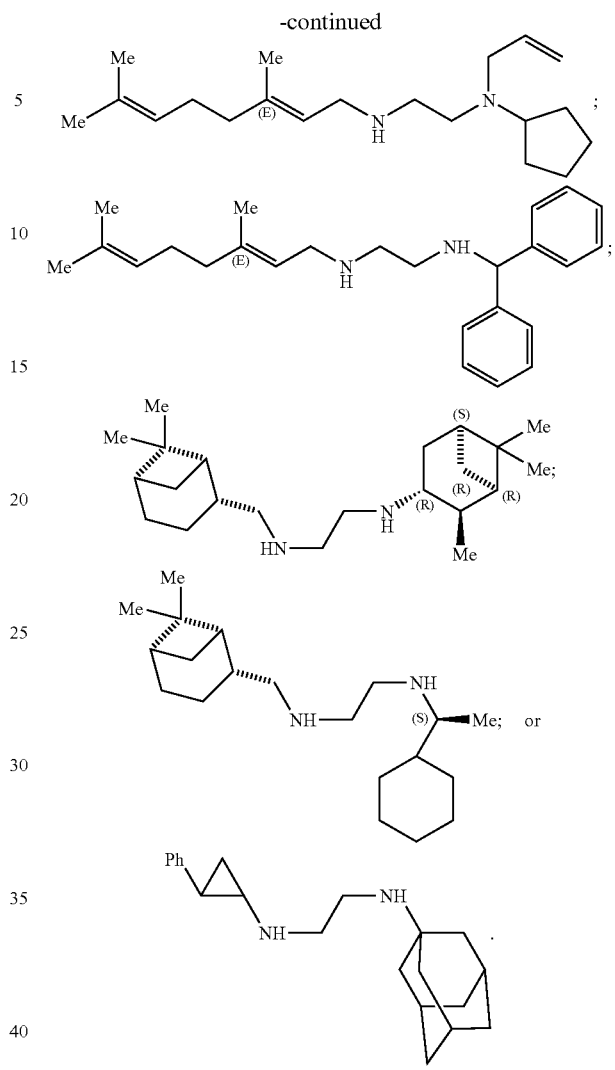
8. The method of claim 1, wherein $NHR_1$ or $NR_2R_3$ of the substituted ethylene diamine has the chemical structure
10. The method of claim 1, wherein the substituted ethylene diamine compound is selected from
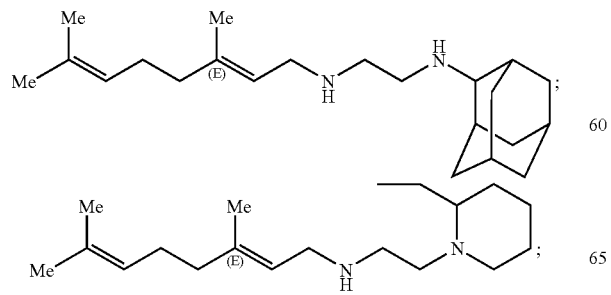
9. The method of claim 8, wherein the substituted ethylene diamine compound is selected from
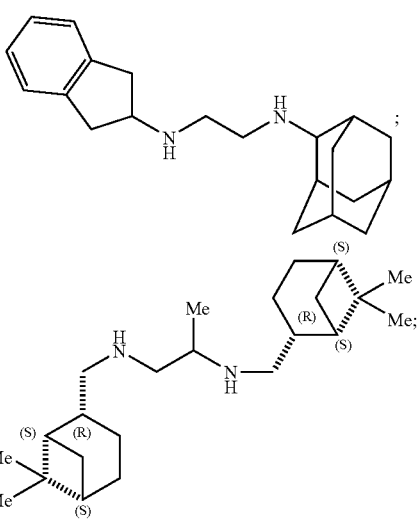

-continued
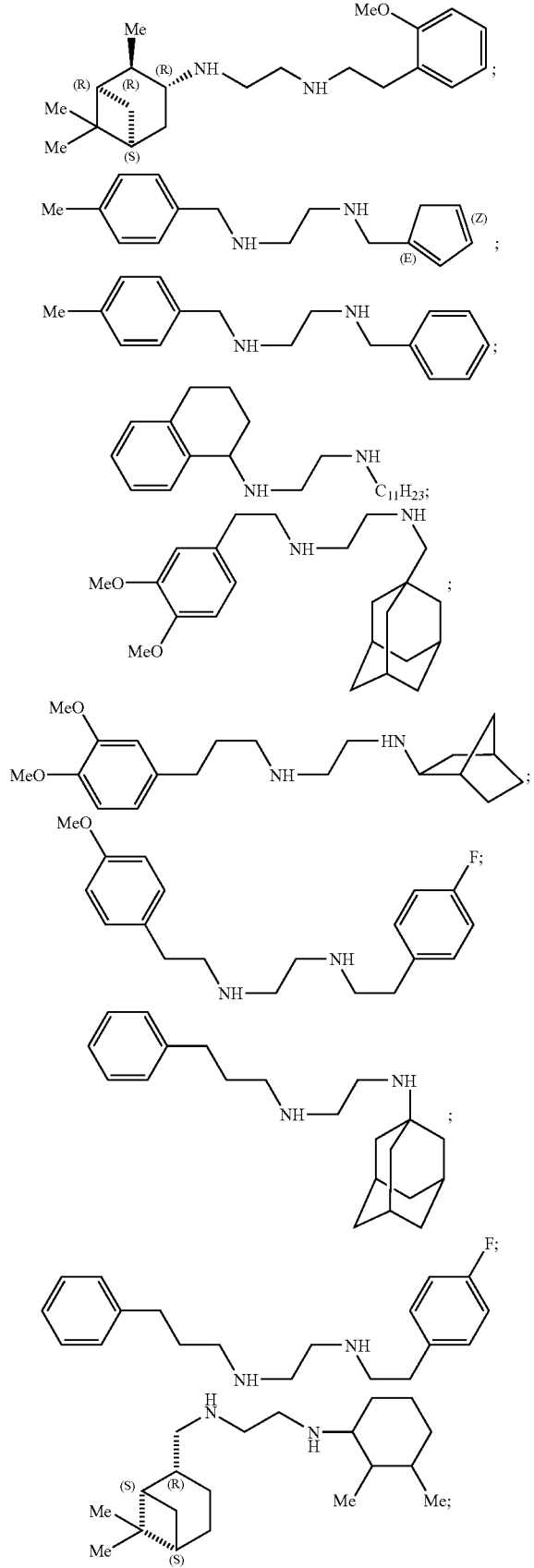
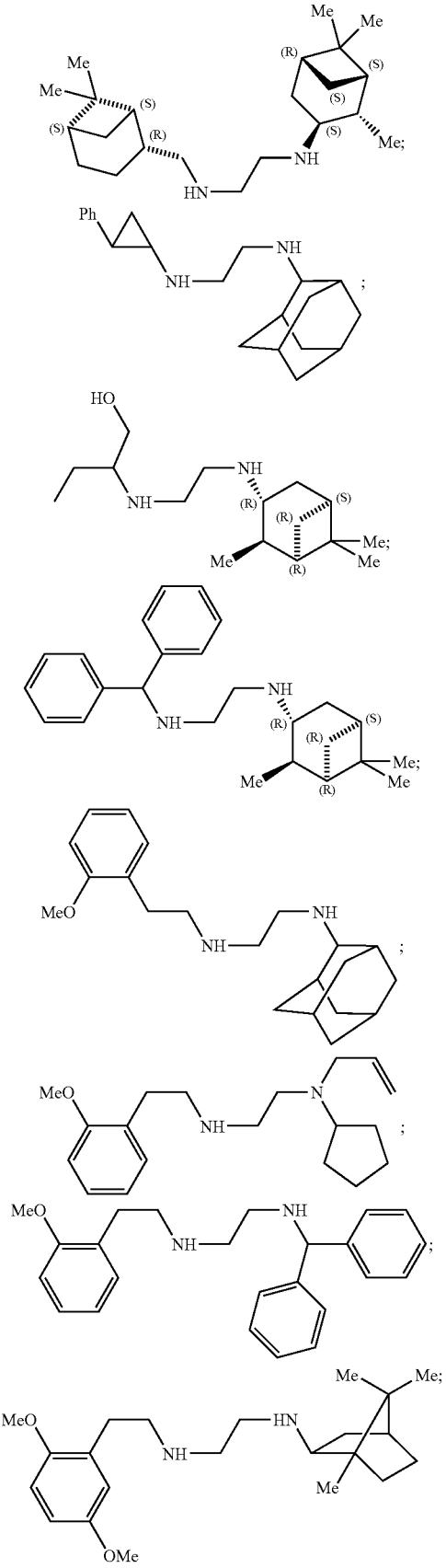

-continued

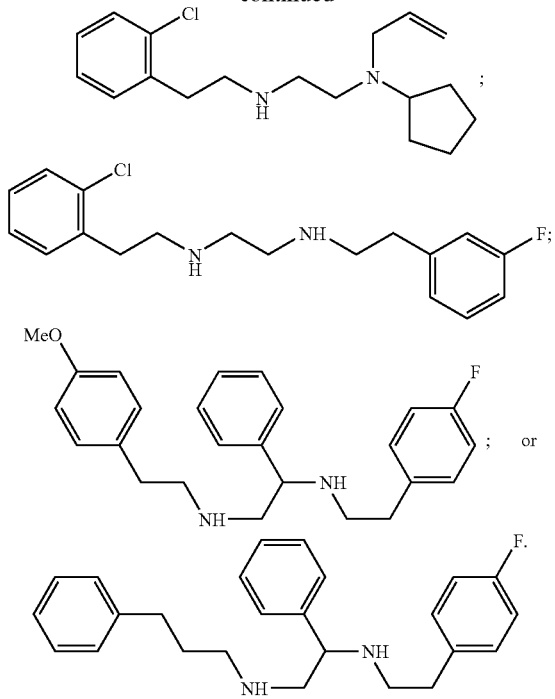

11. The method of claim 1, wherein the mycobacterial agent comprises *M. tuberculosis, M. avium-intracellulare, M. kansarii, M. fortuitum, M. chelonae, M. leprae, M. africanum, M. microti, M. avium paratuberculosis, M. intracellulare, M. scrofulaceum, M. xenopi, M. marinum,* or *M. ulcerans*.

12. The method of claim 1, wherein the infectious disease comprises tuberculosis.

13. A method of treating disease caused by an mycobacterial agent comprising administering an effective amount of a symmetrical substituted ethylene diamine compound of the formula

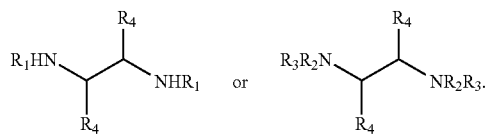

wherein $R_4$ is selected from H, alkyl, aryl, heteroatom substituted alkyl and aryl, alkenyl, alkynyl, aralkyl, aralkynyl, cycloalkyl, cycloalkenyl;

and wherein $R_1$, $R_2$ and $R_3$ are independently selected from H, aryl, alkenyl, alkynyl, aralkenyl, aralkynyl, cycloalkyl, cycloalkenyl, heteroaryl, halide, alkoxy, aryloxy, alkylthio, arylthio, silyl, siloxy, amino.

14. The method of claim 1, wherein $NHR_1$ of the substituted ethylene diamine is selected from 1-adamantanemethylamine, 2,2,-diphenylethylamine, 3,3-diphenylpropylamine, 2-amino-1-butanol, cis-(−)myrtanylamine, cyclooctylamine, 2-adamantamine, (+)-bornylamine, cyclohexyethylamine, undecylamine, geranylamine, (+)-isopinocampheylamine, (−)-isopinocampheylamine, or a combination thereof, or substituted derivatives thereof, or stereoisomers thereof.

15. The method of claim 1, wherein $NR_2R_3$ of the substituted ethylene diamine is selected from 1-adamantanemethylamine, 2,2,-diphenylethylamine, 3,3-diphenylpropylamine, 2-amino-1-butanol, cis-(−)myrtanylamine, cyclooctylamine, 2-adamantamine, (+)-bornylamine, cyclohexyethylamine, undecylamine, geranylamine, (+)-isopinocampheylamine, (−)-isopinocampheylamine, or a combination thereof, or substituted derivatives thereof, or stereoisomers thereof.

16. The method of claim 1, wherein $R_1$, $R_2$, and $R_3$ are selected from isopinocamphenyl; bornyl; norbornyl; adamantanetetyl; cis-(−)myrtanyl; adamantyl; noradamantyl; 6-azabicyclo[3.2.1]octane; or exo-norbomane.

17. The method of claim 1, wherein the infectious agent comprises a drug resistant mycobacterial strain.

18. The method of claim 1, wherein administering the effective amount of substituted ethylene diamine compound comprises topical, oral, peritoneal, implantable, subcutaneous, intramuscular, intraocular, intraarterial or intravenous administration.

19. The method of claim 1, wherein the substituted ethylene diamine compound is administered as a solid, liquid or aerosol.

20. The method of claim 19, wherein the solid comprises pills, creams, soaps or implantable dosage units.

21. The method of claim 19, wherein the liquid comprises liquid formulations adapted for injection, topical or ocular administration.

22. The method of claim 19, wherein the aerosol comprises an inhaler formulation.

23. The method of claim 19, wherein the solid, liquid or aerosol comprises a sustained release matrix.

24. The method of claim 1, wherein the effective amount of substituted ethylene diamine compound comprises from 100 to 0.1 mg per kg of body weight.

25. The method of claim 1, wherein the effective amount of substituted ethylene diamine compound comprises from 50 to 0.2 mg per kg of body weight.

26. The method of claim 1, wherein the effective amount of substituted ethylene diamine compound comprises from 25 to 0.5 mg per kg of body weight.

27. The method of claim 1, wherein the effective amount of substituted ethylene diamine compound comprises from 1 to 1000 mg.

* * * * *